(12) United States Patent
Kurose et al.

(10) Patent No.: US 8,324,265 B2
(45) Date of Patent: *Dec. 4, 2012

(54) HETEROCYCLIC COMPOUNDS HAVING TYPE I 11β HYDROXYSTEROID DEHYDROGENASE INHIBITORY ACTIVITY

(75) Inventors: Noriyuki Kurose, Osaka (JP); Mikayo Hayashi, Naruto (JP); Tomoyuki Ogawa, Osaka (JP); Koji Masuda, Osaka (JP); Eiichi Kojima, Osaka (JP)

(73) Assignee: Shionogi & Co., Ltd., Osaka (JP)

(*) Notice: Subject to any disclaimer, the term of this patent is extended or adjusted under 35 U.S.C. 154(b) by 237 days.

This patent is subject to a terminal disclaimer.

(21) Appl. No.: 12/093,903

(22) PCT Filed: Nov. 20, 2006

(86) PCT No.: PCT/JP2006/323096
§ 371 (c)(1),
(2), (4) Date: May 15, 2008

(87) PCT Pub. No.: WO2007/058346
PCT Pub. Date: May 24, 2007

(65) Prior Publication Data
US 2009/0170832 A1    Jul. 2, 2009

(30) Foreign Application Priority Data

Nov. 21, 2005    (JP) .................. 2005-335995

(51) Int. Cl.
| | |
|---|---|
| A61K 31/551 | (2006.01) |
| A61K 31/5377 | (2006.01) |
| A61K 31/506 | (2006.01) |
| A61K 31/496 | (2006.01) |
| A61K 31/454 | (2006.01) |
| A61K 31/4439 | (2006.01) |
| A61K 31/427 | (2006.01) |
| A61K 31/4245 | (2006.01) |
| A61K 31/4178 | (2006.01) |
| A61K 31/4155 | (2006.01) |
| A61K 31/415 | (2006.01) |
| C07D 417/06 | (2006.01) |
| C07D 417/12 | (2006.01) |
| C07D 413/06 | (2006.01) |
| C07D 413/12 | (2006.01) |
| C07D 409/06 | (2006.01) |
| C07D 409/12 | (2006.01) |
| C07D 401/14 | (2006.01) |
| C07D 401/12 | (2006.01) |
| C07D 401/06 | (2006.01) |
| C07D 403/06 | (2006.01) |
| C07D 403/12 | (2006.01) |
| C07D 231/20 | (2006.01) |
| C07D 231/18 | (2006.01) |

(52) U.S. Cl. ..................... 514/407

(58) Field of Classification Search ............... 548/374.1, 548/369.7, 312.4, 365.7, 364.1, 187, 255, 548/143; 514/407, 397, 341, 254.05, 326, 514/218, 369, 359, 364, 278, 299, 275; 546/276.1, 546/211, 16, 113; 544/371, 295; 540/575
See application file for complete search history.

(56) References Cited

U.S. PATENT DOCUMENTS

| 4,226,877 A | 10/1980 | Arendsen | |
|---|---|---|---|
| 5,948,777 A * | 9/1999 | Bender et al. | 514/235.8 |
| 2005/0059663 A1 | 3/2005 | Martin et al. | |
| 2005/0245532 A1 | 11/2005 | Hoff et al. | |
| 2005/0245533 A1 | 11/2005 | Hoff et al. | |
| 2005/0261302 A1 | 11/2005 | Hoff et al. | |

(Continued)

FOREIGN PATENT DOCUMENTS
DE    19734664 A1 *    2/1999
(Continued)

OTHER PUBLICATIONS

Xiang et al. Biorganic & Medicinal Chemistry 2007, 15, 4396-4405.*
(Continued)

*Primary Examiner* — Joseph Kosack
*Assistant Examiner* — Matthew Coughlin
(74) *Attorney, Agent, or Firm* — Hamre, Schumann, Mueller & Larson, P.C.

(57) ABSTRACT

Disclosed is a compound useful as a type I 11βhydroxysteroid dehydrogenase inhibitor.
A compound represented by the formula:

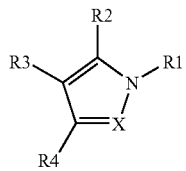

a pharmaceutically acceptable salt or solvate thereof,
wherein
$R^1$ is optionally substituted alkyl or the like,
one of $R^2$ and $R^4$ is a group of formula: —Y—$R^5$,
wherein Y is —O— or the like,
$R^5$ is substituted alkyl (the substituent is optionally substituted cycloalkyl or the like), optionally substituted branched alkyl or the like,
the other of $R^2$ and $R^4$ is hydrogen or optionally substituted alkyl,
$R^3$ is a group of formula: —C(=O)—Z—$R^6$,
wherein Z is —$NR^7$— or —$NR^7$—W—,
$R^6$ is optionally substituted cycloalkyl or the like,
$R^7$ is hydrogen or optionally substituted alkyl,
W is optionally substituted alkylene,
X is =N— or the like,
with the proviso that compounds wherein $R^2$ is 2-(morphorino)ethoxy, $R^3$ is N-(1-adamantyl)carbamoyl and $R^1$ is benzyl are excluded.

14 Claims, No Drawings

U.S. PATENT DOCUMENTS

| | | |
|---|---|---|
| 2005/0277647 A1 | 12/2005 | Link et al. |
| 2006/0148871 A1 | 7/2006 | Rohde et al. |

FOREIGN PATENT DOCUMENTS

| | | |
|---|---|---|
| EP | 0394043 | 10/1990 |
| EP | 0566138 | 10/1993 |
| EP | 1 400 516 A1 | 3/2004 |
| EP | 1 889 842 A1 | 2/2008 |
| EP | 1889842 | 2/2008 |
| EP | 1894919 | 3/2008 |
| EP | 1953145 | 8/2008 |
| EP | 2006286 | 12/2008 |
| EP | 2088136 | 8/2009 |
| JP | 60-214785 A | 10/1985 |
| JP | 01-207289 A | 8/1989 |
| JP | 03-223256 A | 10/1991 |
| JP | 06-025199 A | 2/1994 |
| JP | 2002348280 A * | 12/2002 |
| JP | 2004-065194 | 3/2004 |
| JP | 2007-262022 | 10/2007 |
| WO | WO 93/25535 A1 | 12/1993 |
| WO | 97/07789 | 3/1997 |
| WO | WO 98/14519 A1 | 9/1998 |
| WO | WO 01/23358 A1 | 4/2001 |
| WO | WO 0123358 A1 * | 4/2001 |
| WO | 02/02797 | 1/2002 |
| WO | 02/076435 | 10/2002 |
| WO | WO 03/104208 A1 | 12/2003 |
| WO | 2004/056744 | 7/2004 |
| WO | 2004/056745 | 7/2004 |
| WO | 2004/076418 | 9/2004 |
| WO | 2004/089470 | 10/2004 |
| WO | WO 2004/089470 A2 | 10/2004 |
| WO | 2005/016877 | 2/2005 |
| WO | WO 2005/016877 A2 | 2/2005 |
| WO | WO 2005/061462 A2 | 7/2005 |
| WO | WO 2005/070889 A1 | 8/2005 |
| WO | WO 2005/095350 A1 | 10/2005 |
| WO | WO 2005/097764 A1 | 10/2005 |
| WO | 2005/108368 | 11/2005 |
| WO | WO 2005/108359 A1 | 11/2005 |
| WO | WO 2005/108361 A1 | 11/2005 |
| WO | WO 2005/108368 A1 | 11/2005 |
| WO | WO 2005/112923 A2 | 12/2005 |
| WO | WO 2006/024627 A2 | 3/2006 |
| WO | WO 2006/024628 A1 | 3/2006 |
| WO | WO 2006/048750 A2 | 5/2006 |
| WO | WO 2006/074244 A2 | 7/2006 |
| WO | WO 2006/074330 A2 | 7/2006 |
| WO | WO 2006/100502 A1 | 9/2006 |
| WO | 2006/106052 | 10/2006 |
| WO | WO 2006/106052 A1 | 10/2006 |
| WO | 2007/107470 | 9/2007 |
| WO | WO 2007/107470 A2 | 9/2007 |
| WO | 2007/114125 | 11/2007 |
| WO | 2007/144394 | 12/2007 |
| WO | 2008/012532 | 1/2008 |
| WO | 2008/044656 | 4/2008 |
| WO | 2008/051875 | 5/2008 |
| WO | 2008/053194 | 5/2008 |
| WO | 2008/099145 | 8/2008 |
| WO | 2008/120655 | 10/2008 |
| WO | 2008/142986 | 11/2008 |
| WO | 2009/001817 | 12/2008 |
| WO | 2009/010416 | 1/2009 |
| WO | 2009/013211 | 1/2009 |
| WO | 2009/056881 | 5/2009 |
| WO | 2009/060232 | 5/2009 |
| WO | 2009/098501 | 8/2009 |
| WO | 2009/130496 | 10/2009 |

OTHER PUBLICATIONS

Colagiuri et al. American Journal of Public Health, Sep. 2006, vol. 96, No. 9, pp. 1562-1569.*

Bruno et al. Expert Opinion Emerging Drugs, (2005), 10(4), pp. 747-771.*

Park {Diabetes Research and Clinical Practice 66S (2004), S33-S35}.*

Curtis et al. The Journal of the American Board of Family Practice, vol. 18, pp. 37-43, (2005).*

Souillac, et al., Characterization of Delivery Systems, Differential Scanning Calorimetry, pp. 217-218 (in Encyclopedia of Controlled Drug Delivery, 1999, John Wiley & Sons, pp. 212-227).*

Vippagunta et al. Advanced Drug Delivery Reviews, 48 (2001), pp. 3-26.*

Hussain et al. Diabetes Research and Clinical Practice 2007, 76, 317-326.*

Giron, D. J. Therm. Anal. Cal. 2001, 64, pp. 37-60.*

Giron, D. J. Therm. Anal. Cal. 2002, 68, pp. 335-357.*

B. Rodriquez-Spong et al. Advanced Drug Delivery Reviews, 2004, 56, pp. 241-274.*

Machine translation of the disclosure of Japanese Application Publication No. 2002-348280 by Hirai et al., obtained from http://dossier1.ipdl.inpit.go.jp/AIPN/odse_top_fwi.ipdl?N0000=7401 on Feb. 27, 2012.*

Machine translation of German Application Publication No. DE 197 34 664 A1 by Dollinger et al., obtained from http://worldwide.espacenet.com/numberSearch?locale=en_EP on Feb. 27, 2012.*

English translation of International Search Report for International Application No. PCT/JP2006/323096.

Stewart. 11β-Hydroxysteroid dehydrogenase: implications for clinical medicine. Clinical Endocrinology 44, 1996, p. 493-499.

Kotelevtsev et al. 11β-Hydroxysteroid dehydrogenase type 1 knock-out mice show attenuated glucocortiocoid-inducible responses and resist hyperglycemia on obesity or stress. Proc. Natl. Acad. Sci. USA 99, Dec. 1997, p. 14924-14929.

Walker et al. Carbenoxolone Increases Hepatic Insulin Sensitivity in Man: A Novel Role for 11-Oxosteroid Reductase in Enhancing Glucocorticoid Receptor Activiation. Journal of Clinical Endocrinology and Metabolism 80(11), 1995, p. 3155-3159.

Bujalska et al. Does central obesity reflect "Cushing's disease of the omentum"? The Lancet 349, Apr. 26, 1997, p. 1210-1213.

O'Riordan, "RIO-Diabetes: Rimonabant effective in patients with type 2 diabetes," Medscape News, 2005 (accessed Jun. 29, 2011) <http://www.medscape.com/viewarticle/538697>.

"Rimonabant-studie bestaetigt signifikante verbesserungen der HbA1c-Werte and metabolischen risikofactoren bei patienten mit typ-2-diabetes," Internet Citation, 2005 (accessed on Aug. 4, 2005) <http://www.diabetes-news.de/news/nachrichten-2005/pm050617.htm>.

* cited by examiner

HETEROCYCLIC COMPOUNDS HAVING TYPE I 11β HYDROXYSTEROID DEHYDROGENASE INHIBITORY ACTIVITY

FIELD OF THE INVENTION

This invention relates to a pharmaceutically useful compound with an inhibitory activity to 11βhydroxysteroid dehydrogenase type 1, hereinafter referred to as 11β-HSD-1

BACKGROUND ART

11β-HSD-1 is an enzyme that converts inactive steroids, 11β-dehydrosteroid into its active steroids and is considered to be important in the basal metabolic rate in the living body (Non-patent Document 1). Moreover, 11β-HSD-1 knockout mice have the resistance to hyperglycemia induced by obesity or stress (Non-patent Document 2). In addition, a similar phenomenon was observed in human on administration of 11β-HSD-1 inhibitor, carbenoxolone (Non-patent Document 3). These facts suggest that the 11β-HSD-1 inhibitors could be useful as drugs for the treatment of insulin independent diabetes or obesity (Non-patent Document 4).

Patent document 1 describes that pyrazole derivatives are useful as herbicide. Patent document 2 describes that pyrazole derivatives are useful as pesticide. Patent document 3 describes that pyrazole derivatives are useful as herbicide. Patent document 4 describes that pyrazole derivatives are useful as insecticide. Patent document 5 describes that pyrazole derivatives are useful as insecticide. Patent document 6 describes that pyrazole derivatives are useful as pesticide. Patent document 7 describes that pyrazole derivatives are useful as herbicide. The compounds disclosed in these patents have the carbamoyl group that is substituted with a substituent selected from a group consisting of substituted aryl, substituted arylalkyl, substituted heteroaryl and alkyl at 4-position of the pyrazole ring, and they are different from the compounds in the present invention.

Furthermore the compounds having straight alkyloxy at 5-position on the pyrazole ring are disclosed in patent document 8 and useful for the treatment of schizophrenia, and they are different from the present invention.

Moreover patent document 9 describes that the pyrazole derivatives shown below are useful as a cannabinoid receptor agonist, but does not describe the inhibitory activity to 11β-HSD-1.

[Formula 1]

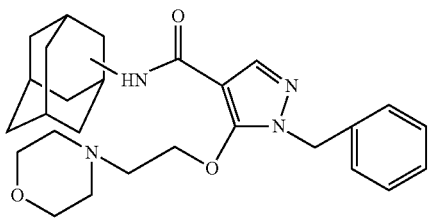

[Non-patent Document 1] Clin. Endocrinol, 1996, 44, 493
[Non-patent Document 2] Proc. Nat. Acad. Sci. USA, 1997, 94, 14924
[Non-patent Document 3] J. Clin. Endocrinol. Metab. 1995, 80, 3155
[Non-patent Document 4] Lancet, 1997, 349, 1210
[Patent Document 1] WO05/070889
[Patent Document 2] WO02/096882
[Patent Document 3] WO93/25535
[Patent Document 4] JP06-025199
[Patent Document 5] JP03-223256
[Patent Document 6] JP01-207289
[Patent Document 7] JP60-214785
[Patent Document 8] U.S. Pat. No. 4,226,877
[Patent Document 9] WO98/41519

DISCLOSURE OF INVENTION

Problems to be Solved by the Invention

The present invention provides useful compounds having an inhibitory activity to 11βhydroxysteroid dehydrogenase type 1.

Means for Solving the Problem

The present invention provides;
(1) A compound represented by formula (I):

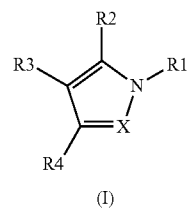

[Formula 2]

(I)

a pharmaceutically acceptable salt or a solvate thereof,
wherein
$R^1$ is optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle,
one of $R^2$ and $R^4$ is a group of formula: —Y—$R^5$,
wherein Y is —O— or —S—, and
$R^5$ is substituted straight alkyl wherein the substituent of said straight alkyl is optionally substituted cycloalkyl, optionally substituted cycloalkenyl, optionally substituted aryl, optionally substituted heteroaryl or optionally substituted heterocycle,
optionally substituted branched alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle,
the other of $R^2$ and $R^4$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle,
$R^3$ is a group of formula: —C(=O)—Z—$R^6$,
wherein Z is —$NR^7$— or —$NR^7$—W—, and
$R^6$ is optionally substituted cycloalkyl, optionally substituted cycloalkenyl, or optionally substituted heterocycle,
$R^7$ is hydrogen or optionally substituted alkyl, or $R^6$ and $R^7$ taken together may form optionally substituted ring,
W is optionally substituted alkylene,
X is =N— or =$CR^8$—, and
$R^8$ is hydrogen or optionally substituted alkyl,
with the proviso that compounds wherein $R^2$ is 2-(morphorino)ethoxy, $R^3$ is N-(1-adamantyl)carbamoyl and $R^1$ is benzyl are excluded,
(2) The compound according to the above (1), a pharmaceutically acceptable salt or a solvate thereof, wherein $R^1$ is substituted alkyl wherein the substituent of said substituted alkyl is optionally substituted amino or optionally substituted heterocycle, (3) The compound according to the above (1), a pharmaceutically acceptable salt or a solvate thereof, wherein $R^1$ is substituted ethyl wherein the substituent of said substituted ethyl is optionally substituted amino or optionally substituted heterocycle, (4) The compound according to the above (1), a pharmaceutically acceptable salt or a solvate thereof, wherein $R^1$ is unsubstituted alkyl, (5) The compound according to the above (1), a pharmaceutically acceptable salt or a solvate thereof, wherein $R^2$ is a group of formula: —Y—$R^5$,
wherein Y and $R^5$ have the same meaning as defined in the above (1), (6) The compound according to the above (5), a pharmaceutically acceptable salt or a solvate thereof, wherein Y is —O—, (7) The compound according to the above (5) or (6), a pharmaceutically acceptable salt or a solvate thereof, wherein $R^5$ is substituted straight alkyl wherein the substituent of said substituted straight alkyl is optionally substituted cycloalkyl, (8) The compound according to the above (7), a pharmaceutically acceptable salt or a solvate thereof, wherein $R^5$ is substituted methyl wherien the substituent of said substituted straight methyl is optionally substituted cycloalkyl, (9) The compound according to the above (7) or (8), a pharmaceutically acceptable salt or a solvate thereof, wherein said optionally substituted cycloalkyl is optionally substituted cyclohexyl,

(10) The compound according to the above (5) or (6), a pharmaceutically acceptable salt or a solvate thereof, wherein $R^5$ is branched alkyl,

(11) The compound according to the above (1), a pharmaceutically acceptable salt or a solvate thereof, wherein Z is —$NR^7$—, and $R^7$ has the same meaning as defined in the above (1),

(12) The compound according to the above (11), a pharmaceutically acceptable salt or a solvate thereof, wherein $R^7$ is hydrogen,

(13) The compound according to the above (1), a pharmaceutically acceptable salt or a solvate thereof, wherein $R^6$ is optionally substituted cycloalkyl,

(14) The compound according to the above (13), a pharmaceutically acceptable salt or a solvate thereof, wherein $R^6$ is adamantyl,

(15) The compound according to the above (13), a pharmaceutically acceptable salt or a solvate thereof, wherein $R^3$ is a group of formula (II):

[Formula 3]

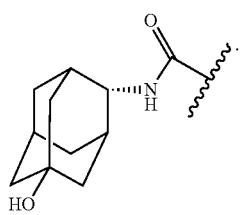

(II)

(16) The compound according to any one of the above (1) to (15), a pharmaceutically acceptable salt or a solvate thereof, wherein X is =N—,

(17) The compound according to the above (1), a pharmaceutically acceptable salt or a solvate thereof, wherein $R^1$ is a group of formula:

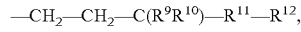

wherein $R^9$ and $R^{10}$ are each independently hydrogen, optionally substituted alkyl or halogen, or $R^9$ and $R^{10}$ taken together with the carbon atom to which they are attached may form an optionally substituted ring,
$R^{11}$ is —(CH$_2$)n-, wherein n is an integer of 0 to 3, and
$R^{12}$ is hydrogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkyloxycarbonyl, optionally substituted arylalkylcarbonyl, optionally substituted carbamoyl, optionally substituted thiocarbamoyl, optionally substituted alkylsulfonyl, optionally substituted arylsulfonyl, optionally substituted sulfamoyl, optionally substituted amino, optionally substituted carbamoyloxy, optionally substituted alkyloxy or optionally substituted alkylthio,
a group of formula: —C(=O)—$NR^{13}R^{14}$,
wherein $R^{13}$ and $R^{14}$ are each independently hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted arylsulfonyl, optionally substituted heteroarylsulfonyl or optionally substituted heterocyclesulfonyl, or $R^{13}$ and $R^{14}$ taken together with the nitrogen atom to which they are attached may form an optionally substituted ring or,
a group of formula: —$NR^{15}R^{16}$,
wherein $R^{15}$ and $R^{16}$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted arylsulfonyl, optionally substituted alkyloxycarbonyl or optionally substituted sulfamoyl, or $R^{15}$ and $R^{16}$ taken together with the nitrogen atom to which they are attached may form optionally substituted ring,

(18) The compound according to the above (1), a pharmaceutically acceptable salt or a solvate thereof, wherein $R^1$ is a group of formula:

—CH$_2$—CH$_2$—C($R^9R^{10}$)—$R^{11}$—$R^{12}$, wherein $R^9$, $R^{10}$, $R^{11}$ and $R^{12}$ have the same meaning as defined in the above (17),

(19) The compound according to the above (17) or (18), a pharmaceutically acceptable salt or a solvate thereof, wherein $R^9$ and $R^{10}$ are each independently optionally substituted alkyl, or $R^9$ and $R^{10}$ taken together with the carbon atom to which they are attached may form optionally substituted ring,

(20) The compound according to any one of the above (17) to (19), a pharmaceutically acceptable salt or a solvate thereof, wherein $R^{11}$ is —$(CH_2)n$-, wherein n is an integer of 0 to 1,

(21) The compound according to any one of the above (17) to (20), a pharmaceutically acceptable salt or a solvate thereof, wherein $R^{12}$ is carboxy, cyano or heterocycle,

(22) The compound according to any one of the above (17) to (20), a pharmaceutically acceptable salt or a solvate thereof, wherein $R^{12}$ is a group of formula: —C(=O)—$NR^{13}R^{14}$, wherein $R^{13}$ and $R^{14}$ are each independently hydrogen, optionally substituted alkyl, optionally substituted aryl, optionally substituted cycloalkyl, optionally substituted alkylsulfonyl, optionally substituted arylsulfonyl, optionally substituted heteroarylsulfonyl, optionally substituted heterocyclesulfonyl or optionally substituted heterocycle, or $R^{13}$ and $R^{14}$ taken together with the nitrogen atom to which they are attached may form an optionally substituted ring,

(23) The compound according to any one of the above (17) to (20), a pharmaceutically acceptable salt or a solvate thereof, wherein $R^{12}$ is a group of formula: —$NR^{15}R^{16}$, wherein $R^{15}$ and $R^{16}$ have the same meaning as defined in the above (17), (24) The compound according to the above (23), a pharmaceutically acceptable salt or a solvate thereof, wherein $R^{15}$ is a group of formula: —C(=O)R', wherein R' is optionally substituted alkyl, optionally substituted alkenyl, optionally substituted cycloalkyl, optionally substituted aryl, optionally substituted amino or optionally substituted alkyloxy,

(25) A pharmaceutical composition which comprises the compound according to any one of the above (1) to (24), a pharmaceutically acceptable salt or a solvate thereof as an active ingredient,

(26) The pharmaceutical composition according to the above (25) for treating and/or preventing diabetes.

The present invention is characterized in the followings.

1) Possess a 5-membered N-containing heteroring,

2) Possess a substituent of formula: —Y—$R^5$ on the above 5-membered heteroring, 3) $R^5$ is substituted straight alkyl wherein the substituent of said substituted alkyl is substituted cycloalkyl, optionally substituted cycloalkenyl, optionally substituted aryl, optionally substituted heteroaryl or optionally substituted heterocycle, optionally substituted branched alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle, optionally substituted branched alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle, 4) Possess a substituent of formula: —C(=O)—Z—$R^6$ on the above 5-membered heteroring, 5) $R^6$ is optionally substituted cycloalkyl, optionally substituted cycloalkenyl, or optionally substituted heterocycle, or $R^6$ and $R^7$ taken together may form an optionally substituted ring, 6) Possess optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle on a nitrogen atom of the above 5-membered heteroring, Effect of the Invention The compounds of the present invention possess an inhibitory activity to 11β hydroxysteroid dehydrogenase type 1 and the pharmaceutical compositions comprising them are very useful for a medicament, especially a medicament for treating and/or preventing hyperlipidemia, diabetes, obesity, arteriosclerosis, atherosclerosis, hyperglycemia and/or syndrome X. Moreover, the compounds of the present invention selectively inhibit 11βhydroxysteroid dehydrogenase type 1. The preferable compounds in the present compounds have a high metabolic stability, a weak drug metabolizing enzyme induction, a weak drug metabolizing enzyme inhibition or a high oral absorption, and they are especially useful for a medicament. In addition, the present invention includes compounds having a low clearance and a long half-life period for exhibiting the drug activity.

BEST MODE FOR CARRYING OUT THE INVENTION

Terms used in the present specification are explained below. Each term has the following meanings alone or together with other terms.

"Alkyl" means a C1 to C10 straight or branched alkyl group, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl, n-decyl or the like. Preferred is a C1 to C6 alkyl or a C1 to C4 alkyl, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl.

"Straight alkyl" means a C1 to C10 straight alkyl group, for example, methyl, ethyl, n-propyl, n-butyl, n-pentyl, n-hexyl, n-heptyl, n-octyl, n-nonyl, n-decyl or the like. Preferred is a C1 to C6 or a C1 to C4 straight alkyl.

"Branched alkyl" means a C3 to C10 branched alkyl group, for example, isopropyl, isobutyl, sec-butyl, tert-butyl, isopentyl, neopentyl, tert-pentyl, isohexyl or the like. Preferred is a C3 to C6 branched alkyl.

"Alkylene" means a di-valent group derived from the above "alkyl", which includes a C1 to C10 straight or branched alkylene. Preferred is methylene, ethylene, propylene, trimethylene, tetramethylene, ethylethylene, pentamethylene, hexamethylene or the like.

"Alkenyl" means a C2 to C8 straight or branched alkenyl group, which includes a group having one or more double bond(s), for example 1 to 3 double bond(s) in the above "alkyl". Exemplified is vinyl, 1-propenyl, 2-propenyl, 1-butenyl, 2-butenyl, 3-butenyl, 1,3-butadienyl, 3-methyl-2-butenyl or the like.

"Alkynyl" means a C2 to C8 straight or branched alkynyl group, which includes a group having one or more triple bond(s), for example 1 to 3 triple bond(s) in the above "alkyl". Exemplified is ethynyl or the like. Moreover, "alkynyl" can possess 1 to 3 double bond(s).

"Cycloalkyl" means a C3 to C15 saturated cyclic hydrocarbon group. Bridged cyclic hydrocarbon group is also included. Exemplified is cyclopropyl, cyclobutyl, cyclopentyl, cyclohexyl, cycloheptyl, cyclooctyl or bridged cyclic hydrocarbon, exemplified as follows.

[Formula 4]

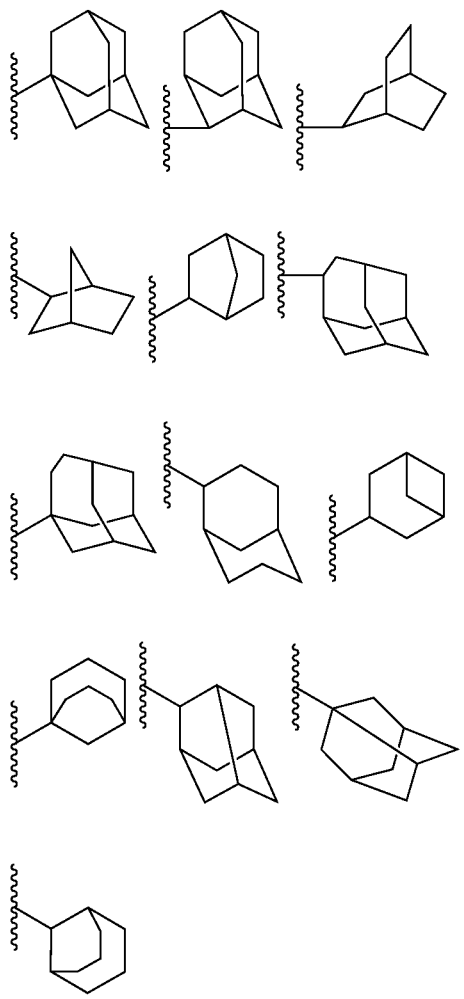

"Cycloalkenyl" means a C3 to C7 unsaturated aliphatic hydrocarbon group, including bridged cyclic hydrocarbon group. Exemplified is cyclopropenyl, cyclobutenyl, cyclopentenyl, cyclohexenyl or cycloheptenyl. Preferred is cyclopropenyl, cyclobutenyl, cyclopentenyl or cyclohexenyl. Furthermore, cycloalkenyl means a group that has unsaturated bond in the above exemplified bridged cyclic hydrocarbon group.

"Aryl" means a monocyclic aromatic hydrocarbon group (e.g., phenyl) or a fused aromatic hydrocarbon group (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl etc.). Preferred is phenyl or naphthyl (1-naphthyl, 2-naphthyl) or the like.

"Heteroaryl" means a monocyclic aromatic heterocyclic group or fused aromatic heterocyclic group.

The monocyclic aromatic heterocyclic group means a group derived from 5 to 8-membered aromatic heterocycle which may contain 1 to 4 oxygen, sulfur and/or nitrogen atom(s) in the ring. The binding bond can be at any substitutable position.

The fused aromatic heterocyclic group means a group derived from 5 to 8-membered aromatic heterocycle which may contain 1 to 4 oxygen, sulfur and/or nitrogen atom(s) in the ring fused with one to four of 5 to 8-membered aromatic carbocycle(s) or other 5 to 8-membered aromatic heterocycle(s). The binding bond can be at any substitutable position.

For example, it is furyl (e.g., furan-2-yl or furan-3-yl), thienyl (e.g., thiophene-2-yl or thiophene-3-yl), pyrrolyl (e.g., pyrrole-1-yl, pyrrole-2-yl or pyrrole-3-yl), imidazolyl (e.g., imidazole-1-yl, imidazole-2-yl or imidazole-4-yl), pyrazolyl (e.g., pyrazole-1-yl, pyrazole-3-yl or pyrazole-4-yl), triazolyl (e.g., 1,2,4-triazole-1-yl, 1,2,4-triazole-3-yl or 1,2,4-triazole-4-yl), tetrazolyl (e.g., tetrazole-1-yl, tetrazole-2-yl or tetrazole-5-yl), oxazolyl (e.g., oxazole-2-yl, oxazole-4-yl or oxazole-5-yl), isoxazolyl (e.g., isoxazole-3-yl, isoxazole-4-yl or isoxazole-5-yl), thiazolyl (e.g., thiazole-2-yl, thiazole-4-yl or thiazole-5-yl), thiadiazolyl, isothiazolyl (e.g., isothiazole-3-yl, isothiazole-4-yl or isothiazole-5-yl), pyridyl (e.g., pyridine-2-yl, pyridine-3-yl or pyridine-4-yl), pyridazinyl (e.g., pyridazine-3-yl or pyridazine-4-yl), pyrimidinyl (e.g., pyrimidine-2-yl, pyrimidine-4-yl or pyrimidine-5-yl), furazanyl (e.g., furazan-3-yl), pyrazinyl (e.g., pyrazine-2-yl), oxadiazolyl (e.g., 1,3,4-oxadiazole-2-yl), benzofuryl (e.g., benzo[b]furan-2-yl, benzo[b]furan-3-yl, benzo[b]furan-4-yl, benzo[b]furan-5-yl, benzo[b]furan-6-yl or benzo[b]furan-7-yl), benzothienyl (e.g., benzo[b]thiophene-2-yl, benzo[b]thiophene-3-yl, benzo[b]thiophene-4-yl, benzo[b]thiophene-5-yl, benzo[b]thiophene-6-yl or benzo[b]thiophene-7-yl), benzimidazolyl (e.g., benzimidazole-1-yl, benzimidazole-2-yl, benzimidazole-4-yl or benzimidazole-5-yl), dibenzofuryl, benzoxazolyl, quinoxalyl (e.g., quinoxaline-2-yl, quinoxaline-5-yl or quinoxaline-6-yl), cinnolyl (e.g., cinnoline-3-yl, cinnoline-4-yl, cinnoline-5-yl, cinnoline-6-yl, cinnoline-7-yl or cinnoline-8-yl), quinazolyl (e.g., quinazoline-2-yl, quinazoline-4-yl, quinazoline-5-yl, quinazoline-6-yl, quinazoline-7-yl or quinazoline-8-yl), quinolyl (e.g., quinoline-2-yl, quinoline-3-yl, quinoline-4-yl, quinoline-5-yl, quinoline-6-yl, quinoline-7-yl or quinoline-8-yl), phthalazinyl (e.g., phthalazine-1-yl, phthalazine-5-yl or phthalazine-6-yl), isoquinolyl (e.g., isoquinoline-1-yl, isoquinoline-3-yl, isoquinoline-4-yl, isoquinoline-5-yl, isoquinoline-6-yl, isoquinoline-7-yl or isoquinoline-8-yl), puryl, pteridinyl (e.g., pteridine-2-yl, pteridine-4-yl, pteridine-6-yl or pteridine-7-yl), carbazolyl, phenanthridinyl, acridinyl (e.g., acridine-1-yl, acridine-2-yl, acridine-3-yl, acridine-4-yl or acridine-9-yl), indolyl (e.g., indole-1-yl, indole-2-yl, indole-3-yl, indole-4-yl, indole-5-yl, indole-6-yl or indole-7-yl), isoindolyl, phenazinyl (e.g., phenazine-1-yl or phenazine-2-yl), phenothiazinyl (e.g., phenothiazine-1-yl, phenothiazine-2-yl, phenothiazine-3-yl or phenothiazine-4-yl) or the like.

"Heterocycle" means a 5 to 8-membered nonaromatic heterocycle group which may contain 1 to 4 oxygen, sulfur and/or nitrogen atom(s) in the ring. The binding bond can be at any substitutable position. Moreover, the nonaromatic heterocycle group can be substituted with a C1 to C5 alkylene chain or a C2 to C5 alkenylene chain to form fused ring (including bicyclic ring) or spiro ring, or can be fused with cycloalkane (preferred is 5 to 6-membered ring) or benzene ring. Heterocycle can be saturated or unsaturated, as long as it is nonaromatic. Preferred is 5 to 8-membered ring. Exemplified is 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl, or the following groups. Each ring can be optionally substituted at any substitutable position.

[Formula 5]

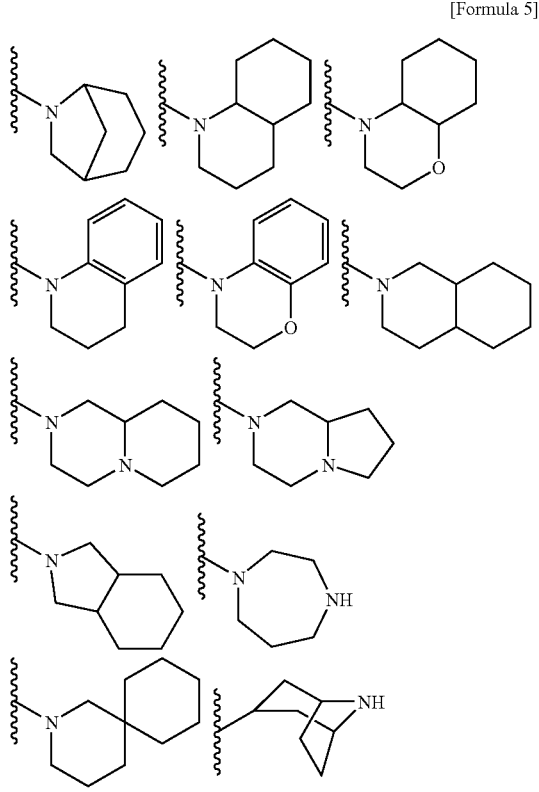

"A ring formed by taking together $R^6$ and $R^7$" means 5 to 8-membered ring including the nitrogen atom attached to $R^7$ in the ring. The above ring is attached to the carbon atom of the carbonyl group through the binding bond from the nitrogen atom attached to $R^7$. The ring is composed of carbon, oxygen, sulfur atom(s) or the like, besides the above nitrogen atom. The ring can contain 1 to 4 oxygen, sulfur and/or nitrogen atom(s) in the ring. Moreover, the ring can be substituted with C1 to C5 alkylene chain or C2 to C5 alkenylene chain to form fused ring (including bicycle ring), spiro ring or can be fused with cycloalkane (preferred is 5 to 6-membered ring) or benzene ring. The ring can be saturated or unsaturated. Preferred is 5 to 8-membered ring, for example, 1-pyrrolinyl, 1-pyrrolidinyl, 1-imidazolinyl, 1-imidazolidinyl, 1-pyrazolinyl, 1-pyrazolidinyl, piperidino, 1-piperadinyl, morpholino, or the following groups. Each ring can be optionally substituted.

[Formula 6]

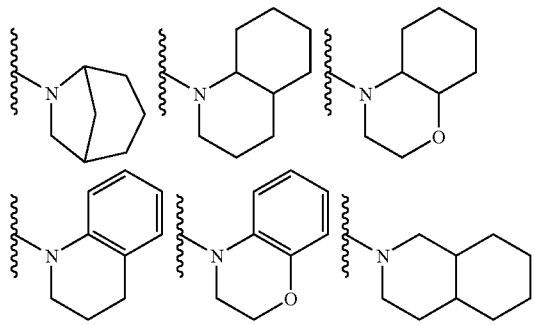

"A ring formed by taking together $R^9$ and $R^{10}$ with the carbon atom to which they are attached" means 3 to 15-membered saturated or unsaturated hydrocarbon ring or 3 to 15-membered saturated or unsaturated hetero ring containing 1 to 4 oxygen, sulfur, and/or nitrogen atom(s) in said hydrocarbon ring. Preferred is nonaromatic ring, for example, cyclopropane, cyclobutane, cyclopentane, cyclohexane, cycloheptane, cyclooctane, cyclopropene, cyclobutene, cyclopentene, cyclohexene, cycloheptene, or the like. Exemplified is saturated or unsaturated hetero ring containing 1 to 4 oxygen, sulfur, and/or nitrogen atom(s) in the hydrocarbon ring.

For example, a group of formula: —C($R^9R^{10}$)—, wherein $R^9$ and $R^{10}$ taken together with the carbon atom to which they are attached may form an optionally substituted ring, is exemplified as follows. Each ring can be optionally substituted.

[Formula 7]

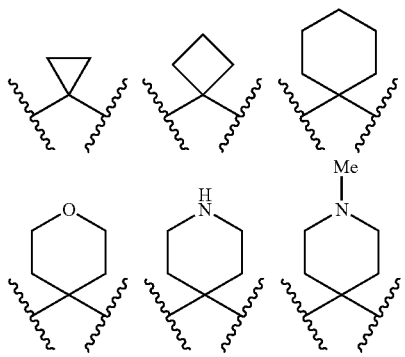

"A ring formed by taking together $R^{13}$ and $R^{14}$ with the nitrogen atom to which they are attached" and "a ring formed by taking together $R^{15}$ and $R^{16}$ with the nitrogen atom to which they are attached" mean 3 to 15-membered nonaromatic hetero ring which may contain 1 to 4 oxygen, sulfur, and/or nitrogen atom(s) besides the above nitrogen atom in the ring. The nonaromatic hetero ring can be bridged with C1 to C4 alkyl chain and be fused with cycloalkane (preferred is 5 to 6-membered ring) or benzene ring. The ring can be saturated or unsaturated, as long as it is nonaromatic. Preferred is 5 to 8-membered ring. For example, a group of formula: —$NR^{13}R^{14}$ wherein $R^{13}$ and $R^{14}$ taken together with the nitrogen atom to which they are attached may form an optionally substituted ring and a group of formula:

—NR$^{15}$R$^{16}$ wherein R$^{15}$ and R$^{16}$ taken together with the nitrogen atom to which they are attached may form an optionally substituted ring are exemplified as follows. 1-Pyrrolinyl, 1-pyrrolidinyl, 1-imidazolinyl, 1-imidazolidinyl, 1-pyrazolinyl, 1-pyrazolidinyl, piperidino, morpholino and the following group are exemplified. Each ring can be optionally substituted.

[Formula 8]

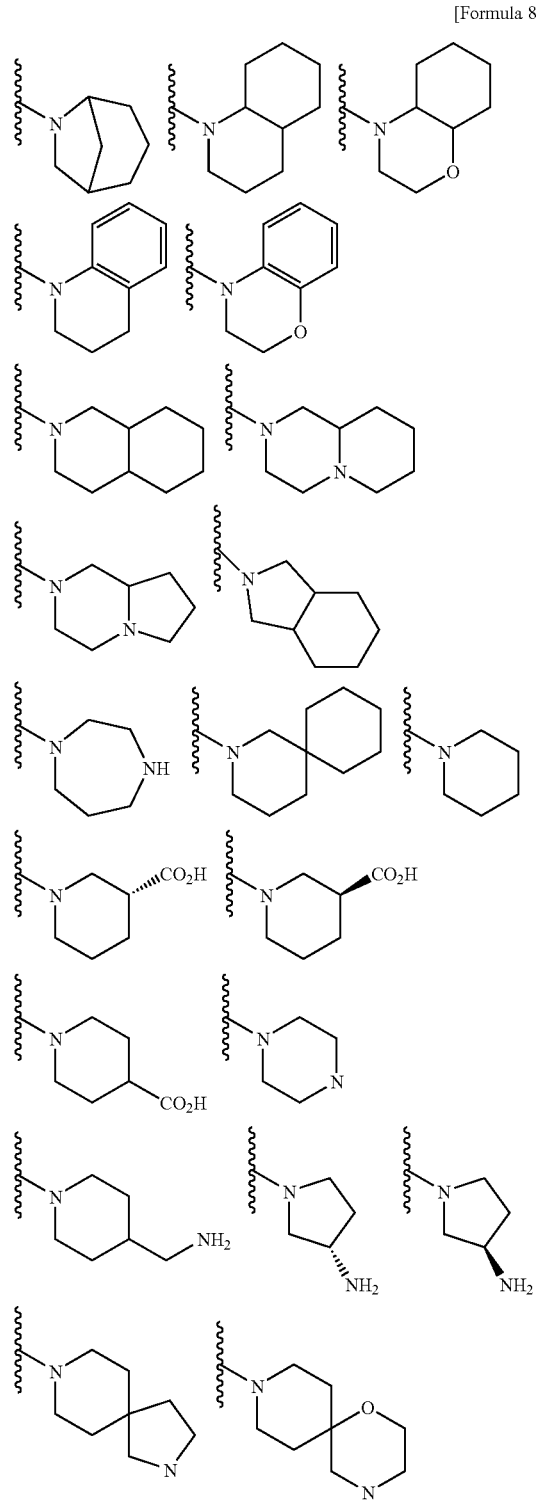

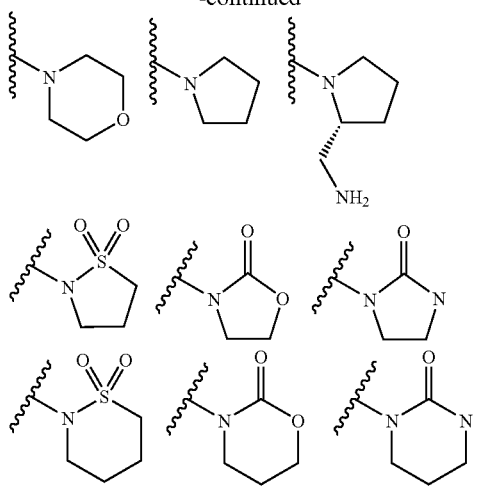

"Optionally substituted cycloalkyl", "optionally substituted cycloalkenyl", "optionally substituted aryl", "optionally substituted heteroaryl", "optionally substituted heterocycle", "optionally substituted alkyl", "optionally substituted alkylene", "optionally substituted alkenyl", "optionally substituted alkynyl", "substituted straight alkyl", "optionally substituted branched alkyl", "a ring formed by taking together R$^6$ and R$^7$", "optionally substituted imino", "a ring formed by taking together R$^9$ and R$^{10}$ with the carbon atom to which they are attached", "a ring formed by taking together R$^{13}$ and R$^{14}$ with the nitrogen atom to which they are attached", "a ring formed by taking together R$^{15}$ and R$^{16}$ with the nitrogen atom to which they are attached" and "optionally substituted methylene" may be substituted with 1 to 4 substituent(s) selected from a group consisting of, for example, hydroxy, carboxy, halogen (e.g.: F, Cl, Br, I),
optionally substituted alkyl (e.g.: methyl, ethyl, isopropyl, tert-butyl,
halogenated alkyl (e.g.: —CF$_3$, —CH$_2$CF$_3$, —CH$_2$CCl$_3$),
optionally substituted alkylthio (e.g.: methylthio),
optionally substituted alkylsulfonyl (e.g.: methansulfonyl, ethansulfonyl),
optionally substituted carbamoyl (e.g.: optionally substituted alkylcarbamoyl (e.g.: methylcarbamoyl, ethylcarbamoyl, dimethylcarbamoyl), optionally substituted alkylsulfonylcarbamoyl),
optionally substituted alkenyl (e.g.: vinyl),
optionally substituted alkenyloxy (e.g.: vinyloxy, allyloxy),
alkynyl (e.g.: ethynyl),
optionally substituted cycloalkyl (e.g.: cyclopropyl),
optionally substituted cycloalkenyl (e.g.: cyclopropenyl),
optionally substituted alkyloxy (e.g.: methoxy, ethoxy, propoxy, butoxy, carboxymethyloxy),
optionally substituted alkyloxycarbonyl (e.g.: methoxycarbonyl, ethoxycarbonyl, tert-butoxycarbonyl), nitro, nitroso,
optionally substituted amino (e.g.: alkylamino (e.g.: methylamino, ethylamino, diethylamino), acylamino (e.g.: optionally substituted alkylcarbonylamino,
optionally substituted arylcarbonylamino, optionally substituted heteroarylcarbonylamino, optionally substituted heterocyclecarbonylamino),
optionally substituted arylalkylamino (e.g.: benzylamino, tritylamino), hydroxyamino, optionally substituted alkyloxycarbonylamino, optionally substituted alkylsulfonylamino, optionally substituted carbamoylamino, optionally substituted arylsulfonylamino, optionally substituted arylamino), azide,
optionally substituted aryl (e.g.: phenyl),
optionally substituted arylalkyl (e.g.: benzyl),
optionally substituted heteroaryl,
optionally substituted heterocycle,
cyano, isocyano, isocyanate, thiocyanate, isothiocyanate, mercapto,
optionally substituted sulfamoyl,
acyl (e.g.: formyl, optionally substituted alkylcarbonyl, optionally substituted alkenylcarbonyl, optionally substituted arylcarbonyl, optionally substituted heteroarylcarbonyl, optionally substituted heterocyclecarbonyl),
formyloxy, haloformyl, oxalo, thioformyl, thiocarboxy, dithiocarboxy, optionally substituted thiocarbamoyl,
sulfino, sulfo, sulfoamino, hydrazino, azide, ureido, amidino, guanidino, phthalimide, oxo, alkylene,
alkylenedioxy (—O—CH$_2$—O—, —O—CH$_2$—CH$_2$—O—, —O—CH$_2$—CH$_2$—CH$_2$—O—, or the like),
optionally substituted heterocyclecarbonyl, phosphoester (e.g., —P(=O)(OEt)$_2$),
optionally substituted cycloalkylthio, optionally substituted arylthio,
optionally substituted heteroarylthio,
optionally substituted heteroaryloxy, optionally substituted aryloxy,
optionally substituted heterocycleoxy, optionally substituted imino,
optionally substituted alkylsulfonyl, optionally substituted arylsulfonyl,
optionally substituted alkylsulfinyl, optionally substituted arylsulfinyl,
optionally substituted alkylcarbonyloxy, optionally substituted arylcarbonyloxy, optionally substituted heteroarylcarbonyloxy, optionally substituted heterocyclcarbonyloxy,
optionally substituted alkylcarbonyl,
optionally substituted arylcarbonyl,
optionally substituted heteroarylcarbonyl,
optionally substituted aryloxycarbonyl,
optionally substituted heteroaryloxycarbonyl,
optionally substituted heterocycleoxycarbonyl,
optionally substituted methylene.

The alkyl part of "optionally substituted alkylsulfonyl", "optionally substituted alkylsulfinyl", "optionally substituted alkyloxy", "optionally substituted alkylsulfonylamino", "optionally substituted alkylcarbonyloxy", "optionally substituted alkylcarbonyl", "optionally substituted alkyloxycarbonyl", "optionally substituted alkyloxycarbonylamino", "optionally substituted alkylthio", "optionally substituted alkylcarbamoyl" and "optionally substituted alkylsulfonylcarbamoyl" is the same as the above "alkyl". The alkyl part can be optionally substituted with the same substituent as the above "optionally substituted alkyl".

The alkenyl part of "optionally substituted alkenylcarbonyl", "optionally substituted alkenyloxy" is the same as the above "alkenyl". The alkenyl part can be optionally substituted with the same substituent as the above "optionally substituted alkenyl".

The cycloalkyl part of "optionally substituted cycloalkylthio" is the same as the above "cycloalkyl". The cycloalkyl part can be optionally substituted with the same substituent as the above "optionally substituted cycloalkyl".

The aryl part of "optionally substituted arylsulfonyl", "optionally substituted arylsulfinyl", "optionally substituted arylsulfonylamino", "optionally substituted arylcarbonyloxy", "optionally substituted aryloxycarbonyl", "optionally substituted arylcarbonyl", "optionally substituted arylamino", "optionally substituted arylthio", "optionally substituted aryloxy" is the same as the above "aryl". The aryl part can be optionally substituted with the same substituent as the above "optionally substituted aryl".

The heteroaryl part of "optionally substituted heteroarylcarbonyloxy", "optionally substituted heteroarylcarbonyl", "optionally substituted heteroaryloxycarbonyl", "optionally substituted heteroarylthio" and "optionally substituted heteroaryloxy" is the same as the above "heteroaryl". The heteroaryl part can be optionally substituted with the same substituent as the above "optionally substituted heteroaryl".

The heterocycle part of "optionally substituted heterocyclecarbonyloxy", "optionally substituted heterocycleoxycarbonyl", "optionally substituted heterocyclecarbonyl" and "optionally substituted heterocycleoxy" is the same as the above "heterocycle". The heterocycle part can be optionally substituted with the same substituent as the above "optionally substituted heterocycle".

The aryl part of "optionally substituted arylalkylamino" is the same as the above "aryl" and the alkyl part is the same as the above "alkyl". The aryl part can be optionally substituted with the same substituent as the above "optionally substituted aryl" and the alkyl part can be optionally substituted with the same substituent as the above "optionally substituted alkyl".

A substituent of "optionally substituted amino", "optionally substituted carbamoylamino", "optionally substituted carbamoyl", "optionally substituted thiocarbamoyl", "optionally substituted sulfamoyl", "optionally substituted imino" includes optionally substituted alkyl, optionally substituted alkenyl, optionally substituted aryl, optionally substituted heteroaryl, acyl, hydroxy, optionally substituted alkylsulfonyl, optionally substituted alkylsulfinyl, optionally substituted arylsulfonyl, optionally substituted arylsulfinyl, optionally substituted amino or the like.

A substituent of "optionally substituted alkylsulfonyl", "optionally substituted alkylsulfinyl", "optionally substituted arylsulfonyl," "optionally substituted arylsulfinyl" includes the same substituent as optionally substituted alkyl or optionally substituted aryl.

"Acyl" means formyl, optionally substituted alkylcarbonyl, optionally substituted alkenylcarbonyl, optionally substituted arylcarbonyl, optionally substituted heteroarylcarbonyl or optionally substituted heterocyclecarbonyl.

A substituent of "optionally substituted alkylcarbonyl", "optionally substituted alkenylcarbonyl", "optionally substituted arylcarbonyl", "optionally substituted heteroarylcarbonyl", "optionally substituted heterocyclecarbonyl" includes the same substituent as optionally substituted alkyl, optionally substituted alkenyl, optionally substituted aryl, optionally substituted heteroaryl, optionally substituted heterocycle.

"Arylalkyl" means the above alkyl which is substituted with 1 to 3 of the above aryl.

$R^1$ is optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle. Preferably $R^1$ is substituted alkyl wherein the substituent of said substituted alkyl is optionally substituted amino or optionally substituted heterocycle, unsubstituted alkyl, a group of formula: —CH=CH—C($R^9R^{10}$)—$R^{11}$—$R^{12}$, or a group of formula: —CH$_2$—CH$_2$—C($R^9R^{10}$)—$R^{11}$—$R^{12}$, wherein $R^9$ and $R^{10}$ are each independently hydrogen, optionally substituted alkyl or halogen, or $R^9$ and $R^{10}$ taken together with the carbon atom to which they are attached may form an optionally substituted ring, $R^{11}$ is —($CH_2$)n- wherein n is an integer of 0 to 3, $R^{12}$ is hydrogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkyloxycarbonyl, optionally substituted arylalkylcarbonyl, optionally substituted carbamoyl, optionally substituted thiocarbamoyl, optionally substituted alkylsulfonyl, optionally substituted arylsulfonyl, optionally substituted sulfamoyl, optionally substituted amino, optionally substituted carbamoyloxy, optionally substituted alkyloxy or optionally substituted alkylthio, a group of formula:—C(=O)—$NR^{13}R^{14}$ wherein $R^{13}$ and $R^{14}$ are each independently hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted arylsulfonyl, optionally substituted heteroarylsulfonyl, optionally substituted heterocyclesulfonyl, or $R^{13}$ and $R^{14}$ taken together with the nitrogen atom to which they are attached may form an optionally substituted ring or, a group of formula: —$NR^{15}R^{16}$ wherein $R^{15}$ and $R^{16}$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted arylsulfonyl, optionally substituted alkyloxycarbonyl, optionally substituted sulfamoyl, or $R^{15}$ and $R^{16}$ taken together with the nitrogen atom to which they are attached may form optionally substituted ring.

One of $R^2$ and $R^4$ is a group of formula: —Y—$R^5$, wherein Y is —O— or —S—, and $R^5$ is substituted straight alkyl wherein the substituent of substituted straight alkyl is optionally substituted cycloalkyl, optionally substituted cycloalkenyl, optionally substituted aryl, optionally substituted heteroaryl or optionally substituted heterocycle, optionally substituted branched alkyl, optionally substituted alkenyl or optionally substituted alkynyl, optionally substituted cycloalkyl, optionally substituted cycloalkenyl, optionally substituted aryl, optionally substituted heteroaryl or optionally substituted heterocycle, the other of $R^2$ and $R^4$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle.

Preferably $R^2$ is a group of formula: —Y—$R^5$ wherein $R^5$ has the same meaning as defined in the above (1). More Preferable as $R^2$ is a a group of formula: —Y—$R^5$ wherein Y is —O—, and $R^5$ is substituted straight alkyl wherein the substituent of said substituted straight alkyl is optionally substituted cycloalkyl. As to said alkyl, methyl, ethyl, propyl (especially, methyl) are preferred. As to said cycloalkyl, cyclopentyl, cyclohexyl, cycloheptyl, cyclooctyl(especially, cyclohexyl) are preferred.

$R^3$ is a group of formula: —C(=O)—Z—$R^6$, wherein Z is —$NR^7$— or —$NR^7$—W—, and $R^6$ is optionally substituted cycloalkyl, optionally substituted cycloalkenyl, or optionally substituted heterocycle, $R^7$ is hydrogen or optionally substituted alkyl, or $R^6$ and $R^7$ taken together may form optionally substituted ring, W is optionally substituted alkylene.

Preferable as Z is —$NR^7$— wherein $R^7$ has the same meaning as defined in the above (1). More preferable as Z is —NH—.

Moreover, as to $R^6$, optionally substituted cycloalkyl is preferable. Adamantyl(especially, 2-adamantyl) is more preferable as $R^6$.

X is =N— or =$CR^8$— wherein $R^8$ is hydrogen or optionally substituted alkyl. Preferable is =N—.

As to $R^1$, for example, the following groups are preferable.

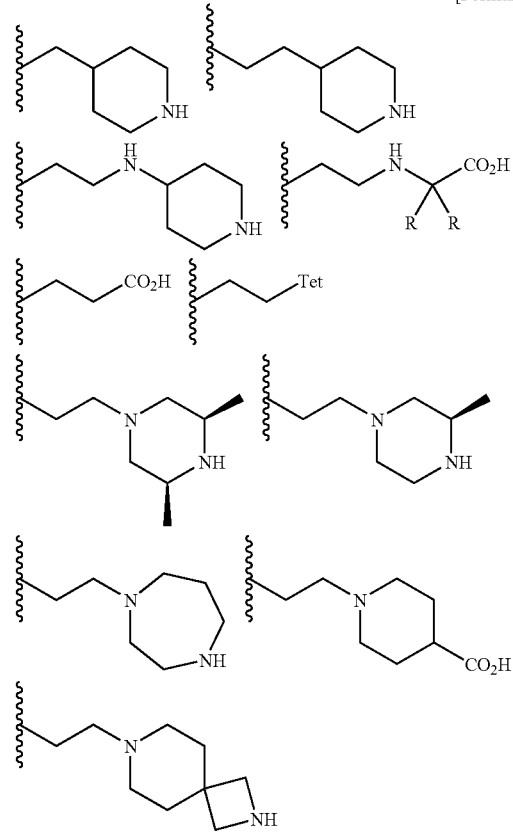

[Formula 9]

wherein R are each independently optionally substituted alkyl, and "Tet" means tetrazoryl.

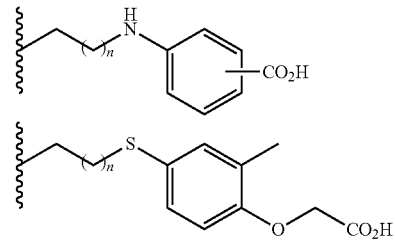

[Formula 10]

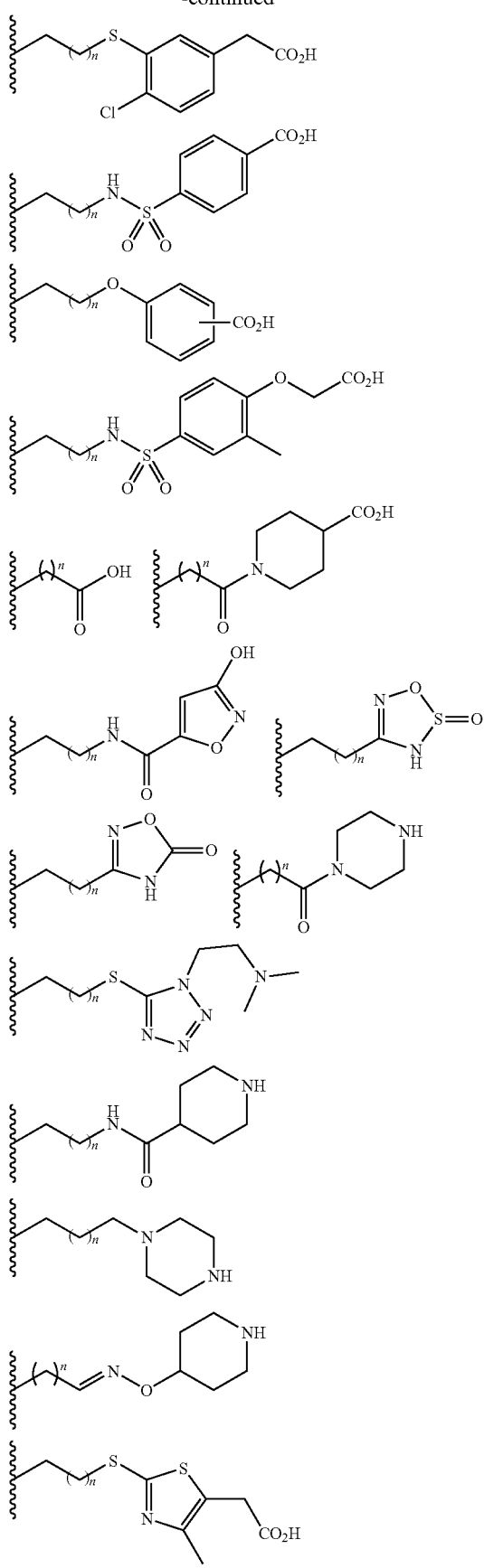
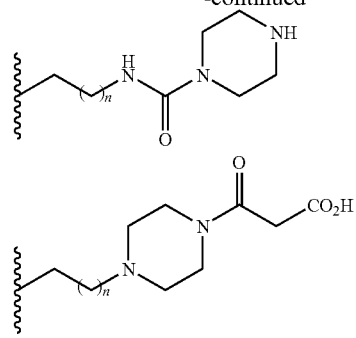
wherein n is an integer of 1 to 3.
[Formula 11]
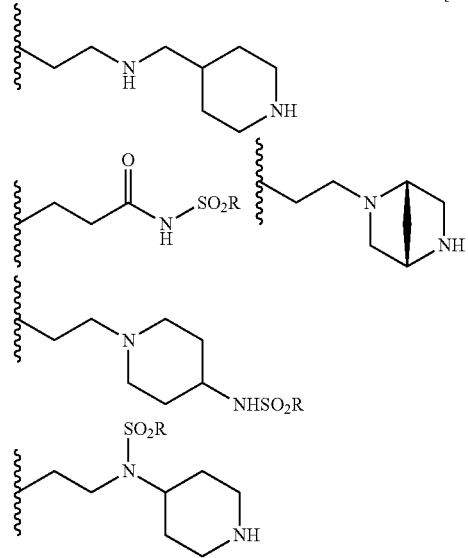
wherein R is optionally substituted alkyl or optionally substituted aryl.
As to a group of formula: —V—R⁵, for example, the following groups are preferable.
[Formula 12]
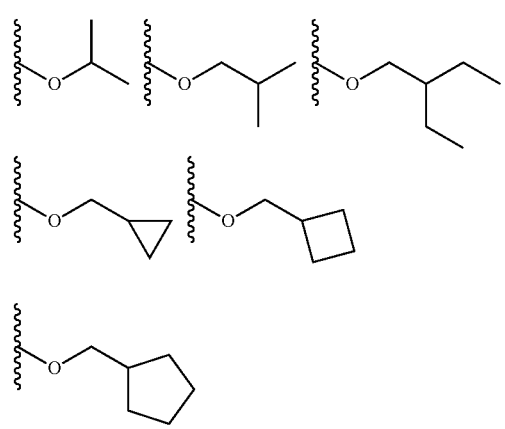

As to the substituent of substituted alkyl of $R^5$, the followings are preferable:

A) optionally substituted cycloalkyl (e.g., cyclopentyl, cyclohexyl, cycloheptyl, cyclooctyl),
B) optionally substituted cycloalkenyl (e.g., cyclopentenyl, cyclohexenyl, cycloheptenyl, cyclooctenyl),
C) optionally substituted aryl (phenyl, naphthyl),
D) heteroaryl (e.g., pyridyl, imidazolyl),
E) optionally substituted heterocycle (e.g., 4-piperidinyl, 2-pyrrolidinyl, morpholino, 2-morpholinyl, piperidino, 3,5-dimethylmorpholino, piperazinyl, N-tert-butoxycarbonyl-3-piperidinyl, 1-pyrrolidinyl, tetrahydropyranyl).

As to optionally substituted cycloalkyl of $R^6$, for example, the following groups are preferable.

[Formula 13]

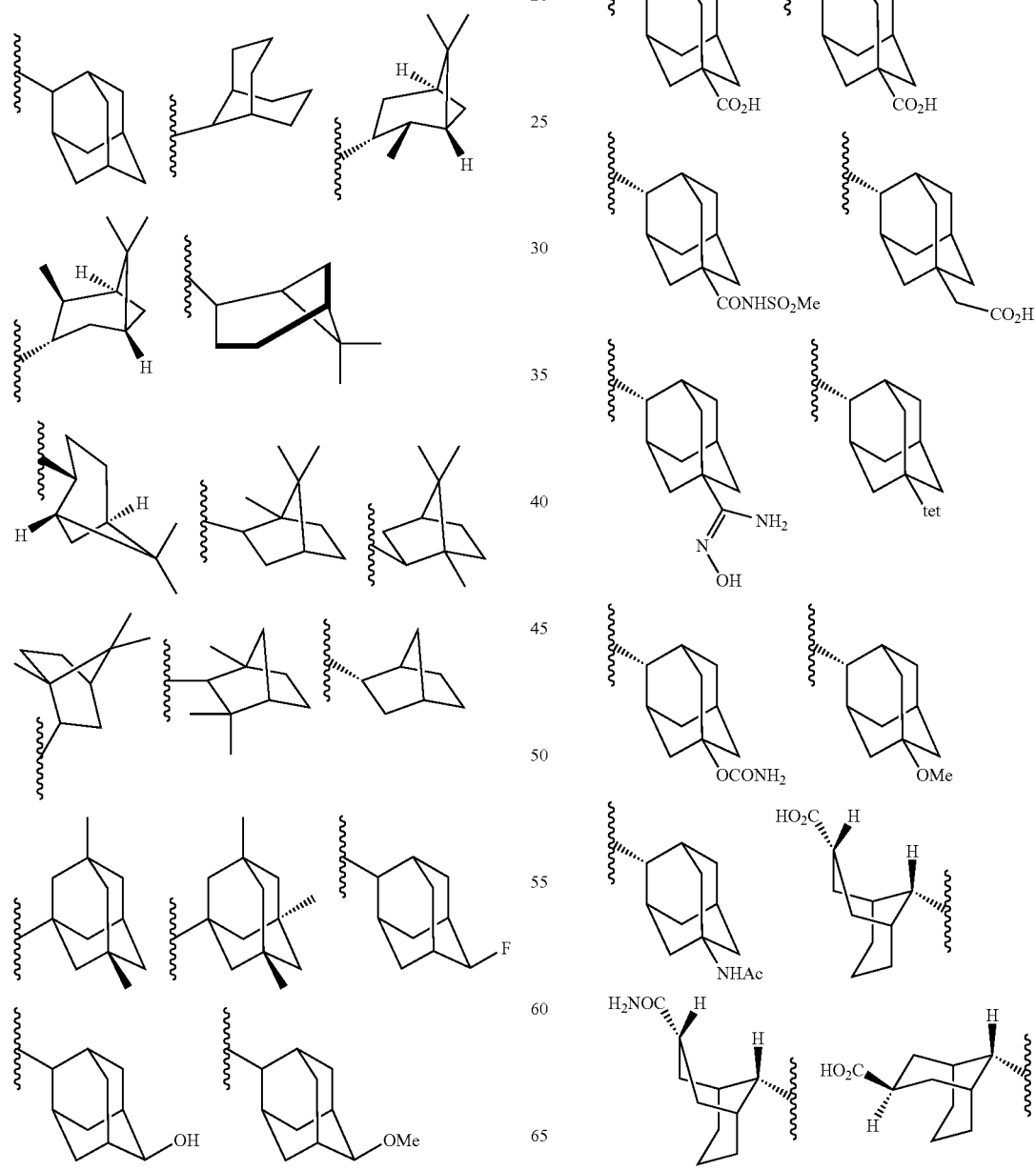

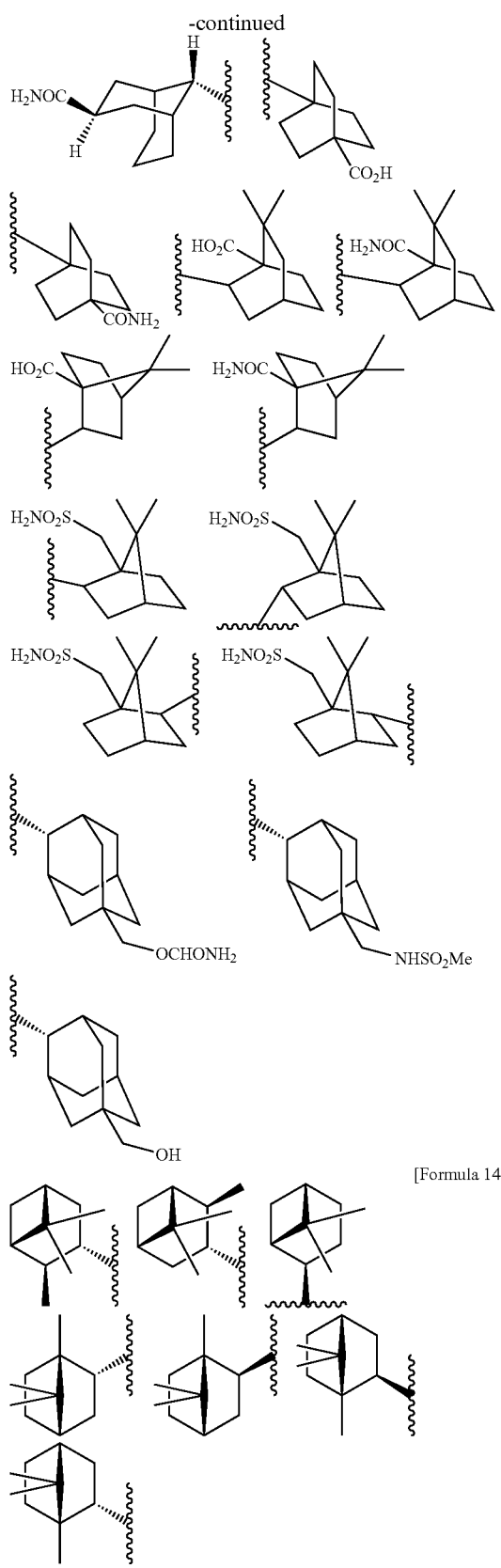

[Formula 14]

Pharmaceutically acceptable salts of the compounds of the present invention are exemplified as follows. Basic salts, for example, are salts of alkali metal such as sodium, potassium or the like; salts of alkaline-earth metal such as calcium, magnesium or the like; salts of ammonium; salts of aliphatic amine such as trimethylamine, triethylamine, dicyclohexylamine, ethanolamine, diethanolamine, triethanolamine, procaine, meglumine, diethanol amine, ethylenediamine or the like; salts of arylalkyl amine such as N,N-dibenzylethylenediamine, benetamine or the like; salts of hetero aromatic amine such as pyridine, picoline, quinoline, isoquinoline or the like; salts of quaternary ammonium such as tetramethylammonium, tetraethylammonium, benzyltrimethylammonium, benzyltriethylammonium, benzyltributylammonium, methyltrioctylammonium, tetrabutylammonium or the like; salts of basic amino acid such as arginine, lysine or the like.

Acidic salts, for example, are salts of inorganic acid such as hydrochloric acid, sulfuric acid, nitric acid, phosphoric acid, carbonic acid, hydrogencarbonic acid, perchloric acid or the like; salts of organic acid such as acetic acid, propionic acid, lactic acid, maleic acid, fumaric acid, tartaric acid, malic acid, citric acid or ascorbic acid; salts of sulfonic acid such as methansulfonic acid, isethionic acid, benzenesulfonic acid, p-toluenesulfonic acid or the like; salts of acidic amino acid such as aspartic acid, glutamic acid or the like.

Solvate means a solvate of a compound of the present invention or a pharmaceutically acceptable salt thereof, for example, alcohol (e.g., ethanol) solvate, hydrate or the like. As to hydrate, monohydrate, dihydrate or the like are exemplified.

A general method for producing a compound of the present invention is explained below. Each symbol is the same as the above (1). In addition, the treatment of the conventional organic synthesis such as extraction, purification and the like can be used for the synthesis of a compound of the present invention.

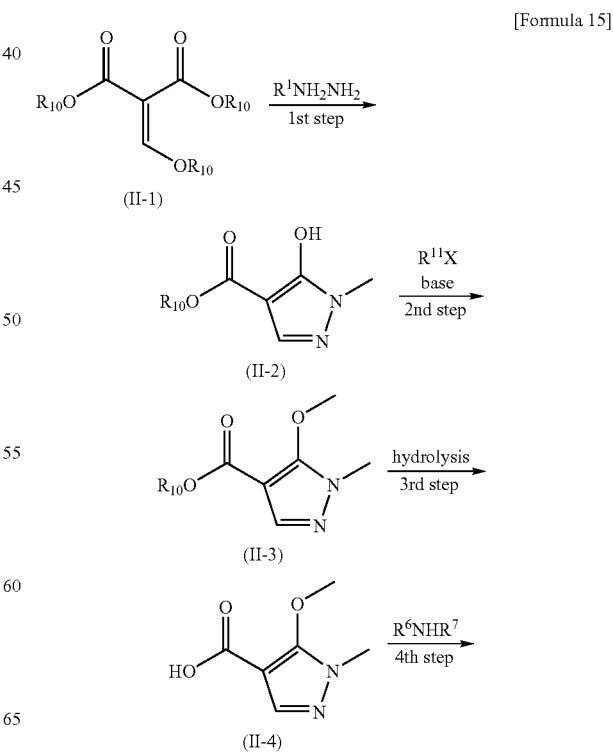

[Formula 15]

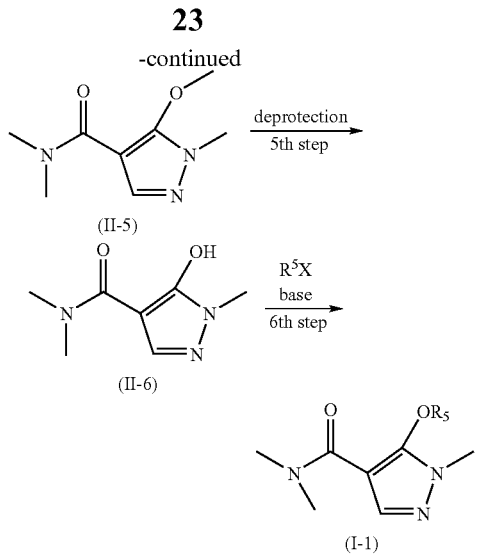

wherein $R^1$, $R^5$ and $R^6$ are the same as the above, $R^{10}$ is a protecting group (e.g., alkyl or the like), $R^{11}$ is a protecting group (e.g., benzyl or the like), and X is a leaving group (e.g., halogen or the like).

1st Step

1st step is a process for manufacturing a compound of formula (II-2) which comprises reacting a compound of formula (II-1) with $R^1NH_2NH_2$.

$R^{10}OH$ can be used as a reaction solvent. This reaction can be performed at room temperature or under refluxing temperature.

2nd Step

2nd step is a process of manufacturing a compound of formula (II-3) which comprises reacting a compound of formula (II-2) with $R^{11}X$.

Benzylhalide can be as $R^{11}X$.

This reaction is preferably performed in the presence of a base and can be carried out at room temperature or under refluxing temperature. Acetone, dimethylformamide or the like can be used as a reaction solvent.

3rd Step

3rd step is a process of manufacturing a compound of formula (II-4) which comprises hydrolyzing a compound of formula (II-3).

This reaction can be performed in a hydrous solvent and in the presence of a base. A hydrous solvent includes hydrous alcohol, hydrous tetrahydrofuran or the like. The mixed solvent of the above can be used. Sodium hydroxide, lithium hydroxide or the like can be used as a base. This reaction can be carried out at room temperature or under refluxing temperature. The preferable reaction temperature is room temperature.

4th Step

4th step is a process of manufacturing a compound of formula (II-5) which comprises reacting a compound of formula (II-4) with $R^6NHR^7$.

This reaction can be performed with the reaction condition known as the condition used for the condensation reaction of carboxylic acid and amine. For example, a condensing agent such as 1,3-dicyclohexylcarbodiimide (DCCD), 1-(3-dimethylaminopropyl)-3-ethylcarbodiimide (WSCI) or the like can be used. 1-Hydroxybenzotriazole (HOBt), 3,4-Dihydrohydroxy-4-oxo-1,2,3-benzotriazine (HOOBt) or the like can be used as an additive.

Dimethylformamide can be used as a solvent. This reaction can be performed at room temperature.

Additionally, after the amidation reaction with $R^6NH_2$, $R^7$ group can be introduced by reacting the obtained compound with $R^7X$ in the presence of a base. Moreover, $R^6WNHR^7$ can be used, instead of $R^6NHR^7$.

5th Step

5th step is a process of manufacturing a compound of formula (II-6) which comprises deprotecting a protective group of a compound of formula (II-5).

When $R^{11}$ is benzyl group, the deprotection reaction can be performed by catalytic reduction.

Alcohol can be used as a solvent. This reaction can be carried out by using palladium-carbon (5~10%) as a catalyst under hydrogen atmosphere.

6th Step

6th step is a process of manufacturing a compound of formula (I-1) which comprises reacting a compound of formula (II-6) with $R^5X$.

This reaction can be performed in the presence of a base. Potassium carbonate, sodium carbonate, sodium hydroxide, lithium hydroxide or the like can be used as a base.

This reaction can be carried out at room temperature or under refluxing temperature. Dimethylformamide can be used as a solvent.

A compound of the present invention wherein X is =$CR^8$— can be synthesized by using a compound having a pyrrole ring instead of a pyrazole ring described in the above formula (II-2) in accordance with the above explained scheme.

Various substituent of a compound of the present invention can be introduced referring to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS, or the like.

A compound of the present invention has a high inhibitory activity to 11β hydroxysteroid dehydrogenase type 1. Therefore, a compound of the present invention can be used for treating and/or preventing a disease concerning 11β hydroxysteroid dehydrogenase type 1, especially, hyperlipidemia, diabetes, obesity, arteriosclerosis, atherosclerosis, hyperglycemia and/or syndrome X. Especially, a compound of the present invention is useful for treating and/or preventing diabetes.

A compound of the present invention can be administrated via oral or parenteral. When the present compound is administrated via oral, the present compound can be used for in any form of the conventional pharmaceutical formulations, for example, solid formulations such as tablets, powders, granules, capsules or the like; aqueous formulations; oleaginous suspensions; or solution formulations such as syrup or elixir. When the present compound is administrated via parenteral, the present compound can be used as an aqueous or oleaginous suspensions injection or nose droops. In the preparation of such formulations, the conventional pharmaceutical excipients, binding agents, lubricants, aqueous solvents, oleaginous solvents, emulsifying agents, suspending agents, preservatives, stabilizers, and the like can be optionally used. Especially, a compound of the present invention is preferably used as oral agents.

A formulation according to the present invention can be manufactured by combining (e.g., admixing) a curatively effective amount of a compound of the present invention with a pharmaceutically acceptable carrier or diluent. The formulation can be manufactured by using of well-known and easily available ingredients in accordance with a known method.

A dosage of a compound of the present invention depends on the administration route, age, body weight, conditions of the patient, and kind of disease, but in case of oral administration, the daily dosage for an adult can be between approximately 0.05 mg~3000 mg, preferably approximately 0.1 mg~1000 mg. The daily dosage can be administered in divisions. When a compound of the present invention is administrated via parenteral, the daily dosage for an adult can be

EXAMPLE 1

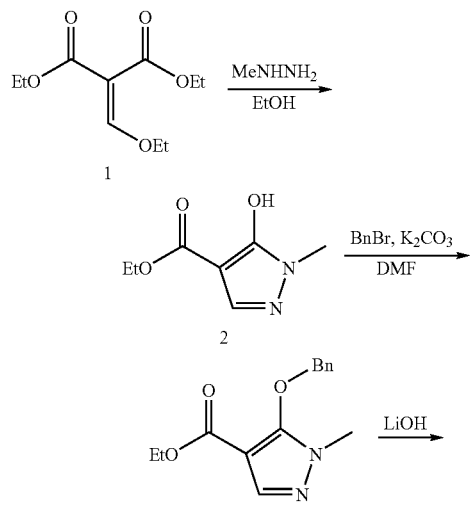

[Formula 16]

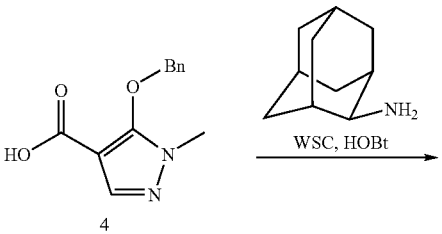

To a solution of Compound 1 (50.0 g) in ethanol was added methylhydrazine (13.5 ml) dropwisely under ice-cooling, then the reaction solution was stirred at room temperature for one hour and refluxed for 4 hours. The solvent was removed under reduced pressure to give a solid. The solid was washed with hexane to give Compound 2 (34.2 g).

To a solution of Compound 2 (20.0 g) in dimethyl formamide (200 ml) were added potassium carbonate (48.7 g) and benzylbromide (15.4 ml), then the resulting mixture was stirred at room temperature for 4 hrs. The insoluble was removed by filtration and the filtrate was poured into a solution of ethyl acetate and 0.1N HCl aquesous soln. and extracted with ethyl acetate. The extraction was washed with 0.1N HCl aqueous soln., $H_2O$ and brine, successively, then dried with sodium sulfate and concentrated in vacuo. The residue was purified by silicagel columnchromatography to give Compound 3 (24.0 g).

To a solution of Compound 3 (24.0 g) in methanol (150 ml)-tetrahydrofuran (30 ml)-$H_2O$ (130 ml) was added 4N lithium hydroxide aqueous soln. (100 ml) under ice-cooling. The resulting solution was stirred at room temperature for 30 min. and at 60° C. for 3 hrs. The solution was neutralized with 2N HCl aqueous soln. under ice-cooling and extracted with ethyl acetate. The extraction was washed with $H_2O$, brine and dried with magnesium sulfate, and concentrated in vacuo to give Compound 4 (18.9 g) as a crystal.

[Formula 17]

To a solution of Compound 4 (2.32 g), 2-aminoadamantane hydrochloride (2.25 g) and 1-hydroxybenztriazole (405 mg) in dimethyl formamide (25 ml) were added triethylamine (3.35 ml) and 1-(3-dimethylaminopropyl)-3-ethylcarbodiimide hydrochloride (2.30 g) successively, then the resulting mixture was stirred at room temperature overnight. The reaction mixture was poured into a solution of 0.1N HCl aqueous soln. and ethyl acetate and extracted with ethyl acetate. The extraction was washed with $H_2O$, brine and dried with magnesium sulfate and concentrated in vacuo. The residue was purified by silicagel columnchromatography to give Compound A-4 (3.12 g).

EXAMPLE 2

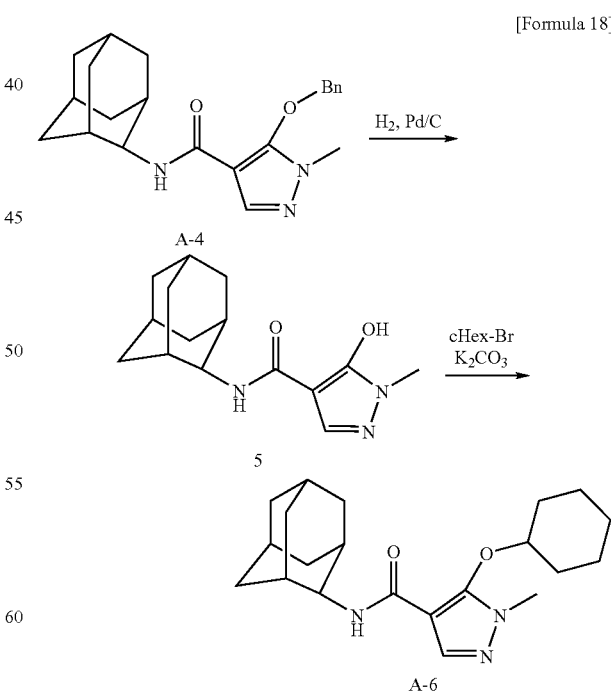

[Formula 18]

To a solution of Compound A-4 (1.00 g) in ethanol (10 ml) was added 5% Pd—C (174 mg), then the resulting mixture was stirred under $H_2$ atmosphere (1 atm) for four hours. The insoluble was removed by filtration using Celite, then the filtrate was concentrated in vacuo to give Compound 5 (711 mg) as a solid.

To a solution of Compound 5 (110 mg) in dimethyl formamide (1.5 ml) were added potassium carbonate (165 mg) and bromocyclohexane (59 μl), then the resulting solution was stirred at 150° C. for 1.5 hrs by using microwave. The reaction solution was poured into a solution of 0.1N HCl aquesous soln. and ethyl acetate and extracted with ethyl acetate. The extraction was washed with H₂O, brine and dried with magnesium sulfate and concentrated in vacuo. The residue was purified by silicagel columnchromatography to give Compound A-6 (16 mg).

EXAMPLE 3

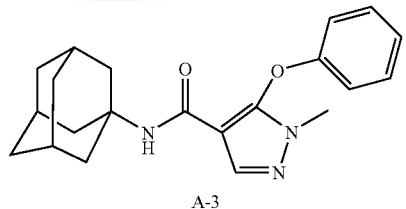

A-3

Compound A-3 was obtained from the reaction with phenol instead of thiophenol described in Example 3.

EXAMPLE 5

[Formula 19]

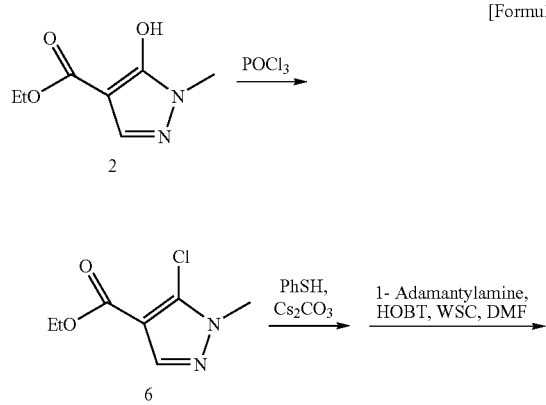

[Formula 21]

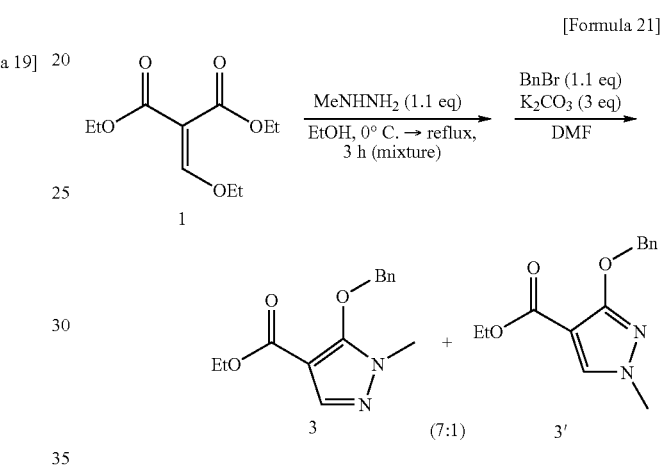

Compound 3 and the regioisomer 3' were synthesized from the same method described in Example 1.

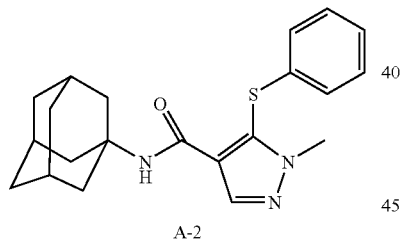

A-2

The reaction of Compound 2 with phosphorus oxychloride gave Compound 6. The reaction of Compound 6 with thiophenol in the presence of cesium carbonate gave Compound A-2.

EXAMPLE 4

[Formula 20]

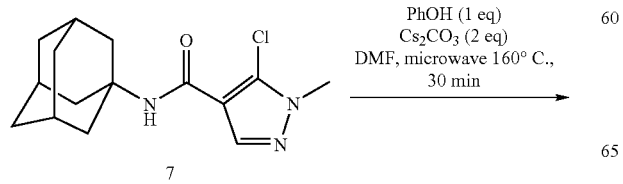

[Formula 22]

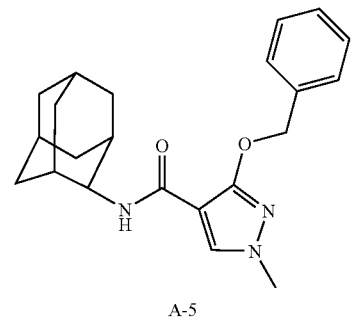

A-5

Compound A-5 was synthesized by using Compound 3'.

EXAMPLE 6

[Formula 23]

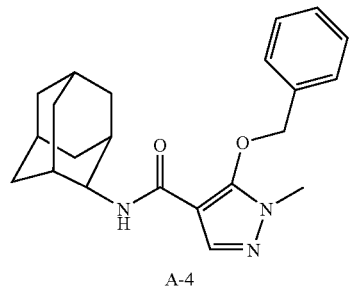

A reaction of catalytic reduction of Compound A-4 gave Compound 5. The obtained compound was reacted with cyclohexylbromide in the presence of potassium carbonate to afford Compound A-6.

EXAMPLE 7

[Formula 24]

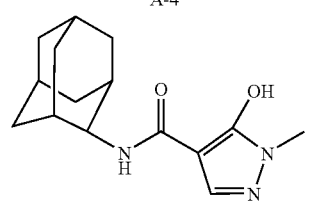

Compound 5 obtained in Example 6 was reacted with phenethylbromide to give Compound A-7. Additionally, a compound of the present invention can be obtained by using various halides as well as the halides shown in Examples 6 and 7. Compounds C-36~38, 41 were synthesized in accordance with the method shown in the above Examples.

EXAMPLE 8

[Formula 25]

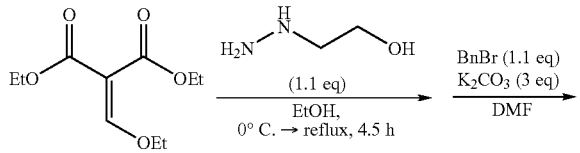

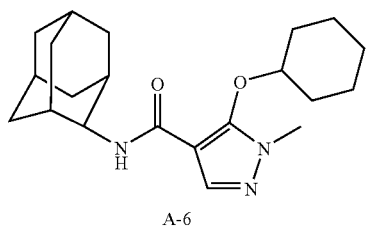

Compounds 8 and 8' were synthesized by using Compound 1 as a starting material and HOCH$_2$CH$_2$NHNH$_2$ instead of MeNHNH$_2$ in Example 1. The obtained 8 was reacted with 2-adamantanamine to give Compound A-8.

EXAMPLE 9

[Formula 26]

-continued

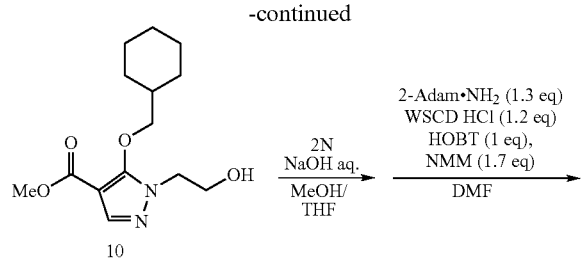

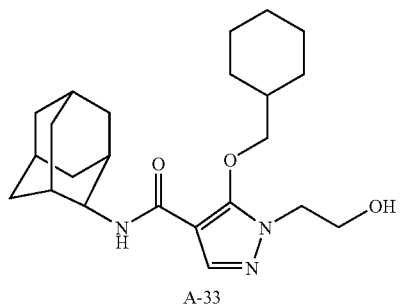

A-33

According to the above scheme, Compound A-33 was prepared. Additionally, Compound C-70 was synthesized by using hydroxy adamantanamine instead of adamantanamine.

EXAMPLE 10

[Formula 27]

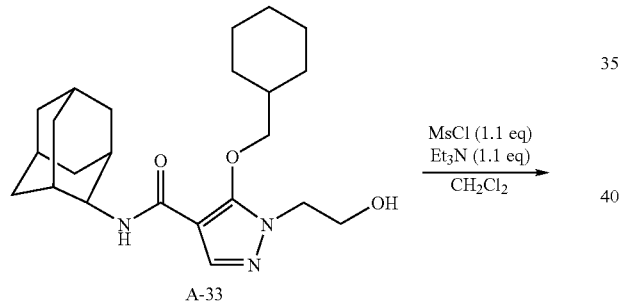

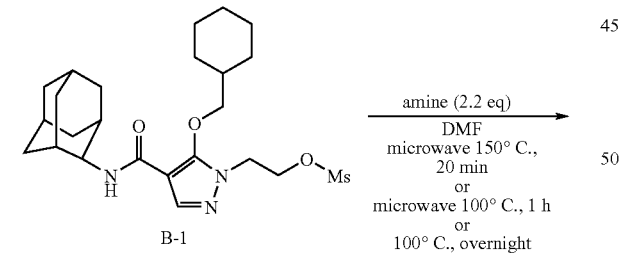

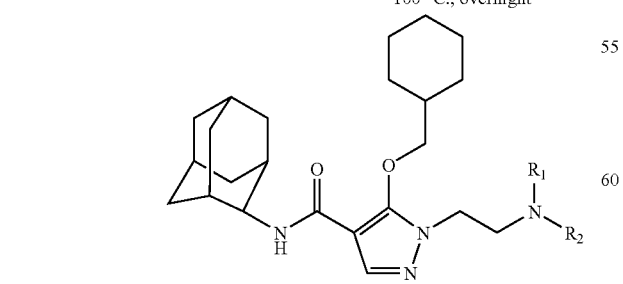

The obtained A-33 was reacted with mesyl chloride in the presence of triethylamine to give Compound B-1. Compound B-1 was reacted with various amines to afford Compounds A-40, A-41, A-42, A-44, A-45 and A-46. Moreover, Compounds C-1, 2, 12 to 28, 51 to 53, 84, 101, 102, 108 to 110 were synthesized from Compound A-33. Moreover, Compounds C-3 to 6, 11 were synthesized from Compound A-44.

EXAMPLE 11

[Formula 28]

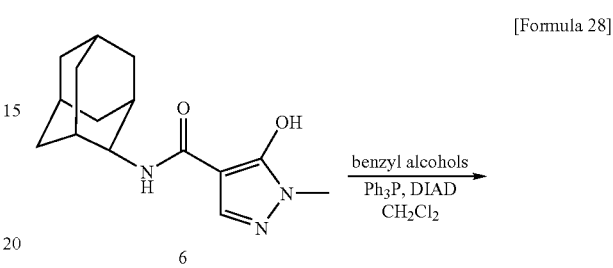

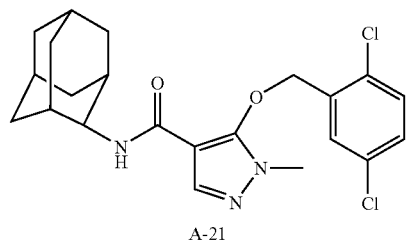

A-21

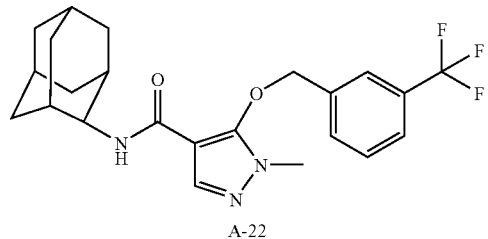

A-22

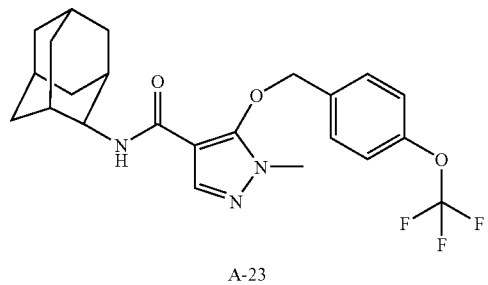

A-23

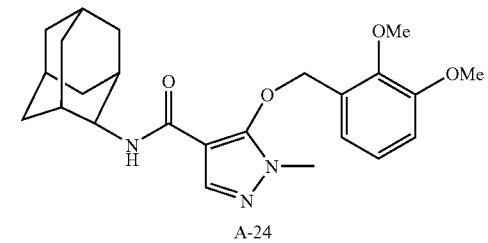

A-24

Compound 6 was reacted with various benzylalcohols to give Compounds A-21, A-22, A-23 and A-24 via Mitsunobu reaction.

EXAMPLE 12

[Formula 29]

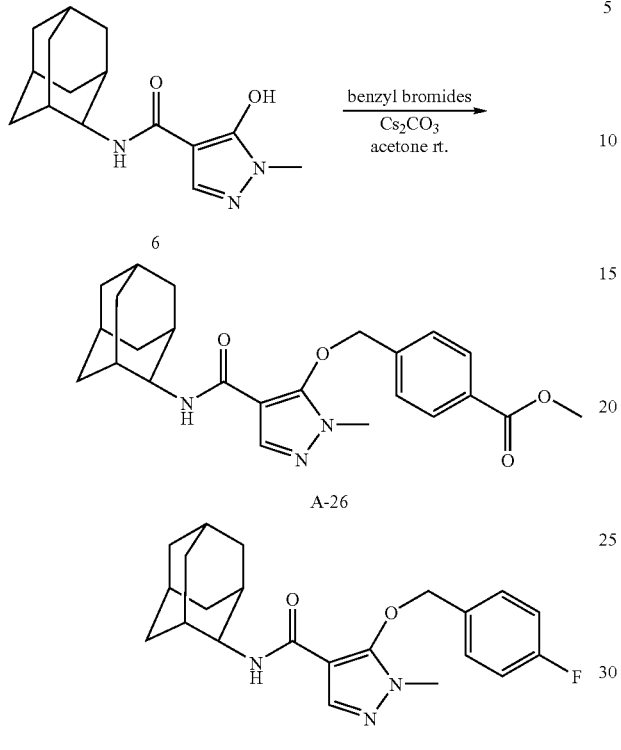

Compound 6 was reacted with various benzylbromides in the presence of cesium carbonate to give Compounds A-26, A-27 and A-28.

EXAMPLE 13

[Formula 30]

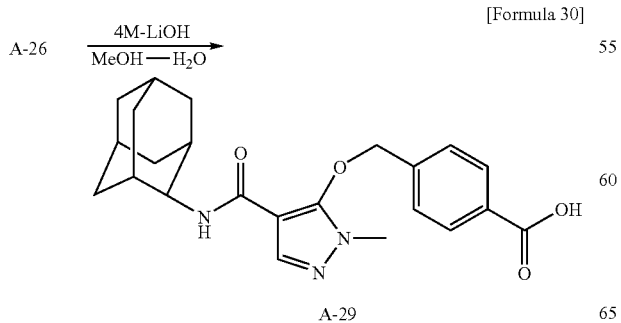

Compound A-26 was hydrolyzed by alkali to afford Compound A-29.

EXAMPLE 14

[Formula 31]

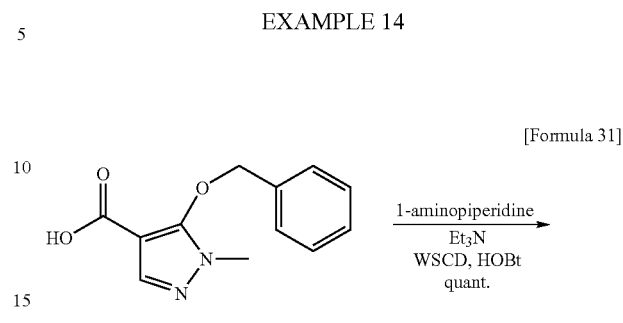

Compound 4 was reacted with 1-aminopiperidine to give Compound A-25. Compounds A-13, A-14, A-19, A-20, A-29, A-34 and A-35 were synthesized in accordance with the above Example.

EXAMPLE 15

[Formula 32]

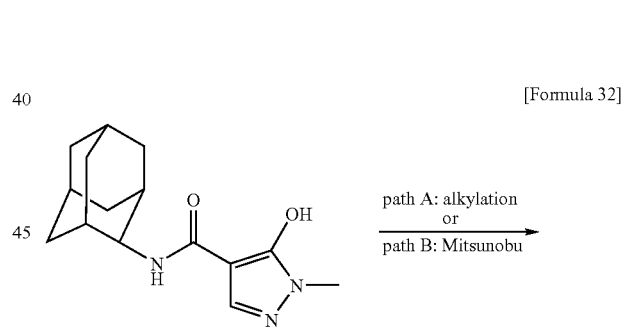

Compounds A-7, A-13, A-14, A-19, A-20, A-22, A-23, A-24, A-26, A-27, A-28, A-29, A-34, A-35, A-51, A-52 and A-59 to 65 were synthesized from Compound 6 via Mitsunobu reaction or alkylation reaction.

EXAMPLE 16

[Formula 33]

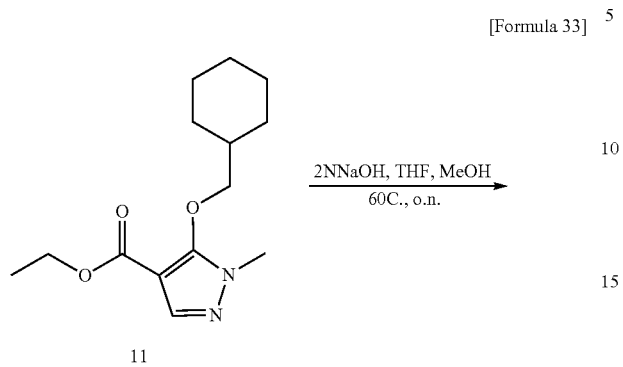

Compound 11 was reacted with sodium hydroxide to give Compound 12.

[Formula 34]

Compound 12 was reacted with various amines in the presence of HOBt and WSC to afford Compound A-36. Compounds A-37, A-38, A-47 to 50, A-53, A-55, A-57, A-58, A-66, A-67, C-7 to 10, 45 and 54 to 58 were synthesized as well as the above Example.

EXAMPLE 17

[Formula 35]

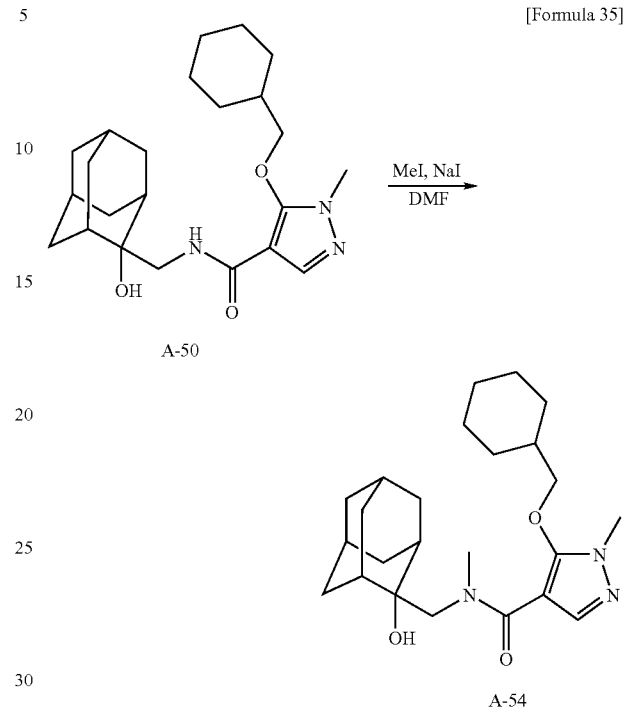

Compound A-50 was reacted with methyliodide and sodiumiodide to give Compounds A-54 and A-55. According to the above method, Compounds A-47 to 49, 57, 58, 66 and 67 were synthesized.

EXAMPLE 18

[Formula 36]

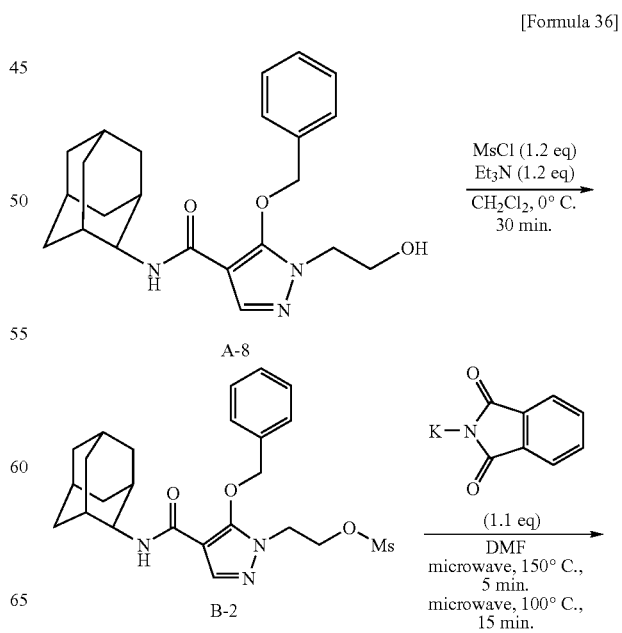

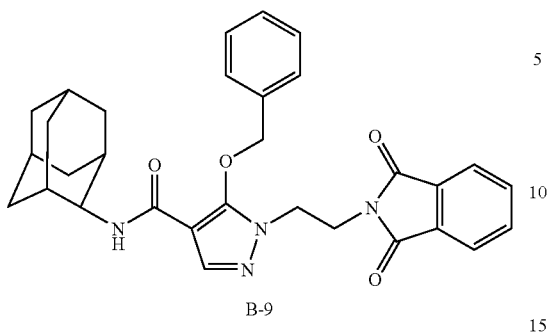

B-9

Compound A-8 was reacted with mesylchloride in the presence of triethylamine to give Compound B-2. Compound B-2 was reacted with potassium phthalimide to afford Compound B-9.

EXAMPLE 19

[Formula 37]

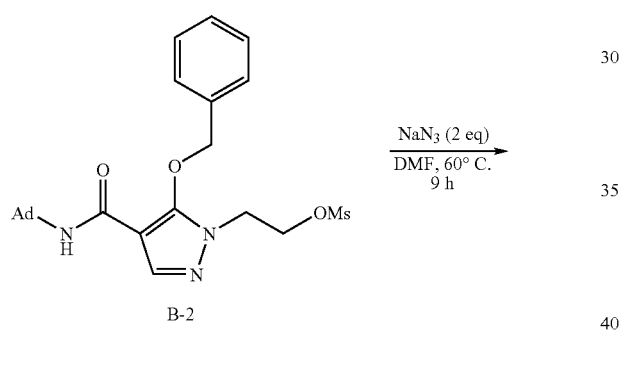

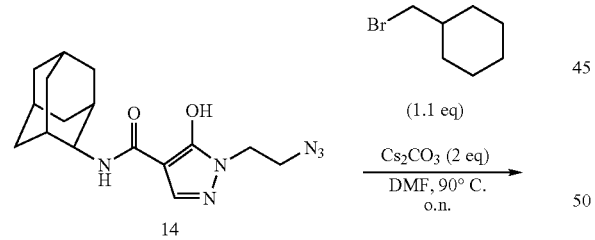

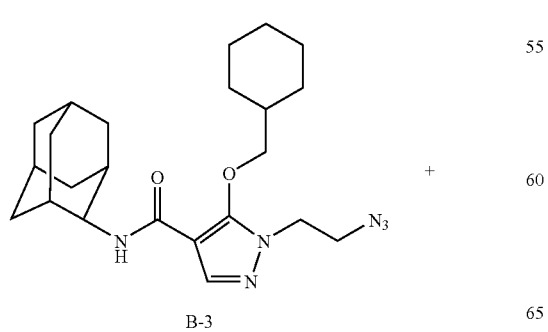

B-3

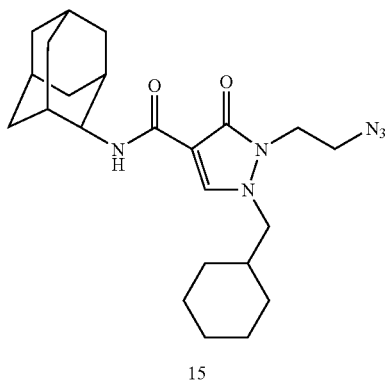

Compound B-2 was reacted with sodium azide to give Compound 14. Compound 14 was reacted with cyclohexylmethylbromide to afford Compound B-3 and Compound 15.

EXAMPLE 20

[Formula 38]

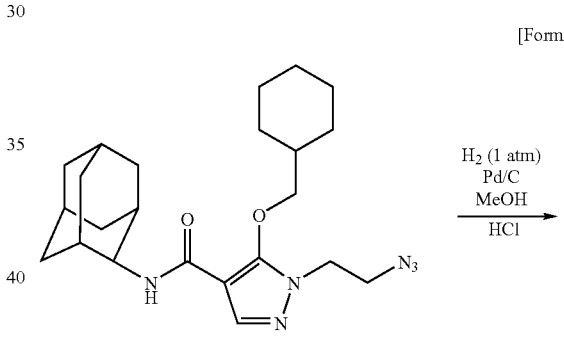

B-3

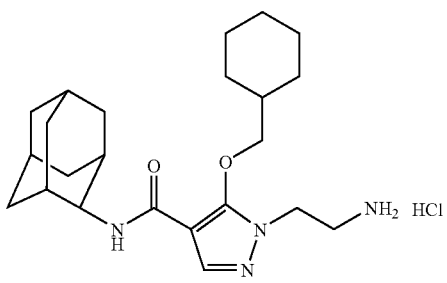

A-30

The catalytic reduction of B-3, followed by treatment with hydrochloric acid to give Compound A-30 (HCl salt). The amidation reaction of the obtained product gave Compounds C-61 and 62.

EXAMPLE 21
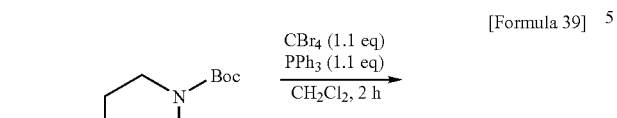
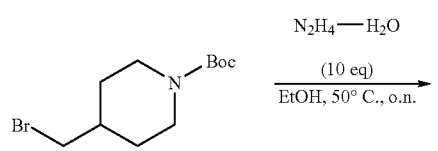
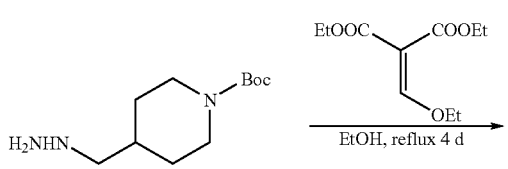
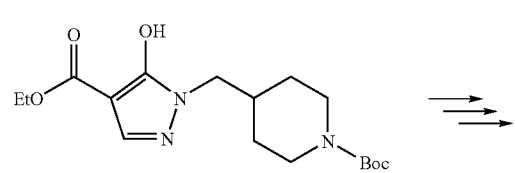
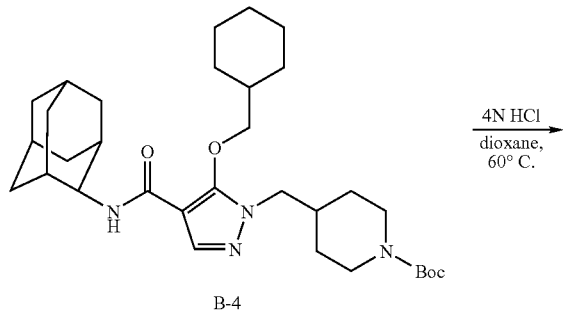
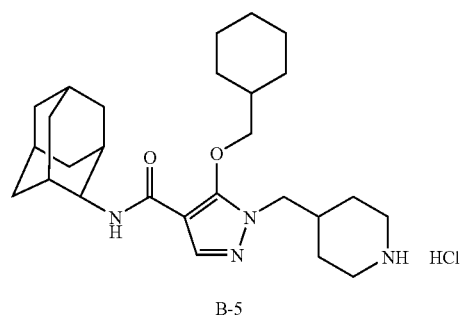
EXAMPLE 22
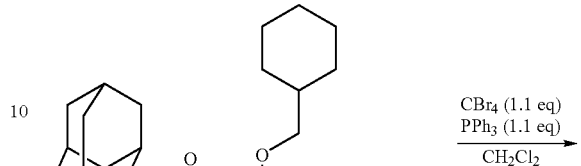
A-33
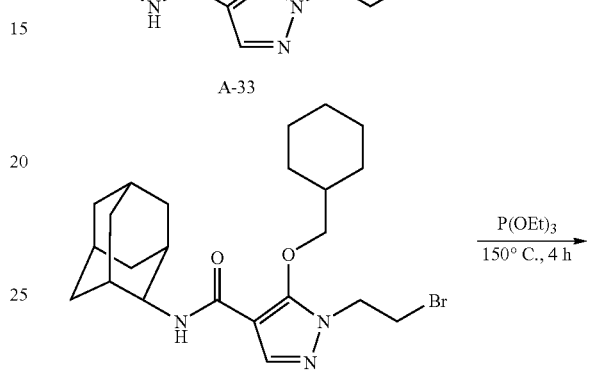
B-6
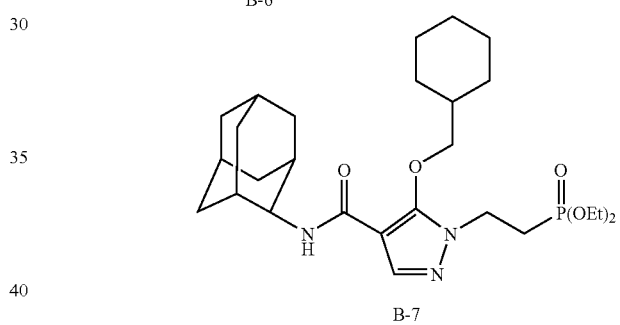
B-7
According to the above scheme, Compounds B-6 and B-7 were synthesized from Compound A-33.
EXAMPLE 23
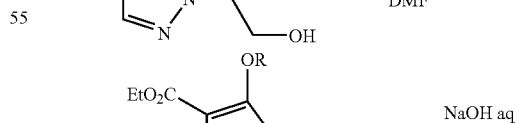
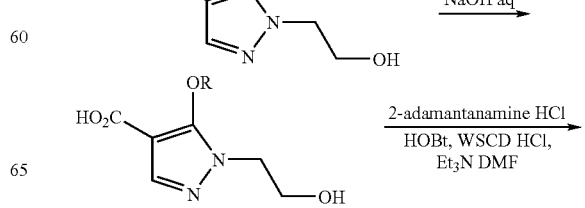

41
-continued
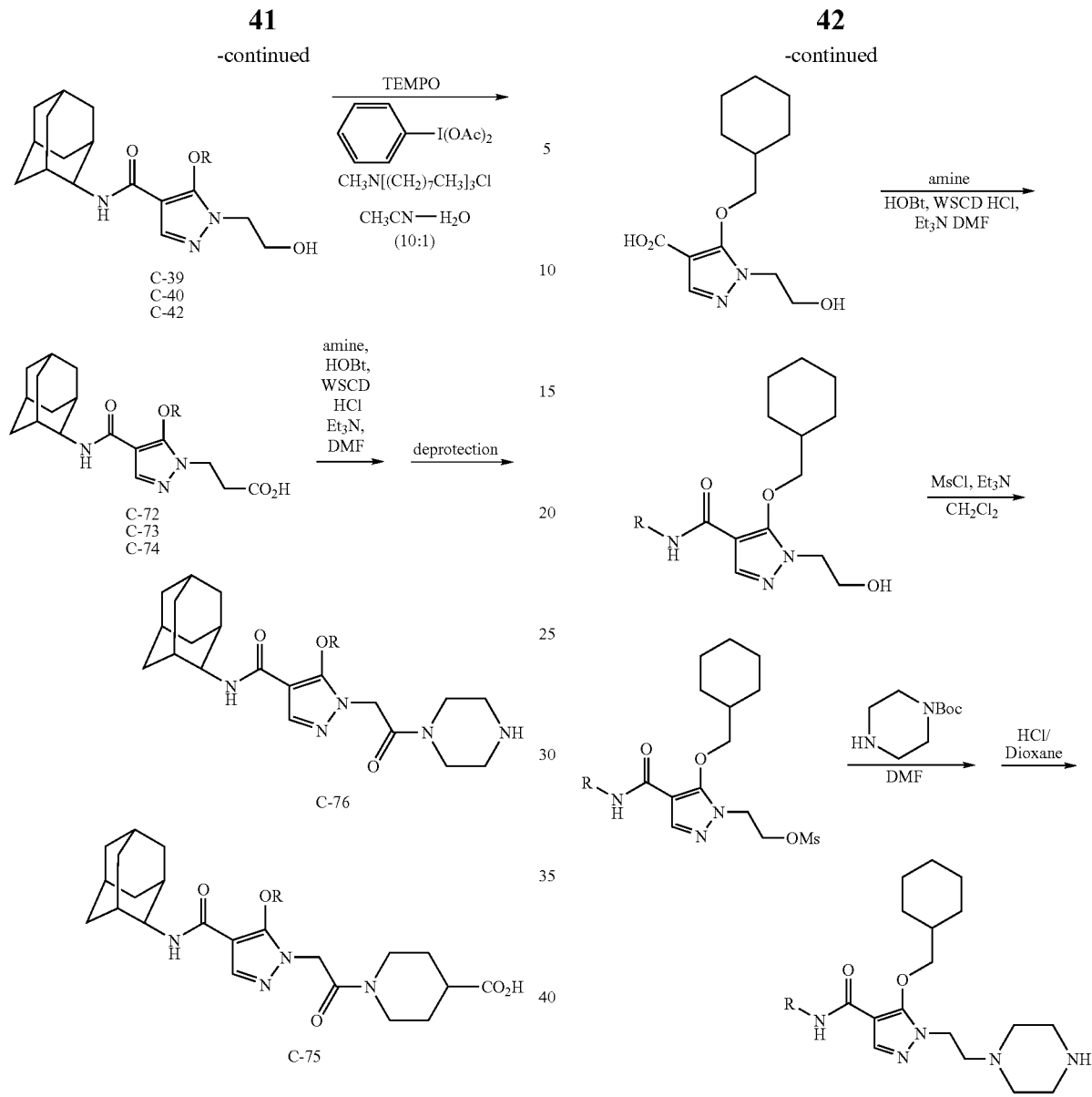
According to the above scheme, Compounds C-39, 40, 42, 72, 73, 74, 75 and 76 were synthesized. Compounds C-79, 81, 151 to 153 were synthesized as well as the above Example.
EXAMPLE 24
42
-continued
According to the above scheme, Compounds C-46, 47, 59 and 60 were synthesized.
EXAMPLE 25
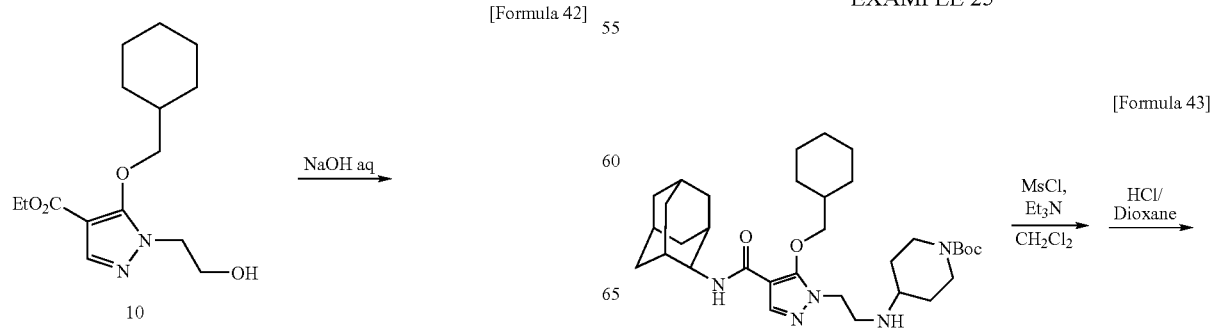

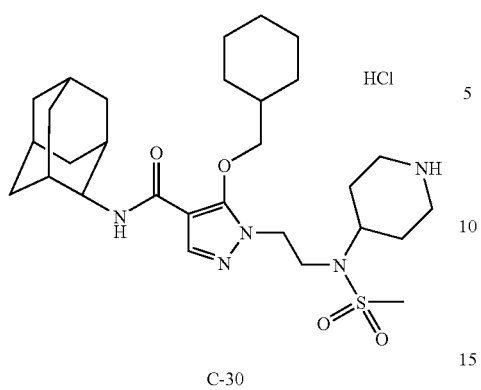
C-30
According to the above scheme, Compound C-30 was synthesized.
EXAMPLE 26
[Formula 44]
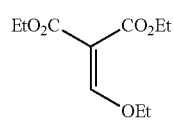
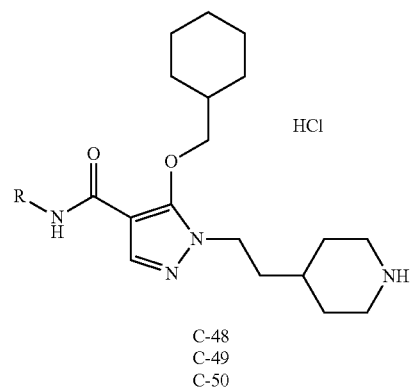
C-48
C-49
C-50
According to the above scheme, Compounds C-48, 49 and 50 were synthesized. Compounds C-126 to 128 were synthesized as well as the above Example.
EXAMPLE 27
[Formula 45]
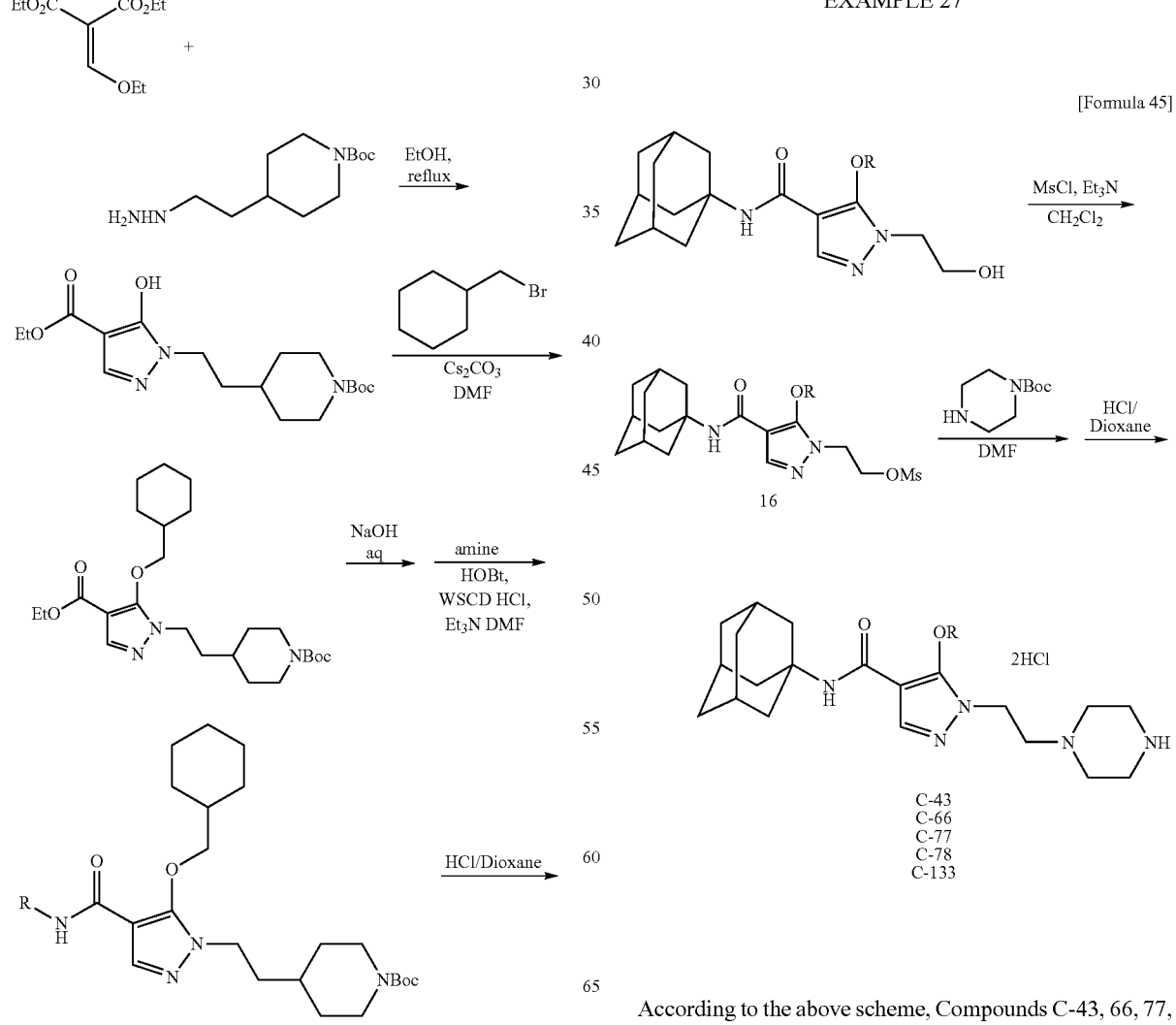
C-43
C-66
C-77
C-78
C-133
According to the above scheme, Compounds C-43, 66, 77, 78 and 133 were synthesized.

EXAMPLE 28
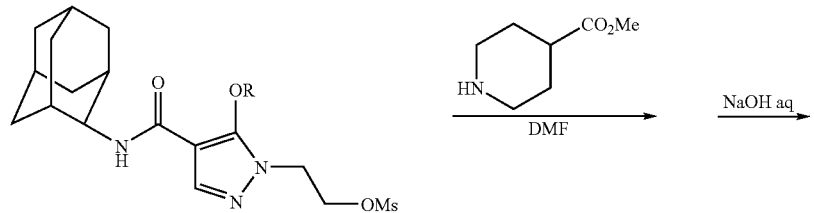
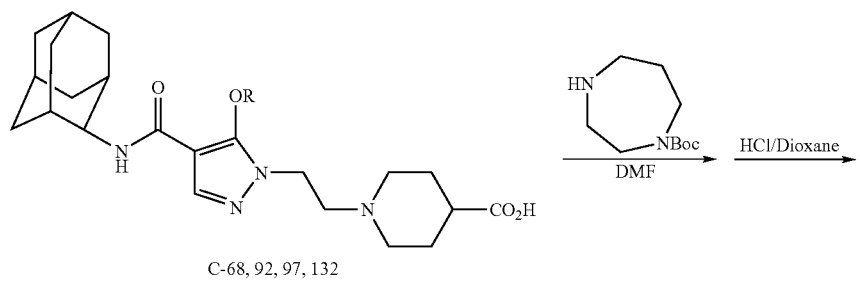
C-68, 92, 97, 132
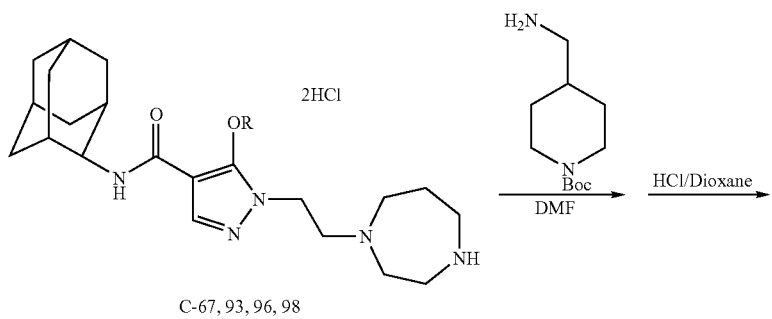
C-67, 93, 96, 98
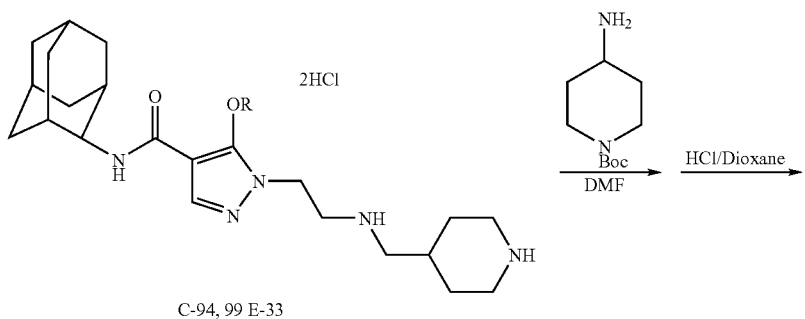
C-94, 99 E-33
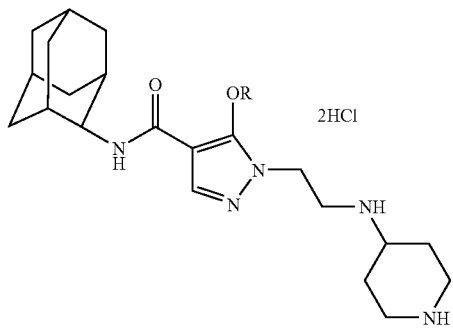
C-69, 95, 100

According to the above scheme, Compounds C-67, 68, 69, 92, 93, 94, 95, 96, 97, 98, 99, 100, 132 and E-33 were synthesized.

EXAMPLE 29

[Formula 47]

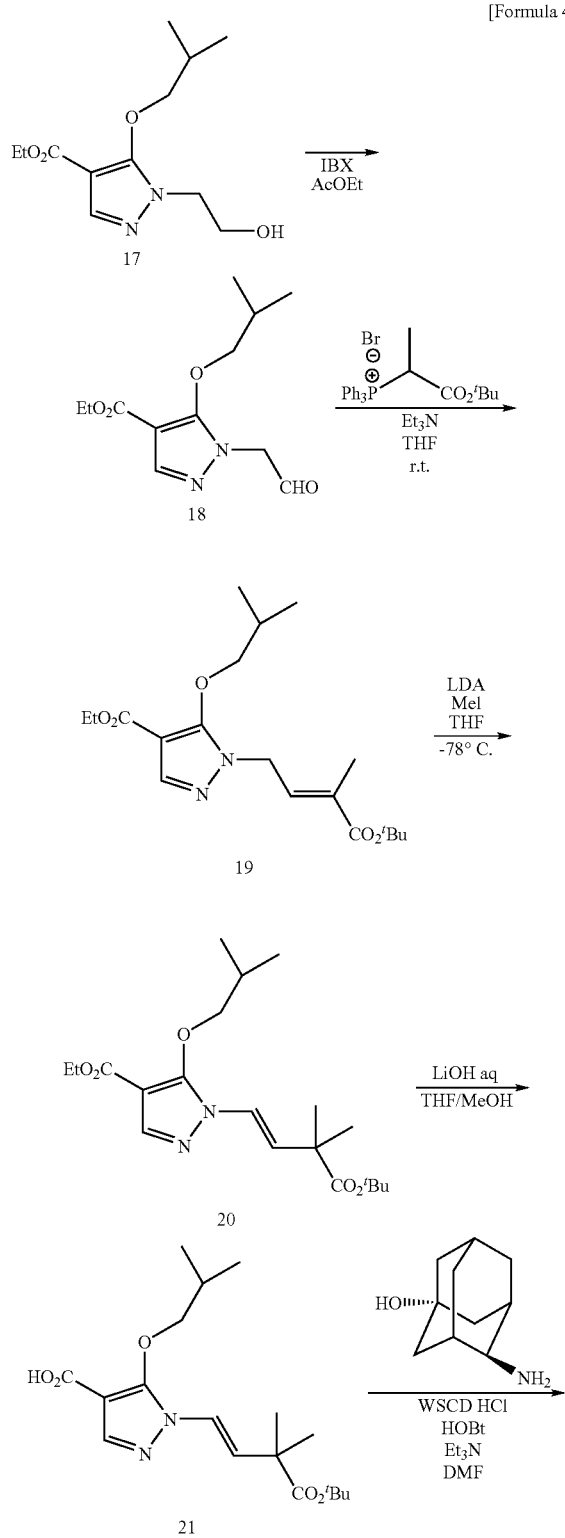

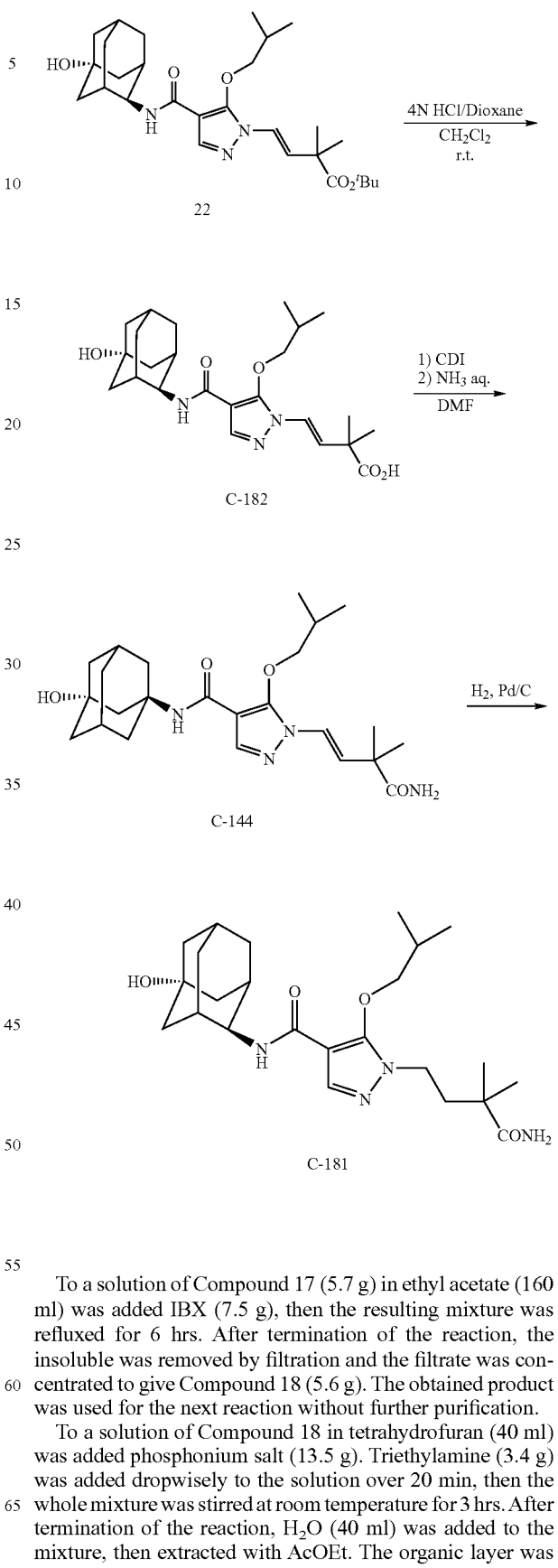

To a solution of Compound 17 (5.7 g) in ethyl acetate (160 ml) was added IBX (7.5 g), then the resulting mixture was refluxed for 6 hrs. After termination of the reaction, the insoluble was removed by filtration and the filtrate was concentrated to give Compound 18 (5.6 g). The obtained product was used for the next reaction without further purification.

To a solution of Compound 18 in tetrahydrofuran (40 ml) was added phosphonium salt (13.5 g). Triethylamine (3.4 g) was added dropwisely to the solution over 20 min, then the whole mixture was stirred at room temperature for 3 hrs. After termination of the reaction, H$_2$O (40 ml) was added to the mixture, then extracted with AcOEt. The organic layer was washed with brine and dried with magnesium sulfate and concentrated. The residue was purified by silicagel columnchromatography to give Compound 19 (5.2 g).

A solution of diisopropylamine (1.3 ml) in tetrahydrofuran (60 ml) was cooled to −78° C., then n-butyllithium (3.25 ml, 2.8M in hexane) was added dropwisely to the solution. After stirring at −78° C. for 30 min, Compound 19 (2.8 g) in tetrahydrofuran (40 ml) was added to the solution and the whole mixture was stirred for 30 min. Iodomethane (1.4 ml) was added to the mixture, then the whole mixture was allowed to gradually warm up to 0° C. After 3 hrs, the mixture was diluted with sat. ammonium chloride aqueous soln. and extracted with ethyl acetate. The organic layer was washed with brine, dried with magnesium sulfate and concentrated. The residue was purified by silicagel columnchromatography to give Compound 20 (2.42 g).

To a solution of Compound 20 (173 mg) in tetrahydrofuran (4 ml)-methanol (2 ml) was added 4N lithium hydroxide aqueous soln. (0.9 ml), then the resulting solution was stirred at room temperature for 24 hrs. After termination of the reaction, the solution was acidified with 2N HCl aqueous soln. and extracted with ethyl acetate. The organic layer was washed with brine and dried with magnesium sulfate and concentrated to give Compound 21 (181 mg). The obtained product was used for the next reaction without further purification.

To a solution of Compound 21 (181 mg) in dimethyl formamide were added hydroxy adamantanamine (94 mg), 1-(3-dimethylaminopropyl)-3-ethylcarbodiimide hydrochloride (118 mg), 1-hydroxybenzotriazole (21 mg) and triethylamine (121 μl), then the resulting solution was stirred at room temperature for 24 hrs. After termination of the reaction, the solution was diluted with 2N HCl aqueous soln. and extracted with ethyl acetate. The organic layer was washed with sat. sodium hydrogencarbonate soln. and brine successively, and dried with magnesium sulfate. The residue was purified by silicagel columnchromatography to give Compound 22 (176 mg). To a solution of Compound 22 (176 mg) in methylene chloride (3 ml) was added 4N HCl/dioxane (2 ml), then the resulting solution was stirred at room temperature for 26 hrs. After termination of the reaction, the solution was diluted with diisopropylether to give crystal. The obtained crystal was collected by filtration and washed with diisopropylether, then dried to give Compound C-182 (120 mg).

To a solution of Compound C-182 (55 mg) in dimethyl formamide (1 ml) was added 1,1'-carbonyldiimidazole (30 mg), then the resulting solution was stirred at room temperature for 45 min. 28% Ammonia aqueous soln. (0.2 ml) was added to the solution and the whole solution was stirred for 1.5 hrs. After termination of the reaction, the solution was diluted with water and extracted with ethyl acetate. The organic layer was washed with 0.1N HCl aqueous soln. and brine successively, and dried with magnesium sulfate and concentrated. The obtained crystal was washed with diisopropylether to afford Compound C-144 (35 mg).

To a solution of Compound C-144 (118 mg) in tetrahydrofuran (4.4 ml)-methanol (0.4 ml) was added 10% Pd—C (40 mg), then the resulting mixture was stirred for 3.5 hrs. under H$_2$ atmosphere. After termination of the reaction, Pd—C was removed by filtration and the solvent was removed to give Compound C-181 (117 mg).

Compounds C-147, 160, 163, 187 and 195 were synthesized as well as the above Example.

EXAMPLE 30

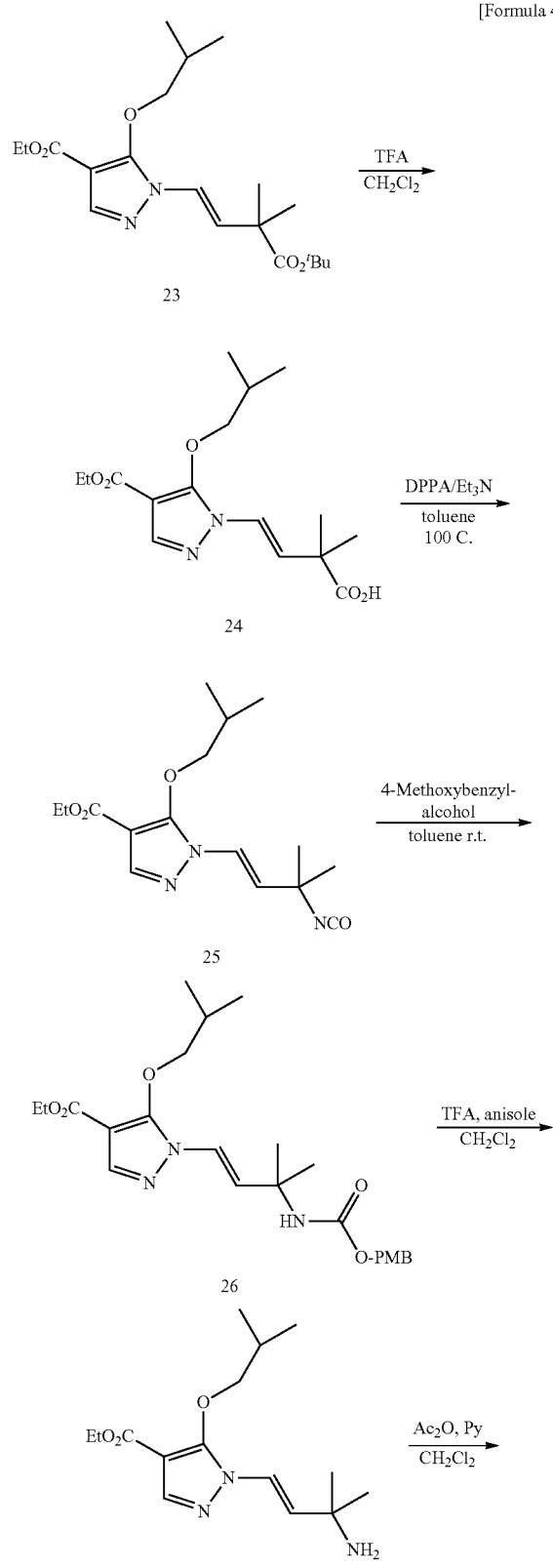

[Formula 48]

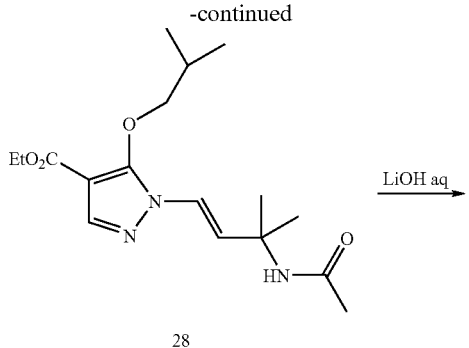

28

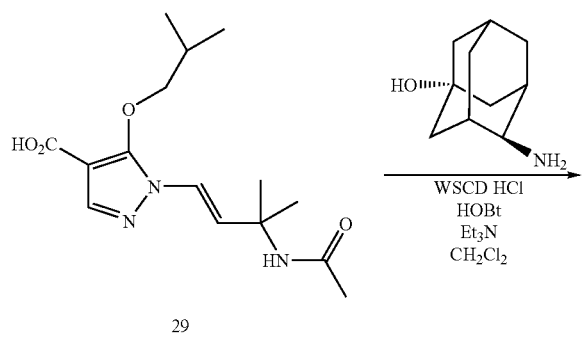

29

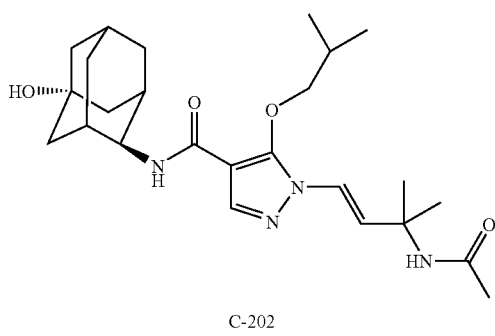

C-202

To a solution of Compound 23 in methylene chloride (100 ml) was added trifluoroacetic acid (50 ml), the resulting solution was stirred at room temperature for 3 hrs. After termination of the reaction, the solvent was removed and the residue was diluted with H₂O (100 ml) and extracted with ethyl acetate. The organic layer was washed with brine and dried with magnesium sulfate and concentrated to give Compound 24 (16.6 g).

To a solution of Compound 24 (16.6 g) in toluene (70 ml) were added triethylamine (5.67 g), diphenylphosphoryl azide (14.7 g), then the resulting solution was stirred at 100° C. for 3 hrs. After termination of the reaction, the solution was diluted with toluene (70 ml) and the organic layer was washed with sat. sodium hydrogencarbonate soln. and brine successively, and dried with magnesium sulfate and concentrated. The obtained product was used for the next reaction without further purification.

According to the above procedure, the obtained 25 was dissolved in toluene (30 ml) and 4-methoxybenzylalcohol (10.6 g) was added to the solution. The solution was stirred at 50° C. for 24 hrs. After termination of the reaction, the solvent was removed and the residue was purified by silicagel columnchromatography to give Compound 26 (19.2 g).

To a solution of Compound 26 in methylene chloride (100 ml) were added anisole (13.6 g) and trifluoroacetic acid (20 ml), then the resulting solution was stirred at room temperature for 2 hrs. After termination of the reaction, the solvent was removed and the residue was diluted with 1N HCl aqueous soln. (50 ml) and H₂O (60 ml). The aqueous layer was washed with hexane and alkalified with 2N NaOH aqueous soln. (30 ml). The solution was extracted with ethyl acetate and the organic layer was washed with brine and dried with magnesium sulfate and concentrated to give Compound 27 (9.6 g).

To a solution of Compound 27 (9.6 g) in methylene chloride (50 ml) were added pyridine (3.9 g) and acetic anhydride (4.0 g), then the resulting solution was stirred at room temperature for 2 hrs. After termination of the reaction, the solution was diluted with chloroform and the organic layer was washed with 2N HCl aqueous soln., sat. sodium hydrogencarbonate soln. and brine successively. The organic layer was dried with magnesium sulfate and concentrated. The residue was purified by silicagel columnchromatography to give Compound 28 (7.1 g).

To a solution of Compound 28 (7.1 g) in tetrahydrofuran (20 ml)-methanol (20 ml) was added 2N LiOH aqueous soln. (21 ml), then the resulting solution was stirred at room temperature for 16 hrs. After termination of the reaction, the solution was acidified with 2N HCl aqueous soln. and extracted with ethyl acetate. The organic layer was washed with brine and dried with magnesium sulfate and concentrated to give Compound 29 (6.3 g).

To a solution of Compound 29 (102 mg) in methylene chloride (2 ml) were added hydroxy adamantanamine (81 mg), 1-(3-dimethylaminopropyl)-3-ethylcarbodiimide hydrochloride (82 mg), 1-hydroxybenzotriazole (14 mg) and triethylamine (115 µl), then the resulting solution was stirred at room temperature for 13 hrs. After termination of the reaction, the solution was acidified with 2N HCl aqueous soln. and extracted with methylene chloride. The organic layer was washed with sat. sodium hydrogencarbonate soln. and brine successively, and dried with sodium sulfate. The residue was purified by silicagel columnchromatography to afford Compound C-202 (123 mg).

Compounds C-194 and 204 were synthesized as well as the above Example.

EXAMPLE 31

[Formula 49]

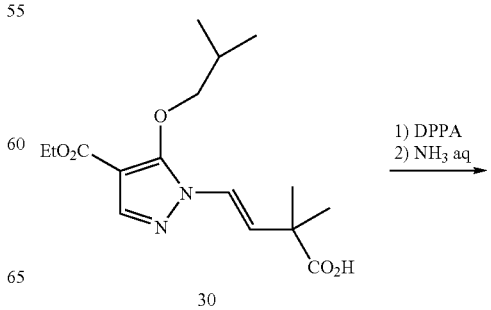

30

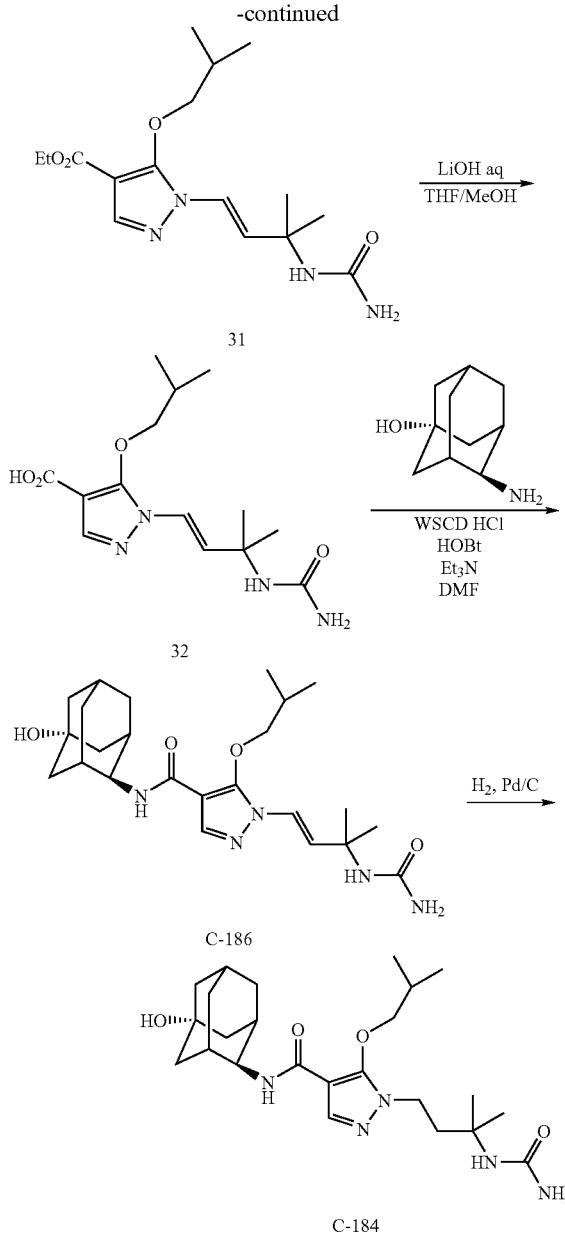

HCl aqueous soln., and extracted with ethyl acetate-tetrahydrofuran. The organic layer was washed with brine and dried with sodium sulfate and concentrated. The obtained crystal was washed with ethyl acetate-hexane to afford Compound 32 (193 mg).

To a solution of Compound 32 (193 mg) in dimethyl formamide (4 ml) were added hydroxy adamantanamine (152 mg), 1-(3-dimethylaminopropyl)-3-ethylcarbodiimide hydrochloride (155 mg), 1-hydroxybenzotriazole (26 mg) and triethylamine (217 μl), then the resulting solution was stirred at room temperature for 18 hrs. After termination of the reaction, the solution was acidified with 2N HCl aqueous soln. and extracted with methylene chloride. The organic layer was washed with sat. sodium hydrogencarbonate soln. and brine successively, and dried with sodium sulfate. The residue was purified by silicagel columnchromatography to give Compound C-186 (36 mg).

To a solution of Compound C-186 (25 mg) in tetrahydrofuran (1 ml)-methanol (0.1 ml) was added 10% Pd—C (12 mg), then the resulting mixture was stirred for 24 hrs under $H_2$ atmosphere. After termination of the reaction, Pd—C was removed by filtration and the solvent was removed to afford Compound C-184 (25 mg).

Compounds C-183, 185, 198 and 199 were synthesized as well as the above Example.

EXAMPLE 32

[Formula 50]

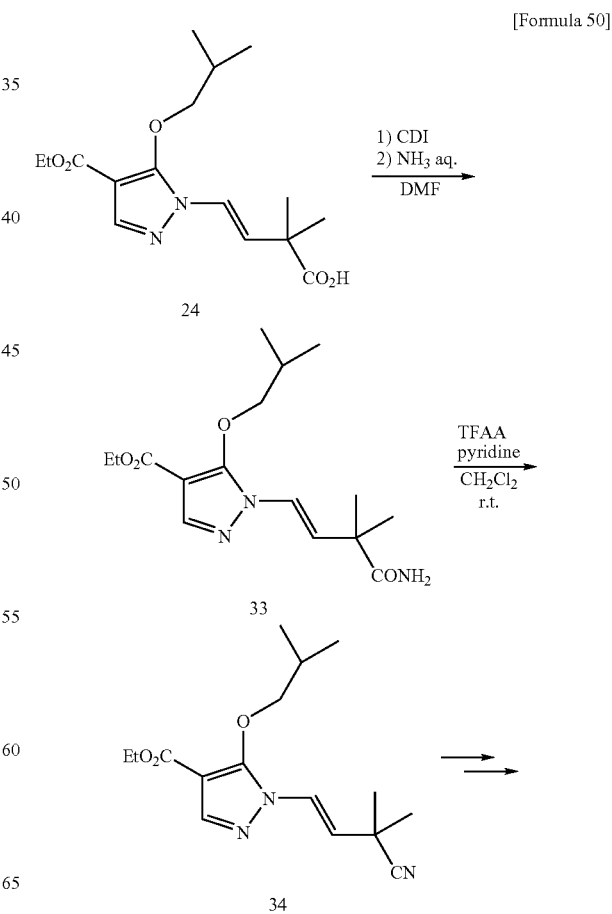

To a solution of Compound 30 (400 mg) in toluene (8 ml) were added triethylamine (180 μl) and diphenylphosphoryl azide (279 μl), then the resulting solution was stirred at 100° C. for 2 hrs. After cooling to 0° C., 28% ammonia aqueous soln. (2 ml) was added to the solution and the whole solution was stirred at room temperature for 80 min. After termination of the reaction, $H_2O$ was added to the solution and extracted with ethyl acetate. The organic layer was washed with sat. sodium hydrogencarbonate soln. and brine, and dried with sodium sulfate and concentrated. The residue was purified by silicagel columnchromatography to give Compound 31 (303 mg).

To a solution of Compound 31 (303 mg) in tetrahydrofuran (3 ml)-methanol (1.5 ml) was added 2N LiOH aqueous soln. (0.68 ml), then the resulting solution was stirred at room temperature for 19 hrs. After termination of the reaction, the solution was diluted with $H_2O$ and the organic layer was washed with diethylether. The mixture was acidified with 2N

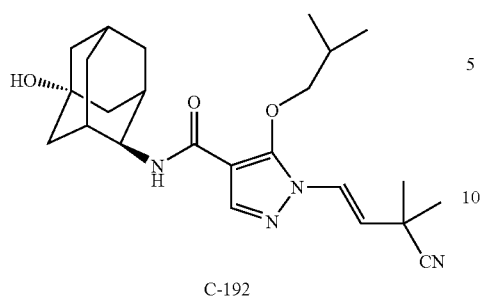

C-192

According to Example 29, Compound 33 was synthesized from Compound 24. To a solution of Compound 33 (149 mg) in methylene chloride (3 ml) were added pyridine (74 μl) and anhydrous trifluoroacetic acid (98 μl), then the resulting solution was stirred at room temperature for 45 min. After termination of the reaction, HCl aqueous soln. was added to the solution. The mixture was extracted with ethyl acetate and the organic layer was washed with sat. sodium hydrogencarbonate soln. and brine successively, and dried with sodium sulfate and concentrated to give Compound 34 (141 mg).

According to the above procedure, Compound C-192 was synthesized.

EXAMPLE 33

[Formula 51]

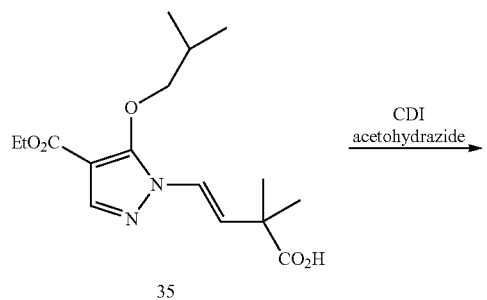

35

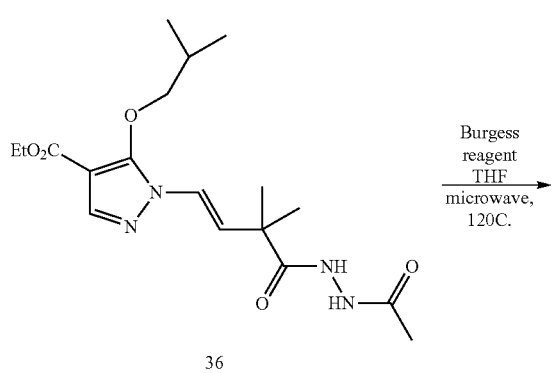

36

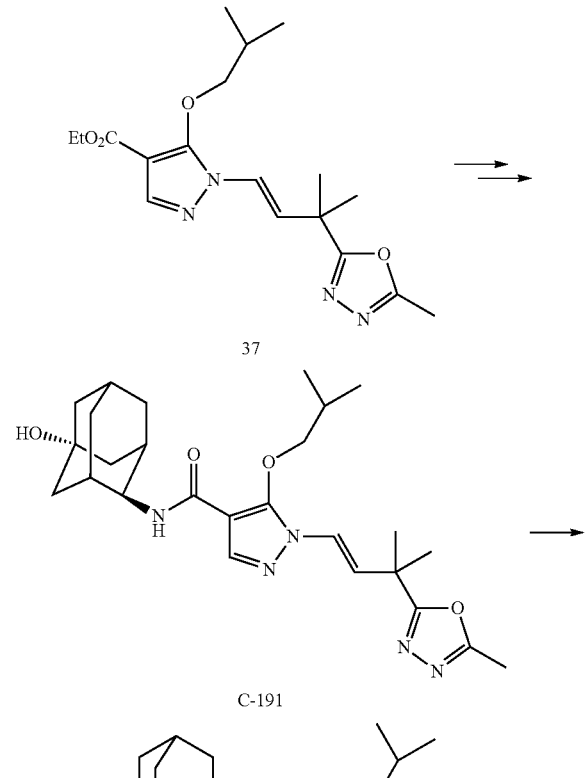

37

C-191

C-190

To a solution of Compound 35 in methylene chloride (4 ml) was added 1,1'-carbonyldiimidazole (200 mg), then the resulting solution was stirred at room temperature for 2 hrs and cooled to 0° C. Acetohydrazide (69 mg) in methylene chloride (2 ml) was added to the solution and the whole mixture was stirred at room temperature for 2 hrs. After termination of the reaction, HCl aqueous soln. was added to the mixture. The extraction was carried with ethyl acetate and the organic layer was washed with sat. sodium hydrogencarbonate soln. and brine, successively and dried with sodium sulfate. The solvent was removed to give a crystal. The obtained crystal was washed with hexane to give Compound 36 (190 mg).

To a solution of Compound 36 (140 mg) in tetrahydrofuran (2.8 ml) was added Burgess Reagent (259 mg), then the resulting solution was stirred at 120° C. for 15 min. by using microwave. After termination of the reaction, the solvent was removed and the residue was purified by silicagel columnchromatography to afford Compound 37 (126 mg).

According to the above procedure, Compounds C-190 and 191 were synthesized.

EXAMPLE 34

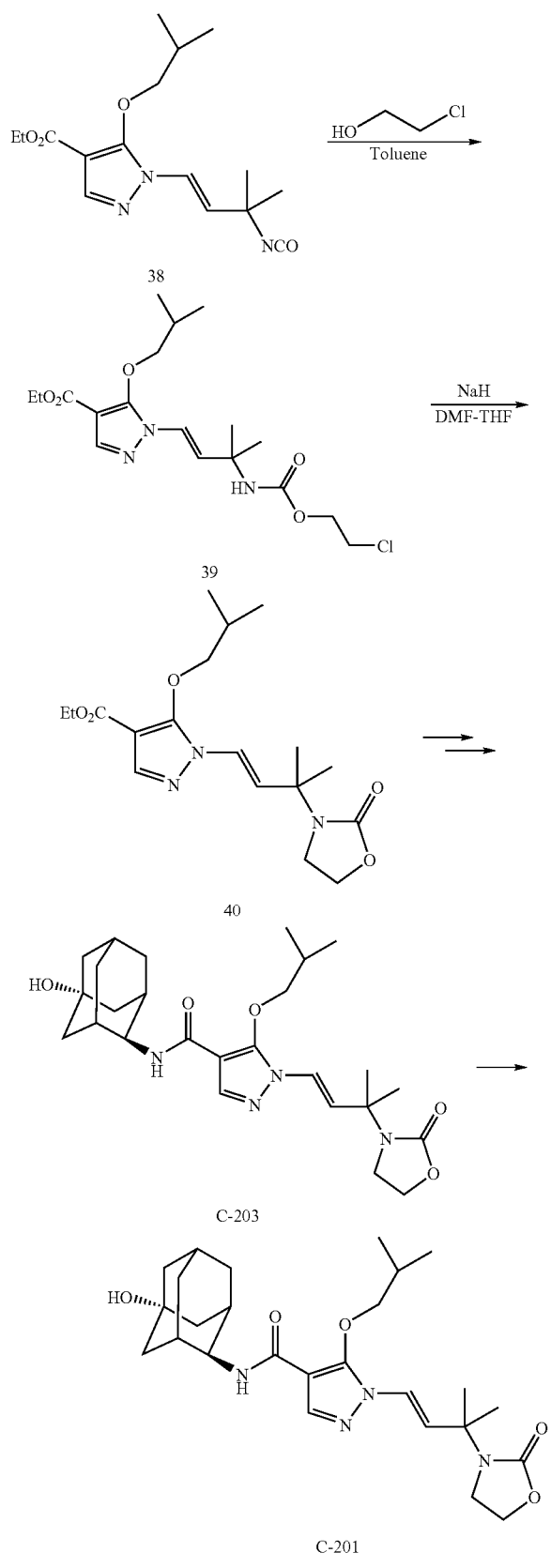

To a solution of Compound 38 in toluene (2 ml) were added 2-chloroethanol (103 μl), triethylamine (2 drops), then the resulting solution was stirred at room temperature for 24 hrs. After termination of the reaction, the solvent was removed and the residue was purified by silicagel columnchromatography to give Compound 39 (215 mg).

To a solution of Compound 39 (211 mg) in tetrahydrofuran (4 ml)-dimethyl formamide (4 ml) was added sodium hydride (32 mg, 60% oil suspension), then the resulting solution was stirred at room temperature for 140 min. After termination of the reaction, HCl aqueous soln. was added to the solution. The extraction was carried out with ethyl acetate and the organic layer was washed with brine and dried with sodium sulfate and concentrated. The residue was purified by silicagel columnchromatography to give Compound 40 (191 mg).

According to the above procedure, Compounds C-201 and 203 were synthesized.

EXAMPLE 35

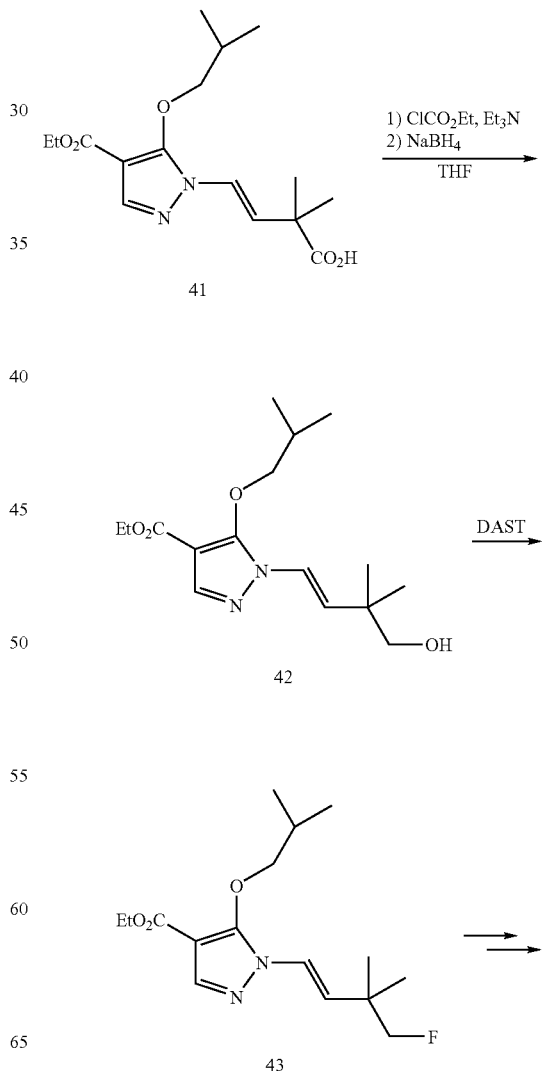

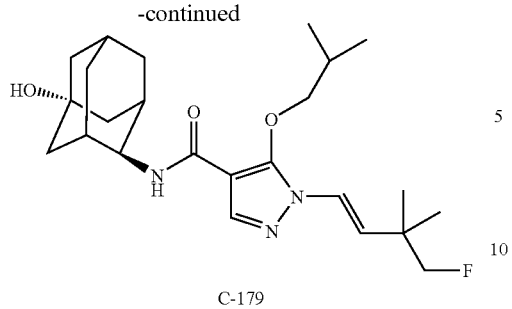

C-179

To a solution of Compound 41 (237 mg) in tetrahydrofuran (3 ml) were added triethylamine (152 µl) and ethyl chlorocarbonate (84 µl) at 0° C., then the resulting solution was stirred at room temperature for 1 hr. Sodium borohydride (69 mg) and H₂O (1 ml) were added to the solution at 0° C. and the whole mixture was stirred for 20 min. After termination of the reaction, HCl aqueous soln. was added to the mixture. The extraction was carried out with ethyl acetate and the organic layer was washed with brine and dried with sodium sulfate and concentrated. The residue was purified by silicagel columnchromatography to afford 42 (185 mg).

To a solution of 42 (185 mg) in methylene chloride (5 ml) was added DAST (102 µl) at −78° C., then the resulting solution was stirred at the same temperature for 30 min. After termination of the reaction, sat. ammonium chloride soln. was added to the solution. The extraction was carried out with ethyl acetate and the organic layer was dried with sodium sulfate and concentrated. The residue was purified by silicagel columnchromatography to afford Compound 43 (62 mg).

According to the above procedure, Compound C-179 was synthesized.

EXAMPLE 36

[Formula 54]

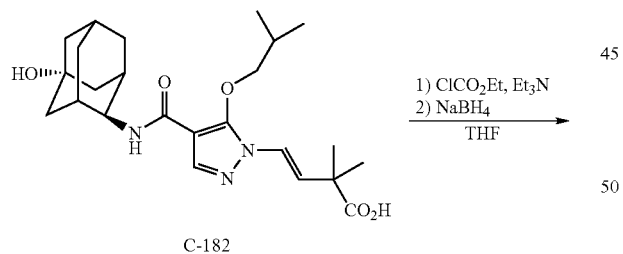

C-182

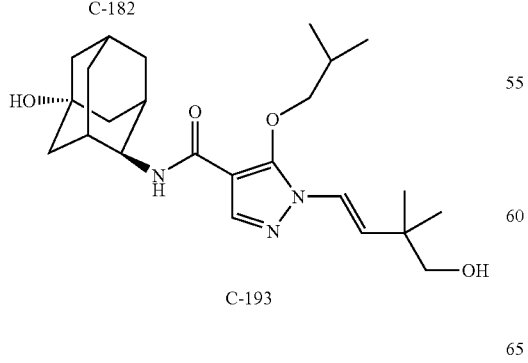

C-193

According to the above procedure, the reduction of carboxylic acid, Compound C-182 gave Compound C-193.

Compound C-162 was synthesized as well as the above Example. According to Example 29, Compound C-164 was synthesized from Compound C-162.

EXAMPLE 37

[Formula 55]

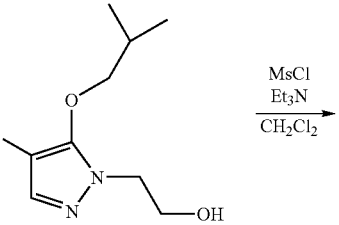

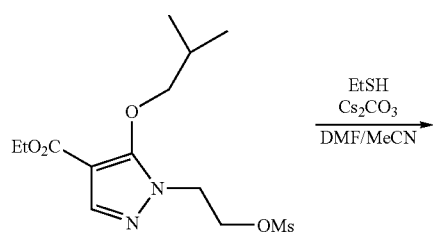

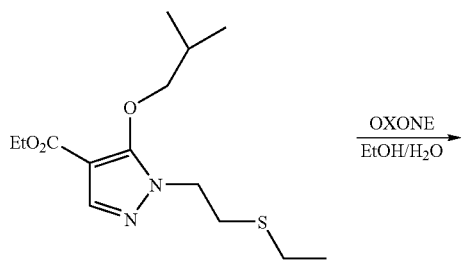

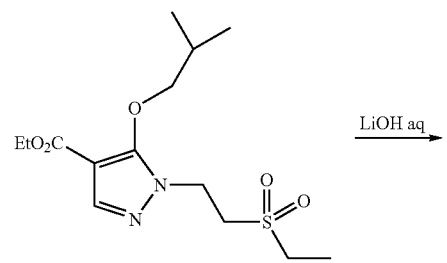

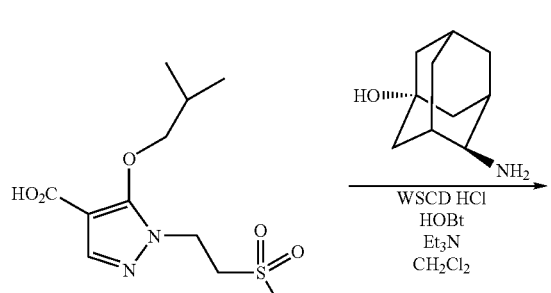

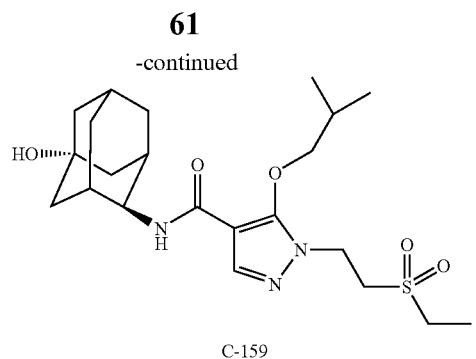
C-159
According to the above scheme, Compound C-159 was synthesized.
EXAMPLE 38
[Formula 56]
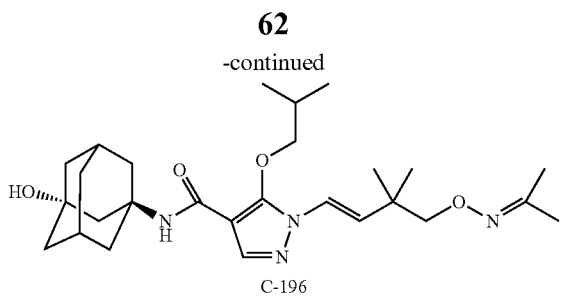
C-196
According to the above scheme, Compound C-196 was synthesized.
EXAMPLE 39
[Formula 57]
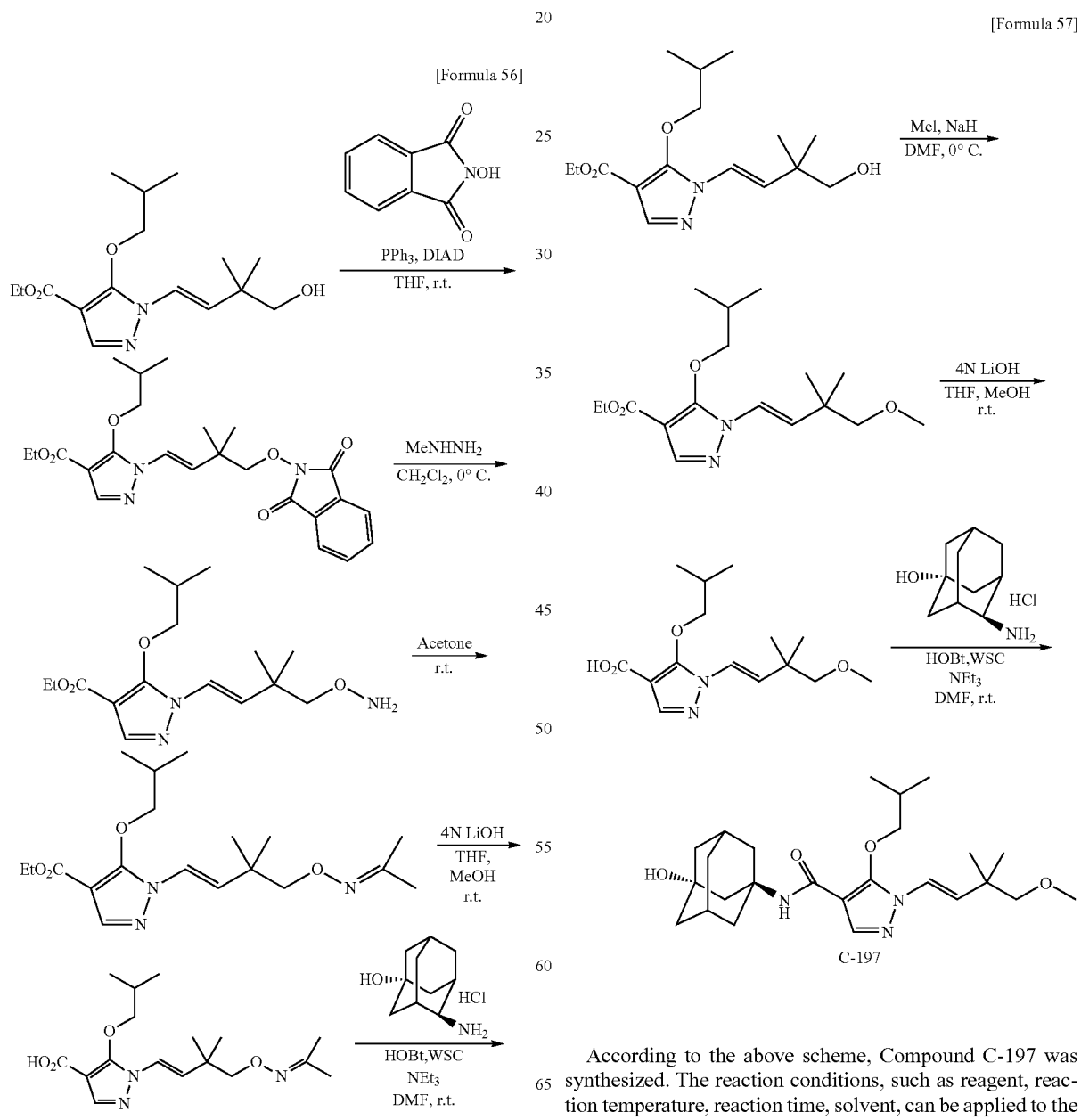
C-197
According to the above scheme, Compound C-197 was synthesized. The reaction conditions, such as reagent, reaction temperature, reaction time, solvent, can be applied to the conventional condition.

EXAMPLE 40

[Formula 58]

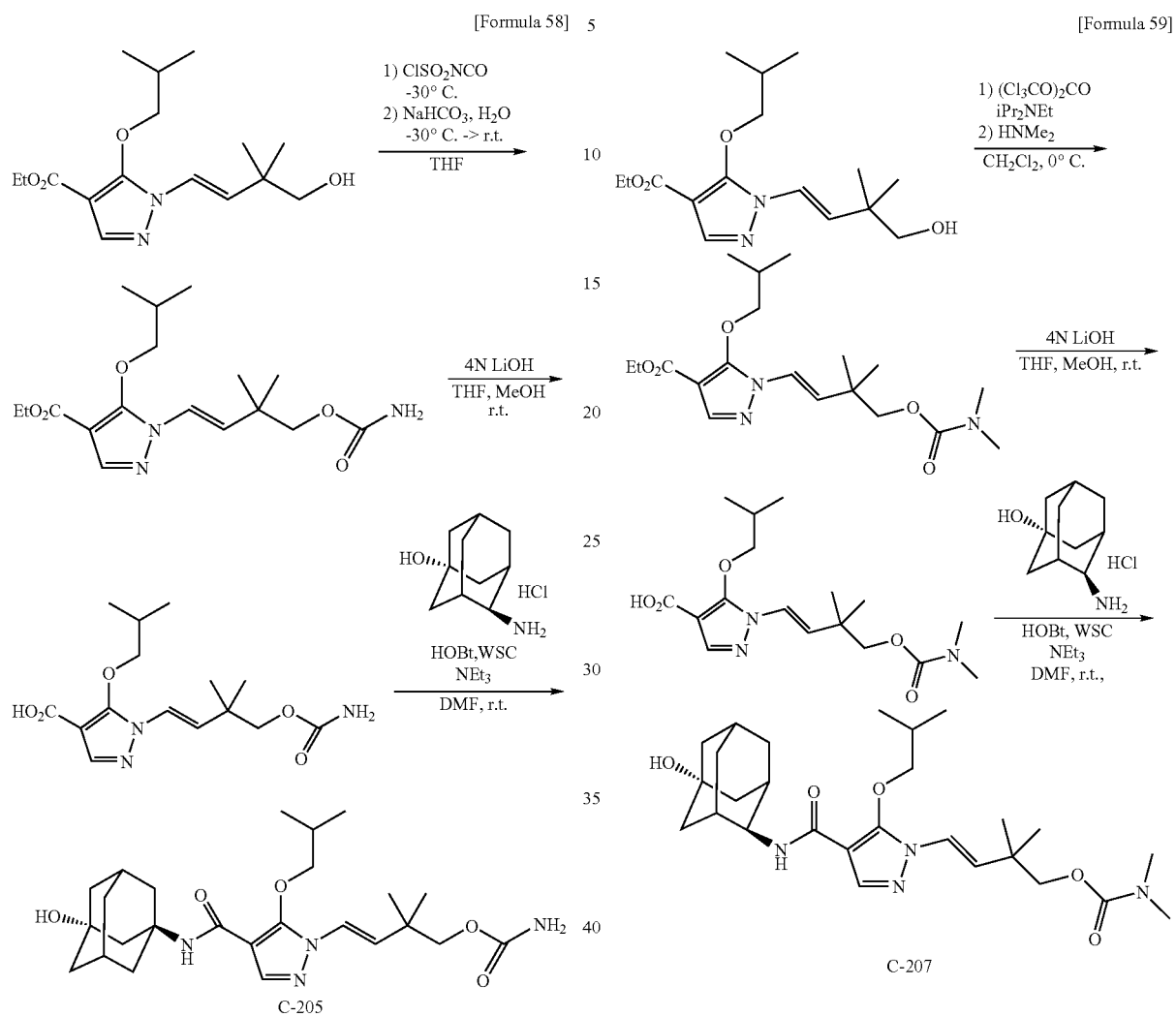

According to the above scheme, Compound C-205 was synthesized. The reaction conditions, such as reagent, reaction temperature, reaction time, solvent, can be applied to the conventional condition.

EXAMPLE 41

[Formula 59]

According to the above scheme, Compound C-207 was synthesized. The reaction conditions, such as reagent, reaction temperature, reaction time, solvent, can be applied to the conventional condition.

EXAMPLE 42

[Formula 60]

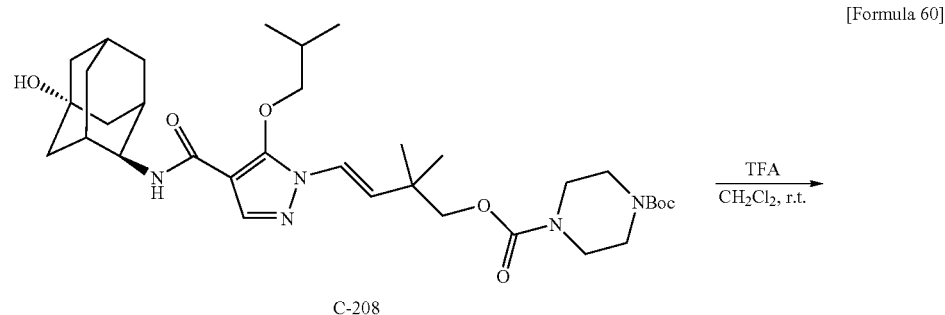

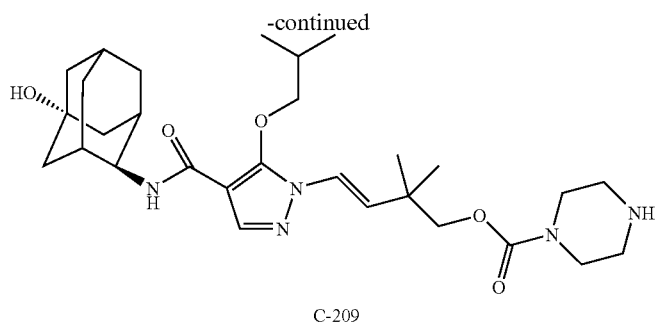

C-209

According to the above scheme, Compound C-209 was synthesized from Compound C-208. The reaction conditions, such as reagent, reaction temperature, reaction time, solvent, can be applied to the conventional condition.

EXAMPLE 43

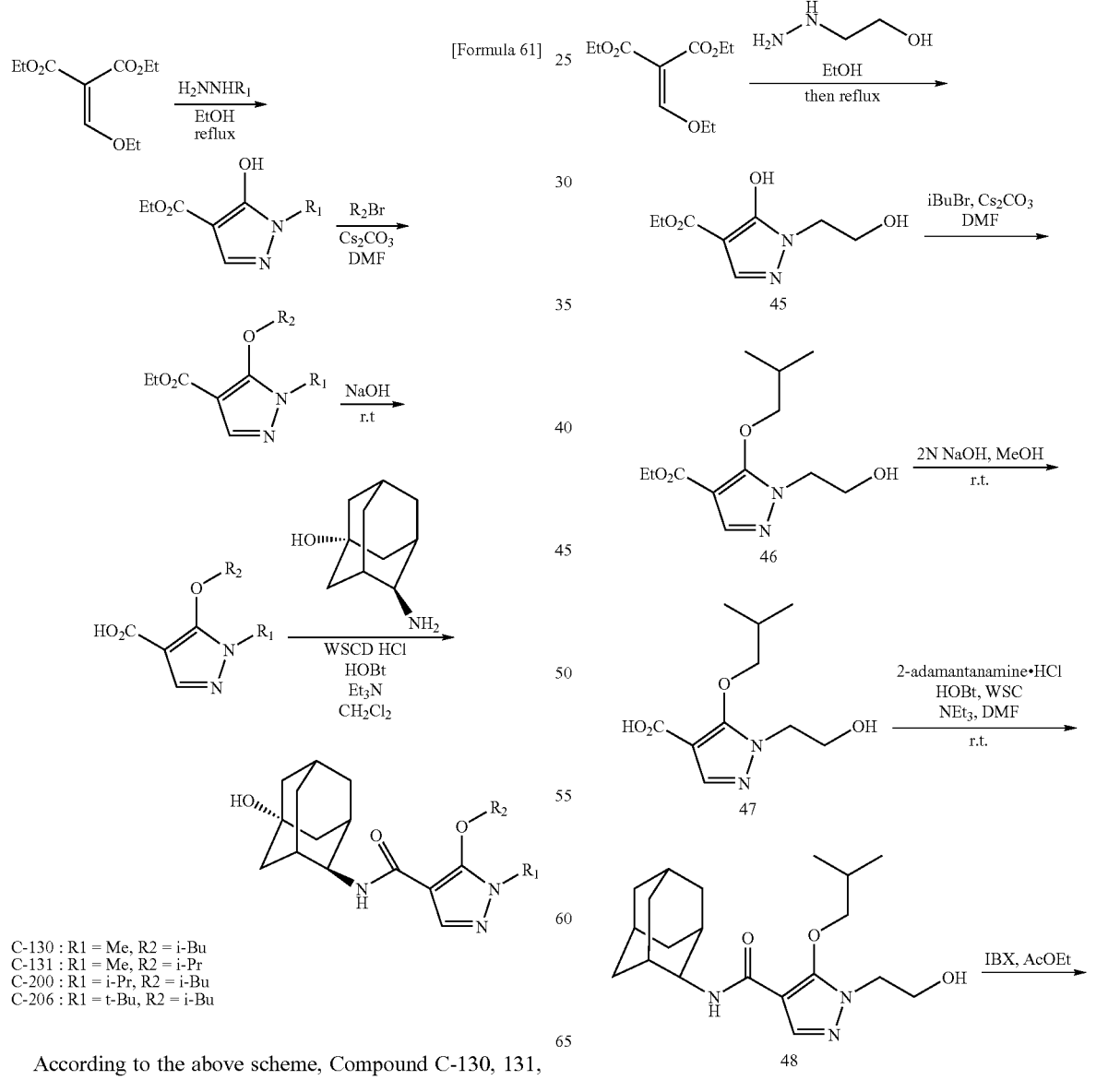

According to the above scheme, Compound C-130, 131, 200 and 206 were synthesized. The reaction conditions, such as reagent, reaction temperature, reaction time, solvent, can be applied to the conventional condition.

EXAMPLE 44

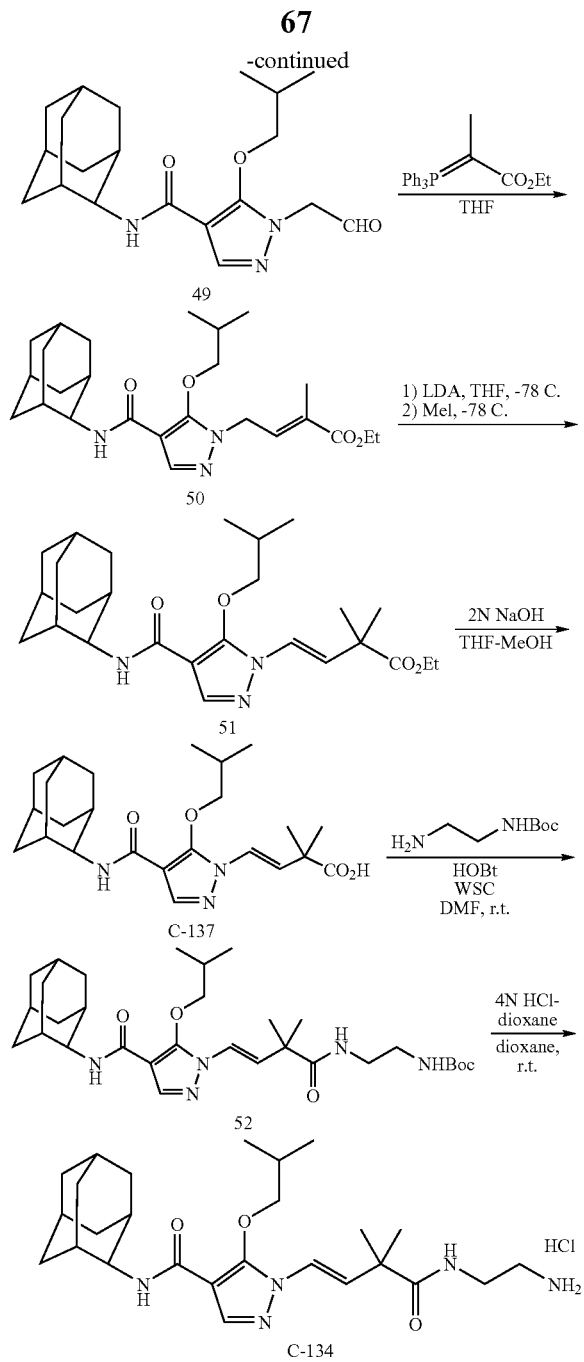

To a solution of diethyl ethoxymethylenemalonate (21.6 g) in ethanol (80 ml) was added dropwise hydrazine ethanol (8 g) in ethanol (20 ml) over 30 min at −4° C. The resulting solution was stirred at 40° C. for 1 hr and the solvent was removed. The residue was dissolved in chloroform and the organic layer was washed with sat. sodium hydrogencarbonate soln. and dried with magnesium sulfate and concentrated. The residue was dissolved in ethanol (80 ml) and the solution was refluxed for 18 hrs. After the termination of the reaction, the solvent was removed to give Compound 45 (18.5 g).

To a solution of Compound 45 (6.3 g) in dimethyl formamide (30 ml) were added cesium carbonate (15.4 g) and isobutyl bromide (5.6 ml), then the resulting mixture was stirred at 70° C. for 3 hrs. After termination of the reaction, H₂O (60 ml) was added to the mixture. The extraction was carried out with ethyl acetate and the organic layer was washed with brine and dried with magnesium sulfate and concentrated to give Compound 46 (5.7 g).

To a solution of Compound 46 (8.0 g) in methanol (70 ml) was added 2N NaOH aqueous soln. (60 ml), then the resulting solution was stirred at room temperature for 24 hrs. After termination of the reaction, the solution was acidified with 2N HCl aqueous soln. (65 ml) and extracted with ethyl acetate. The organic layer was washed with brine and dried with magnesium sulfate and concentrated. The obtained crystal was washed with diisopropylether to afford Compound 47 (6.0 g).

To a solution of Compound 47 (5.0 g) in dimethyl formamide (50 ml) were added 2-adamantanamine hydrochloride (5.35 g), 1-(3-dimethylaminopropyl)-3-ethylcarbodiimide hydrochloride (5.04 g), 1-hydroxybenzotriazole (3.55 g) and triethylamine (7.6 ml), then the resulting solution was stirred at room temperature for 24 hrs. After termination of the reaction, the solution was diluted with 2N HCl aqueous soln. and extracted with ethyl acetate. The organic layer was washed with sat. sodium hydrogencarbonate soln. and brine, and dried with sodium sulfate and concentrated. The residue was purified by silicagel columnchromatography to give Compound 48 (4.0 g).

To a solution of Compound 48 (4.0 g) in ethyl acetate (80 ml) was added IBX (6.2 g), then the resulting mixture was refluxed for 6 hrs. After termination of the reaction, the insoluble matter was removed by filtration and the solvent was concentrated to give Compound 49 (4.0 g). The obtained product was used for the next reaction without further purification.

To a solution of Compound 49 (4.0 g) in tetrahydrofuran (50 ml) was added (carbethoxyethylidene)triphenylphosphorane (5.27 g), then the resulting solution was stirred at room temperature for 4 hrs. After termination of the reaction, the solution was diluted with H₂O and extracted with ethyl acetate. The organic layer was washed with brine and dried with sodium sulfate and concentrated. The residue was purified by silicagel columnchromatography to give Compound 50 (3.9 g).

To a solution of diisopropylamine (2.72 ml) in tetrahydrofuran (40 ml) was added dropwise n-BuLi (12.2 ml, 1.59M in hexane) at −78° C. After stirring at the same temperature for 45 min, 50 (3.9 g) in tetrahydrofuran (40 ml) was added to the solution and the whole solution was stirred for 1 h. Iodomethane (0.6 ml) was added to the solution, then the solution was stirred for 1.5 hrs. After termination of the reaction, the solution was diluted with 2N HCl aqueous soln. and extracted with ethyl acetate. The organic layer was washed with brine and dried with sodium sulfate and concentrated. The residue was purified by silicagel columnchromatography to afford Compound 51 (2.4 g).

To a solution of Compound 51 (280 mg) in tetrahydrofuran (2.5 ml)-methanol (2.5 ml) was added 2N NaOH aqueous soln. (2.5 ml), then the resulting solution was stirred at room temperature for 1 h. After termination of the reaction, the solution was acidified with 2N HCl aqueous soln. and extracted with ethyl acetate. The organic layer was washed with brine and dried with sodium sulfate. The solvent was removed to give Compound C-137 (259 mg).

To a solution of Compound C-137 (141 mg) in dimethyl formamide (3 ml) were added tert-butyl-2-aminoethylcarbamate (68 mg), 1-(3-dimethylaminopropyl)-3-ethylcarbodiimide hydrochloride (76 mg) and 1-hydroxybenzotriazole (53 mg), then the resulting solution was stirred at room temperature for 24 hrs. After termination of the reaction, the solution was diluted with 2N HCl aqueous soln. and extracted with ethyl acetate. The organic layer was washed with sat.

sodium hydrogencarbonate soln. and brine successively, and dried with sodium sulfate. The solvent was removed and the residue was purified by silicagel columnchromatography to give Compound 52 (146 mg).

To a solution of Compound 52 (146 mg) in dioxane (1.5 ml) was added 4N HCl/dioxane (1.5 ml), then the resulting solution was stirred at room temperature for 3 hrs. After termination of the reaction, the solution was diluted with diisopropylether to give crystal. The crystal was collected by filtration and washed with diisopropylether and dried to afford Compound C-134 (94 mg).

Compounds C-129, D-13 to 35 were synthesized from the same method.

EXAMPLE 45

[Formula 63]

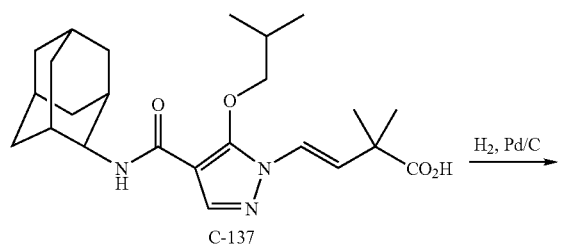

To a solution of Compound C-137 (118 mg) in ethanol (3 ml) was added 10% Pd—C (12 mg), then the resulting mixture was stirred for 5 hrs under $H_2$ atmosphere. After termination of the reaction, Pd—C was removed by filtration. The filtrate was concentrated to give Compound C-138 (116 mg). According to the conventional procedure, Compound C-135 was synthesized.

Additionally, Compounds C-139, D1 to 12 were synthesized as well as the above Example.

EXAMPLE 46

[Formula 64]

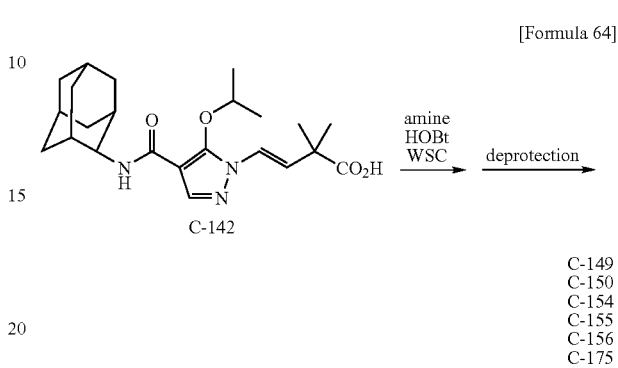

According to the synthetic procedure of Compounds C-137 and C-142 were synthesized. Compound C-142 was converted to Compounds C-149, 150, 154 to 156 and 175 by the conventional procedure.

EXAMPLE 47

[Formula 65]

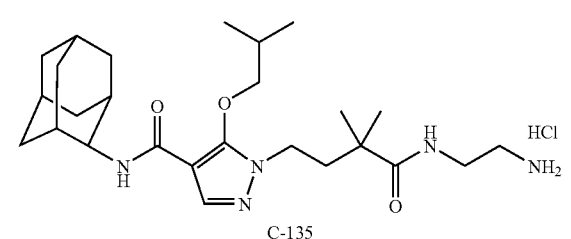

According to the synthetic procedure of Compounds C-137 and C-143 was synthesized. Compound C-143 was converted to Compounds C-147, 148 and 157 by the conventional procedure.

EXAMPLE 48

[Formula 66]

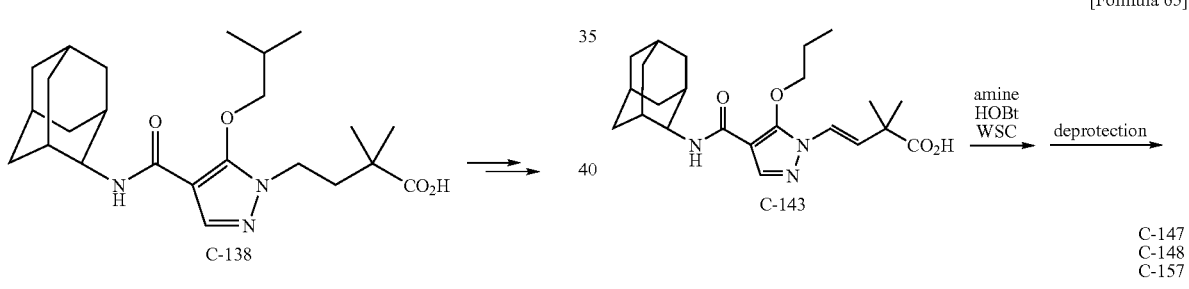

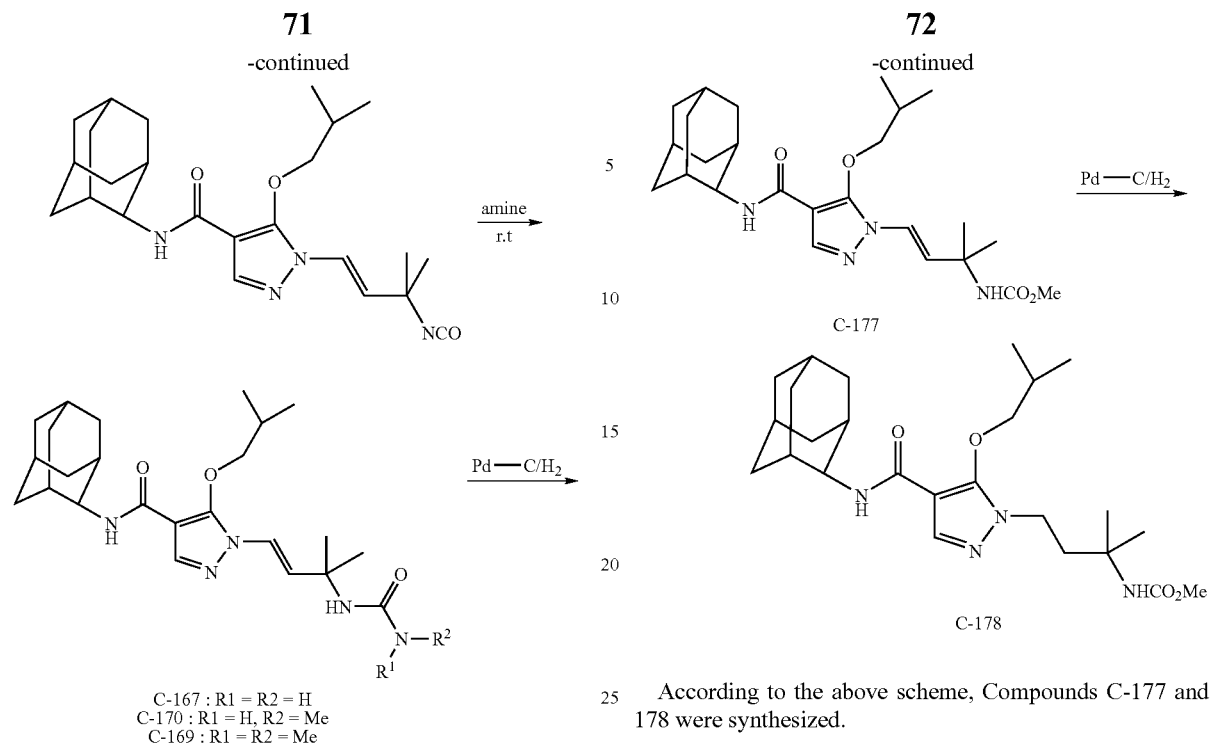
C-167 : R1 = R2 = H
C-170 : R1 = H, R2 = Me
C-169 : R1 = R2 = Me
C-171 : R1 = R2 = H
C-174 : R1 = H, R2 = Me
C-173 : R1 = R2 = Me
According to the synthetic procedure of Compound C-184 (Example 31), the above compounds were synthesized from Compound C-137.
EXAMPLE 49
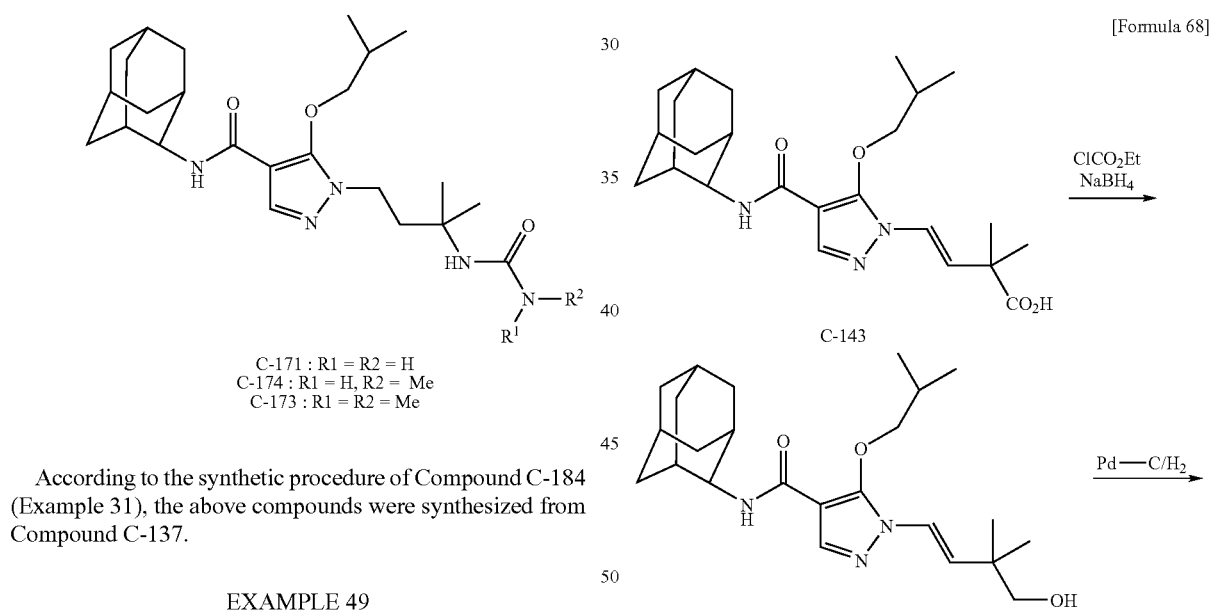
According to the above scheme, Compounds C-177 and 178 were synthesized.
EXAMPLE 50
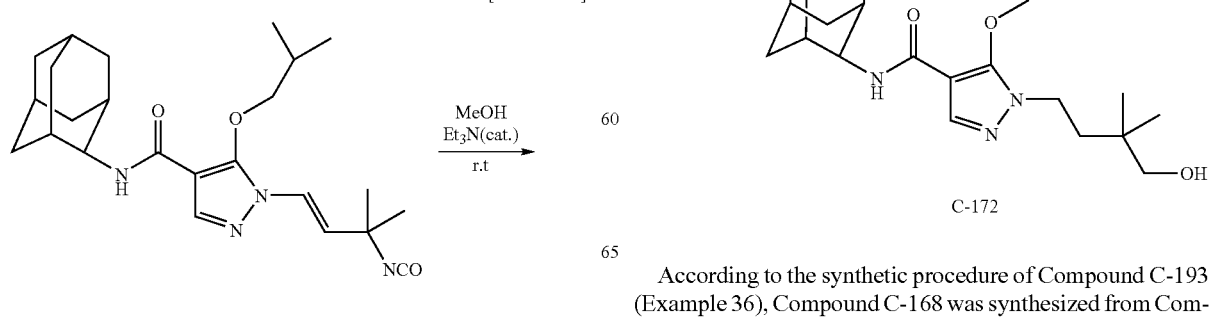
According to the synthetic procedure of Compound C-193 (Example 36), Compound C-168 was synthesized from Compound C-137. Additionally, Compound C-168 was converted to Compound C-172 by the above procedure.
EXAMPLE 51
[Formula 69]
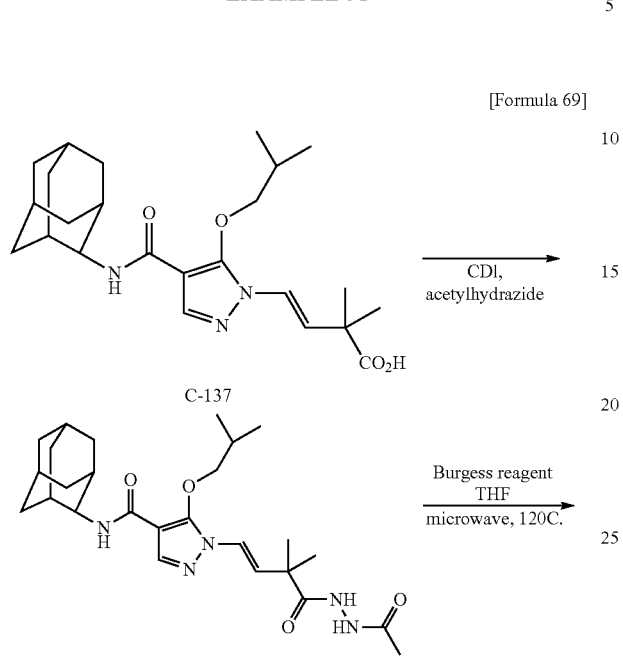
According to the synthetic procedure of Compound C-191 (Example 33), Compound C-180 was synthesized from Compound C-137.
EXAMPLE 52
[Formula 70]
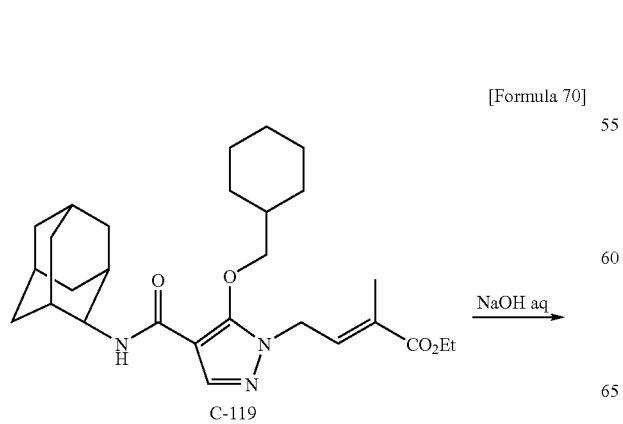
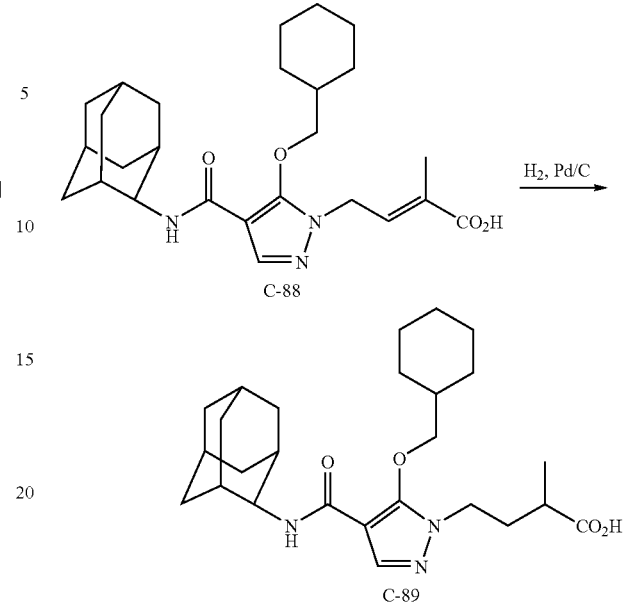
Hydrolysis of Compound C-119 gave Compound C-88, followed by the catalytic reduction of Compound C-88 gave Compound C-89.
EXAMPLE 53
[Formula 71]
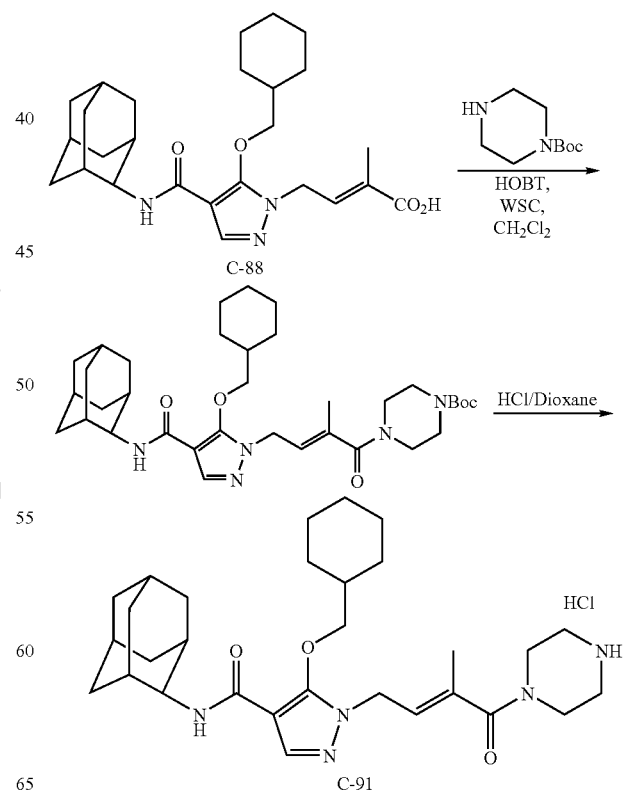

According to the above scheme, Compound C-91 was synthesized from Compound C-88.
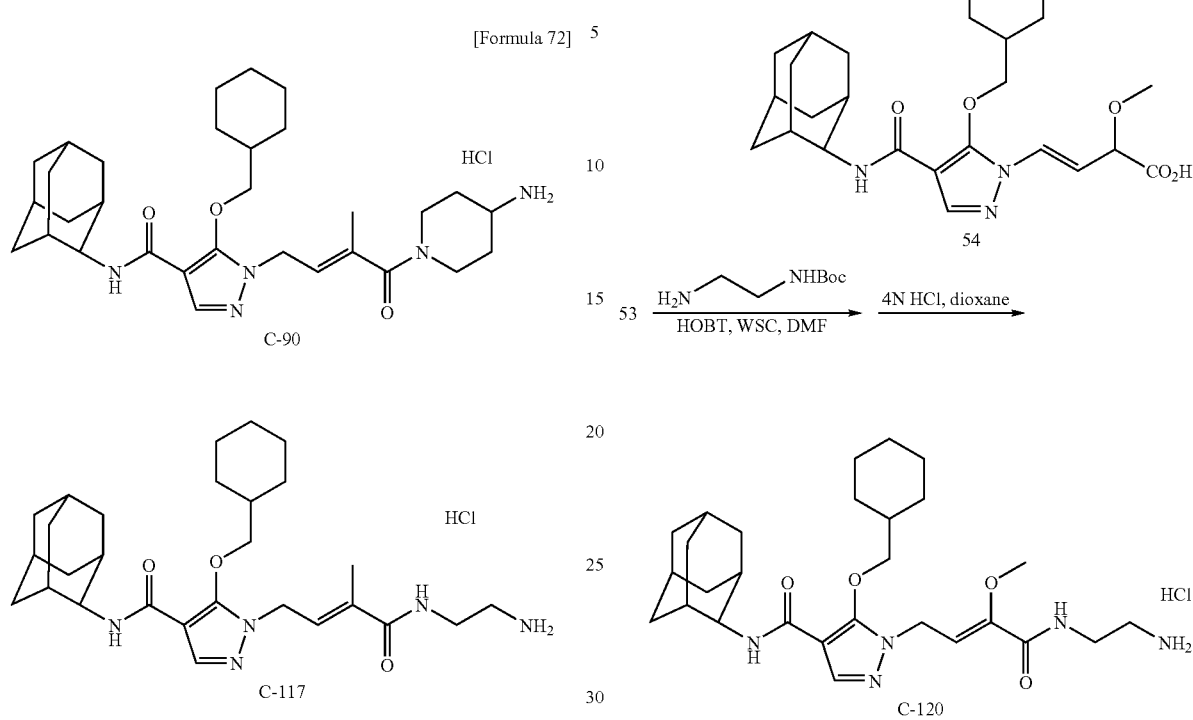
According to the above procedure, the following compounds were synthesized.
EXAMPLE 54
According to the above scheme, Compounds 53 and 54 were synthesized. Compound C-120 was synthesized from Compound 53.
EXAMPLE 55
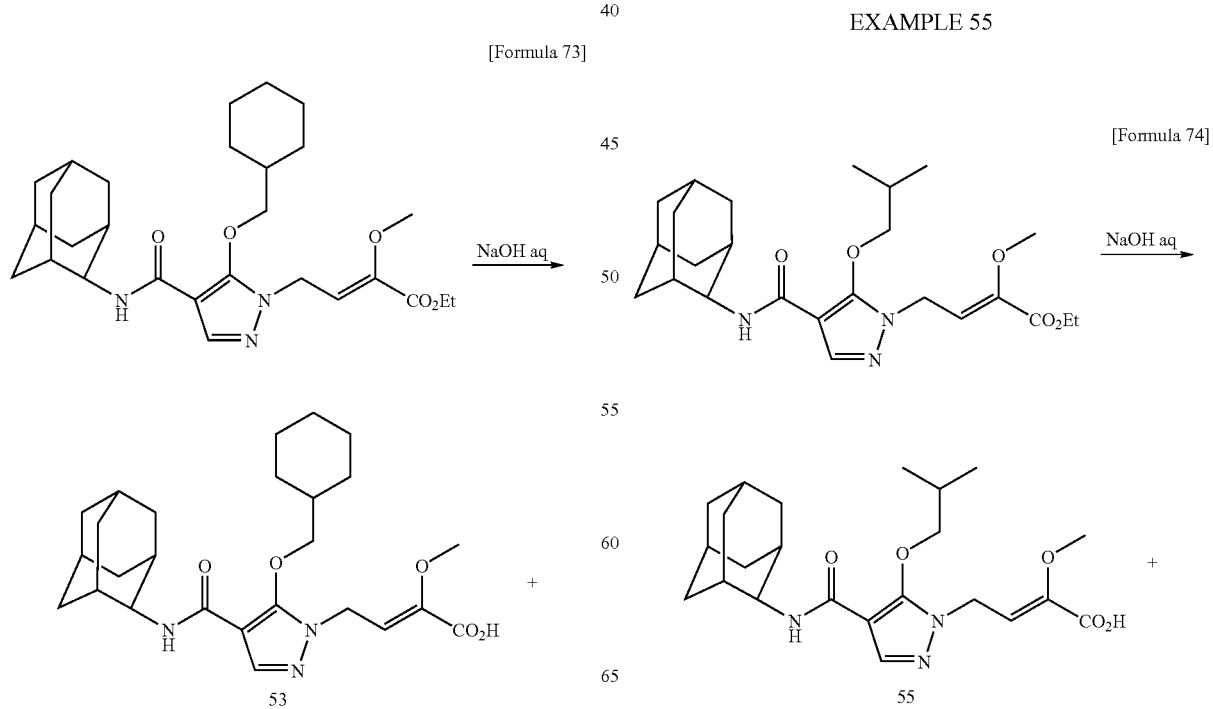

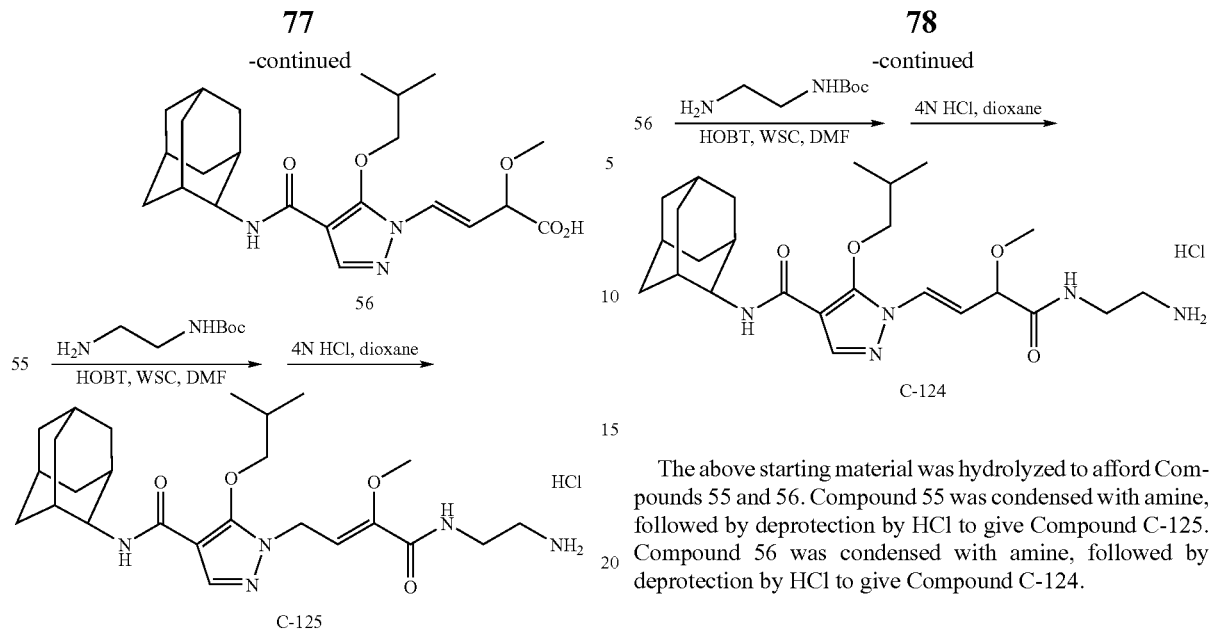
The above starting material was hydrolyzed to afford Compounds 55 and 56. Compound 55 was condensed with amine, followed by deprotection by HCl to give Compound C-125. Compound 56 was condensed with amine, followed by deprotection by HCl to give Compound C-124.
EXAMPLE 56
[Formula 75]
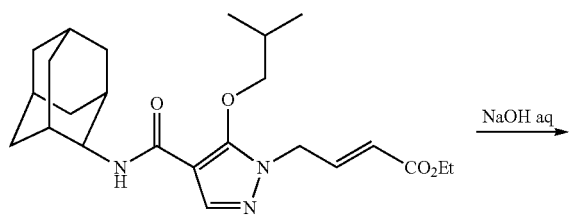
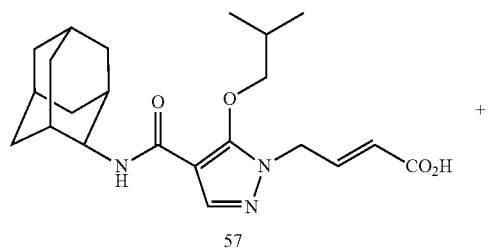
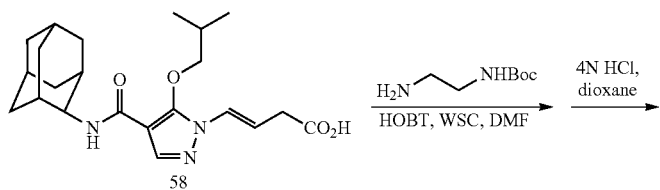
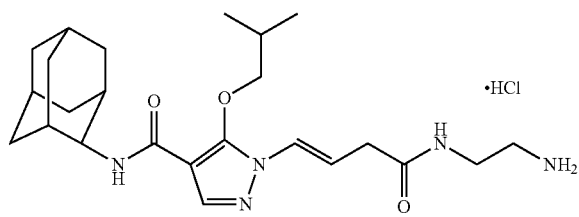

According to the above scheme, Compound C-121 was obtained.
According to the above scheme, Compounds C-123 and 122 were obtained.
EXAMPLE 57
EXAMPLE 58
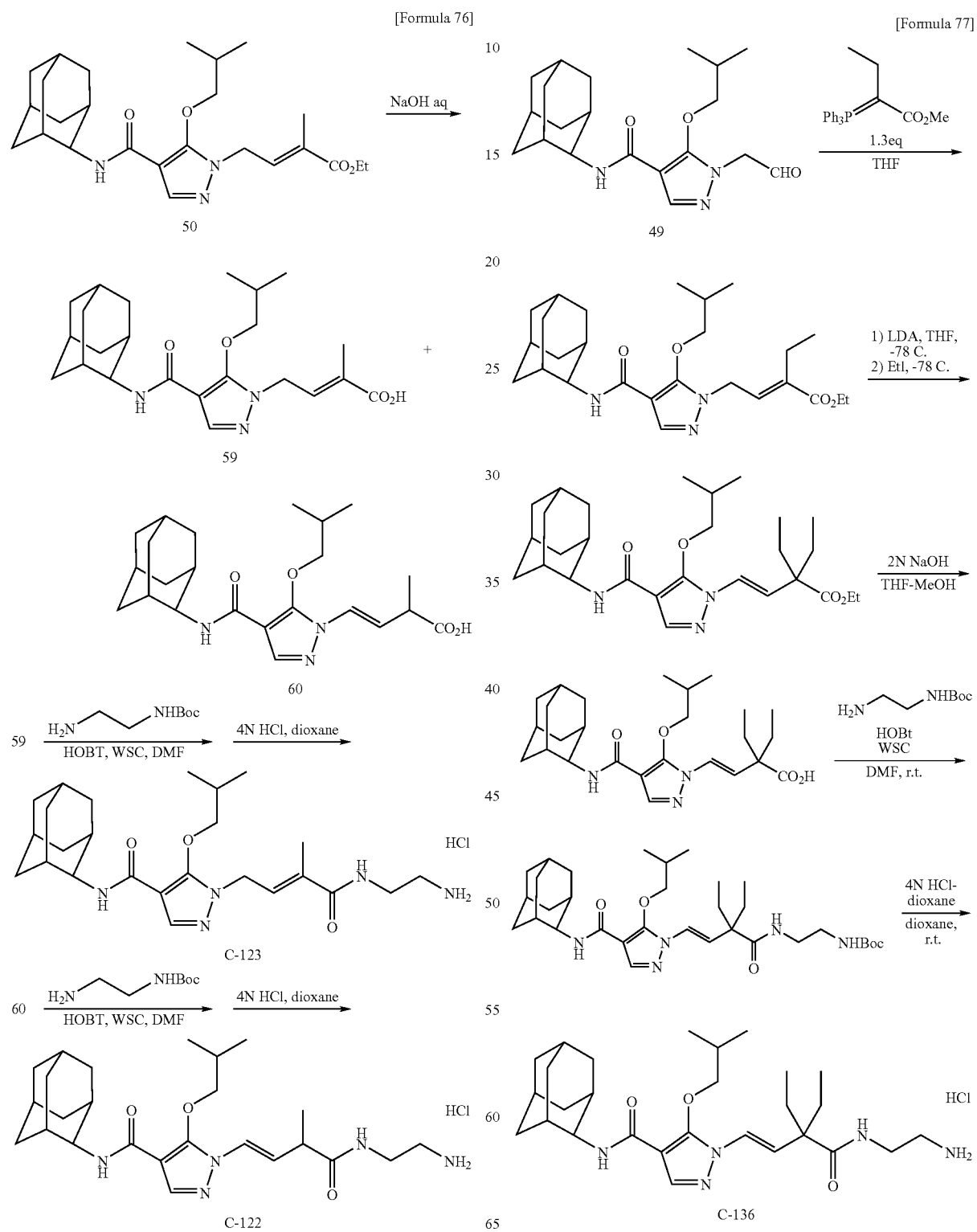

According to the above scheme, Compound C-136 was obtained.
EXAMPLE 59
[Formula 78]
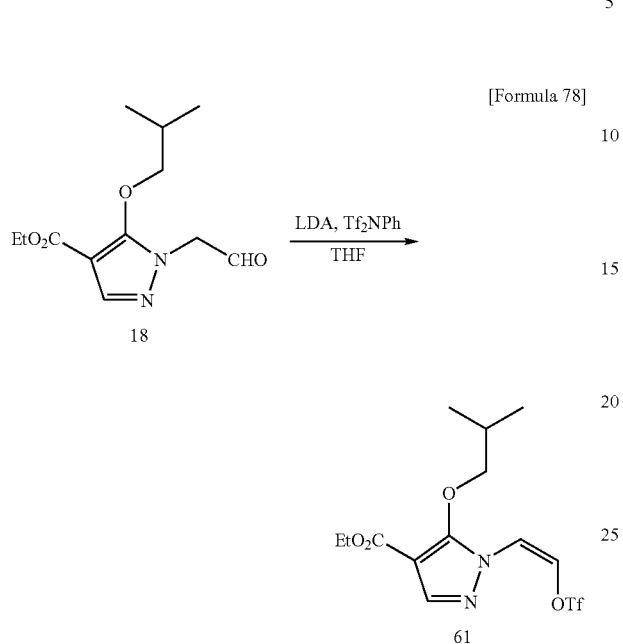
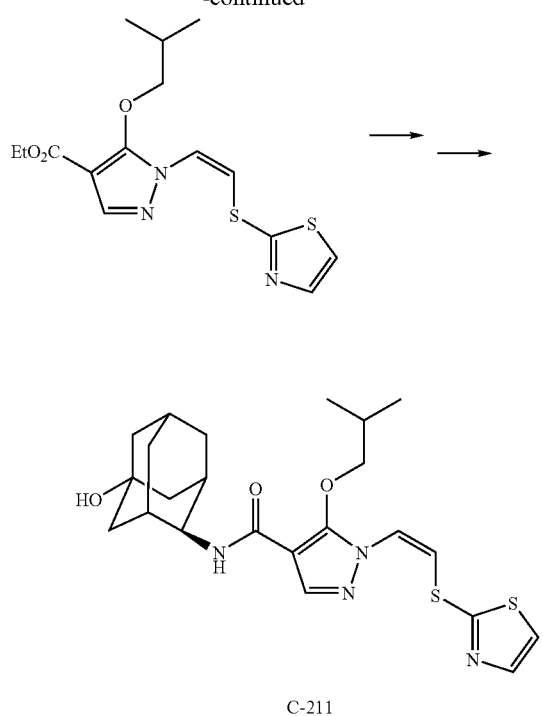
According to the above scheme, Compounds C-210 and 211 were obtained.
EXAMPLE 60
[Formula 79]
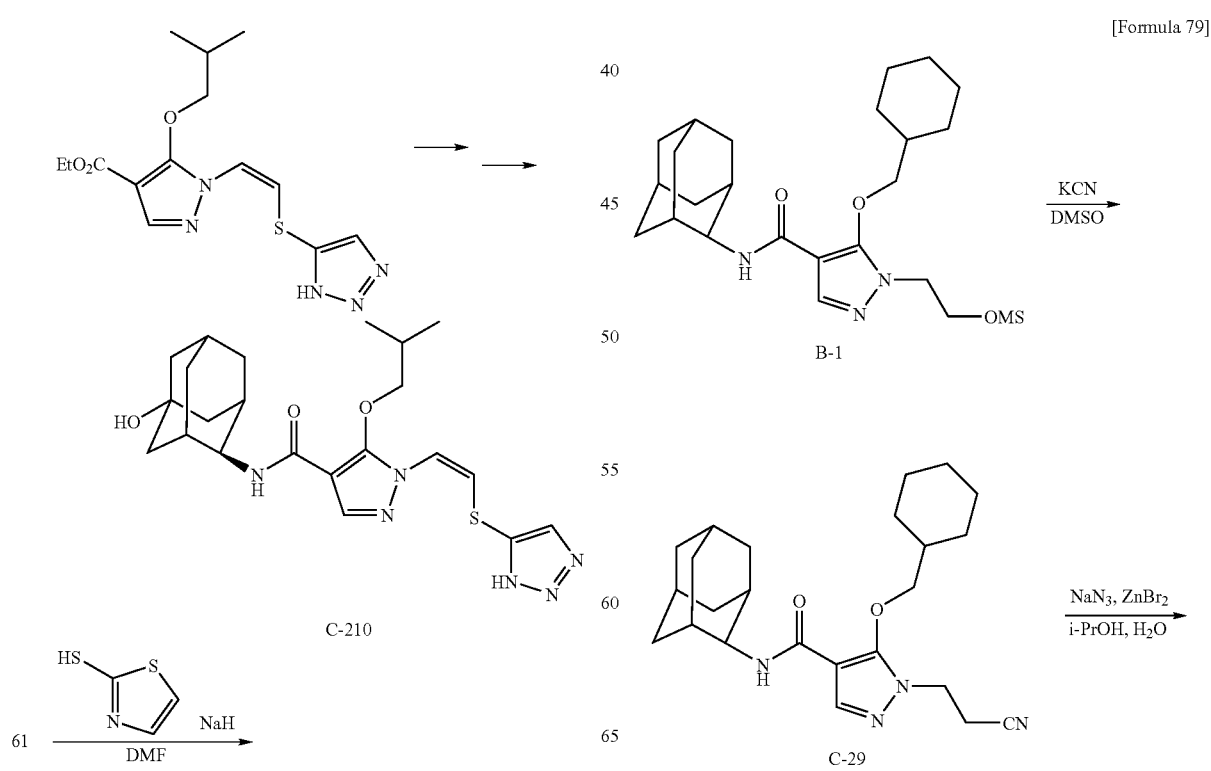

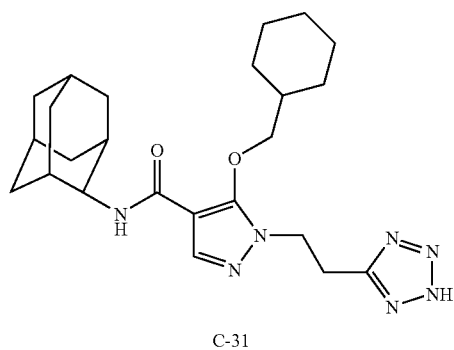

C-31

According to the above scheme, Compounds C-29 and 31 were obtained. Compound C-104 was synthesized as well as the above-mentioned execution example.

EXAMPLE 61

[Formula 80]

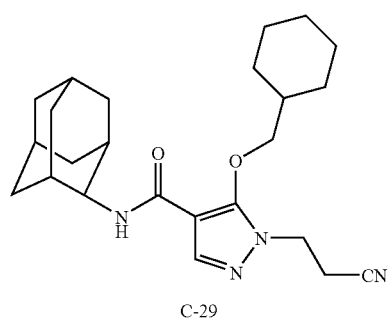

C-29

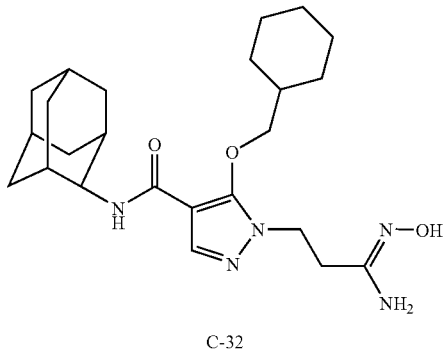

C-32

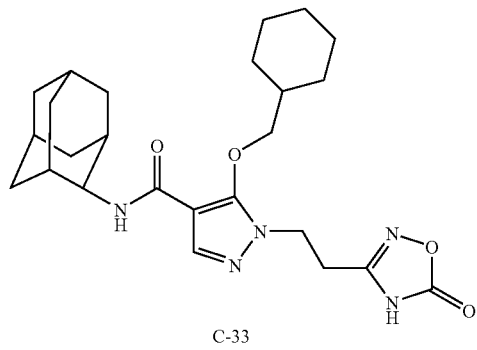

C-33

According to the above scheme, Compound C-32 was synthesized, followed by reaction with 1,1'-carbonyldiimidazole to give Compound C-33.

EXAMPLE 62

[Formula 81]

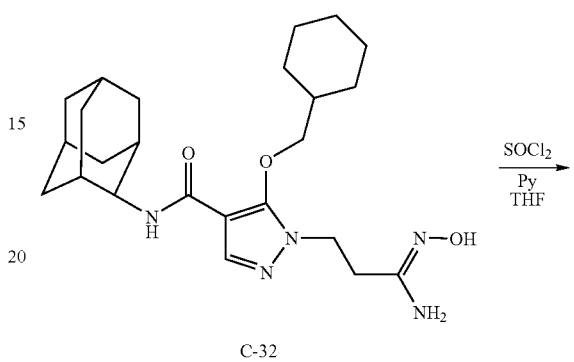

C-32

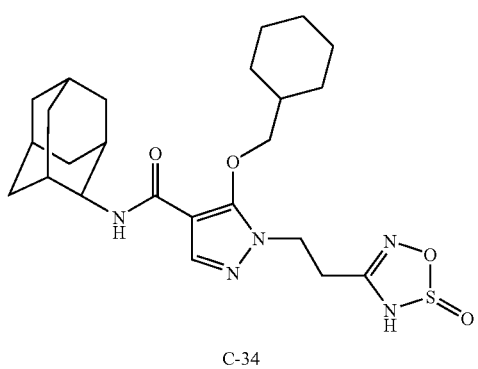

C-34

Compound C-32 was reacted with thionyl chloride in the presence of pyridine to afford Compound C-34.

EXAMPLE 63

[Formula 82]

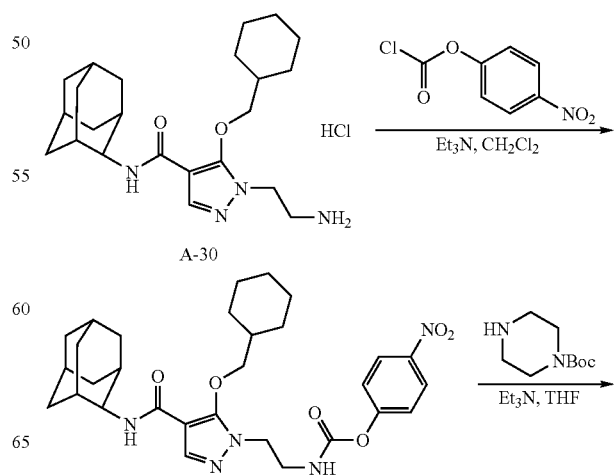

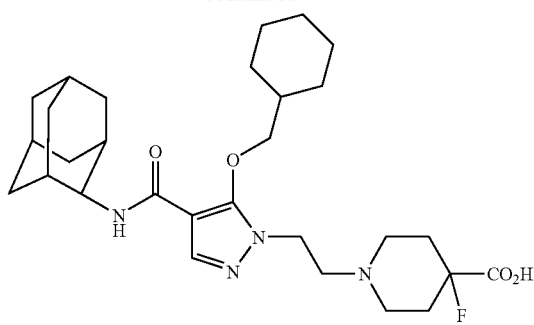
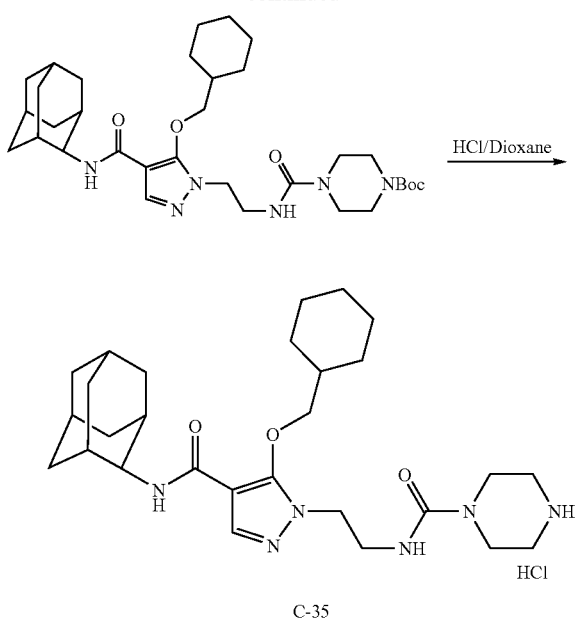
C-35
According to the above scheme, Compound C-35 was synthesized.
EXAMPLE 64
[Formula 83]
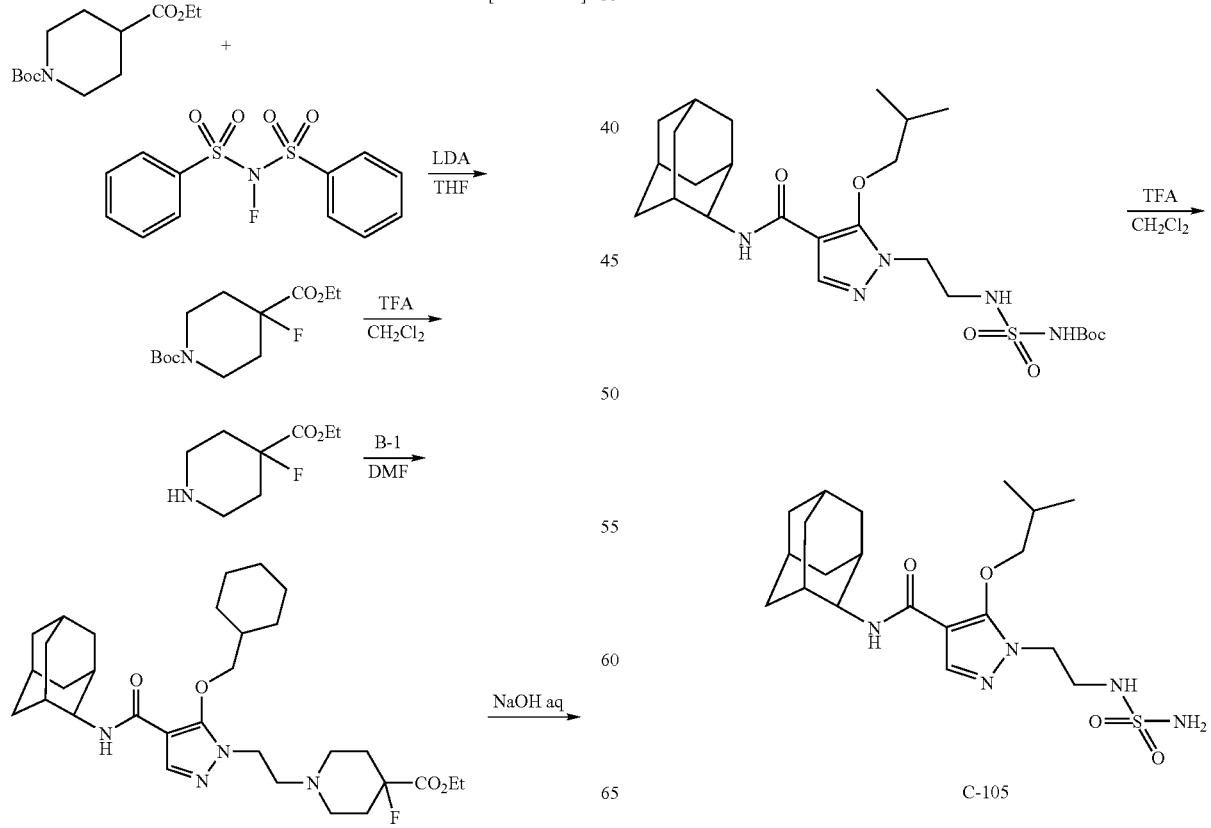
C-65
According to the above scheme, Compound C-65 was synthesized.
EXAMPLE 65
[Formula 84]
C-105

87
According to the above scheme, Compound C-105 was synthesized.
EXAMPLE 66
[Formula 85]
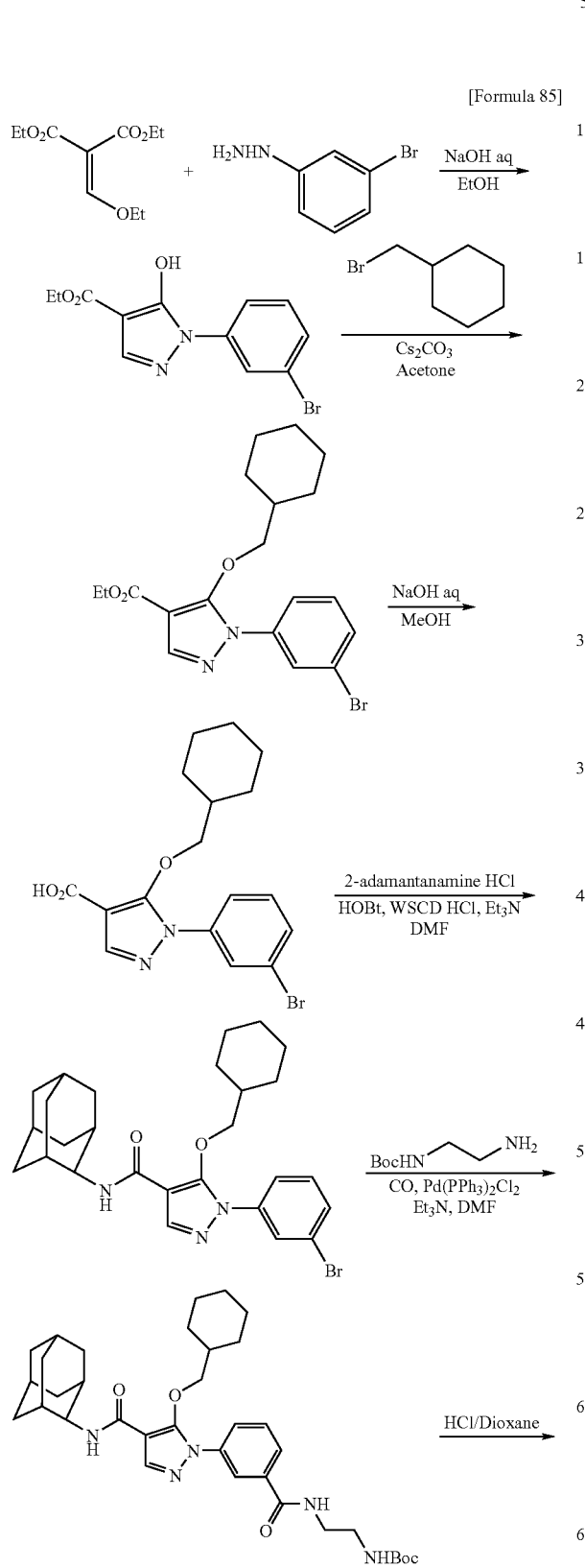
88
-continued
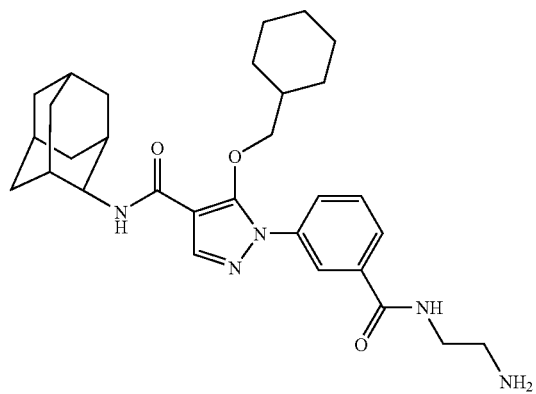
C-106
According to the above scheme, Compound C-106 was synthesized.
EXAMPLE 67
[Formula 86]
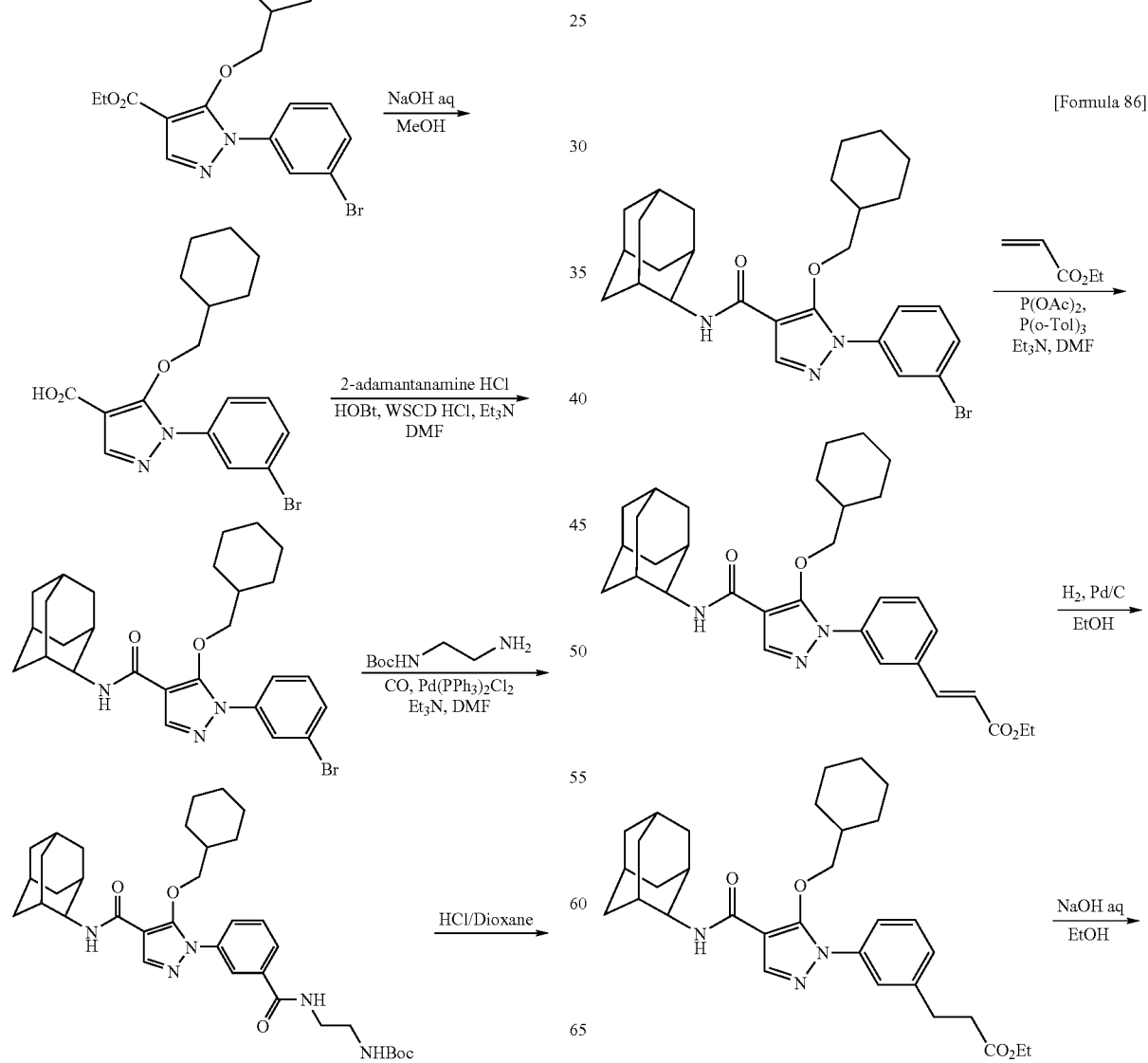

-continued

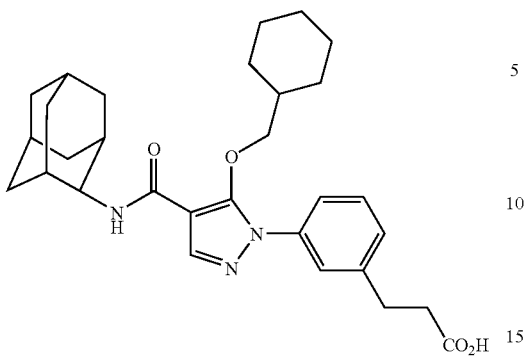

C-107

According to the above scheme, Compound C-107 was synthesized.

EXAMPLE 68

[Formula 87]

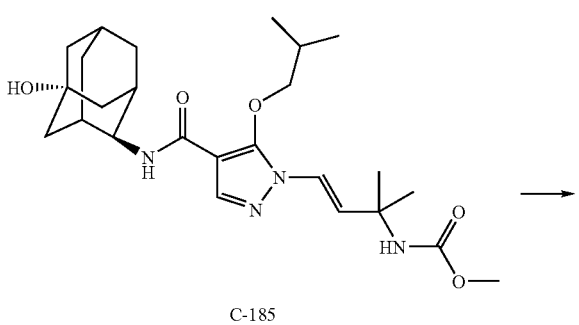

C-185

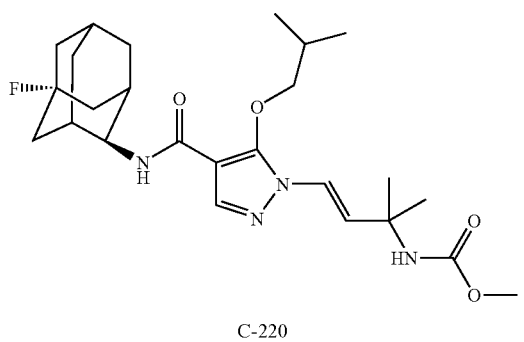

C-220

To a solution of Compound C-185 (300 mg) in methylene chloride (20 ml) was added DAST (168 μl) at −78° C., then the resulting solution was at the same temperature for 1 h. After termination of the reaction, the solution was poured into sat. sodium hydrogencarbonate soln. and extracted with ethyl acetate. The organic layer was washed with brine and dried with magnesium sulfate and concentrated. The residue was purified by silicagel columnchromatography to give Compound C-220 (270 mg).

Compound C-219 was synthesized from Compound C-144 by the same procedure.

EXAMPLE 69

[Formula 88]

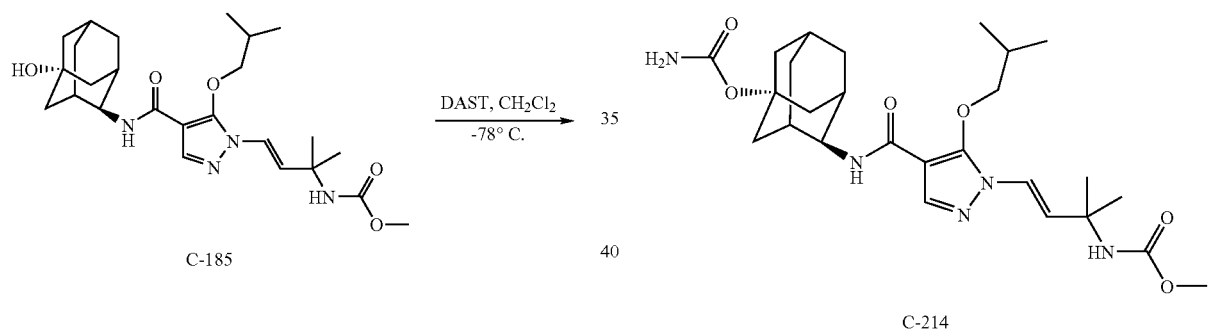

To a solution of Compound C-185 (250 mg) in tetrahydrofuran (2.5 ml) was added chlorosulfonyl isocyanate (69 μl) at −45° C., then the resulting solution was stirred at −25° C. for 3 hrs. Sodium hydrogencarbonate (221 mg) and H$_2$O (50 μl) were added to the solution and the whole mixture was stirred at room temperature for 1 h. The mixture was extracted with ethyl acetate and the organic layer was washed with brine and dried with sodium sulfate and concentrated. The residue was purified by silicagel columnchromatography to give Compound C-214 (220 mg).

Compound C-231 was synthesized from Compound C-202, and Compound C-236 was obtained from Compound C-216 as well as the above Example.

The following compounds were synthesized as well as the above Example. "ClH" has the same meaning as "HCl" in the following table. The measurement results of NMR, MS and m.p. were disclosed.

TABLE 1

| No. | Structure | NMR (CDCl3 or d6-DMSO), MS or m.p. |
|---|---|---|
| A-1 | 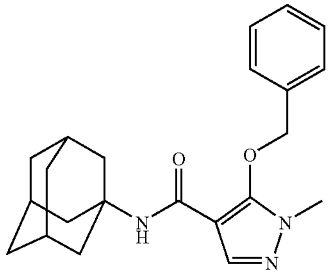 | 1H-NMR (DMSO-d6) δ: 1.64 (br s, 6 H), 2.00-2.02 (br m, 10 H), 3.48 (s, 3 H), 5.34 (s, 2 H), 6.86 (s, 1 H), 7.40-7.41 (m, 5 H), 7.69 (s, 1 H). |
| A-2 | 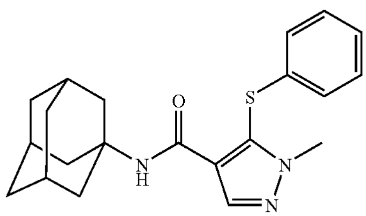 | 1H-NMR (CDCl3) δ: 1.57 (br s, 2 H), 1.64-1.67 (br m, 5 H), 1.98-2.04 (br m, 8 H), 3.88 (s, 3 H), 6.99 (s, 1 H), 7.06 (d, J = 6.9 Hz, 2 H), 7.27-7.29 (m, 9 H), 8.12 (s, 1 H). |
| A-3 | 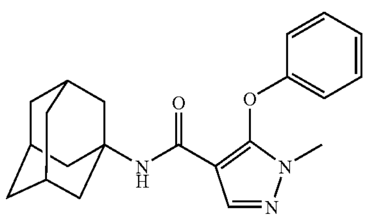 | 1H-NMR (DMSO-d6) δ: 1.57-1.62 (br m, 7 H), 1.82 (br s, 6 H), 1.95 (br s, 3 H), 2.02 (br s, 1 H), 3.59 (s, 3 H), 6.62 (s, 1 H), 6.92 (d, J = 8.1 Hz, 2 H), 7.14 (t, J = 7.3 Hz, 1 H), 7.39 (t, J = 8.0 Hz, 2 H), 7.86 (s, 1 H). |
| A-4 | 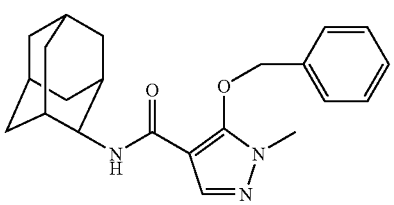 | 1H-NMR (DMSO-d6) δ: 1.48 (d, J = 12.1 Hz, 2 H), 1.81 (dt, J = 56.8, 20.7 Hz, 12 H), 3.52 (s, 3 H), 3.99 (s, 1 H), 5.36 (s, 2 H), 7.23 (d, J = 7.1 Hz, 1 H), 7.39-7.41 (m, 5 H), 7.82 (s, 1 H). |
| A-5 | 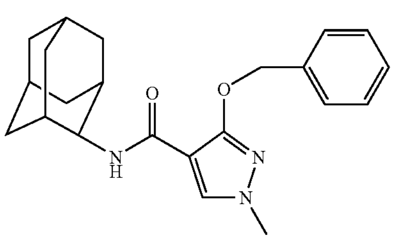 | 1H-NMR (DMSO-d6) δ: 1.39-1.70 (m, 14 H), 3.74 (s, 3 H), 3.95 (d, J = 8.3 Hz, 1 H), 5.26 (s, 2 H), 7.10 (d, J = 9.1 Hz, 1 H), 7.39-7.40 (m, 3 H), 7.50 (d, J = 7.1 Hz, 2 H), 7.99 (s, 1 H). |
| A-6 | 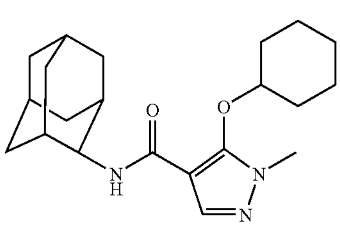 | 1H-NMR (CDCl3) δ: 1.25-1.28 (m, 2 H), 1.48-1.52 (m, 2 H), 1.71-1.95 (m, 20 H), 3.70 (s, 3 H), 4.19-4.22 (m, 1 H), 4.31-4.41 (m, 1 H), 6.42 (d, J = 7.0 Hz, 1 H), 7.27 (s, 1 H), 7.74 (s, 1 H). |

TABLE 2

| No. | Structure | NMR (CDCl3 or d6-DMSO), MS or m.p. |
|---|---|---|
| A-7 | 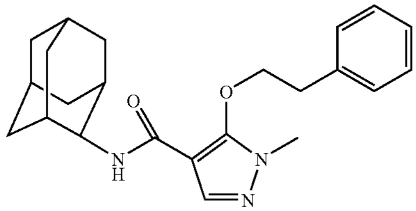 | 1H-NMR (CDCl3) δ: 1.72-2.04 (m, 16 H), 3.15 (t, J = 6.8 Hz, 2 H), 3.49 (s, 3 H), 4.24-4.26 (m, 1 H), 4.51 (t, J = 6.8 Hz, 2 H), 6.46 (d, J = 7.6 Hz, 1 H), 7.28-7.40 (m, 5 H), 7.73 (s, 1 H). |
| A-8 | 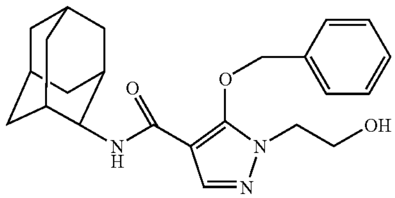 | 1H-NMR (CDCl3) δ: 1.61-1.98 (m, 16 H), 2.72 (br s, 1 H), 3.80 (t, J = 4.5 Hz, 2 H), 3.88 (t, J = 4.6 Hz, 2 H), 4.20-4.22 (m, 1 H), 5.34 (s, 2 H), 6.49 (d, J = 8.1 Hz, 1 H), 7.27 (s, 1 H), 7.35-7.40 (m, 5 H), 7.78 (s, 1 H). |
| A-9 | 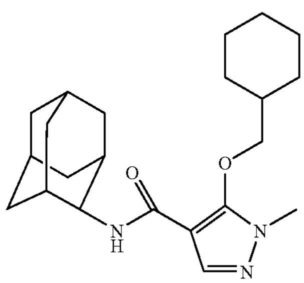 | 1H-NMR (CDCl3) δ: 1.05-1.28 (m, 4 H), 1.74-1.92 (br m, 26 H), 3.69 (t, J = 6.8 Hz, 3 H), 3.98 (t, J = 5.3 Hz, 2 H), 3.99 (d, J = 6.3 Hz, 2 H), 6.46 (d, J = 7.0 Hz, 1 H), 7.73 (s, 1 H). |
| A-10 | 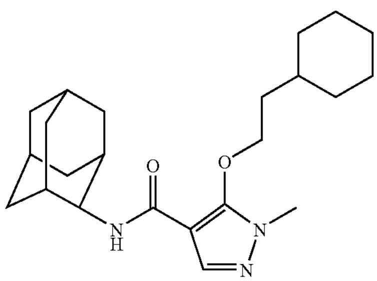 | 1H-NMR (DMSO-d6) δ: 0.92-0.94 (m, 2 H), 1.15-1.20 (m, 2 H), 1.42-1.99 (m, 20 H), 3.61 (s, 3 H), 3.96 (s, 1 H), 4.29 (t, J = 6.9 Hz, 2 H), 7.20 (d, J = 7.1 Hz, 1 H), 7.76 (s, 1 H). |
| A-11 | 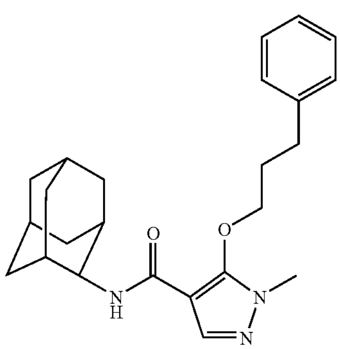 | 1H-NMR (CDCl3) δ: 1.66-1.98 (br m, 14 H), 2.17 (tt, J = 7.2, 2.9 Hz, 2 H), 2.79 (q, J = 7.2 Hz, 2 H), 3.39 (t, J = 10.5 Hz, 2 H), 3.67 (s, 3 H), 4.17-4.27 (m, 3 H), 6.43 (d, J = 8.4 Hz, 1 H), 7.13-7.32 (m, 5 H), 7.71 (s, 1 H). |
| A-12 | 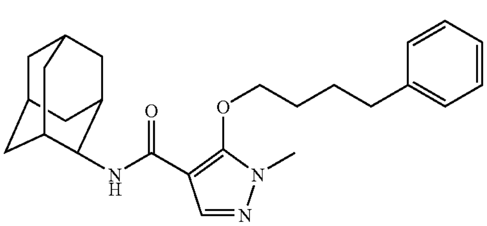 | 1H-NMR (DMSO-d6) δ: 1.50 (d, J = 13.4 Hz, 2 H), 1.75-1.90 (m, 16 H), 2.61-2.64 (br m, 2 H), 3.60 (s, 3 H), 3.94-3.96 (br m, 1 H), 4.25-4.27 (br m, 2 H), 7.19-7.21 (m, 3 H), 7.28 (t, J = 7.6 Hz, 2 H), 7.77 (s, 1 H). |

TABLE 3

| No. | Structure | NMR (CDCl3 or d6-DMSO), MS or m.p. |
|---|---|---|
| A-13 | 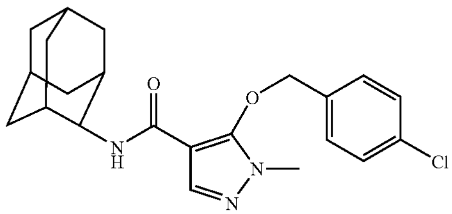 | DMSO-d6 δ 1.42-1.95 (m, 14 H), 3.55 (s, 3 H), 3.97-4.00 (m, 1 H), 5.36 (s, 2 H), 7.25 (d, J = 7.2 hz, 1 H), 7.42-7.52 (m, 4 H), 7.85 (s, 1 H). |
| A-14 | 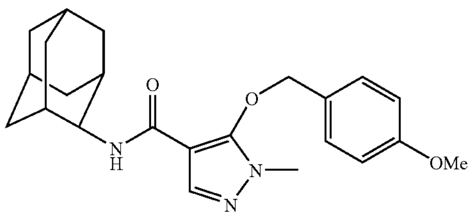 | DMSO-d6 δ 1.50-1.98 (m, 14 H), 3.03 (s, 3 H), 3.13 (d, 1 H, J = 9.2), 3.31 (d, J = 13.6, 1 H), 3.71 (s, 3 H), 3.79-3.88 (m, 1 H), 6.80 (d, J = 8.8 Hz, 2 H), 7.04 (d, J = 8.8 Hz, 2 H), 7.52 (d, J = 7.6 Hz, 1 H), 7.73 (s, 1 H). |
| A-15 | 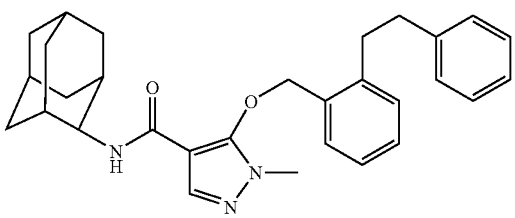 | DMSO-d6 δ 1.39-2.00 (m, 14 H), 2.77-2.86 (m, 2 H), 2.94-3.01 (m, 2 H), 3.48 (s, 3 H), 3.98-4.07 (m, 1 H), 5.43 (s, 2 H), 7.14-7.44 (m, 10 H), 7.87 (s, 1 H). |
| A-16 | 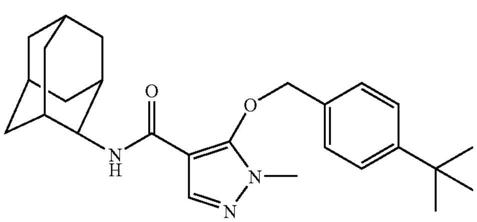 | DMSO-d6 δ 1.28 (s, 9 H), 1.41-1.92 (m, 14 H), 3.53 (s, 3 H), 3.91-4.04 (m, 1 H), 5.34 (s, 2 H), 7.18 (d, J = 7.2 Hz, 1 H), 7.32-7.43 (m, 4 H), 7.81 (s, 1 H). |
| A-17 | 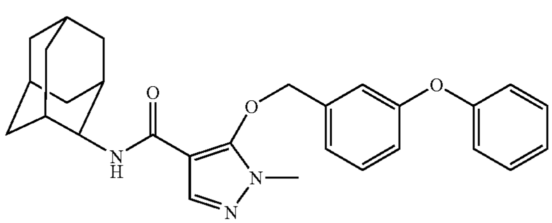 | DMSO-d6 δ 1.42-1.99 (m, 14 H), 3.51 (s, 3 H), 3.94-3.96 (m, 1 H), 5.35 (s, 2 H), 6.94-7.08 (m, 4 H), 7.12-7.22 (m, 3 H), 7.37-7.43 (m, 3 H), 7.84 (s, 1 H). |
| A-18 | 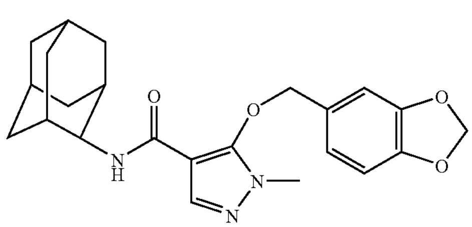 | DMSO-d6 δ 1.50-1.88 (m, 14 H), 3.06 (s, 3 H), 3.13 (d, J = 13.2 Hz, 1 H), 3.29 (d, J = 13.2 Hz, 1 H), 3.78-3.83 (m, 1 H), 5.97 (d, J = 4.8 Hz, 2 H), 6.56-6.80 (m, 3 H), 7.50 (d, J = 7.6 Hz, 1 H), 7.76 (s, 1 H). |

TABLE 4

| No. | Structure | NMR (CDCl3 or d6-DMSO), Ms or m.p. |
|---|---|---|
| A-19 | 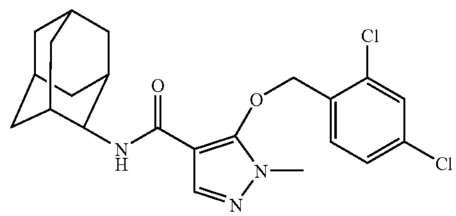 | DMSO-d6 δ 1.40-2.00 (m, 14 H), 3.55 (s, 3 H), 3.95-4.02 (m, 1 H), 5.47 (s, 2 H), 7.31 (d, J = 6.8 Hz, 1 H), 7.46-7.72 (m, 3 H), 7.88 (s, 1 H). |
| A-20 | 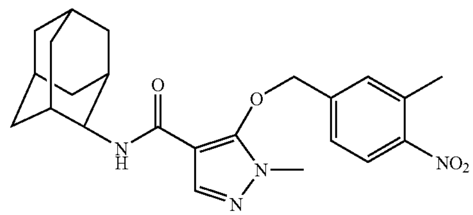 | DMSO-d6 δ 1.50-1.85 (m, 14 H), 2.46 (s, 3 H), 3.08 (s, 3 H), 3.32 (s, 2 H), 3.79-3.83 (m, 1 H), 7.18-7.49 (m, 3 H), 7.79-7.98 (m, 2 H). |
| A-21 | 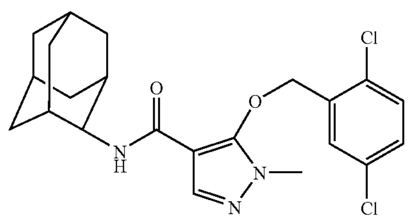 | DMSO-d6 δ 1.39-2.01 (m, 14 H), 3.58 (s, 3 H), 3.97-4.05 (m, 1 H), 5.47 (s, 2 H), 7.27-7.32 (m, 1 H), 7.45-7.66 (m, 3 H), 7.88 (s, 1 H). |
| A-22 | 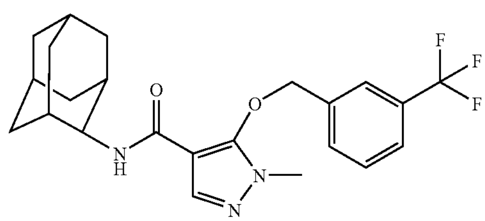 | DMSO-d6 δ 1.40-1.99 (m, 14 H), 3.58 (s, 3 H), 3.96-4.04 (m, 1 H), 5.47 (s, 2 H), 7.26 (d, J = 6.8 Hz, 1 H), 7.61-7.87 (m, 5 H). |
| A-23 | 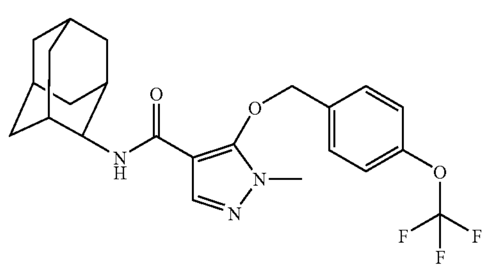 | DMSO-d6 δ 1.39-1.97 (m, 14 H), 3.56 (s, 3 H), 3.96-4.04 (m, 1 H), 5.38 (s, 2 H), 7.19-7.28 (m, 1 H), 7.32-7.44 (m, 2 H), 7.55-7.63 (m, 2 H), 7.86 (s, 1 H). |
| A-24 | 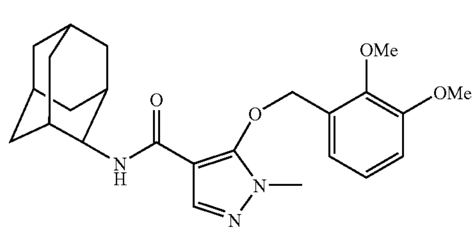 | DMSO-d6 δ 1.52-1.96 (m, 15 H), 3.07 (s, 3 H), 3.31 (s, 3 H), 3.72 (s, 3 H), 3.78 (s, 2 H), 6.55-6.63 (m, 1 H), 6.85-6.93 (m, 2 H), 7.52-7.58 (m, 2 H). |

TABLE 5

| No. | Structure | NMR (CDCl3 or d6-DMSO), MS or m.p. |
|---|---|---|
| A-25 | 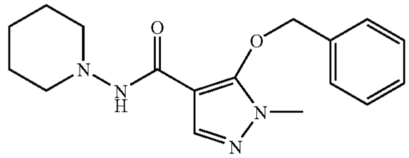 | DMSO-d6 δ 1.04-1.32 (m, 10 H), 2.32 (s, 3 H), 2.61-2.72 (m, 2 H), 4.65-4.89 (m, 2 H), 7.39-7.55 (m, 3 H), 7.84-7.95 (m, 2 H), 9.37 (s, 1 H). |
| A-26 | 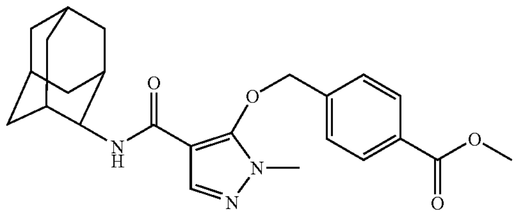 | DMSO-d6 δ 1.41-2.00 (m, 14 H), 3.56 (s, 3 H), 3.86 (s, 3 H), 3.96-4.02 (m, 1 H), 5.46 (s, 2 H), 7.27 (d, J = 7.2 Hz, 1 H), 7.59 (d, J = 8.0 Hz, 2 H), 7.86 (s, 1 H), 7.98 (d, J = 8.0 Hz, 2 H). |
| A-27 | 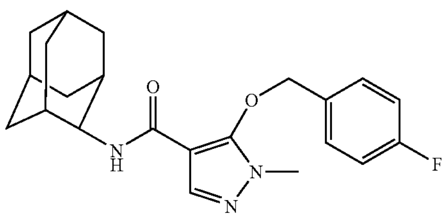 | mp 110-111° C. |
| A-28 | 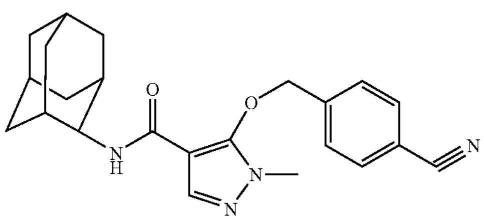 | mp 173-174° C. |
| A-29 | 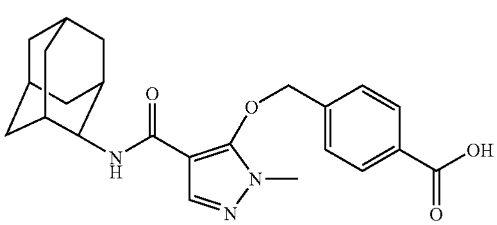 | mp 202-203° C. |
| A-30 | 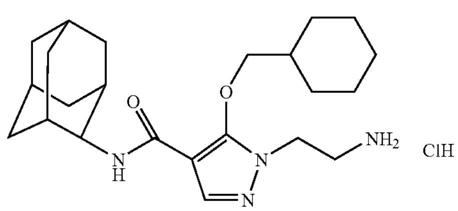 | 1H-NMR (DMSO-d6) δ: 1.02-1.25 (m, 4 H), 1.53 (d, J = 11.9 Hz, 2 H), 1.74-1.95 (br m, 19 H), 3.18 (t, J = 5.9 Hz, 2 H), 3.97 (s, 1 H), 4.11 (d, J = 6.1 Hz, 2 H), 4.18 (t, J = 6.1 Hz, 2 H), 7.30 (d, J = 7.6 Hz, 1 H), 7.89 (s, 1 H). |

TABLE 6

| No. | Structure | NMR (CDCl3 or d6-DMSO), MS or m.p. |
|---|---|---|
| A-31 | 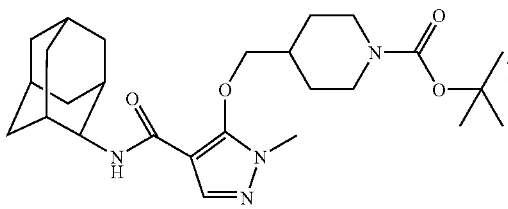 | 1H-NMR (CDCl3) δ: 1.07-1.11 (m, 2 H), 1.41 (s, 13 H), 1.55-1.81 (m, 16 H), 2.55 (t, J = 12.8 Hz, 2 H), 3.51 (s. 3 H), 3.91-3.99 (m, 4 H), 6.10 (d, J = 7.5 Hz, 1 H), 7.48 (s, 1 H). |
| A-32 | HCl | 1H-NMR (DMSO-d6) δ: 2.03-1.50 (m, 17 H), 2.93-2.84 (q, 4 H), 3.30-3.27 (m, 2 H), 3.61 (s, 3 H), 3.96 (m, 1 H), 4.16-4.15 (d J = 7.5 Hz, 2 H), 7.30-7.28 (d, J = 8.0 Hz, 1 H), 7.86 (s, 1 H), 8.98 (br s, 1 H), 9.06 (br s, 1 H), |
| A-33 | 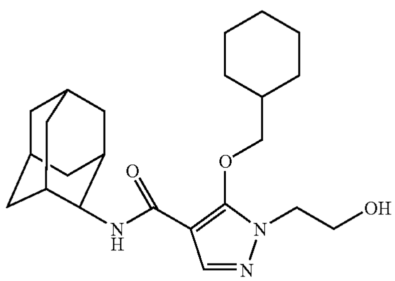 | 1H-NMR (CDCl3) δ: 1.04-1.40 (m, 4 H), 1.72-2.21 (m, 21 H), 4.04-4.15 (m, 5 H), 4.23-4.26 (m, 1 H), 6.48 (d, J = 7.8 Hz, 1 H), 7.80 (s, 1 H). |
| A-34 | 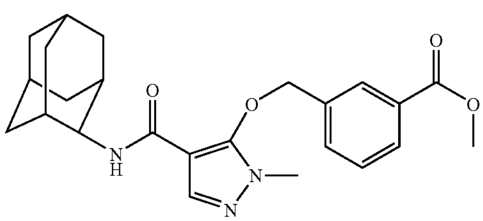 | mp 128-129° C. |
| A-35 | 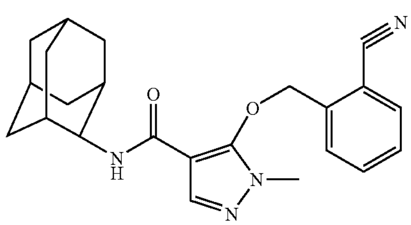 | mp 107-108° C. |
| A-36 | 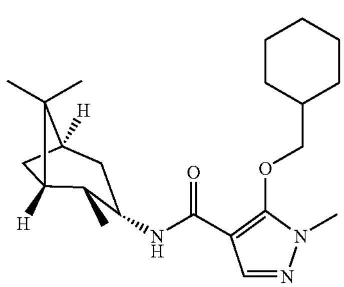 | 300 MHz (CDCl3) 1.08 (s, 3 H), 1.15 (d, J = 7.2 Hz, 3 H) 1.24 (3 H,s), 1.22-2.05 (m, 16 H) 2.42-2.49 (m, 1 H), 2.63-2.73 (m, 1 H), 3.72 (s, 3 H), 4.00 (d, J = 6.3 Hz, 2 H), 4.38-4.49 (m, 1 H) 6.04 (d, J = 8.4 Hz, 1 H), 7.76 (s, 1 H) |

TABLE 7

| No. | Structure | NMR (CDCl3 or d6-DMSO), MS or m.p. |
| --- | --- | --- |
| A-37 | 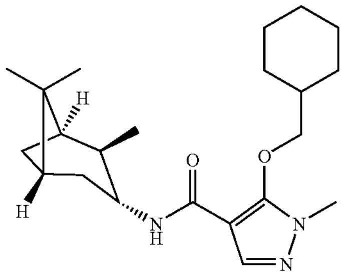 | 300 MHz (CDCl3) 1.08 (s, 3 H), 1.15 (d, J = 7.2 Hz, 3 H) 1.24 (3 H, s), 1.22-2.10 (m, 16 H) 2.41-2.49 (m, 1 H), 2.63-2.72 (m, 1 H), 3.71 (s, 3 H), 4.00 (d, J = 6.3 Hz, 2 H), 4.38-4.52 (m, 1 H) 6.02 (d, J = 8.4 Hz, 1 H), 7.75 (s, 1 H) |
| A-38 | 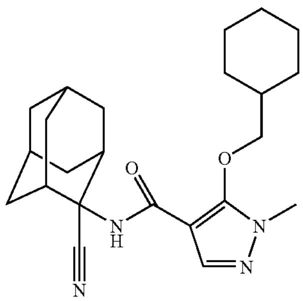 | 300 MHz (CDCl3) 1.07-1.99 (m, 23 H) 2.33 (m, 1 H) 2.62 (s, 1 H) 3.72 (s, 3 H) 4.01 (d, J = 6.3 Hz, 2 H) 6.25 (s, 1 H) 7.74 (s, 1 H) |
| A-39 | 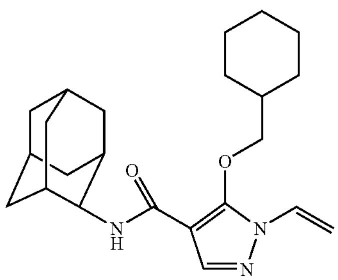 | 1H-NMR (CDCl3) δ: 1.40-1.04 (m, 4 H), 2.21-1.72 (m, 21 H), 4.03-4.01 (m, 2 H), 4.25-4.16 (m, 1 H), 4.96-4.93 (d, J = 8.1 Hz, 1 H), 5.80-5.76 (d, J = 11.2 Hz, 1 H), 7.00-6.92 (dd, J = 11.3 Hz, J = 8.2 Hz, 1 H), 7.83 (s, 1 H). |
| A-40 | 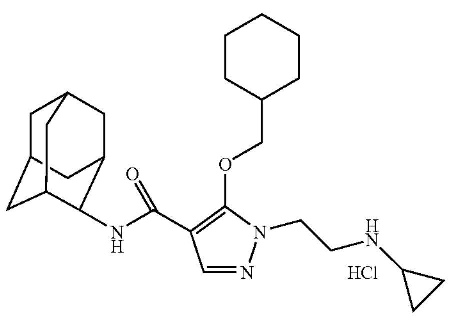 | 1H-NMR (DMSO-d6) δ: 0.73 (q, J = 6.6 Hz, 2 H), 1.00-1.04 (m, 4 H), 1.14-1.25 (m, 3 H), 1.51-2.03 (m, 20 H), 2.51 (s, 2 H), 2.74-2.77 (m, 1 H), 3.36 (d, J = 5.6 Hz, 2 H), 3.97 (s, 1 H), 4.12 (d, J = 6.1 Hz, 2 H), 4.33 (t, J = 6.9 Hz, 2 H), 7.32 (d, J = 6.6 Hz, |
| A-41 | 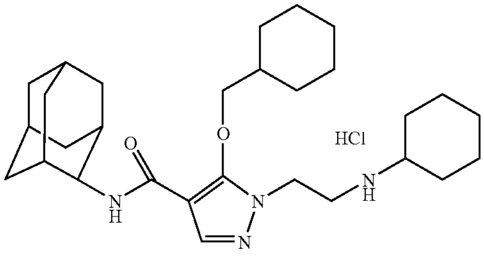 | 1H-NMR (DMSO-d6) δ: 1.03-1.39 (m, 10 H), 1.51-2.03 (m, 27 H), 3.03 (s, 1 H), 3.27 (s, 2 H), 3.97 (1 H, s, 1 H), 4.13 (d, J = 5.8 Hz, 2 H), 4.34 (t, J = 6.8 Hz, 2 H), 7.32 (d, J = 6.8 Hz, 1 H), 7.89 (s, 1 H), 9.46 (s, 2 H). |

TABLE 7-continued

| No. | Structure | NMR (CDCl3 or d6-DMSO), MS or m.p. |
|---|---|---|
| A-42 | 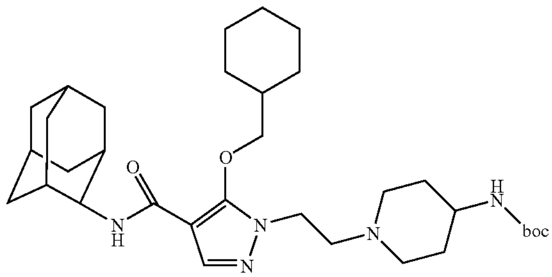 | 1H-NMR (DMSO-d6) δ: 1.03-1.41 (m, 14 H), 1.52 (d, J = 13.1 Hz, 2 H), 1.63-2.09 (m, 21 H), 2.50 (s, 3 H), 2.62 (t, J = 6.4 Hz, 2 H), 2.77 (dd, J = 11.7, 6.7 Hz, 2 H), 3.17 (s, 1 H), 3.97 (t, J = 6.2 Hz, 3 H), 4.08 (d, J = 6.3 Hz, 2 H), 6.73 (d, J = 7.1 Hz, 1 |

TABLE 8

| No. | Structure | NMR (CDCl3 or d6-DMSO), MS or m.p. |
|---|---|---|
| A-43 | 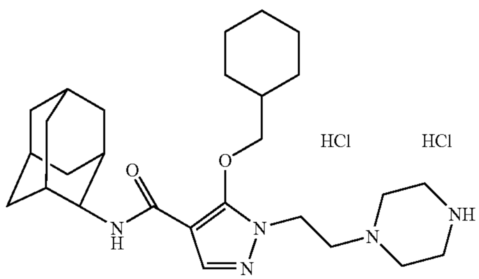 | 1H-NMR (DMSO-d6) δ: 1.14 (dt, J = 56.3, 21.5 Hz, 4 H), 1.77 (tt, J = 95.5, 27.9 Hz, 18 H), 3.51-3.58 (m. 14 H), 3.98 (d, J = 6.3 Hz, 1 H), 4.14 (d, J = 5.8 Hz, 2 H), 4.46 (t, J = 6.6 Hz, 2 H), 7.37 (d, J = 6.8 Hz, 1 H), 7.89 (s, 1 H), 10.08 (s, 2 H). |
| A-44 | 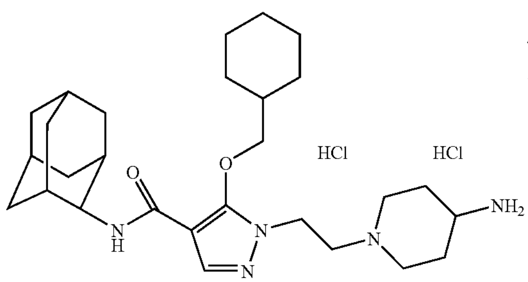 | 1H-NMR (DMSO-d6) δ: 1.00-1.29 (m, 4 H), 1.50-2.18 (m, 19 H), 3.08-3.57 (m, 8 H), 3.97-4.01 (m, 1 H), 4.20-4.40 (m, 5 H), 7.37 (d, J = 6.8 Hz, 1 H), 7.90 (s, 1 H), 8.64 (br s, 2 H), 11.42 (br s, 1 H). |
| A-45 | 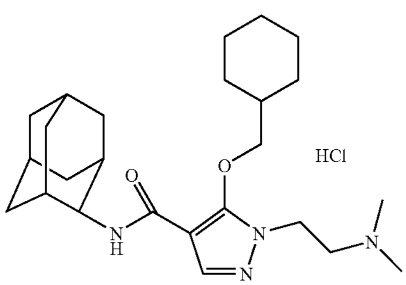 | 1H-NMR (DMSO-d6) δ: 1.03-1.26 (m, 8 H), 1.63-1.91 (m, 22 H), 2.80 (d, J = 4.2 Hz, 6 H), 3.48 (d, J = 5.7 Hz, 2 H), 3.97-3.98 (m, 1 H), 4.14 (d, J = 6.0 Hz, 2 H), 4.34 (t, J = 6.5 Hz, 2 H), 7.35 (d, J = 7.0 Hz, 1 H), 7.92 (s, 1 H). |
| A-46 | 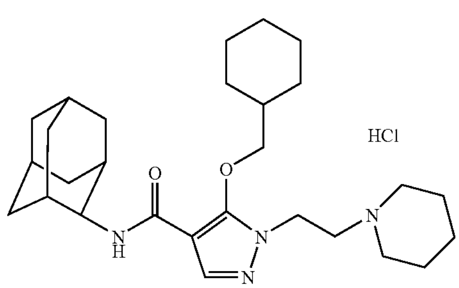 | 1H-NMR (DMSO-d6) δ: 1.05 (t, J = 12.1 Hz, 2 H), 1.18-1.38 (m, 4 H), 1.77 (ddd, J = 122.7, 76.0, 22.0 Hz, 27 H), 2.91-2.93 (br m, 2 H), 3.42-3.45 (m, 4 H), 3.97 (s, 1 H), 4.14 (d, J = 6.1 Hz, 2 H), 4.42 (t, J = 6.9 Hz, 2 H), 7.35 (d, J = 6.3 Hz, 1 H), 7.90 ( |

TABLE 8-continued

| No. | Structure | NMR (CDCl3 or d6-DMSO), MS or m.p. |
|---|---|---|
| A-47 | 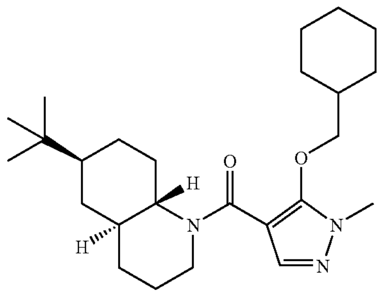 | 300 MHz (CDCl3) 0.86 (s, 9 H), 1.00-1.82 (m, 23 H), 2.28-2.32 (1 H), 3.32-3.47 (m, 2 H) |
| A-48 | 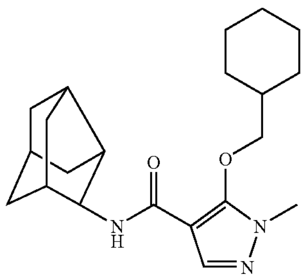 | 400 MHz (DMSO) 1.01-1.29 (m, 5 H), 1.50-.211 (m, 16 H), 2.21 (br, 2 H), 2.43 (t, J = J = 6.4 Hz, 1 H), 3.59 (s, 3 H), 4.07 (d, J = 6.0 Hz, 2 H), 7.50 (s, 1 H), 7.68 (s, 1 H) |

TABLE 9

| No. | Structure | NMR (CDCl3 or d6-DMSO), MS or m.p. |
|---|---|---|
| A-49 | 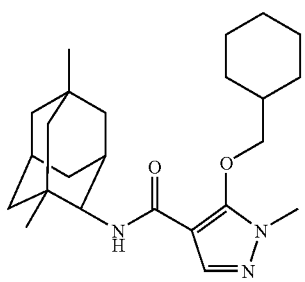 | 400 MHz (DMSO) 0.82 (s, 6H), 1.01-1.35 (m, 11 H), 1.56-1.84 (m, 1 2 H), 2.09 (brs, 1 H), 3.58 (s, 3 H), 4.04 (d, J = 6.4 Hz. 2 H), 6.82 (s, 1 H), 7.63 (s, 1 H) |
| A-50 | 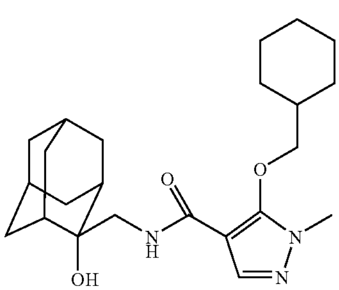 | 300 MHz (CDCl3) 1.05-2.15 (m, 25 H) 3.67 (d, J = 6.0 Hz, 2 H) 3.70 (s, 3 H) 3.98 (d, J = 6.0 Hz, 2 H) 6.52 (s, 1 H) 7.74 (s, 1 H) |
| A-51 | 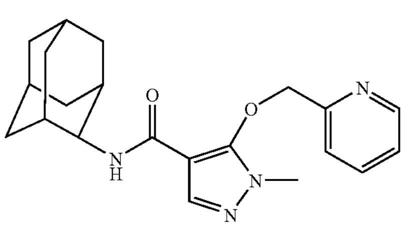 | DMSO-d6 δ 1.42-1.96 (m, 14 H), 3.60 (s, 3 H), 3.95-3.99 (m, 1 H), 5.41 (s, 2 H), 7.24-7.30 (m, 1 H), 7.32-7.40 (m, 1 H), 7.50-7.56 (m, 1 H) 7.78-7.88 (m, 2 H), 8.56 (d, J = 4.4 Hz, 1 H). |

TABLE 9-continued

| No. | Structure | NMR (CDCl3 or d6-DMSO), MS or m.p. |
|---|---|---|
| A-52 | 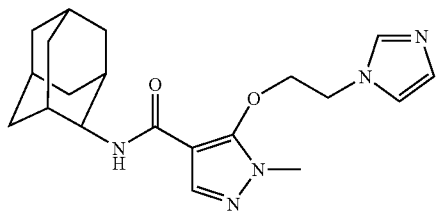 | DMSO-d6 δ 1.42-2.10 (m, 14 H), 3.34 (s, 3 H), 3.91-4.03 (m, 1 H), 4.30-4.41 (m, 2 H), 4.47-4.62 (m, 2 H), 6.92 (s, 1 H), 7.24-7.34 (m, 2 H), 7.71 (s, 1 H), 7.86 (s, 1 H). |
| A-53 | 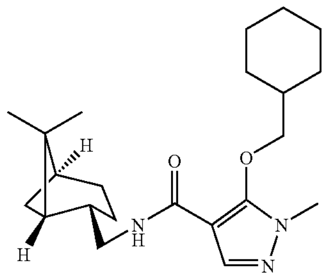 | 300 MHz (CDCl3) 1.07 (s, 3 H) 1.20 (s, 3 H) 1.12-1.99 (m, 18 H) 2.23-2.29 (m, 1 H) 2.34-2.42 (m, 1 H) 3.30-3.75 (m, 2 H) 3.71 (s, 3 H) 3.96 (d, J = 6.3 Hz, 2 H) 6.12 (s, 1 H) 7.73 (s, 1 H) |
| A-54 | 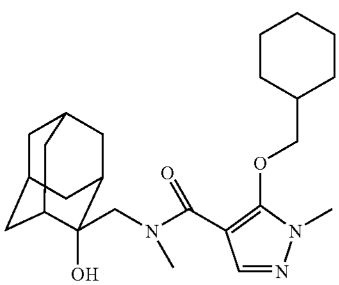 | 300 MHz (CDCl3) 1.00-1.88 (m, 24 H), 2.27-2.31 (m, 1 H) 3.22 (s, 3 H) 3.66 (s, 3 H) 3.80 (s, 2 H) 3.99 (d, J = 6.3 Hz, 2 H) 7.43 (s, 1 H) |

TABLE 10

| No. | Structure | NMR (CDCl3 or d6-DMSO), MS or m.p. |
|---|---|---|
| A-55 | 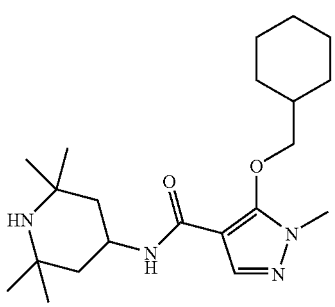 | 300 MHz (CDCl3) 0.99-2.00 (m, 15 H) 1.20 (s, 6 H) 1.32 (s, 6 H) 3.70 (s, 3 H) 3.96 (d, J = 5.7 Hz, 2 H) 4.40-4.43 (m, 1 H) 5.86 (d, J = 7.8 Hz, 1 H) 7.70 (s, 1 H) |
| A-56 | 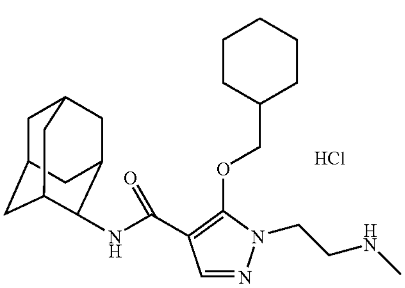 | 1H-NMR (CDCl3) δ: 1.71-2.02 (m, 22 H), 2.47 (s, 3 H), 3.05 (t, J = 6.0 Hz, 2 H), 4.02 (d, J = 6.3 Hz, 2 H), 4.10 (t, J = 5.9 Hz, 2 H), 4.18-4.21 (m, 1 H), 6.41 (d, J = 8.9 Hz, 1 H), 7.73 (s, 1 H). |

TABLE 10-continued

| No. | Structure | NMR (CDCl3 or d6-DMSO), MS or m.p. |
|---|---|---|
| A-57 | 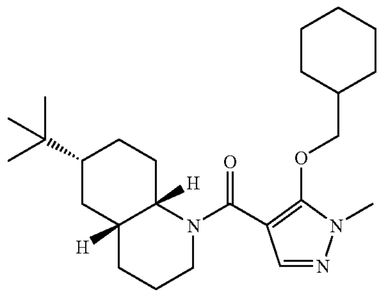 | 400 MHz (DMSO) 0.81 (s, 9 H), 0.90-2.03 (m, 23 H), 2.99 (t, J = 10.8 Hz, 1 H), 3.58 (s, 3 H), 3.82 (d, J = 10.8 Hz, 1 H), 3.91 (d, J = 6.4 Hz, 2 H), 4.33 (br, 1 H), 7.31 (s, 1 H) |
| A-58 | 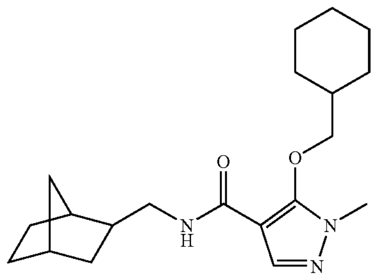 | (DMSO) 0.64-0.68 (m, 0.4 H), 0.99-2.17 (m, 20.6 H), 2.89-3.02 (m, 1.2 H), 3.08-3.23 (m, 0.8 H), 3.58 (s, 3 H), 4.09 (d, J = 7.2 Hz, 2 H), 7.59 (t, J = 4.8 Hz, 0.4 H), 7.68 (s, 0.6 H), 7.69 (s, 0.4 H), 7.74 (t, J = 5.6 Hz, 0.6 H) |
| A-59 | 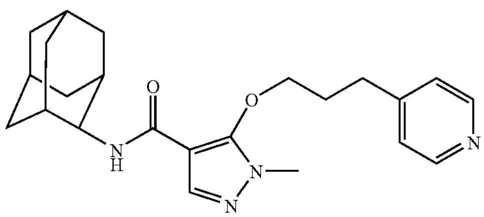 | DMSO-d6 δ 1.51-2.01 (m, 15 H), 2.41-2.66 (m, 3 H), 3.33 (s, 3 H), 3.93-4.11 (m, 3 H), 7.19-7.26 (m, 2 H), 8.21 (s, 1 H), 8.45 (s, 2 H), 8.83 (d, J = 8.8 Hz, 1 H). |
| A-60 | 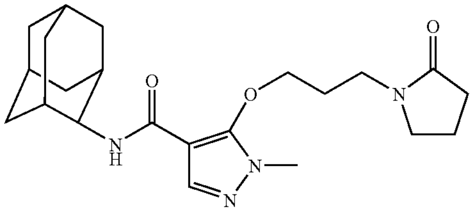 | DMSO-d6 δ 1.41-2.01 (m, 20 H), 2.19-2.36 (m, 2 H), 3.22-3.48 (m, 2 H), 3.63 (s, 3 H), 3.96-3.98 (m, 1 H), 4.25-4.26 (m, 2 H), 7.24 (d, J = 6.8 Hz, 1 H), 7.81 (s, 1 H). |

TABLE 11

| No. | Structure | NMR (CDCl3 or d6-DMSO), MS or m.p. |
|---|---|---|
| A-61 | 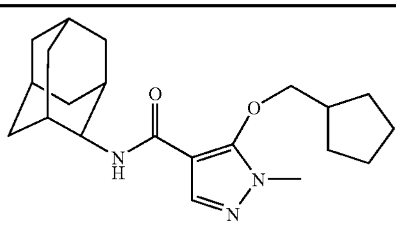 | mp 116-117° C. |
| A-62 | 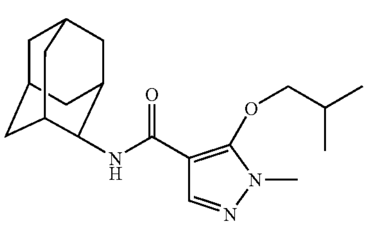 | mp 119-120° C. |

TABLE 11-continued
| No. | Structure | NMR (CDCl3 or d6-DMSO), MS or m.p. |
|---|---|---|
| A-63 | 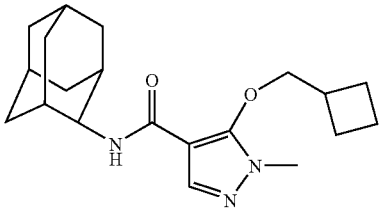 | mp 84-85° C. |
| A-64 | 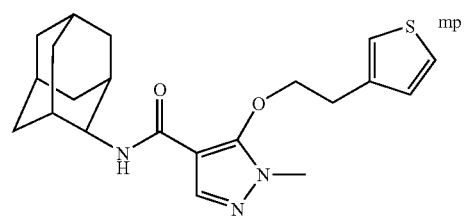 | mp 68-69° C. |
| A-65 | 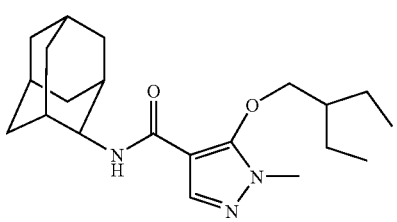 | mp 89-90° C. |
| A-66 | 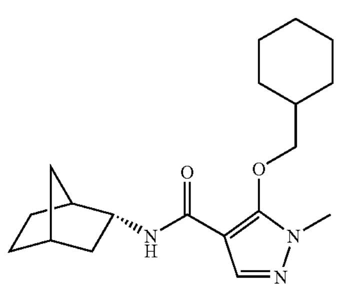 | 400 MHz (DMSO) 0.99-1.90 (m, 19 H), 2.16 (brs, 1 H), 2.35 (brs, 1 H), 3.59 (s, 3 H), 4.02-4.15 (m, 3 H), 7.49 (d, J = 6.8 Hz, 1 H), 7.75 (s, 1 H) |
| A-67 | 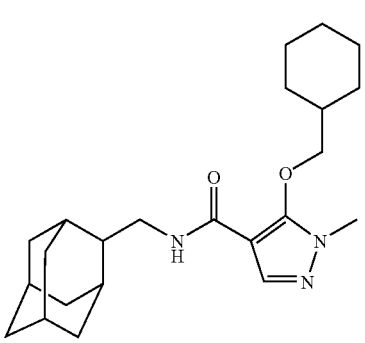 | 400 MHz (DMSO) 0.98-1.28 (m, 5 H), 1.46-1.93 (m, 21 H), 3.29-3.33 (m, 2 H), 3.58 (s, 3 H), 4.08 (d, J = 6.4 Hz, 2 H), 7.67 (br, 2 H) |

TABLE 12

| No. | Structure |
|---|---|
| B-1 | (chemical structure) |
| B-2 | (chemical structure) |
| B-3 | (chemical structure) |
| B-4 | (chemical structure) |
| B-5 | (chemical structure) |

TABLE 12-continued

| No. | Structure |
|---|---|
| B-6 | (chemical structure) |
| B-7 | (chemical structure) |
| B-8 | (chemical structure) |
| B-9 | (chemical structure) |

TABLE 13

| No. | Structure | NMR (CDCl3 or d6-DMSO) |
|---|---|---|
| C-1 | 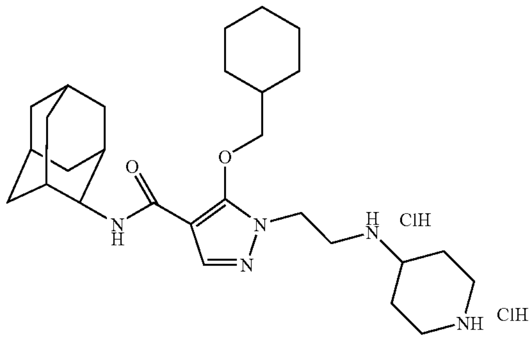 | (DMSO-d6): 0.97-2.26 (m, 29 H), 2.83-2.96 (m, 2 H), 3.25-3.44 (m, 5 H), 3.93-4.01 (m, 1 H), 4.13 (d, J = 6.4 Hz, 2 H), 4.35 (t, J = 7.2 Hz, 2 H), 7.32 (d, J = 6.8 Hz, 1 H), 7.89 (s, 1 H), 9.15 (br.s, 1 H), 9.37 (br.s, 1 H), 9.84 (br.s, 2 H) |
| C-2 | 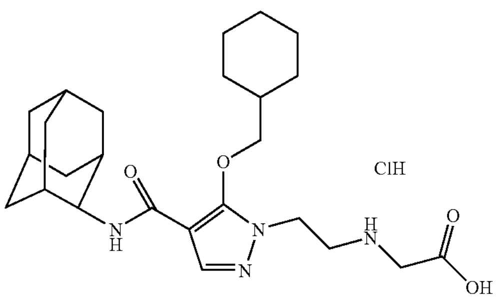 | (DMSO-d6): 0.96-2.06 (m, 25 H), 3.30-3.39 (m, 2 H), 3.87-4.03 (m, 3 H), 4.12 (d, J = 6.0 Hz, 2 H), 4.31 (t, J = 6.0 Hz, 2 H), 7.33 (d, J = 6.8 Hz, 1 H), 7.91 (s, 1 H), 9.42 (br.s, 2 H) |
| C-3 | 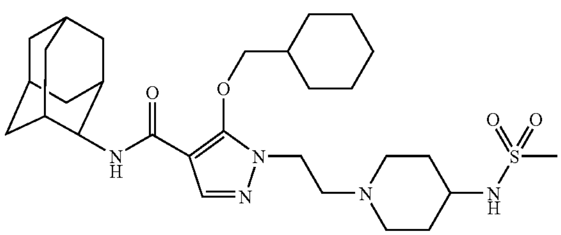 | (DMSO-d6): 0.99-2.11 (m, 32 H), 2.59-2.67 (m, 2 H), 2.72-2.80 (m, 2 H), 2.89 (s, 3 H), 3.93-4.00 (m, 3 H), 4.09 (d, J = 4.2 Hz, 2 H), 7.01 (d, J = 7.2 Hz, 1 H), 7.26 (d, J = 6.0 Hz, 1 H), 7.79 (s, 1 H) |
| C-4 | 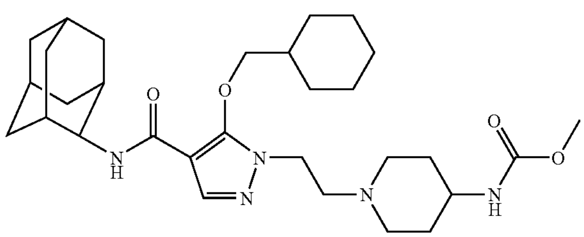 | (DMSO-d6): 1.01-2.08 (m, 32 H), 2.60-2.67 (m, 2 H), 2.73-2.80 (m, 2 H), 3.50 (s, 3 H), 3.94-4.00 (m, 3 H), 4.08 (d, J = 6.0 Hz, 2 H), 7.04-7.08 (m, 1 H), 7.26 (d, J = 6.8 Hz, 1 H), 7.79 (s, 1 H) |
| C-5 | 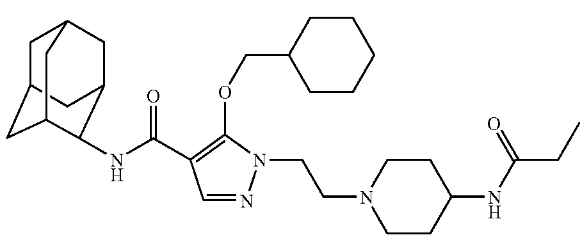 | (DMSO-d6): 0.97 (t, J = 7.6 Hz, 3 H), 1.01-2.10 (m, 32 H), 2.60-2.68 (m, 2 H), 2.74-2.81 (m, 2 H), 3.42-3.53 (m, 2 H), 3.94-4.02 (m, 3 H), 4.09 (d, J = 6.0 Hz, 2 H), 7.26 (d, J = 6.8 Hz, 1 H), 7.61 (d, J = 7.2 Hz, 1 H), 7.80 (s, 1 H) |
| C-6 | 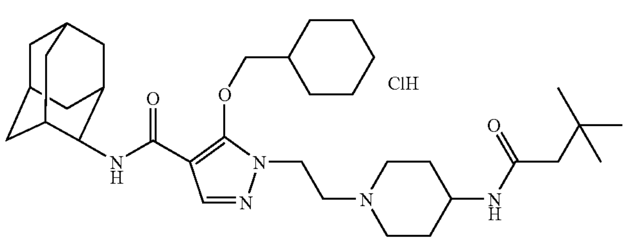 | (DMSO-d6): 0.91-2.08 (m, 41 H), 3.01-3.13 (m, 2 H), 3.32-4.00 (m, 1 H), 4.41-4.49 (m, 2 H), 7.36 (d, J = 7.2 Hz, 1 H), 7.89 (s, 1 H), 7.99 (d, J = 7.2 Hz, 1 H), 11.32 (br.s, 1 H) |

TABLE 14

| No. | Structure | NMR (CDCl3 or d6-DMSO) |
|---|---|---|
| C-7 | 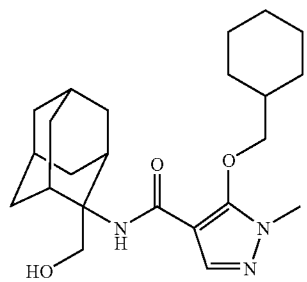 | (CDCl3): 1.05-1.32 (m, 11 H), 1.70-2.33 (m, 14 H), 3.15 (bs, 1 H), 3.75 (s, 3 H), 4.01 (d, J = 6.0 Hz, 2 H), 4.05 (s, 2 H), 6.39 (s, 1 H), 7.79 (s, 1 H) |
| C-8 | 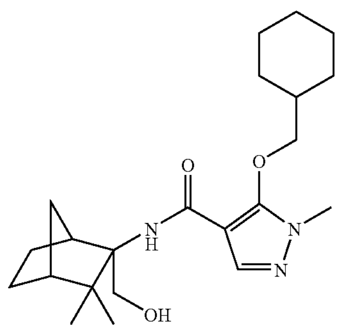 | (CDCl3); 1.07 (s, 3 H), 1.14 (s, 3 H), 1.23-1.90 (m, 18 H), 2.51-2.52 (m, 1 H), 3.62 (bs, 1 H), 3.73 (s, 3 H), 3.82 (d, J = 11.7 Hz, 1 H), 3.95-4.09 (m, 2 H), 4.36 (d, J = 11.7 Hz, 1 H), 6.15 (s, 1 H), 7.72 (s, 1 H) |
| C-9 | 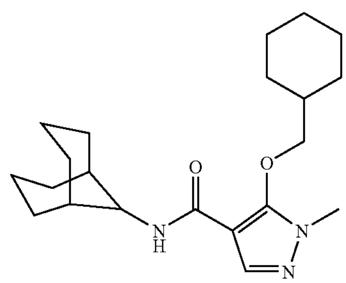 | (DMSO-d6); 1.00-1.92 (m, 25 H), 3.62 (s, 3 H), 3.79 (brs, 1 H), 4.06 (d, J = 6.0 Hz, 2 H), 7.12 (d, J = 6.4 Hz, 1 H), 7.73 (s, 1 H) |
| C-10 | 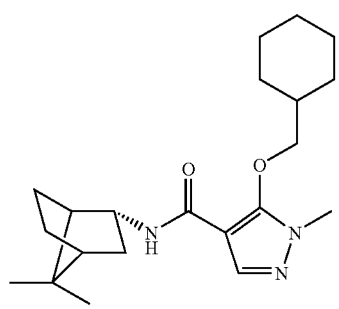 | (DMSO-d6); 0.96-2.28 (m, 25 H), 3.59 (s, 3 H), 4.00-4.12 (m, 2 H), 4.27 (brs, 1 H), 7.19 (d, J = 6.0 Hz, 1 H), 7.69 (s, 1 H) |
| C-11 | 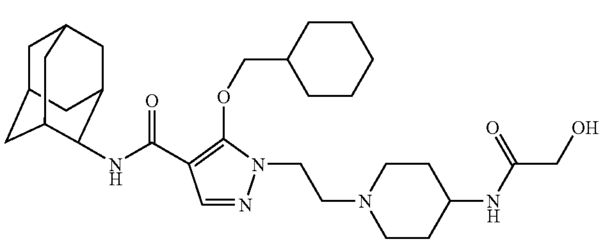 | (DMSO-d6): 0.99-2.11 (m, 32 H), 2.61-2.69 (m, 2 H), 2.74-2.81 (m, 2 H), 3.76 (d, J = 6.0 Hz, 2 H), 3.95-4.02 (m, 3 H), 4.09 (d, J = 6.0 Hz, 2 H), 5.37 (t, J = 6.0 Hz, 1 H), 7.26 (d, J = 6.4 Hz, 1 H), 7.49 (d, J = 7.6 Hz, 1 H), 7.79 (s, 1 H) |

TABLE 14-continued
| No. | Structure | NMR (CDCl3 or d6-DMSO) |
|---|---|---|
| C-12 | 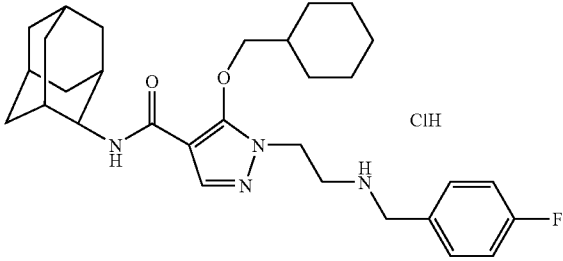 | (DMSO-d6): 0.93-2.03 (m, 25 H), 2.82 (t, J = 6.4 Hz, 2 H), 3.66 (s, 2 H), 3.94-4.00 (m, 3 H), 4.04 (d, J = 6.0 Hz, 2 H), 7.10 (t, J = 8.8 Hz, 2 H), 7.22 (d, J = 7.2 Hz, 1 H), 7.30 (t, J = 6.8 Hz, 2 H), 7.78 (s, 1 H) |
TABLE 15
| No. | Structure | NMR (CDCl3 or d6-DMSO) |
|---|---|---|
| C-13 | 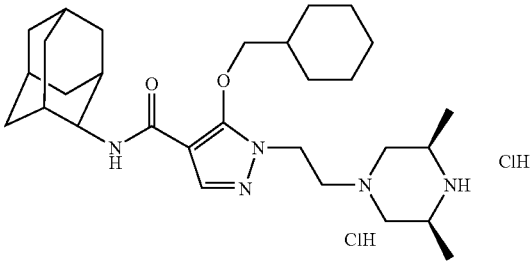 | (DMSO-d6): 0.96-2.07 (m, 31 H), 2.32-2.56 (m, 1 H), 2.87-3.66 (m, 6 H), 3.93-4.21 (m, 6 H), 7.31 (d, J = 7.2 Hz, 1 H), 7.84 (s, 1 H), 9.78 (br.s, 1 H) |
| C-14 | 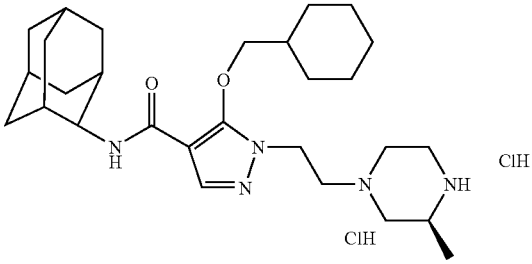 | (DMSO-d6): 0.80-2.17 (m, 28 H), 2.27-2.38 (m, 1 H), 2.65-2.93 (m, 5 H), 2.99-3.18 (m, 2 H), 3.93-4.13 (m, 6 H), 7.27 (d, J = 6.8 Hz, 1 H), 7.82 (s, 1 H), 8.32 (s, 1 H) |
| C-15 | 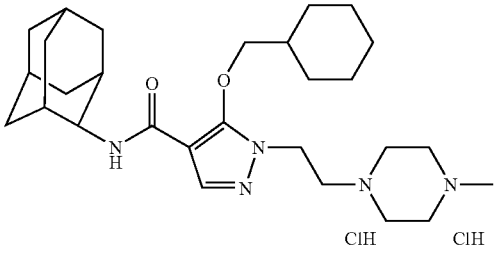 | (DMSO-d6): 0.96-2.07 (m, 27 H), 2.57-3.20 (m, 11 H), 3.93-4.15 (m, 5 H), 7.29 (d, J = 6.8 Hz, 1 H), 7.83 (s, 1 H) |
| C-16 | 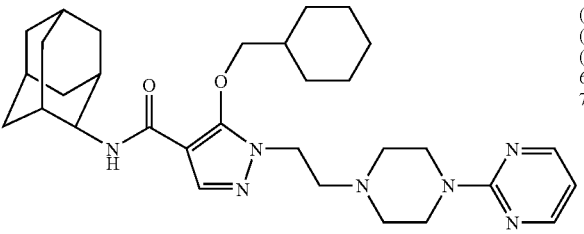 | (DMSO-d6): 1.01-2.04 (m, 27 H), 2.43-2.49 (m, 2 H), 2.69-2.75 (m, 2 H), 3.65-3.71 (m, 4 H), 3.94-4.12 (m, 5 H), 6.61 (t, J = 4.8 Hz, 1 H), 7.27 (d, J = 7.6 Hz, 1 H), 7.80 (s, 1 H), 8.34 (d, J = 4.8 Hz, 1 H) |

TABLE 15-continued

| No. | Structure | NMR (CDCl3 or d6-DMSO) |
|---|---|---|
| C-17 | 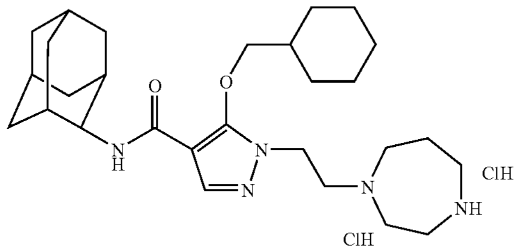 | (DMSO-d6): 0.99-2.23 (m, 29 H), 3.16-3.78 (m, 8 H), 3.93-4.01 (m, 1 H), 4.13 (d, J = 6.0 Hz, 2 H), 4.43 (m, 2 H), 7.36 (d, J = 6.8 Hz, 1 H), 7.89 (s, 1 H) |
| C-18 | 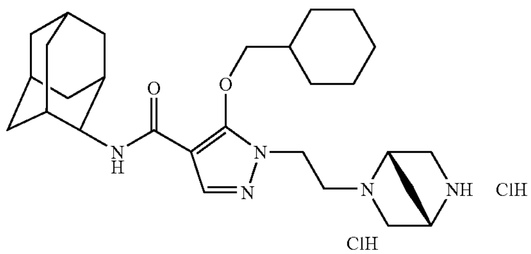 | (DMSO-d6): 0.97-2.46 (m, 27 H), 3.26-4.58 (m, 13 H), 7.37 (d, J = 6.8 Hz, 1 H), 7.89 (s, 1 H), 9.83-10.02 (br, 1 H), 10.26-10.39 (br, 1 H) |

TABLE 16

| No. | Structure | NMR (CDCl3 or d6-DMSO) |
|---|---|---|
| C-19 | 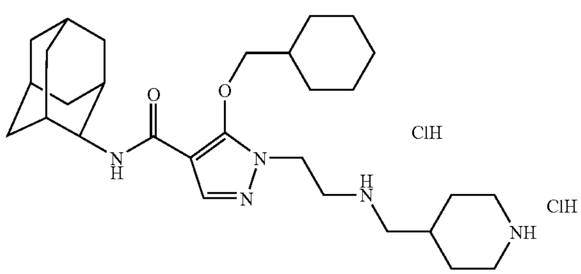 | (DMSO-d6): 0.97-2.12 (m, 30 H), 2.77-2.96 (m, 4 H), 3.19-3.35 (m, 4 H) 3.93-4.01 (m, 1 H), 4.12 (d, J = 6.0 Hz, 2 H), 4.31-4.40 (m, 2 H), 7.33 (d, J = 6.8 Hz, 1 H), 7.89 (s, 1 H), 8.92-9.05 (br, 1 H), 9.08-9.19 (br, 1 H), 9.36-9.51 (br, 1 H) |
| C-20 | 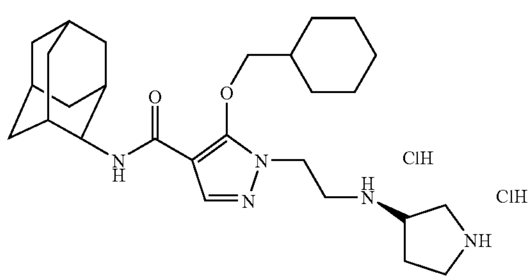 | (DMSO-d6): 0.97-2.39 (m, 27 H), 3.16-3.62 (m, 6 H), 3.91-4.01 (m, 4 H), 4.13 (d, J = 6.0 Hz, 2 H), 4.32 (t, J = 6.8 Hz, 2 H), 7.33 (d, J = 7.2 Hz, 1 H), 7.89 (s, 1 H), 9.39-9.53 (br, 1 H), 9.66-9.79 (br, 1 H), 9.88-10.16 (br, 1 H) |
| C-21 | 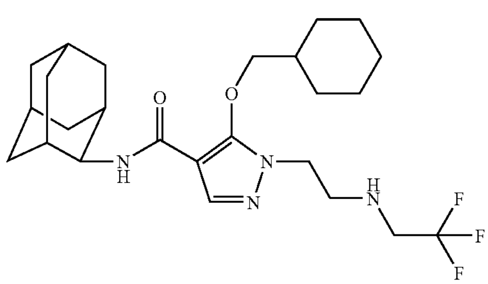 | (CDCl3): 1.04-2.01 (m, 27 H), 3.99-4.05 (m, 4 H), 4.07-4.12 (m, 2 H), 4.17-4.24 (m, 1 H), 6.44 (d, J = 7.2 Hz, 1 H), 7.77 (s, 1 H) |

TABLE 16-continued
| No. | Structure | NMR (CDCl3 or d6-DMSO) |
|---|---|---|
| C-22 | 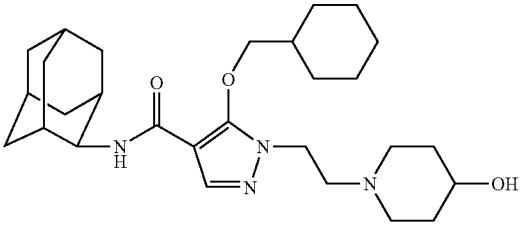 | (DMSO-d6): 0.98-2.14 (m, 29 H), 2.59-3.46 (m, 7 H), 3.92-4.01 (m, 3 H), 4.09 (d, J = 5.6 Hz, 2 H), 4.52 (s, 1 H), 7.25 (d, J = 7.2 Hz, 1 H), 7.79 (s, 1 H) |
| C-23 | 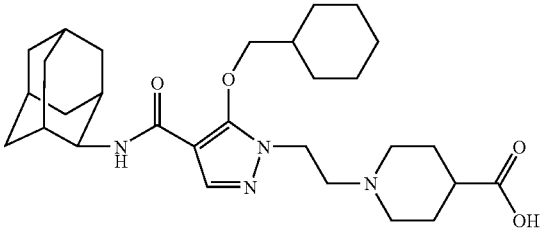 | (DMSO-d6): 0.96-2.33 (m, 30 H), 2.65-3.62 (m, 6 H), 3.93-4.16 (m, 5 H), 7.27 (d, J = 6.4 Hz, 1 H), 7.81 (s, 1 H) |
| C-24 | 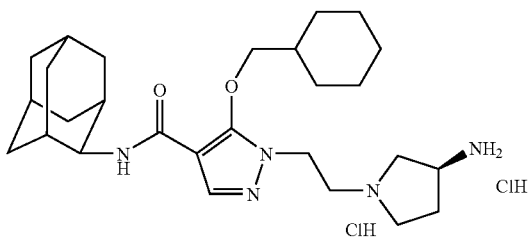 | (DMSO-d6): 0.93-2.07 (m, 27 H), 3.47-3.76 (m, 7 H), 3.91-4.17 (m, 3 H), 4.28-4.41 (m, 2 H), 7.30-7.39 (m, 1 H), 7.87 (s, 1 H), 8.63-8.90 (br, 2 H) |
TABLE 17
| No. | Structure | NMR (CDCl3 or d6-DMSO) |
|---|---|---|
| C-25 | 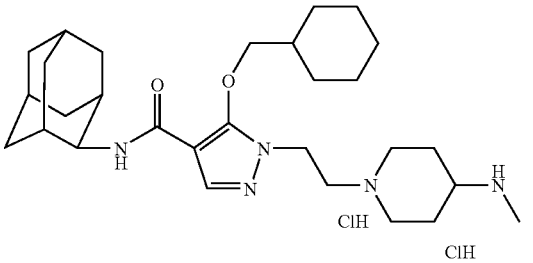 | (DMSO-d6): 0.98-2.32 (m, 29 H), 3.00-4.29 (m, 13 H), 4.41-4.49 (m, 2 H), 7.36 (d, J = 6.4 Hz, 1 H), 7.90 (s, 1 H), 9.48-9.59 (br, 1 H) |
| C-26 | 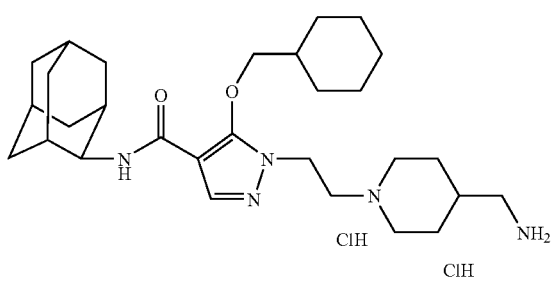 | (DMSO-d6): 0.97-2.07 (m, 30 H), 2.65-4.00 (m, 9 H), 4.13 (d, J = 7.2 Hz, 2 H), 4.41-4.51 (m, 2 H), 7.37 (d, J = 6.4 Hz, 1 H), 7.89 (s, 1 H), 8.26-8.44 (br, 3 H), 11.21-11.37 (br, 1 H) |

TABLE 17-continued

| No. | Structure | NMR (CDCl3 or d6-DMSO) |
|---|---|---|
| C-27 | 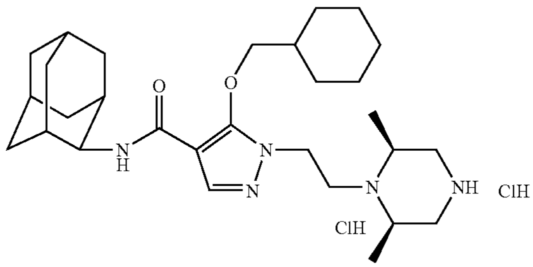 | (DMSO-d6): 0.96-2.08 (m, 31 H), 3.21-3.34 (m, 2 H), 3.44-4.00 (m, 7 H), 4.16 (d, J = 6.0 Hz, 2 H), 4.30-4.39 (m, 2 H), 7.42 (d, J = 6.8 Hz, 1 H), 7.90 (s, 1 H), 9.91-10.03 (br, 1 H), 10.12-10.26 (br, 1 H) |
| C-28 | 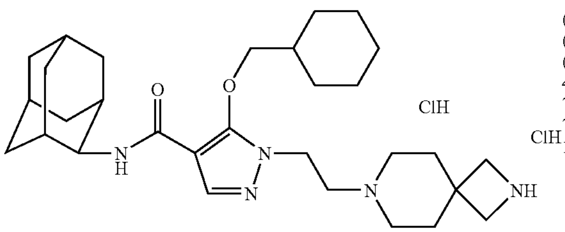 | (DMSO-d6): 0.99-2.26 (m, 29 H), 2.93-3.05 (m, 2 H), 3.35-3.47 (m, 4 H), 3.67-3.81 (m, 4 H), 3.93-4.00 (m, 1 H), 4.13 (d, J = 6.0 Hz, 2 H), 4.40-4.47 (m, 2 H), 7.36 (d, J = 6.4 Hz, 1 H), 7.36 (d, J = 6.4 Hz, 1 H), 7.89 (s, 1 H), 9.39-9.50 (br, 2 H), 11.20-11.30 (br, 1 H) |
| C-29 | 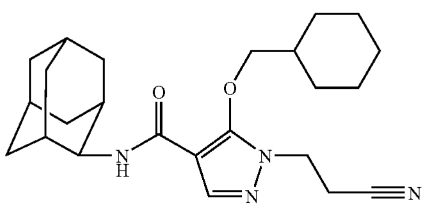 | (DMSO-d6): 0.97-2.09 (m, 25 H), 3.02 (t, J = 6.0 Hz, 2 H), 3.95-4.00 (m, 1 H), 4.14 (d, J = 6.0 Hz, 2 H), 4.17 (t, J = 6.0 Hz, 2 H), 7.36 (d, J = 6.8 Hz, 1 H), 7.88 (s, 1 H) |
| C-30 | 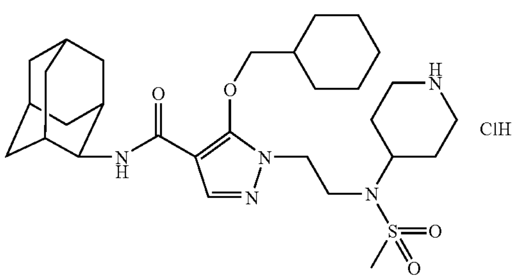 | (CDCl3): 1.05-2.04 (m, 31 H), 2.62-2.76 (m, 2 H), 2.63-2.76 (m, 2 H), 2.91 (s, 3 H), 3.51 (t, J = 6.9 Hz, 2 H), 3.62-3.74 (m, 1 H), 4.03 (d, J = 6.3 Hz, 2 H), 4.14-4.24 (m, 3 H), 6.44 (d, J = 7.8 Hz, 1 H), 7.75 (s, 1 H) |

TABLE 18

| No. | Structure | NMR (CDCl3 or d6-DMSO) |
|---|---|---|
| C-31 | 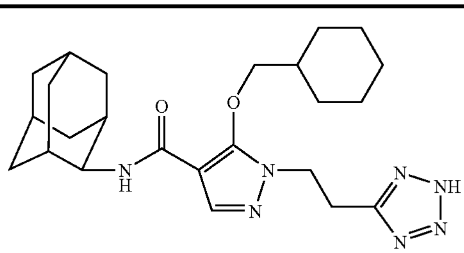 | (CDCl3): 1.03-2.04 (m, 25 H), 3.56 (t, J = 6.0 Hz, 2 H), 3.96 (d, J = 6.0 Hz, 2 H), 4.16-4.22 (m, 1 H), 4.40 (t, J = 6.0 Hz, 2 H), 6.41 (d, J = 7.5 Hz, 1 H), 7.78 (s, 1 H) |

TABLE 18-continued

| No. | Structure | NMR (CDCl3 or d6-DMSO) |
| --- | --- | --- |
| C-32 | 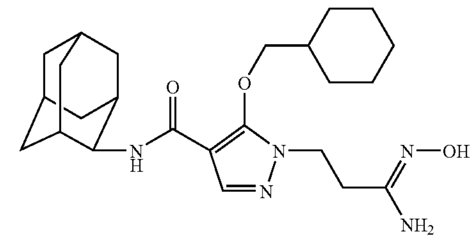 | (CDCl3): 1.03-2.05 (m, 25 H), 2.78 (t, J = 6.3 Hz, 2 H), 3.99 (d, J = 6.3 Hz, 2 H), 4.15-4.25 (m, 3 H), 5.25-5.38 (br, 1 H), 6.44 (d, J = 7.5 Hz, 1 H), 7.77 (s, 1 H) |
| C-33 | 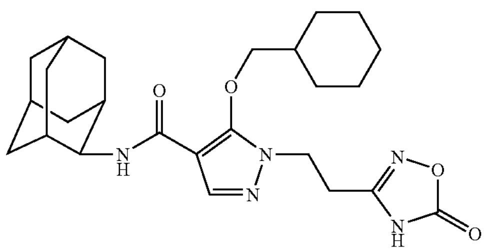 | (DMSO-d6): 0.94-2.06 (m, 25 H), 2.98 (t, J = 6.4 Hz, 2 H), 3.93-4.00 (m, 1 H), 4.08 (d, J = 6.0 Hz, 2 H), 4.24 (t, J = 6.4 Hz, 2 H), 7.31 (d, J = 6.8 Hz, 1 H), 7.81 (s, 1 H) |
| C-34 | 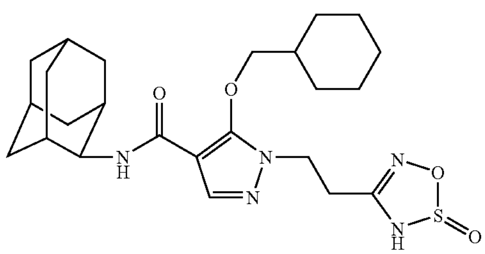 | (DMSO-d6): 0.96-2.07 (m, 25 H), 2.85 (t, J = 6.4 Hz, 2 H), 3.94-4.00 (m, 1 H), 4.10 (d, J = 6.0 Hz, 2 H), 4.29 (t, J = 6.4 Hz, 2 H), 7.33 (d, J = 6.8 Hz, 1 H), 7.86 (s, 1 H), 10.99 (s, 1 H) |
| C-35 | 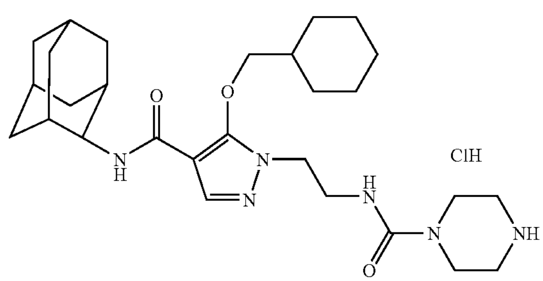 | (DMSO-d6): 0.91-2.06 (m, 25 H), 2.88-3.05 (m, 4 H), 3.28-3.38 (m, 2 H), 3.46-3.61 (m, 4 H), 3.90-4.11 (m, 5 H), 7.23 (d, J = 6.4 Hz, 1 H), 7.86 (s, 1 H), 9.48-9.66 (m, 2 H) |
| C-36 | 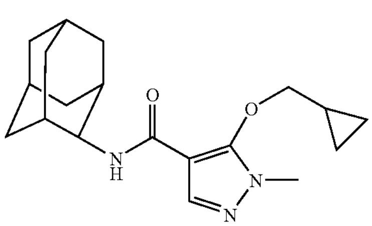 | (DMSO-d6); 1.41-2.08 (m, 14 H), 2.38-2.47 (m, 2 H), 3.60 (s, 3 H), 3.93-4.02 (m, 1 H), 4.25-4.38 (m, 2 H), 5.00-5.21 (m, 2 H), 5.76-5.92 (m, 1 H), 7.22 (d, J = 10.0 Hz, 1 H), 7.81 (s, 1 H). |

TABLE 19

| No. | Structure | NMR (CDCl3 or d6-DMSO) |
|---|---|---|
| C-37 | 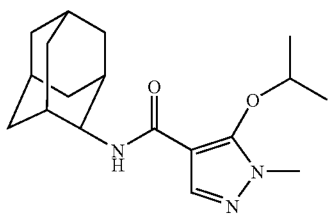 | (DMSO-d6); 1.26 (s, 3 H), 1.28 (s, 3 H), 1.53 (d, J = 12.4 Hz, 2 H), 1.60-2.04 (m, 12 H), 3.61 (s, 3 H), 3.92-4.03 (m, 1 H), 4.80-4.94 (m, 1 H), 7.15 (d, J = 6.8 Hz, 1 H), 7.83 (s, 1 H). |
| C-38 | 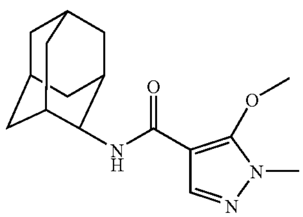 | (DMSO-d6); 1.41-2.11 (m, 14 H), 3.37 (s, 3 H), 3.64 (s, 1 H), 3.89-4.04 (m, 1 H), 8.10 (s, 1 H), 8.83 (d, J = 8.8 Hz, 1 H). |
| C-39 | 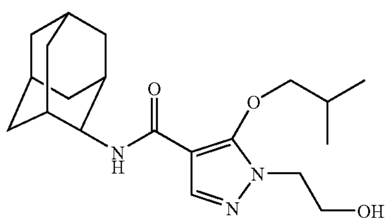 | (DMSO-d6); 0.97 (s, 3 H), 0.99 (s, 3 H). 1.53 (d, J = 12.4 Hz, 2 H), 1.61-2.10 (m, 13 H), 3.63-3.78 (m, 2 H), 3.85-4.01 (m, 3 H), 4.02-4.09 (m, 2 H), 4.79-4.92 (m, 1 H), 7.19 (d, J = 6.8 Hz, 1 H), 7.82 (s, 1 H). |
| C-40 | 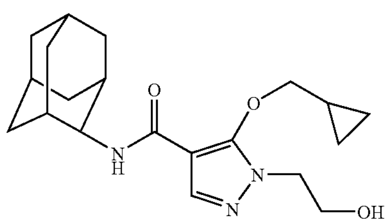 | (DMSO-d6); 0.23-0.37 (m, 2 H), 0.46-0.59 (m, 2 H), 1.12-1.28 (m, 1 H), 1.42-2.06 (m, 14 H), 3.64-3.79 (m, 2 H), 3.90-4.06 (m, 3 H), 4.14 (d, J = 7.6 Hz, 2 H), 4.80-4.91 (m, 1 H), 7.18 (d, J = 7.2 Hz, 1 H), 7.85 (s, 1 H). |
| C-41 | 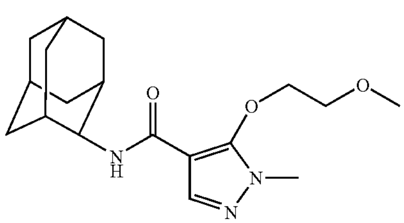 | (DMSO-d6); 1.18 (t, J = 7.2 Hz, 2 H), 1.45-2.06 (m, 14 H), 3.12-3.40 (m, 7 H), 3.92-4.08 (m, 2 H), 8.09 (s, 1 H), 8.83 (d, J = 8.0 Hz, 1 H). |
| C-42 | 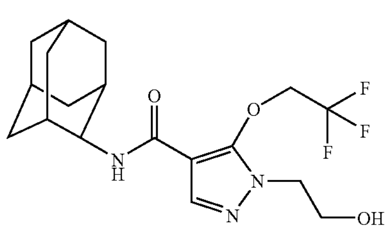 | (DMSO-d6); 1.51 (d, J = 12.4 Hz, 2 H), 1.60-2.12 (m, 12 H), 3.60-3.73 (m, 2 H), 3.90-4.03 (m, 3 H), 4.82-4.96 (m, 1 H), 4.98-5.12 (m, 2 H), 7.44 (d, J = 6.8 Hz, 1 H), 8.30 (s, 1 H). |

TABLE 20
| No. | Structure | NMR(CDCl3 or d6-DMSO) |
| --- | --- | --- |
| C-43 | 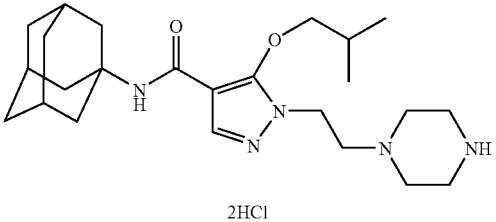 2HCl | (DMSO-d6); 0.97 (s, 3H), 0.99 (s, 3H), 1.51 (d, J = 12.4 Hz, 2H), 1.60-2.11 (m, 12H), 3.25-3.62 (m, 12H), 3.90-4.01 (m, 1H), 4.11 (d, J = 6.8 Hz, 2H), 4.35-4.49 (m, 2H), 7.39 (d, J = 6.8 Hz, 1H), 7.91 (s, 1H), 9.98 (brs, 2H). |
| C-44 | 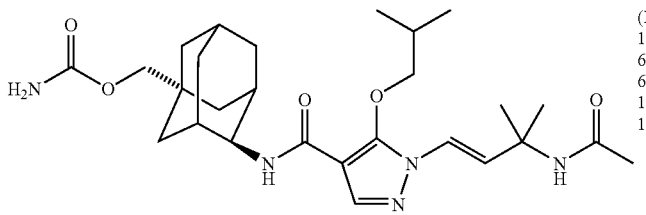 | (DMSO-d6); 0.97 (d, J = 6.0 Hz, 6H), 1.40-1.58 (m, 14H), 1.79 (s, 3H), 1.89-2.02 (m, 6H), 3.56 (s, 2H), 3.91 (brs, 1H), 4.08 (d, J = 6.4 Hz, 2H), 6.30-6.53 (brm, 3H), 6.77 (d, J = 14.4 Hz, 1H), 7.44 (d, J = 6.0 Hz, 1H), 7.78 (s, 1H), 7.96 (s, 1H) |
| C-45 | 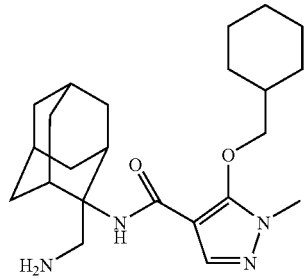 | (CDCl3); 1.06-1.32 (m, 11H), 1.68-2.46 (m, 14H) 2.22 (bs, 2H), 3.61 (s, 2H), 3.73 (s, 3H), 4.09-4.11 (m, 2H),, 6.39 (s, 1H), 7.79 (s, 1H) |
| C-46 | 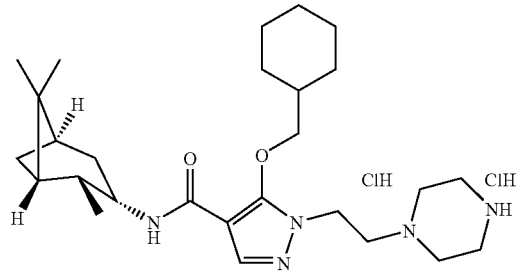 | (DMSO-d6); 1.00 (s, 3H), 1.04 (d, J = 4.5 Hz, 3H), 1.22 (s, 3H), 1.10-2.42 (m, 18H), 3.46-3.71 (m, 8H), 4.13-4.23 (m, 2H), 4.26-4.38 (m, 2H), 4.32 (d, J = 6.9 Hz, 2H) 7.78 (d, J = 8.7 Hz, 1H), 7.87 (s, 1H), 9.52 (bs, 2H) |
| C-47 | 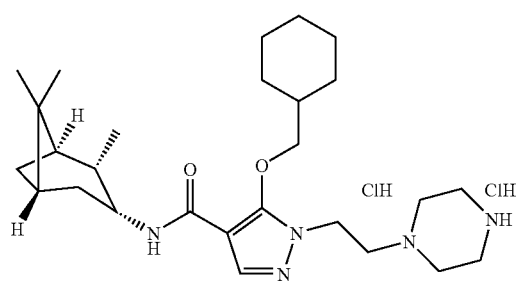 | (DMSO-d6): 1.00 (s, 3H), 1.04 (d, J = 4.5 Hz, 3H), 1.22 (s, 3H), 1.09-2.42 (m, 18H), 3.46-3.71 (m, 8H), 4.13-4.23 (m, 2H), 4.26-4.38 (m, 2H), 4.33 (d, J = 6.9 Hz, 2H) 7.78 (d, J = 8.4 Hz, 1H), 7.87 (s, 1H), 9.58 (bs, 2H) |

TABLE 20-continued

| No. | Structure | NMR(CDCl3 or d6-DMSO) |
| --- | --- | --- |
| C-48 | 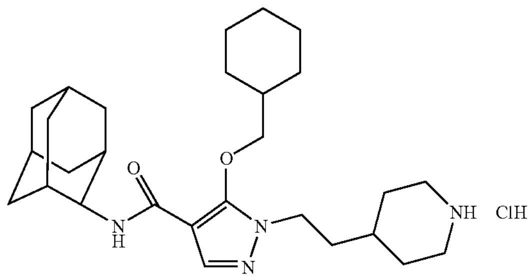 | (DMSO-d6); 1.01-2.03 (m, 32H), 2.73-2.84 (m, 2H), 3.19-3.23 (m, 2H), 3.92-3.97 (m, 3H), 4.08 (d, J = 6.3 Hz, 2H), 7.30 (d, J = 7.2 Hz, 1H), 7.82 (s, 1H), 8.61 9.00 (m, 2H) |

TABLE 21

| No. | Structure | NMR(CDCl3 or d6-DMSO) |
| --- | --- | --- |
| C-49 | 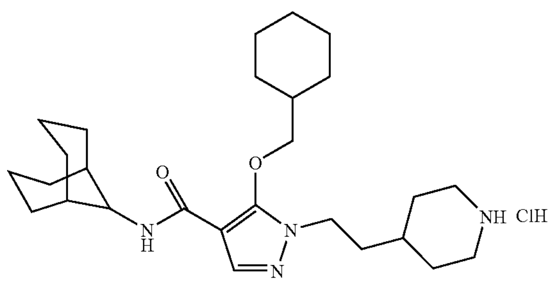 | (DMSO-d6); 1.02-1.93 (m, 32H), 2.77-2.84 (m, 2H), 3.20-3.24 (m, 2H), 3.78-3.90 (m, 1H) 3.95 (t, J = 7.2 Hz,, 2H), 4.08 (d, J = 6.0 Hz, 2H), 7.23 (d, J = 6.6 Hz, 1H), 7.80 (s, 1H), 8.61-9.00 (m, 2H) |
| C-50 | 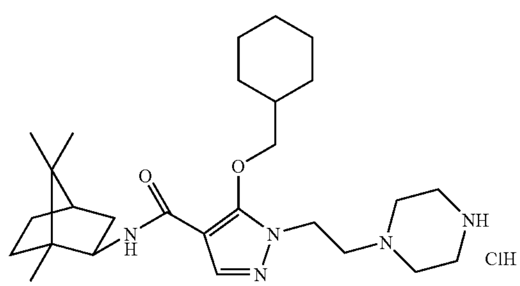 | (DMSO-d6); 0.77 (s, 3H), 0.78 (s, 3H), 0.94 (s, 3H), 0.94-1.83 (m, 25H), 2.74-2.85 (m, 2H), 3.17-3.24 (m, 2H), 3.83-3.96 (m, 3H), 4.01-4.15 (m, 2H), 6.92 (d, J = 7.8 Hz, 1H), 7.73 (s, 2H), 8.48-8.73 (m, 2H) |
| C-51 | 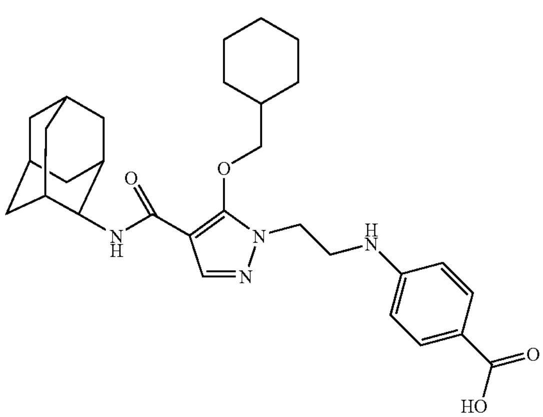 | (DMSO-d6); 0.77-1.25 (m, 11H), 1.50-1.99 (m, 14H), 3.51-3.54 (m, 2H), 3.89 (d, J = 6.3 Hz, 2H), 3.95-3.97 (m, 1H), 4.01-4.06 (m, 2H), 6.59 (d, J = 8.7 Hz, 2H), 7.17 (d, J = 6.9 Hz, 1H), 7.68 (d, J = 8.7 Hz, 2H), 7.87 (s, 1H), 12.00 (bs, 1H) |

TABLE 21-continued

| No. | Structure | NMR(CDCl3 or d6-DMSO) |
|---|---|---|
| C-52 | 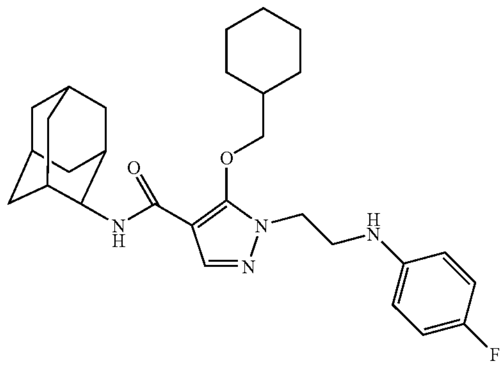 | (CDCl3); 0.86-1.31 (m, 11H), 1.67-2.04 (m, 14H), 3.64-3.68 (m, 2H), 3.95 (d, J = 6.0 Hz, 2H), 4.16-4.21 (m, 1H), 4.26-4.29 (m, 2H), 6.35 (d, J = 8.4 Hz, 1H), 6.91-7.06 (m, 4H), 7.77 (s, 1H) |
| C-53 | 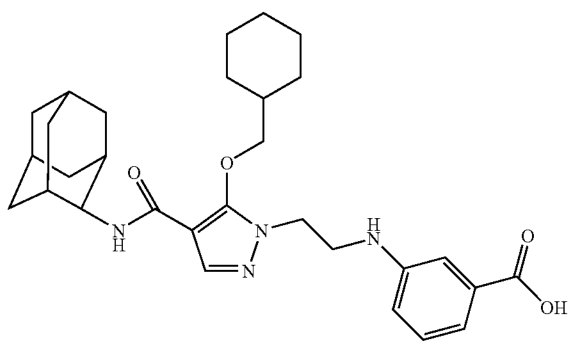 | (DMSO-d6); 0.76-1.17 (m, 11H), 1.50-2.00 (m, 14H), 3.47-3.52 (m, 2H), 3.90 (d, J = 6.3 Hz, 2H), 3.94-3.98 (m, 1H), 4.01-4.06 (m, 2H), 6.06 (t, J = 6.0 Hz, 1H), 6.78-6.81 (m, 1H), 7.12-7.21 (m, 3H), 7.86 (s, 1H), 12.62 (bs, 1H) |
| C-54 | 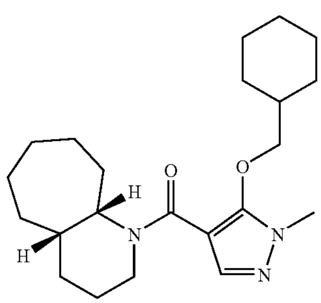 | (DMSO-d6); 0.92-1.99 (m, 24H), 2.50-2.92 (m, 1H), 3.59 (s, 3H), 3.65-4.58 (m, 4H), 7.29 (s, 1H) |

TABLE 22

| No. | Structure | NMR(CDCl3 or d6-DMSO) |
|---|---|---|
| C-55 | 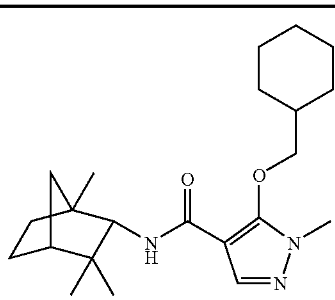 | (DMSO-d6); 0.77 (s, 3H), 1.00-1.79 (m, 24H), 3.62 (s, 3H), 3.67 (d, J = 9.2 Hz, 1H), 4.07 (d, J = 6.0 Hz, 2H), 6.78 (d, J = 9.6 Hz, 1H), 7.73 (s, 1H) |

TABLE 22-continued

| No. | Structure | NMR(CDCl3 or d6-DMSO) |
|---|---|---|
| C-56 | 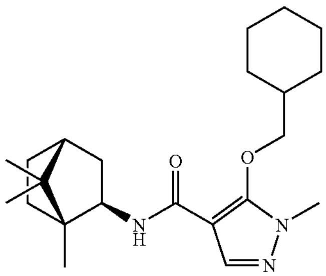 | (DMSO-d6); 0.78 (s, 6H), 0.94 (s, 3H), 1.00-1.80 (m, 18H), 3.60 (s, 3H), 3.89-4.11 (m, 3H), 6.80 (d, J = 8.0 Hz, 1H), 7.68 (s, 1H) |
| C-57 | 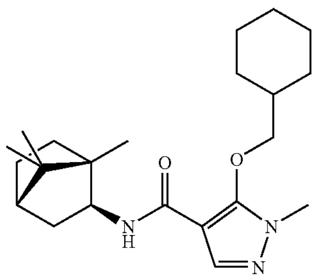 | (DMSO-d6); 0.78 (s, 6H), 0.94 (s, 3H), 0.98-1.80 (m, 18H), 3.60 (s, 3H), 3.89-4.12 (m, 3H), 6.79 (d, J = 8.0 Hz, 1H), 7.68 (s, 1H) |
| C-58 | 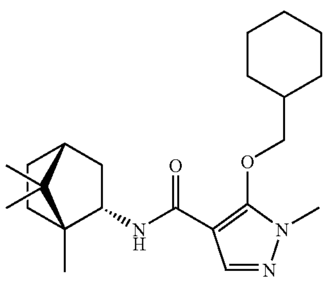 | (DMSO-d6); 0.72 (s, 3H), 0.84 (s, 3H), 0.93 (s, 3H), 0.99-1.80 (m, 17H), 2.14 (brt, J = 10.4 Hz, 1H), 3.60 (s, 3H), 4.03 (t, J = 8.0 Hz, 1H), 4.12 (t, J = 7.6 Hz, 1H), 4.28 (brs, 1H), 7.36 (d, J = 8.0 Hz, 1H), 7.76 (s, 1H) |
| C-59 | Chiral | (DMSO-d6); 0.78 (s, 6H), 0.94 (s, 3H), 0.98-1.80 (m, 18H), 2.32 (brs, 4H), 2.57-2.68 (brm, 6H), 3.89-4.14 (m, 5H), 6.87 (d, J = 7.2 Hz, 1H), 7.70 (s, 1H) |
| C-60 | 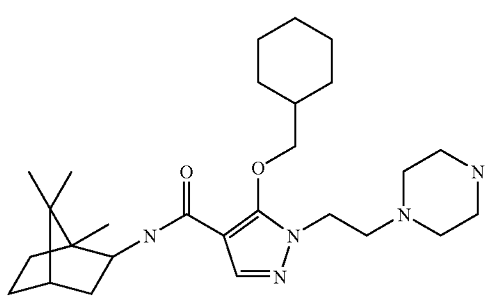 | (DMSO-d6); 0.78 (s, 6H), 0.94 (s, 3H), 0.98-1.80 (m, 18H), 2.31 (brs, 4H), 2.57-2.66 (brm, 6H), 3.89-4.14 (m, 5H), 6.87 (d, J = 7.2 Hz, 1H), 7.70 (s, 1H) |

TABLE 23
| No. | Structure | NMR(CDCl3 or d6-DMSO) |
|---|---|---|
| C-61 | 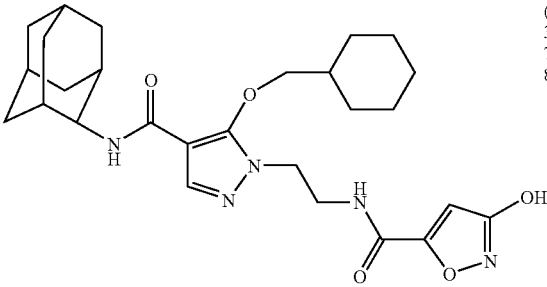 | (DMSO-d6): 0.88-2.04 (m, 25H), 3.50-3.59 (m, 2H), 3.94-4.12 (m, 5H), 6.52 (s, 1H), 7.19 (d, J = 6.8 Hz, 1H), 7.84 (s, 1H), 8.94 (t, J = 5.6 Hz, 1H), 11.66 (br.s, 1H) |
| C-62 | 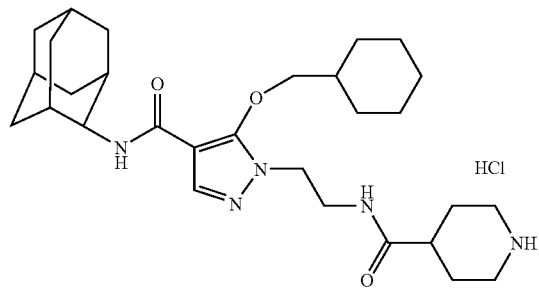 | (DMSO-d6): 0.97-2.04 (m, 29H), 2.34-2.44 (m, 1H), 2.77-2.90 (m, 2H), 3.15-3.26 (m, 2H), 3.33-3.43 (m, 2H), 3.93-4.02 (m, 3H), 4.06 (d, J = 6.0 Hz, 2H), 7.23 (d, J = 6.8 Hz, 1H), 7.86 (s, 1H), 8.14 (t, J = 5.6 Hz, 1H), 8.96-9.10 (br, 1H), 9.31-9.44 (br, 1H) |
| C-63 | 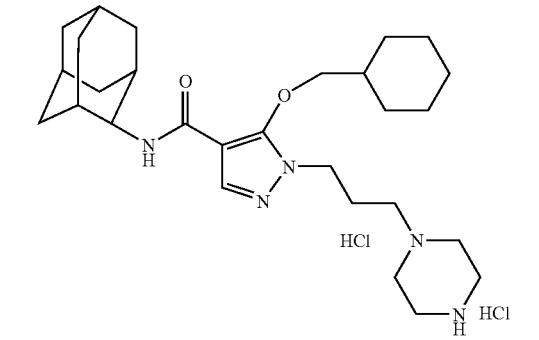 | (DMSO-d6): 0.97-2.31 (m, 27H), 3.10-4.23 (m, 14H), 7.29 (d, J = 6.8 Hz, 1H), 7.84 (s, 1H), 9.83-10.12 (br, 1H) |
| C-64 | 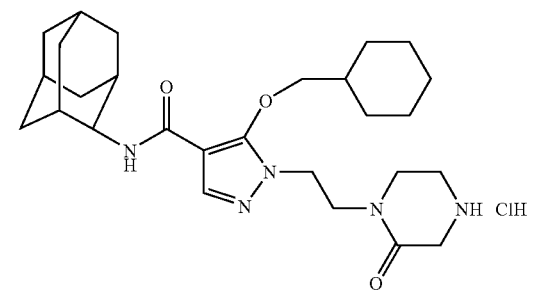 | (DMSO-d6): 0.95-2.07 (m, 29H), 3.22-3.31 (m, 2H), 3.35-3.43 (m, 2H), 3.93-3.99 (m, 1H), 4.03-4.14 (m, 4H), 7.30 (d, J = 6.0 Hz, 1H), 7.84 (s, 1H), 9.89-10.05 (br, 1H) |
| C-65 | 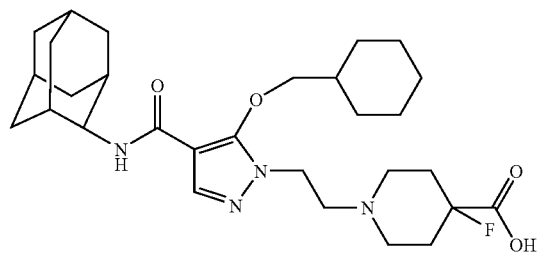 | (CDCl3): 1.05-2.05 (m, 29H), 2.20-2.33 (m, 3H), 3.05-3.20 (m, 2H), 3.50-3.61 (m, 2H), 4.11 (d, J = 6.0 Hz, 2H), 4.16-4.21 (m, 1H), 4.56-4.63 (m, 2H), 6.54 (d, J = 8.1 Hz, 1H), 7.71 (s, 1H) |

TABLE 23-continued
| No. | Structure | NMR(CDCl3 or d6-DMSO) |
|---|---|---|
| C-66 | 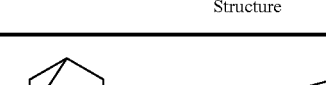 | (DMSO-d6): 0.97 (t, J = 7.6 Hz, 3H), 1.48-2.02 (m, 16H), 2.26-2.74 (m, 10H), 3.93-4.06 (m, 3H), 4.22 (t, J = 6.4 Hz, 2H), 7.25 (d, J = 6.4 Hz, 1H), 7.97 (s, 1H) |
TABLE 24
| No. | Structure | NMR(CDCl3 or d6-DMSO) |
|---|---|---|
| C-67 | 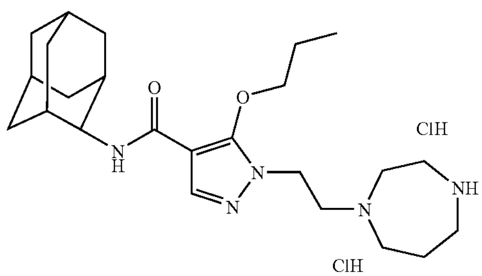 | (DMSO-d6): 1.18 (t, J = 7.2 Hz, 3H), 1.47-2.04 (m, 18H), 2.54-2.69 (m, 6H), 2.72 (t, J = 6.4 Hz, 2H), 2.84 (t, J = 6.4 Hz, 2H), 3.87-4.04 (m, 3H), 4.23 (t, J = 6.4 Hz, 2H), 7.22 (d, J = 6.4 Hz, 1H), 7.78-7.82 (br, 1H) |
| C-68 | 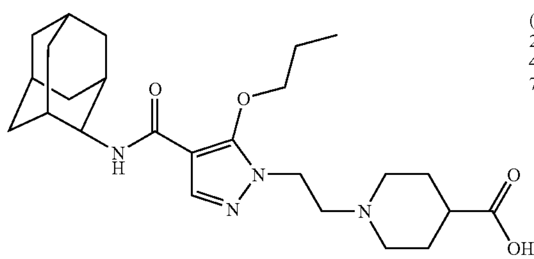 | (DMSO-d6): 0.97 (t, J = 7.6 Hz, 3H), 1.43-2.31 (m, 21H), 2.59-3.44 (m, 6H), 3.93-4.15 (m, 3H), 4.24 (t, J = 6.4 Hz, 2H), 7.26 (d, J = 6.0 Hz, 1H), 7.83 (s, 1H) |
| C-69 | 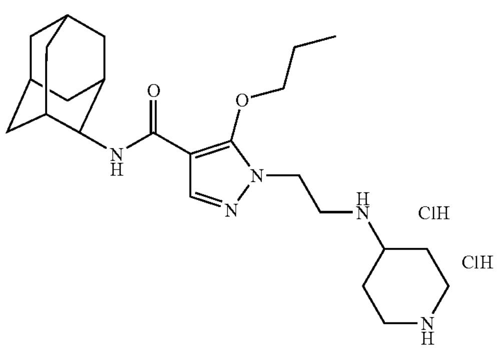 | (DMSO-d6): 0.97 (t, J = 7.2 Hz, 3H), 1.44-2.29 (m, 20H), 2.82-2.98 (m, 2H), 3.21-3.48 (m, 5H), 3.93-4.03 (m, 1H), 4.27 (t, J = 6.4 Hz, 2H), 4.34-4.44 (m, 2H), 7.31 (d, J = 7.2 Hz, 1H), 7.93 (s, 1H), 9.12-9.27 (br, 1H), 9.49-9.62 (br, 1H), 9.93-10.05 (br, 2H) |
| C-70 | Chiral | (CDCl3): 1.01-2.25 (m, 24H), 3.98-4.05 (m, 4H), 4.07-4.12 (m, 2H), 4.14-4.20 (m, 1H), 6.34 (d, J = 7.8 Hz, 1H), 7.76 (s, 1H) |

TABLE 24-continued

| No. | Structure | NMR(CDCl3 or d6-DMSO) |
|---|---|---|
| C-71 | 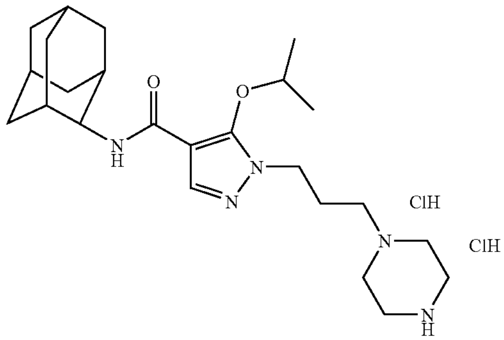 | (CDCl3): 1.36 (d, J = 6.3 Hz, 6H), 1.65-2.07 (m, 16H), 2.35 (t, J = 6.9 Hz, 2H), 2.37-2.45 (m, 4H), 2.90 (t, J = 4.8 Hz, 4H), 4.01 (t, J = 7.2 Hz, 2H), 4.18-4.23 (m, 1H), 4.76-4.84 (m, 1H), 6.40 (d, J = 7.5 Hz, 1H), 7.74 (s, 1H) |
| C-72 | 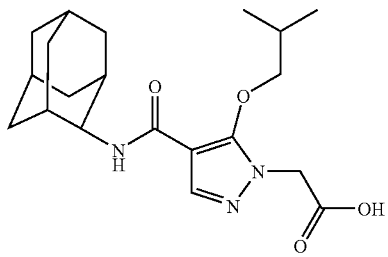 | (DMSO-d6); 0.92 (s, 3H), 0.93 (s, 3H), 1.51 (d, J = 12.4 Hz, 2H), 1.61-2.08 (m, 13H), 3.92-4.00 (m, 1H), 4.06 (d, J = 6.4 Hz, 2H), 4.67-4.76 (m, 2H), 7.35 (d, J = 6.8 Hz, 1H), 7.84 (s, 1H), 13.2 (brs, 1H), |

TABLE 25

| No. | Structure | NMR(CDCl3 or d6-DMSO) |
|---|---|---|
| C-73 | 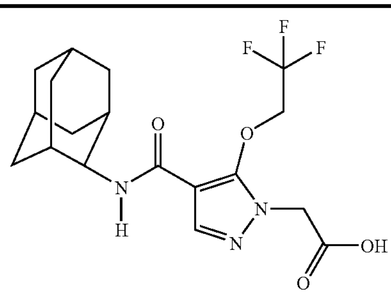 | (DMSO-d6); 1.51 (d, J = 12.4 Hz, 2H), 1.60-2.14 (m, 12H), 3.94-4.02 (m, 1H), 4.77 (s, 2H), 4.94-5.11 (m, 2H), 7.54 (d, J = 6.4 Hz, 1H), 8.08 (s, 1H), 13.3 (brs, 1H). |
| C-74 | 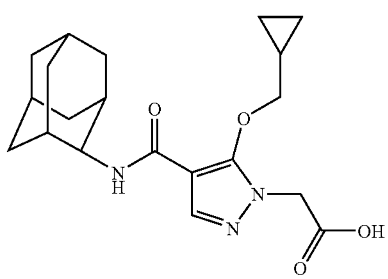 | (DMSO-d6); 0.19-0.31 (m, 2H), 0.44-0.56 (m, 2H), 1.08-1.21 (m, 1H), 1.52 (d, J = 12.8 Hz, 2H), 1.61-2.09 (m, 12H), 3.92-4.01 (m, 1H), 4.12 (d, J = 7.6 Hz, 2H), 4.76 (s, 2H), 7.30 (d, J = 7.2 Hz, 1H), 7.88 (s, 1H), 13.3 (brs, 1H). |
| C-75 | 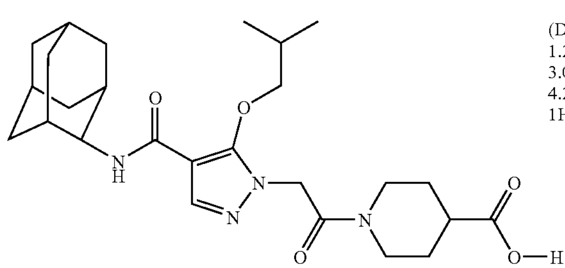 | (DMSO-d6); 0.89 (s, 3H), 0.91 (s, 3H), 1.25-2.10 (m, 16H), 2.67-2.85 (m, 1H), 3.01-3.22 (m, 1H), 3.49-3.66 (m, 2H), 3.73-4.21 (m, 5H), 4.76-5.03 (m, 4H), 7.26 (s, 1H), 7.83 (s, 1H), 11.93 (brs, 1H). |

TABLE 25-continued

| No. | Structure | NMR(CDCl3 or d6-DMSO) |
|---|---|---|
| C-76 | 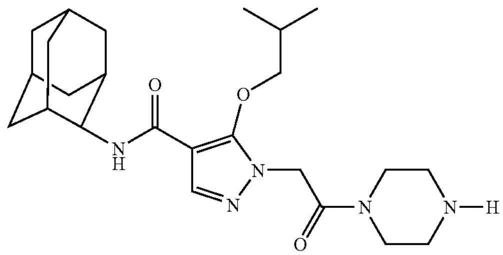 | (DMSO-d6); 0.91 (s, 3H), 0.93 (s, 3H), 1.53 (d, J = 12.8 Hz, 2H), 1.61-2.09 (m, 13H), 2.56-2.75 (m, 5H), 3.28-3.48 (m, 4H), 3.91-4.08 (m, 3H), 4.84-4.96 (m, 2H), 7.26 (d, J = 6.4 Hz, 1H), 7.83 (s, 1H). |
| C-77 | 2HCl | (DMSO-d6); 1.51 (d, J = 12.4 Hz, 2H), 1.59-2.14 (m, 12H), 3.26-3.71 (m, 11H), 3.92-4.04 (m, 1H), 4.35-4.51 (m, 2H), 5.10-5.26 (m, 2H), 7.57 (d, J = 6.4 Hz, 1H), 8.18 (s, 1H), 10.06 (brs, 2H). |
| C-78 | 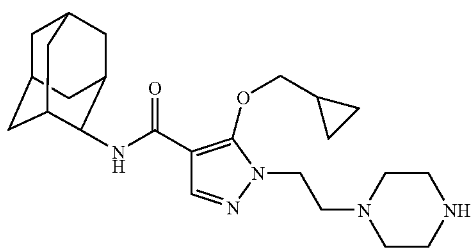 | (DMSO-d6); 0.25-0.30 (m, 4H), 0.49-0.53 (m, 4H), 1.52 (d, J = 11.8 Hz, 2H), 1.63-2.12 (m, 19H), 3.81-4.28 (m, 6H), 7.23 (s, 1H), 7.83 (s, 1H), |

TABLE 26

| No. | Structure | NMR(CDCl3 or d6-DMSO) |
|---|---|---|
| C-79 | 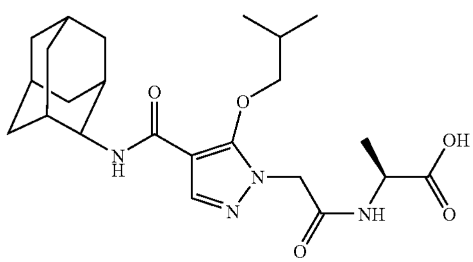 | (DMSO-d6); 0.92 (s, 3H), 0.94 (s, 3H), 1.10-1.21 (m, 1H), 1.23-1.37 (m, 3H), 1.53 (d, J = 11.6 Hz, 2H), 1.61-2.11 (m, 12H), 3.85-4.11 (m, 3H), 4.12-4.33 (m, 1H), 4.53-4.75 (m, 2H), 7.26 (d, J = 6.0 Hz, 1H), 7.83 (s, 1H), 8.46 (d, J = 6.0 Hz, 1H), 12.5 (brs, 1H). |
| C-80 | 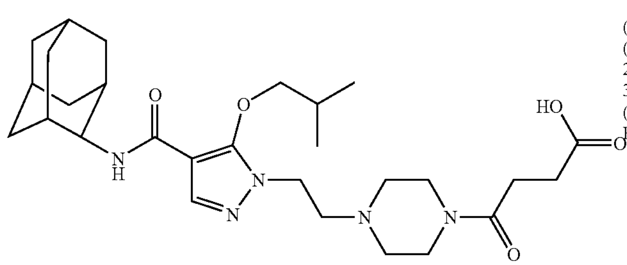 | (DMSO-d6); 0.97 (s, 3H), 0.99 (s, 3H), 1.52 (d, J = 11.6 Hz, 2H), 1.62-2.12 (m, 12H), 2.37-2.62 (m, 6H), 2.85-3.25 (m, 3H), 3.38-3.61 (m, 4H), 3.90-4.01 (m, 1H), 4.02-4.18 (m, 3H), 4.35-4.51 (m, 3H), 7.37 (d, J = 6.8 Hz, 1H), 7.91 (s, 1H), 11.72 (brs, 1H). |

TABLE 26-continued

| No. | Structure | NMR(CDCl3 or d6-DMSO) |
|---|---|---|
| C-81 | 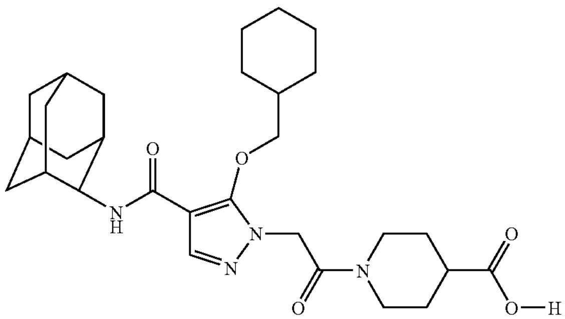 | (DMSO-d6); 0.80-1.03 (m, 2H), 1.05-1.28 (m, 4H), 1.29-1.42 (m, 1H), 1.43-2.07 (m, 22H), 2.48-2.58 (m, 1H), 2.67-2.83 (m, 1H), 3.03-3.19 (m, 1H), 3.77-4.23 (m, 5H), 4.80-5.02 (m, 2H), 7.24 (d, J = 6.8 Hz, 1H), 7.81 (s, 1H), 12.29 (brs, 1H). |
| C-82 | 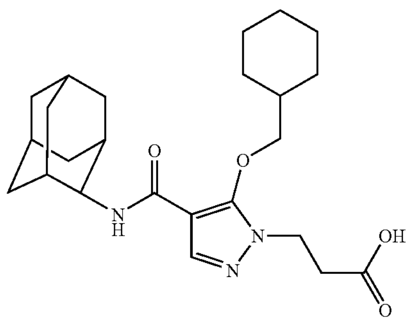 | (DMSO-d6); 0.90-1.31 (m, 6H), 1.52 (d, J = 12.4 Hz, 2H), 1.57-2.07 (m, 17H), 2.69-2.81 (m, 2H), 3.88-4.00 (m, 1H), 4.02-4.18 (m, 4H), 7.25 (d, J = 7.2 Hz, 1H), 7.78 (s, 1H), 12.33 (brs, 1H). |
| C-83 | 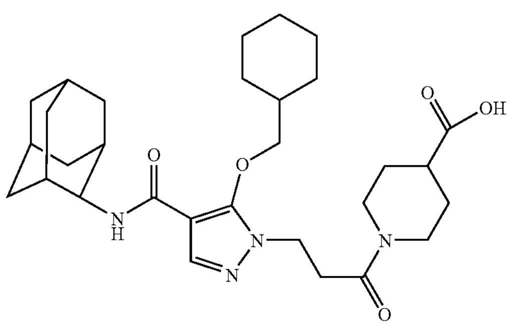 | (DMSO-d6); 0.92-2.05 (m, 28H), 2.40-2.49 (m, 1H), 2.64-2.78 (m, 1H), 2.79-2.91 (m, 2H), 2.97-3.12 (m, 1H), 3.65-3.80 (m, 1H), 3.85-4.22 (m, 7H), 7.19 (d, J = 6.8 Hz, 1H), 7.78 (s, 1H), 12.23 (brs, 1H). |
| C-84 | 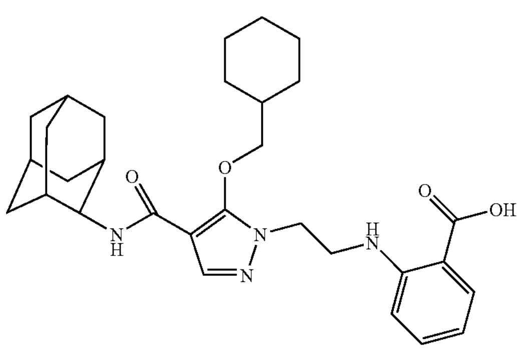 | (CDCl3); 0.90-1.28 (m, 11H), 1.58-2.11 (m, 14H), 3.71-3.81 (m, 2H), 3.94 (d, J = 5.7 Hz, 2H), 4.12-4.23 (m, 1H), 4.23-4.27 (m, 2H), 6.43 (d, J = 6.9 Hz, 1H), 6.73-6.78 (m, 1H), 6.88-6.91 (m, 1H), 7.39-7.44 (m, 1H), 7.82 (s, 1H), 7.98-8.01 (m, 1H) |

TABLE 27

| No. | Structure | NMR(CDCl3 or d6-DMSO) |
|---|---|---|
| C-85 | 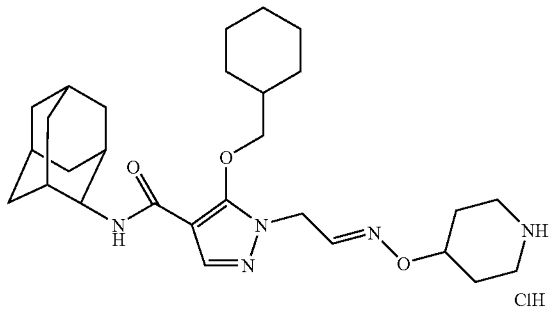 | (DMSO-d6); 0.99-1.25 (m, 11H), 1.50-2.03 (m, 18H), 2.94-3.10 (m, 2H), 3.10-3.25 (m, 2H), 3.96-3.98 (m, 1H), 4.08-4.12 (m,, 2H), 4.23-4.36 (m, 1H), 4.71 (d, J = 4.8 Hz, 2H), 6.99-7.02 (m, 1H), 7.32-7.36 (m, 1H), 7.84 (s, 1H), 8.76-8.85 (m, 2H) |
| C-86 | 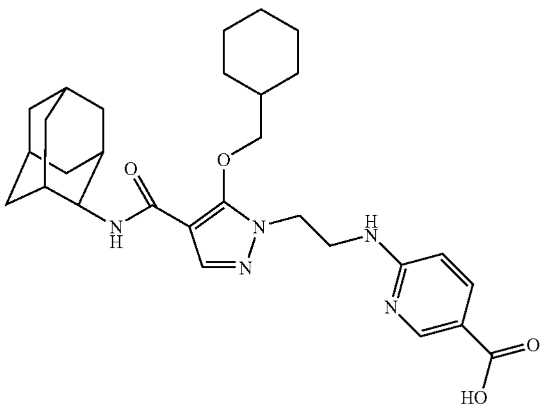 | (CDCl3); 0.86-1.28 (m, 11H), 1.66-1.98 (m, 14H), 3.89-4.01 (m, 4H), 4.11-4.23 (m, 1H), 4.23-4.35 (m, 2H), 6.47 (d, J = 8.1 Hz, 1H), 6.65 (d, J = 8.1 Hz, 1H), 7.76 (s, 1H), 8.14 (d, J = 8.1 Hz, 1H), 8.61 (s, 1H) |
| C-87 | 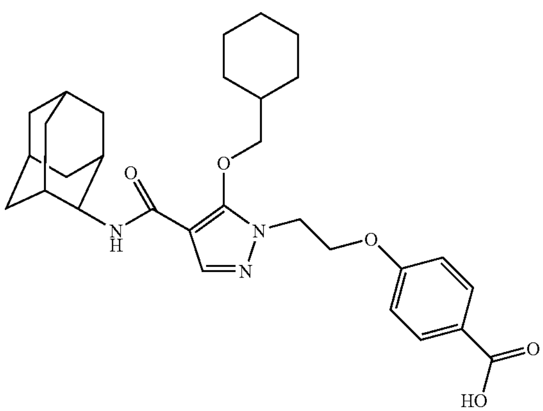 | (CDCl3): 1.04-1.32 (m, 11H), 1.68-2.06 (m, 14H), 4.12 (d, J = 7.2 Hz, 2H), 4.19-4.22 (m, 1H), 4.37-4.40 (m, 2H), 4.45-4.49 (m, 2H), 6.41 (d, J = 8.1 Hz, 1H), 6.89 (d, J = 9.0 Hz, 2H), 7.79 (s, 1H), 8.03 (d, J = 9.0 Hz, 2H) |
| C-88 | 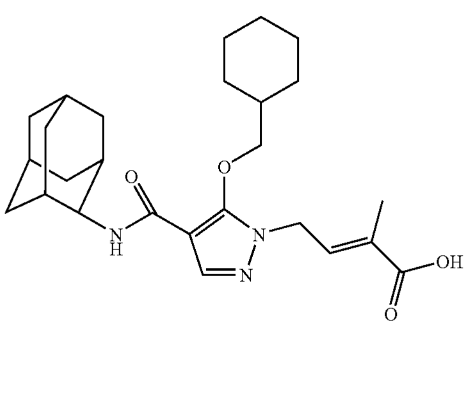 | (CDCl3); 0.96-1.33 (m, 11H), 1.27 (s, 3H), 1.41-2.00 (m, 14H), 4.03 (d, J = 6.3 Hz, 2H), 4.18-4.22 (m, 1H), 4.78 (d, J = 6.0 Hz, 2H), 6.34 (d, J = 8.7 Hz, 1H), 6.84-6.91 (m, 1H), 7.74 (s, 1H) |

TABLE 27-continued

| No. | Structure | NMR(CDCl3 or d6-DMSO) |
|---|---|---|
| C-89 | 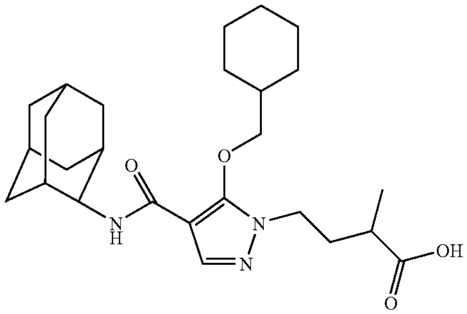 | (CDCl3); 0.86-1.43 (m, 14H), 1.61-2.00 (m, 14H), 2.01-2.22 (m, 2H), 2.48-2.40 (m, 1H), 3.95-4.25 (m, 3H), 6.37 (bs, 1H), 7.74 (s, 1H) |
| C-90 | 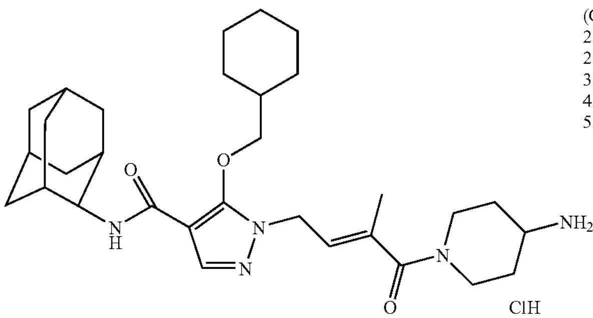 | (CDCl3): 1.00-1.35 (m, 11H), 1.59-2.11 (m, 16H) 2.09 (s, 3H), 2.20-2.38 (m, 2H), 2.77-3.12 (m, 4H), 3.41-3.60 (m, 1H), 4.12-4.20 (m, 1H) 4.21-4.54 (m, 2H), 4.85-5.11 (m, 2H), 5.68-5.74 (m, 1H), 7.43 (bs, 1H), 8.52-8.74 (m, 3H) |

TABLE 28

| No. | Structure | NMR(CDCl3 or d6-DMSO) |
|---|---|---|
| C-91 | 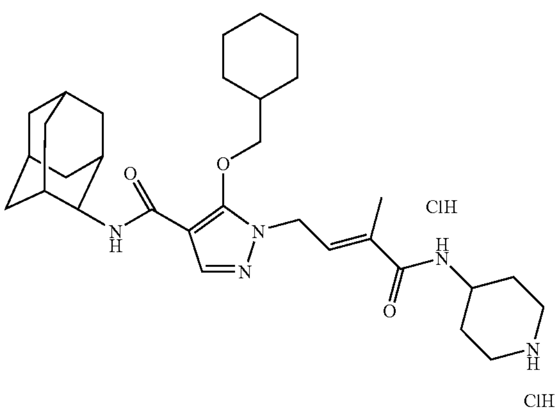 | (CDCl3); 1.02-1.33 (m, 11H), 1.66-2.10 (m, 18H), 1.88 (s, 3H), 2.70-3.09 (m, 4H), 3.42-3.60 (m, 1H), 4.06-4.10 (m, 5H), 4.73 (d, J = 5.4 Hz, 1H), 6.41-6.03 (m, 1H), 6.75 (d, J = 7.2 Hz, 1H), 7.27-7.40 (m, 1H), 8.91 (s, 1H), 9.36 (bs, 1H), 9.57 (bs, 1H) |
| C-92 | 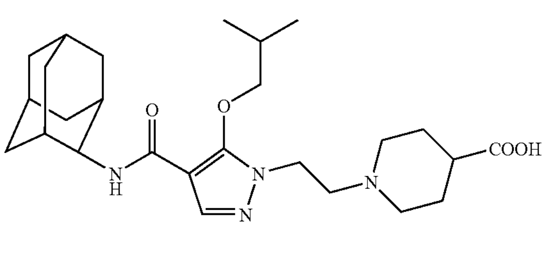 | (DMSO-d6); 0.98 (d, J = 6.6 Hz, 6H), 1.50-2.09 (m, 20H), 2.93-3.61 (m, 6H), 3.98 (d, J = 6.3 Hz, 1H), 4.10 (d, J = 6.3 Hz, 2H), 4.39 (m, 2H), 7.38 (m, 1H), 7.90 (s, 1H), 12.35 (br, 1H) |

TABLE 28-continued

| No. | Structure | NMR(CDCl3 or d6-DMSO) |
|---|---|---|
| C-93 | 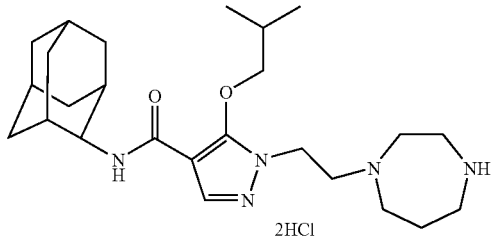 | (DMSO-d6); 0.98 (d, J = 6.6 Hz, 6H), 1.50-1.54 (m, 2H), 1.71-2.18 (m, 17H), 3.29 (m, 4H), 3.72 (m, 4H), 3.98 (m, 1H), 4.11 (d, J = 6.6 Hz, 2H), 4.44 (t, J = 6.6 Hz, 2H), 7.40 (d, J = 6.6 Hz, 1H), 7.92 (s, 1H), 9.49-9.71 (m, 2H), 11.79 (br, 1H) |
| C-94 | 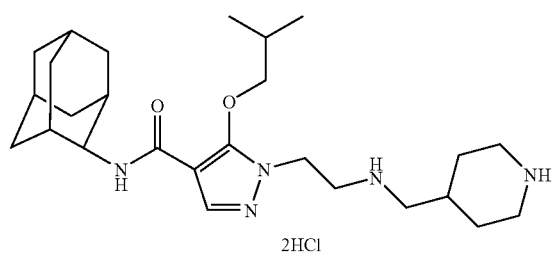 | (DMSO-d6); 0.98 (d, J = 6.3 Hz, 6H), 1.36-1.54 (m, 4H), 1.31-2.11 (m, 16H), 2.80-2.90 (m, 4H), 3.24-3.29 (m, 4H), 3.96-3.99 (m, 1H), 4.10 (d, J = 6.6 Hz, 2H), 4.34 (t, J = 6.6 Hz, 2H), 7.37 (d, J = 6.9 Hz, 1H), 7.92 (s, 1H), 8.87-9.01 (m, 2H), 9.33 (br, 2H) |
| C-95 | 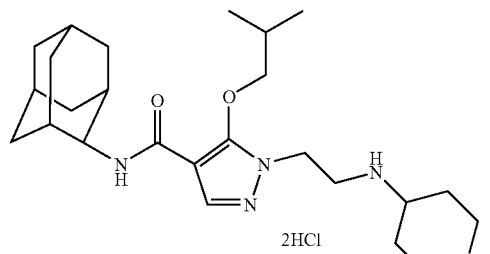 | (DMSO-d6); 0.98 (d, J = 6.6 Hz, 6H), 1.50-1.54 (m, 2H), 1.71-2.12 (m, 15H), 2.19-2.23 (m, 2H), 2.83-2.95 (m, 2H), 3.35-3.39 (m, 5H), 3.98 (d, J = 6.9 Hz, 1H), 4.10 (d, J = 6.6 Hz, 2H), 4.34 (t, J = 6.6 Hz, 2H), 7.36 (d, J = 6.9 Hz, 1H), 7.92 (s, 1H), 9.09-9.26 (m, 2H), 9.74 (br, 2H) |
| C-96 | 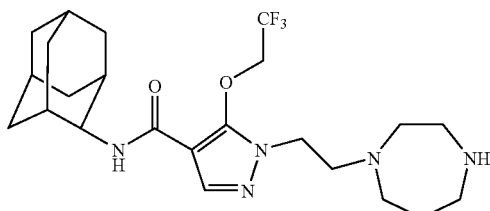 | (DMSO-d6); 1.49-2.16 (m, 16H), 3.21-3.71 (m, 10H), 4.00 (d, J = 6.6 Hz, 1H), 4.43 (m, 2H), 5.19 (q, J = 9.0 Hz, 2H), 7.58 (d, J = 6.6 Hz, 1H), 8.18 (s, 1H), 9.49-9.70 (m, 2H), 11.66 (m, 1H) |

TABLE 29

| No. | Structure | NMR(CDCl3 or d6-DMSO) |
|---|---|---|
| C-97 | 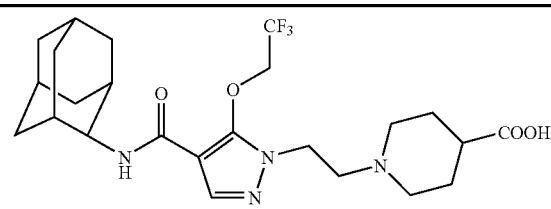 | (DMSO-d6); 1.47-2.07 (m, 21H), 3.17-3.40 (m, 4H), 3.97-4.40 (m, 3H), 5.13 (q, J = 8.4 Hz, 2H), 7.51 (d, J = 6.9 Hz, 1H), 8.11 (s, 1H), 12.35 (br, 1H) |
| C-98 | 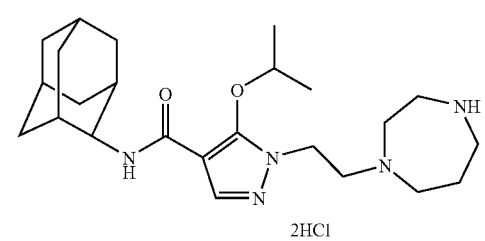 | (DMSO-d6); 1.29 (d, J = 6.0 Hz, 6H), 1.51-2.15 (m, 16H), 3.24-3.51 (m, 10H), 3.98 (d, J = 7.2 Hz, 1H), 4.40 (m, 2H), 4.93-5.02 (m, 1H), 7.31 (d, J = 7.2 Hz, 1H), 7.97 (s, 1H), 9.45 (brs, 2H), 11.77 (brs, 1H) |

TABLE 29-continued
| No. | Structure | NMR(CDCl3 or d6-DMSO) |
|---|---|---|
| C-99 | 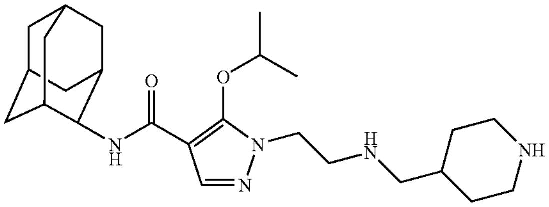 | (DMSO-d6); 1.29 (d, J = 6.3 Hz, 6H), 1.40-1.56 (m, 4H), 1.71-2.03 (m, 15H), 2.80-2.91 (m, 4H), 3.26-3.29 (m, 4H), 3.99 (d, J = 6.9 Hz, 1H), 4.35 (t, J = 6.9 Hz, 2H), 4.91-5.00 (m, 1H), 7.30 (d, J = 6.9 Hz, 1H), 7.98 (s, 1H), 8.80-8.94 (m, 2H), 9.27 (m, 2H) |
| C-100 | 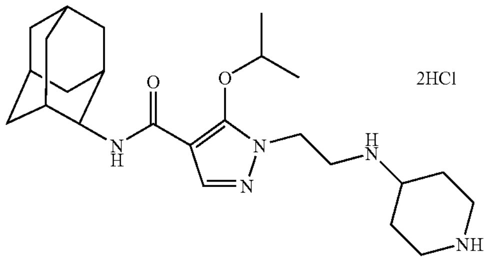 | (DMSO-d6); 1.30 (d, J = 6.0 Hz, 6H), 1.52-2.24 (m, 18H), 2.88-2.92 (m, 2H), 3.30-3.41 (m, 5H), 4.01 (m, 1H), 4.35 (t, J = 6.9 Hz, 2H), 4.92-5.00 (m, 1H), 7.31 (d, J = 6.6 Hz, 1H), 8.00 (s, 1H), 9.05-9.17 (m, 2H), 9.72 (m, 2H) |
| C-101 | 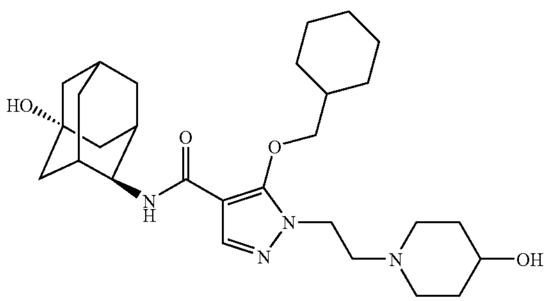 | (DMSO-d6): 0.96-2.12 (m, 30H), 2.57-2.72 (m, 4H), 3.36-3.47 (m, 1H), 3.84-3.91 (m, 1H), 3.97 (t, J = 6.4 Hz, 2H), 4.08 (d, J = 6.0 Hz, 2H), 4.43 (s, 1H), 4.54 (d, J = 4.0 Hz, 1H), 7.23 (d, J = 6.8 Hz, 1H), 7.79 (s, 1H) |
| C-102 | 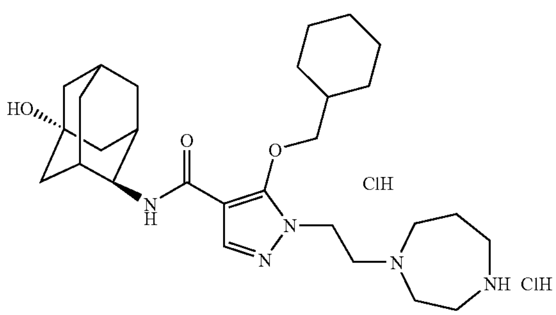 | (DMSO-d6): 0.93-2.30 (m, 28H), 3.06-3.94 (m, 9H), 4.07-4.21 (m, 2H), 4.36-4.54 (m, 2H), 7.35 (br.s, 1H), 7.90 (s, 1H), 9.67-10.19 (m, 2H), 11.87-12.18 (br, 1H) |
TABLE 30
| No. | Structure | NMR(CDCl3 or d6-DMSO) |
|---|---|---|
| C-103 | 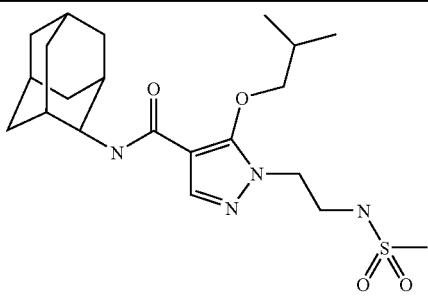 | (CDCl3): 1.05 (d, J = 6.6 Hz, 6H), 1.66-2.05 (m, 15H), 2.94 (s, 3H), 3.60-3.67 (m, 2H), 4.08 (d, J = 6.9 Hz, 2H), 4.17-4.24 (m, 3H), 6.41 (d, J = 7.8 Hz, 1H), 7.78 (s, 1H) |

TABLE 30-continued

| No. | Structure | NMR(CDCl3 or d6-DMSO) |
| --- | --- | --- |
| C-104 | 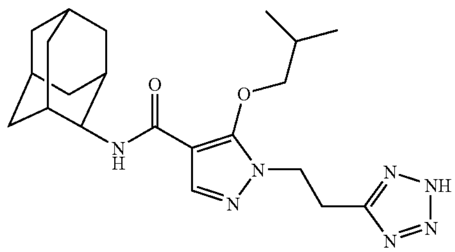 | (CDCl3): 1.04 (d, J = 6.6 Hz, 6H), 1.67-2.19 (m, 15H), 3.59 (t, J = 6.6 Hz, 2H), 4.12 (d, J = 6.6 Hz, 2H), 4.15-4.21 (m, 1H), 4.59 (t, J = 6.6 Hz, 2H), 7.72 (d, J = 8.4 Hz, 1H), 8.06 (s, 1H) |
| C-105 | 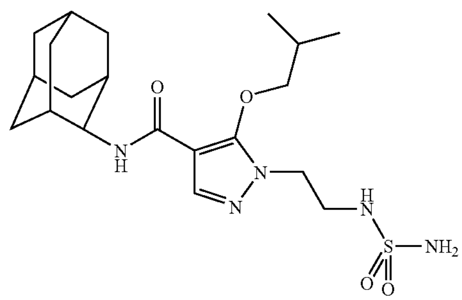 | (CDCl3): 1.05 (d, J = 6.6 Hz, 6H), 1.65-2.19 (m, 15H), 3.59 (t, J = 5.4 Hz, 2H), 4.09 (d, J = 6.6 Hz, 2H), 4.16-4.28 (m, 3H), 6.47 (d, J = 7.2 Hz, 1H), 7.79 (s, 1H) |
| C-106 | 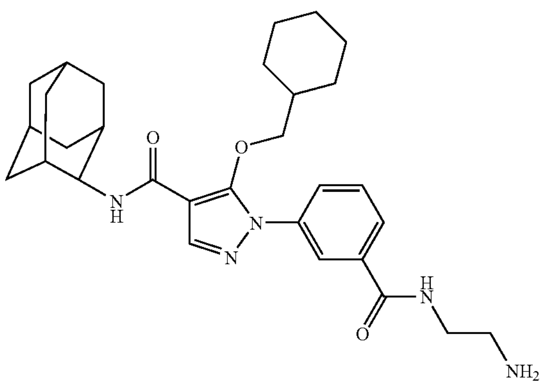 | (DMSO-d6): 0.76-2.11 (m, 25H), 3.04-3.40 (m, 4H), 3.94-4.07 (m, 3H), 7.45-7.93 (m, 4H), 8.04 (s, 1H), 8.14 (s, 1H), 8.56-8.65 (br, 1H) |
| C-107 | 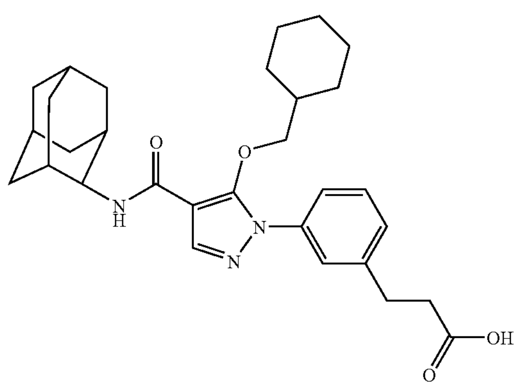 | (DMSO-d6): 0.80-2.08 (m, 25H), 2.57 (t, J = 7.6 Hz, 2H), 2.90 (t, J = 7.6 Hz, 2H), 3.93-4.06 (m, 3H), 7.24-7.31 (m, 1H), 7.38-7.51 (m, 4H), 7.98 (s, 1H), 12.15 (br.s, 1H) |

TABLE 30-continued

| No. | Structure | NMR(CDCl3 or d6-DMSO) |
|---|---|---|
| C-108 | 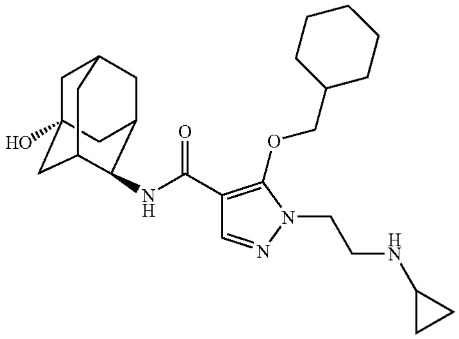 | (CDCl3): 0.42-0.51 (m, 4H), 1.01-2.24 (m, 25H), 3.18 (d, J = 6.3 Hz, 2H), 4.02 (d, J = 6.3 Hz, 2H), 4.09-4.20 (m, 3H), 6.28 (d, J = 7.5 Hz, 1H), 7.73 (s, 1H) |

TABLE 31

| No. | Structure | NMR(CDCl3 or d6-DMSO) |
|---|---|---|
| C-109 | 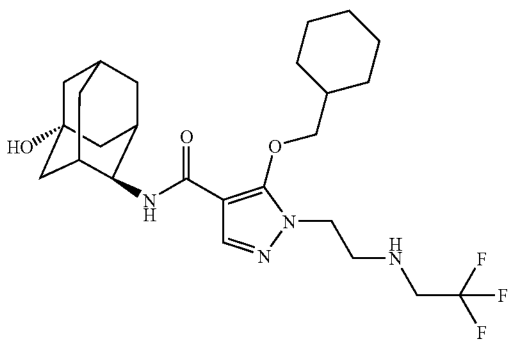 | (DMSO-d6): 0.94-2.08 (m, 24H), 2.90-3.01 (m, 2H), 3.16-3.31 (m, 2H), 3.84-4.01 (m, 3H), 4.08 (d, J = 5.2 Hz, 2H), 4.33-4.46 (br, 1H), 7.21 (d, J = 6.4 Hz, 1H), 7.80 (s, 1H) |
| C-110 | 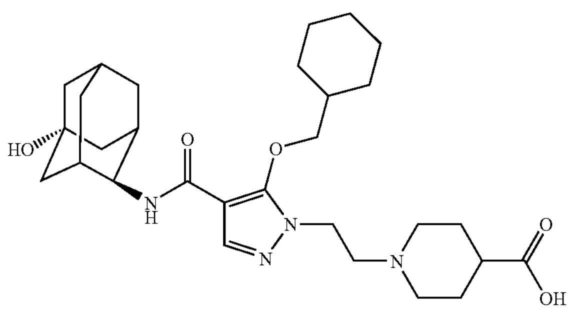 | (DMSO-d6): 0.92-2.27 (m, 31H), 2.56-2.88 (m, 4H), 3.79-4.18 (m, 6H), 7.22 (br.s, 1H), 7.80 (s, 1H) |
| C-111 | 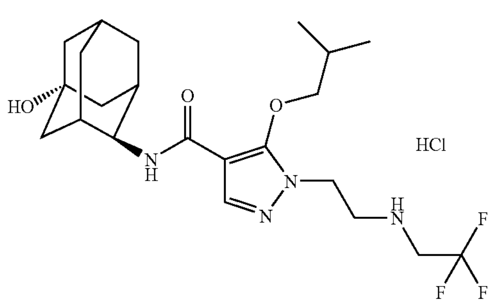 | (CDCl3): 1.04 (d, J = 6.6 Hz, 6H), 1.51-2.24 (m, 14H), 3.16-3.26 (m, 4H), 4.03 (d, J = 6.6 Hz, 2H) <4.10 (t, J = 5.4 Hz, 2H), 4.13-4.20 (m, 1H), 6.23 (d, J = 6.3 Hz, 1H), 7.72 (s, 1H) |

TABLE 31-continued

| No. | Structure | NMR(CDCl3 or d6-DMSO) |
|---|---|---|
| C-112 | 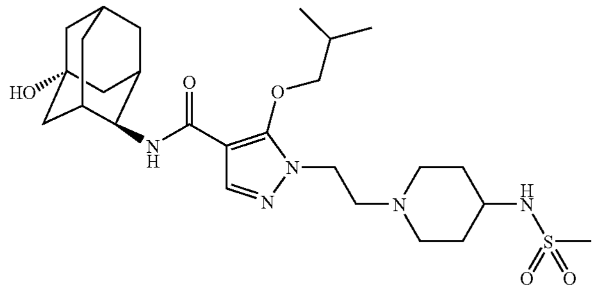 | (CDCl3): 1.06 (d, J = 6.6 Hz, 6H), 1.44-2.23 (m, 22H), 2.39-2.56 (m, 2H), 3.02-3.53 (m, 3H), 4.07 (d, J = 6.6 Hz, 2H), 4.12-4.19 (m, 1H), 4.22-4.40 (br, 1H), 6.21-6.32 (br, 1H), 7.69 (s, 1H) |
| C-113 | 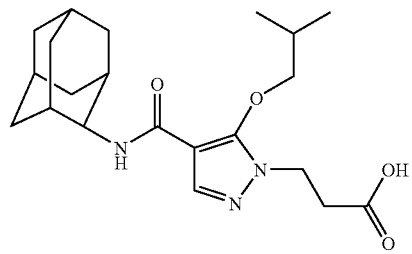 | (DMSO-d6): 0.97 (s, 3H), 0.99 (s, 3H), 1.52 (d, J = 12.0 Hz, 2H), 1.60-2.09 (m, 13H), 2.76 (t, J = 6.8 Hz), 3.88-4.01 (m, 1H), 4.06 (d, J = 6.8 Hz, 2H), 4.13 (t, J = 6.8 Hz, 2H), 7.27 (d, J = 6.8 Hz, 1H), 7.80 (s, 1H), 12.33 (brs, 1H), |
| C-114 | 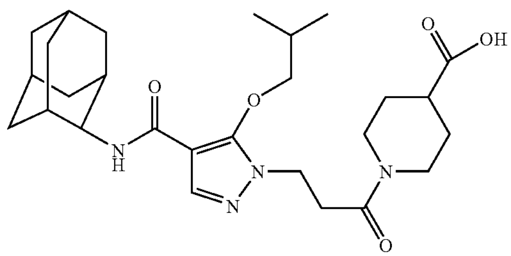 | (DMSO-d6); 0.97 (s, 3H), 0.98 (s, 3H), 1.19-1.57 (m, 5H), 1.61-2.09 (m, 15H), 2.62-2.78 (m, 1H), 2.79-2.90 (m, 2H), 2.96-3.11 (m, 1H), 3.65-3.80 (m, 1H), 3.90-4.22 (m, 6H), 7.22 (d, J = 6.4 Hz, 1H), 7.80 (s, 1H), 12.23 (brs, 1H), |

TABLE 32

| No. | Structure | NMR(CDCl3 or d6-DMSO) |
|---|---|---|
| C-115 | 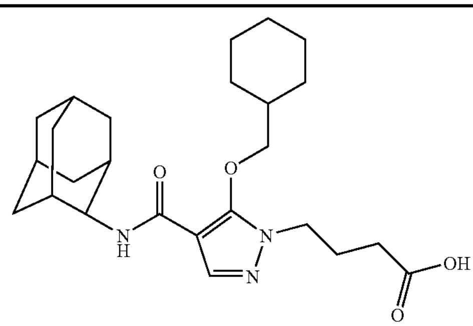 | (CDCl3); 1.00-1.35 (m, 11H), 1.67-1.88 (m, 14H), 3.27 (d, J = 6.0 Hz, 2H), 4.01 (d, J = 6.0 Hz, 2H), 4.18-4.21 (m, 1H), 6.37 (dt, J = 6.0, 14.1 Hz, 1H), 6.48 (d, J = 7.8 Hz, 1H), 6.86 (d, J = 14.1 Hz, 1H), 7.84 (s, 1H) |
| C-116 | 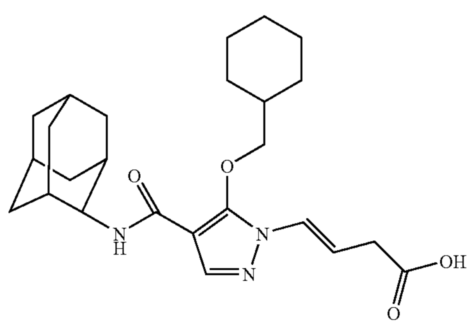 | (CDCl3); 1.01-1.39 (m, 11H), 1.35-2.05 (m, 14H), 2.05-2.17 (m, 2H), 2.37-2.42 (m, 2H), 4.02 (d, J = 6.3 Hz, 2H), 4.06-4.11 (m, 2H), 4.18-4.21 (m, 1H), 6.38 (d, J = 7.8 Hz, 1H), 7.73 (s, 1H) |

TABLE 32-continued

| No. | Structure | NMR(CDCl3 or d6-DMSO) |
|---|---|---|
| C-117 | 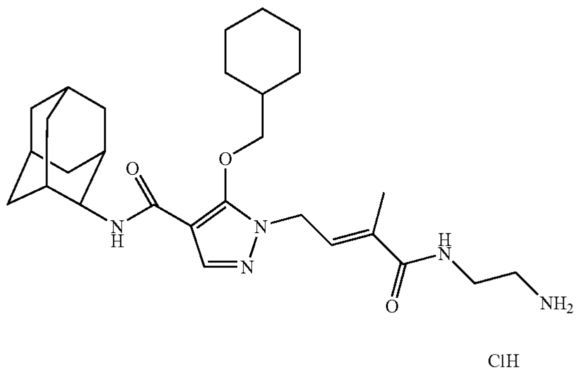 | (DMSO-d6); 0.99-1.24 (m, 11H), 1.50-2.03 (m, 14H), 1.91 (s, 3H), 2.84-2.90 (m, 2H), 3.36-3.50 (m, 2H), 3.96-4.00 (m, 1H), 4.08 (d, J = 6.0 Hz, 2H), 4.71 (d, J = 6.0 Hz, 2H), 6.30 (t, J = 6.0 Hz, 1H), 7.31 (d, J = 7.2 Hz, 1H), 7.83 (s, 1H), 7.89 (bs, 2H), 8.10-8.18 (m, 1H) |
| C-118 | 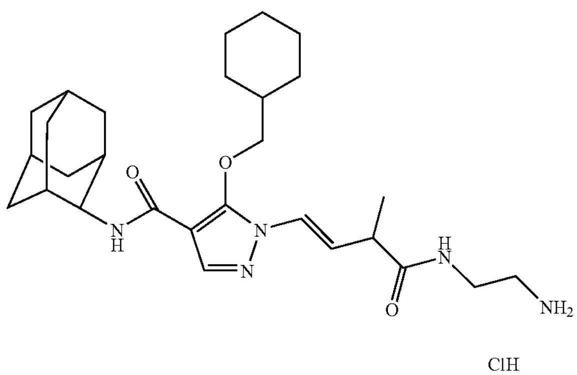 | (DMSO-d6); 1.03-1.22 (m, 11H), 1.50-2.04 (m, 17H), 2.81-2.96 (m, 2H), 3.19-3.50 (m, 2H), 3.60-3.72 (m, 1H), 3.94-4.00 (m, 1H), 4.12 (d, J = 5.1 Hz, 2H), 6.18 (dd, J = 8.4, 14.4 Hz, 1H), 6.89 (d, J = 14.4 Hz, 1H), 7.44 (d, J = 6.9 Hz, 1H), 7.95 (s, 1H), 8.01 (bs, 1H), 8.27 (t, J = 5.4 Hz, 1H) |
| C-119 | 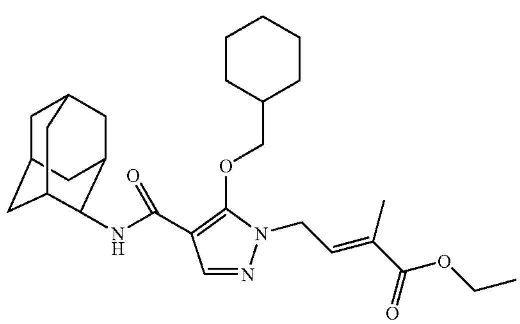 | (CDCl3); 1.02-1.34 (m, 14H), 1.67-2.00 (m, 14H), 1.98 (s, 3H), 4.03 (d, J = 6.3 Hz, 2H), 4.16-4.21 (m, 1H), 4.19 (q, J = 6.9 Hz, 2H), 4.76 (d, J = 6.3 Hz, 2H), 6.35 (d, J = 8.1 Hz, 1H), 6.76 (t, J = 6.3 Hz, 1H), 7.73 (s, 1H) |
| C-120 | 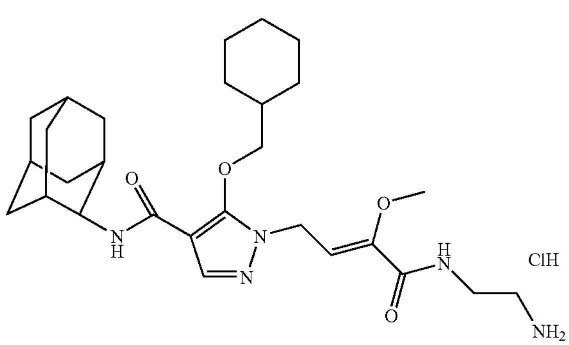 | (DMSO-d6); 1.03-1.26 (m, 11H), 1.56-2.02 (m, 14H), 2.92-3.00 (m, 2H), 3.24-3.21 (m, 2H), 3.39 (s, 3H), 3.46-3.57 (m, 2H), 3.99-4.02 (m, 1H), 4.48-4.51 (m, 2H), 4.64-4.70 (m, 1H) 7.90 (d, J = 7.5 Hz, 1H), 8.22 (bs, 2H), 9.08 (t, J = 6.0 Hz, 1H), 9.20 (s, 1H) |

TABLE 33

| No. | Structure | NMR(CDCl3 or d6-DMSO) |
|---|---|---|
| C-121 | 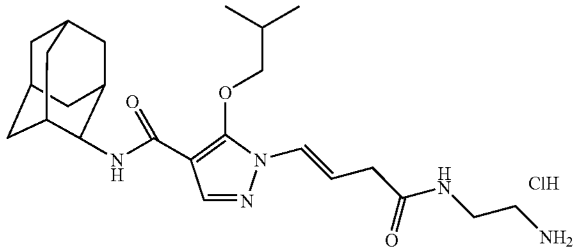 | (DMSO-d6); 0.96 (d, J = 6.6 Hz, 6H), 1.49-2.07 (m, 15H), 2.83-2.91 (m, 2H), 3.07 (d, J = 6.9 Hz, 2H), 3.28-3.40 (m, 2H), 3.96-4.00 (m, 1H), 4.10 (d, J = 6.6 Hz, 2H), 6.20 (dt, J = 6.9, 14.1 Hz, 1H), 6.94 (d, J = 14.1 Hz, 1H), 7.48 (d, J = 6.9 Hz, 1H), 7.92 (s, 1H), 7.96 (bs, 2H), 8.28 (t, J = 6.0 Hz, 1H) |
| C-122 | 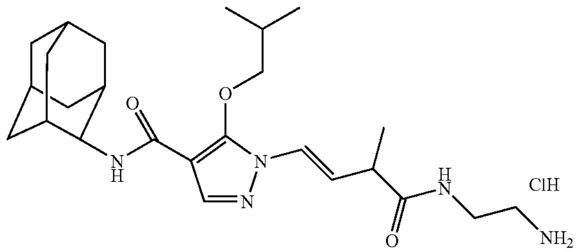 | (DMSO-d6); 0.96 (d, J = 6.6 Hz, 6H), 1.21 (d, J = 6.9 Hz, 3H), 1.71-2.04 (m, 14H), 2.82-2.88 (m, 2H), 3.20-3.40 (m, 4H), 3.95-3.98 (m, 1H), 4.10 (d, J = 6.3 Hz, 2H), 6.19 (dd, J = 8.1, 14.1 Hz, 1H), 6.90 (d, J = 14.1 Hz, 1H) 7.46 (d, J = 7.2 Hz, 1H), 7.97 (bs, 2H), 8.25 (t, J = 5.5 Hz, 1H) |
| C-123 | 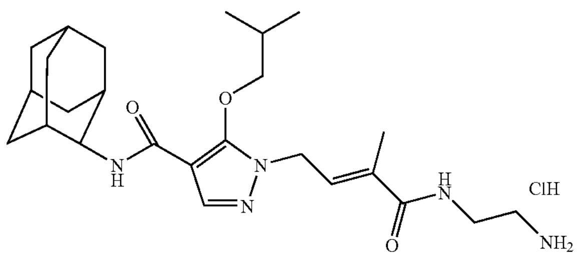 | (DMSO-d6); 0.95 (d, J = 6.9 Hz, 6H), 1.50-2.05 (m, 18H), 2.84-2.90 (m, 2H), 3.32-3.38 (m, 2H), 3.95-3.98 (m, 1H), 4.06 (d, J = 6.6 Hz, 2H), 4.73 (d, J = 6.6 Hz, 2H), 6.31 (t, J = 6.6 Hz, 1H), 7.34 (d, J = 6.9 Hz, 1H), 7.86 (s, 1H), 7.97 (bs, 2H), 8.15 (t, J = 5.4 Hz, 1H) |
| C-124 | 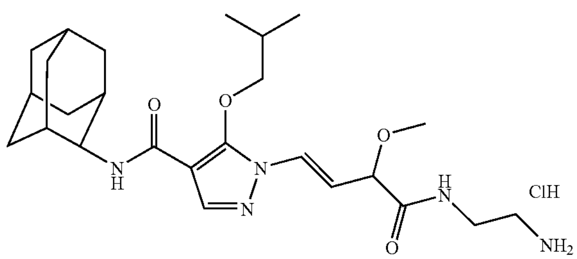 | (DMSO-d6); 0.95 (d, J = 6.9 Hz, 6H), 1.49-2.06 (m, 15H), 2.84-2.97 (m, 2H), 3.19-3.35 (m, 2H), 3.34 (s, 3H), 3.96-3.99 (m, 1H), 4.14 (d, J = 6.6 Hz, 2H), 4.01-4.20 (m, 1H), 6.06 (dd, J = 7.6, 14.1 Hz, 1H), 7.12 (d, J = 14.1 Hz, 1H), 7.54 (d, J = 6.6 Hz, 1H), 7.96 (bs, 2H), 7.99 (s, 1H), 8.28 (t, J = 6.0 Hz, 1H) |
| C-125 | 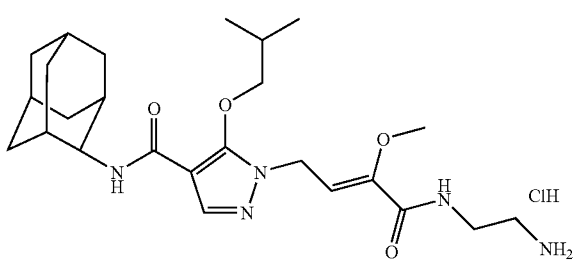 | (DMSO-d6); 0.99 (d, J = 6.6 Hz, 6H), 1.53-2.13 (m, 15H), 2.95-3.00 (m, 2H), 3.15-3.23 (m, 2H), 3.40 (s, 3H), 4.01-4.04 (m, 1H), 4.40-4.81 (m, 5H), 8.02 (d, J = 6.9 Hz, 1H), 8.28 (bs, 2H), 9.11 (t, J = 5.4 Hz, 1H), 9.25 (s, 1H) |
| C-126 | 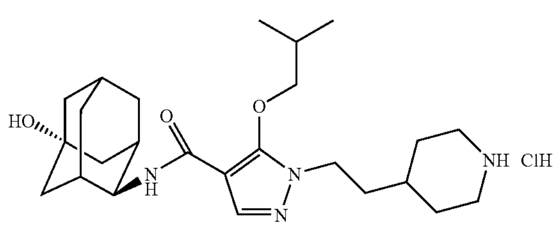 | (DMSO-d6); 0.97 (d, J = 6.9 Hz, 6H), 1.32-2.07 (m, 21H), 2.73-2.89 (m, 2H), 3.19-3.24 (m, 2H), 3.83-3.90 (m, 1H), 3.95 (t, J = 6.9 Hz, 2H), 4.06 (d, J = 6.3 Hz, 2H), 7.27 (d, J = 6.3 Hz, 1H), 7.84 (s, 1H), 8.70 (bs, 1H), 8.92 (bs, 1H) |

TABLE 34

| No. | Structure | NMR(CDCl3 or d6-DMSO) |
|---|---|---|
| C-127 | 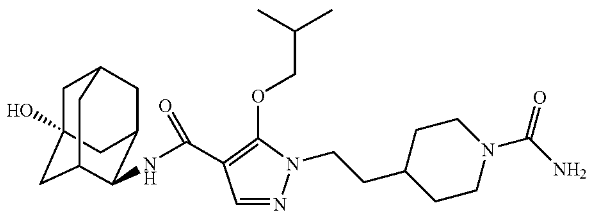 | (CDCl3); 1.05 (d, J = 6.6 Hz, 6H), 1.14-2.20 (m, 21H), 2.75-2.85 (m, 2H), 3.92-4.04 (m, 4H), 4.00 (d, J = 6.9 Hz, 2H), 6.21 (d, J = 7.5 Hz, 1H), 7.68 (s, 1H) |
| C-128 | 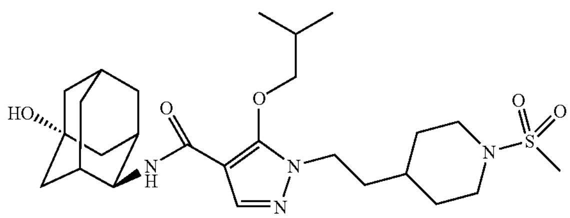 | (CDCl3); 1.06 (d, J = 6.9 Hz, 6H), 1.32-2.20 (m, 21H), 2.59-2.67 (m, 2H), 2.76 (s, 3H), 3.76-3.81 (m, 2H), 4.12 (d, J = 6.9 Hz, 2H) 4.01-4.06 (m, 2H), 4.13-4.18 (m, 1H), 6.21 (d, J = 7.5 Hz, 1H), 7.69 (s, 1H) |
| C-129 | 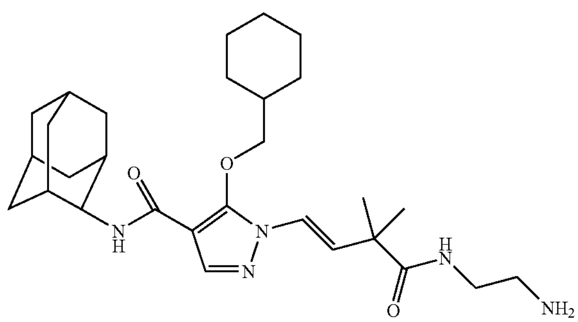 | (DMSO-d6); 1.02-1.31 (m, 11H), 1.31 (s, 6H), 1.50-2.04 (m, 14H) 2.83 (t, J = 6.6 Hz, 2H), 3.25-3.30 (m, 2H), 3.96-3.98 (m, 1H), 4.12 (d, J = 6.0 Hz, 2H), 6.36 (d, J = 14.4 Hz, 1H), 6.79 (d, J = 14.4 Hz, 1H), 7.38 (d, J = 7.2 Hz, 1H), 7.78 (t, J = 6.6 Hz, 1H), 7.84 (bs, 1H), 7.97 (s, 1H) |
| C-130 | 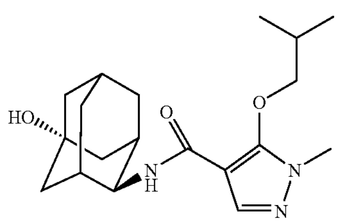 | (CDCl3); 1.06 (d, J = 6.6 Hz, 6H), 1.53-2.20 (m, 14H), 3.72 (s, 3H), 3.98 (d, J = 6.6 Hz, 2H), 6.25-6.30 (m, 1H), 7.71 (s, 1H) |
| C-131 | 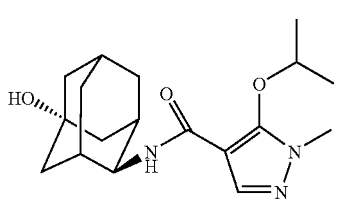 | (CDCl3); 1.38 (d, J = 6.0 Hz, 6H), 1.54-2.20 (m, 13H), 3.71 (s, 3H), 4.12-4.20 (m, 1H), 4.69-4.78 (m, 1H), 6.30-6.38 (m, 1H), 7.75 (s, 1H) |
| C-132 | 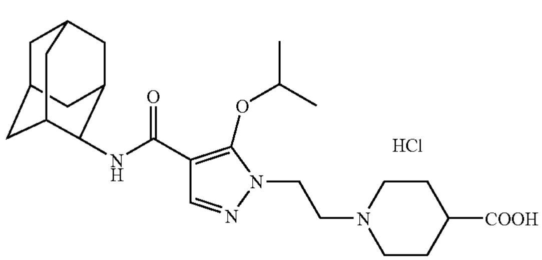 | (DMSO-d6); 1.27 (d, J = 6.3 Hz, 6H), 1.51-2.03 (m, 19H), 2.99-3.32 (m, 6H), 3.97-3.99 (m, 1H), 4.34 (m, 2H), 4.93-5.02 (m, 1H), 7.29 (d, J = 6.9 Hz, 1H), 7.93 (s, 1H), 10.49 (brs, 1H), 12.32 (brs, 1H) |

TABLE 35

| No. | Structure | NMR (CDCl3 or d6-DMSO) |
|---|---|---|
| C-133 | 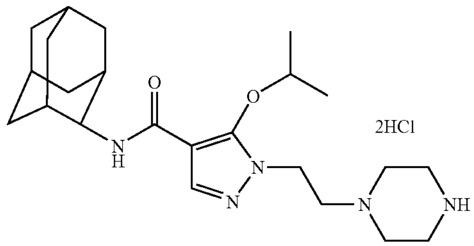 | (DMSO-d6); 1.28 (d, J = 6.3 Hz, 6 H), 1.51-2.04 (m, 14 H), 3.37 (m, 10 H), 3.97-3.99 (m, 1 H), 4.35 (m, 2 H), 4.93-5.01 (m, 1 H), 7.31 (d, J = 7.2 Hz, 1 H), 7.95 (s, 1 H), 9.49 (m, 3 H) |
| C-134 | 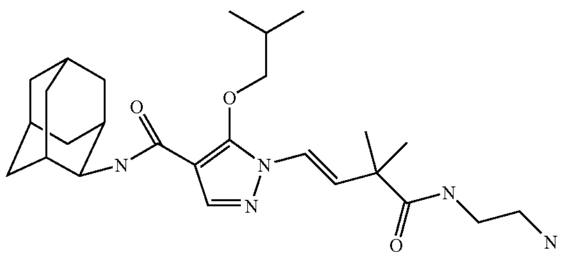 | (CDCl3); 1.05 (d, J = 6.6 Hz, 6 H), 1.41 (s, 6 H), 1.65-1.99 (m, 14 H), 2.03-2.20 (m, 1 H), 3.12-3.29 (m, 2 H), 3.54-3.70 (m, 2 H), 4.06 (d, J = 5.4 Hz, 2 H), 4.11-4.20 (m, 1 H), 6.52 (d, J = 13.8 Hz, 1 H), 6.66-6.73 (m, 1 H), 6.84 (d, J = 13.8 Hz, 1 H), 7.50-7.64 (m, 1 H), 7.93 (s, 1 H), 8.32 (bs, 2 H) |
| C-135 | 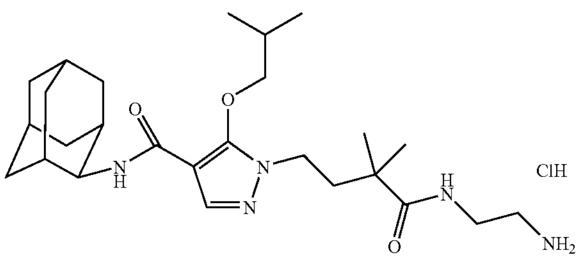 | (DMSO-d6); 0.98 (d, J = 6.6 Hz, 6 H), 1.15 (s, 6 H), 1.50-2.04 (m, 17 H), 2.82-2.88 (m, 2 H), 3.26-3.33 (m, 2 H), 3.81-3.89 (m, 2 H), 3.95-3.98 (m, 1 H), 4.03 (d, J = 6.6 Hz, 2 H), 7.25 (d, J = 6.9 Hz, 1 H), 7.81 (s, 1 H), 7.81-7.87 (m, 1 H), 7.87 (bs, 2 H) |
| C-136 | 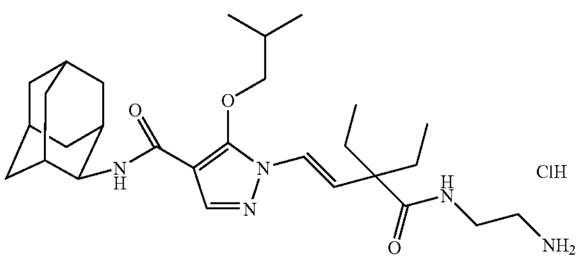 | (DMSO-d6); 0.76 (t, J = 7.2 Hz, 6 H), 0.97 (d, J = 6.6 Hz, 6 H), 1.50-2.04 (m, 19 H), 2.78-2.90 (m, 2 H), 3.33-3.41 (m, 2 H), 3.96-4.03 (m, 1 H), 4.11 (d, J = 6.6 Hz, 2 H), 6.31 (d, J = 11.7 Hz, 1 H), 6.83 (d, J = 11.7 Hz, 1 H), 7.44 (d, J = 6.9 Hz, 1 H), 7.86-7.94 (m, 1 H), 7.98 (s, 1 H), 8.07 (bs, 2 H) |
| C-137 | 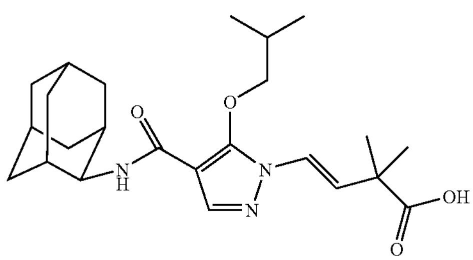 | (CDCl3): 1.06 (d, J = 6.6 Hz, 6 H), 1.45 (s, 6 H), 1.67-2.05 (m, 14 H), 2.08-2.17 (m, 1 H), 3.99 (d, J = 6.9 Hz, 2 H), 4.19-4.22 (m, 1 H), 6.46 (d, J = 8.1 Hz, 1 H), 6.54 (d, J = 14.4 Hz, 1 H), 6.86 (d, J = 14.4 Hz, 1 H), 7.84 (s, 1 H) |
| C-138 | 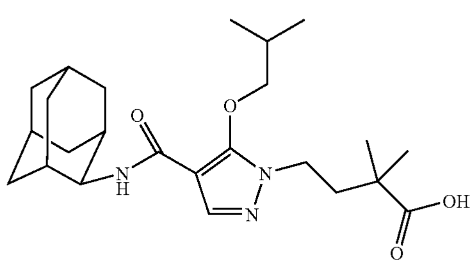 | (CDCl3); 1.05 (d, J = 6.6 Hz, 6 H), 1.28 (s, 6 H), 1.66-1.99 (m, 16 H), 2.02-2.16 (m, 1 H), 4.00 (d, J = 6.6 Hz, 2 H), 4.04-4.08 (m, 2 H), 4.16-4.20 (m, 1 H), 6.38 (d, J = 7.8 Hz, 1 H), 7.73 (s, 1 H) |

TABLE 36

| No. | Structure | NMR (CDCl3 or d6-DMSO) |
|---|---|---|
| C-139 | 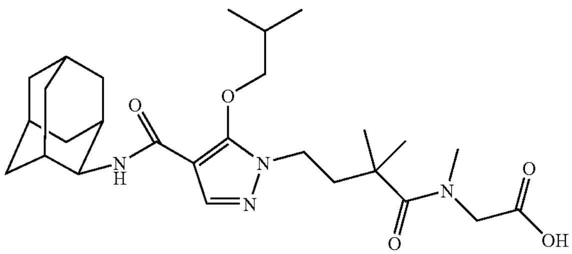 | (CDCl3); 1.04 (d, J = 6.6 Hz, 6 H), 1.37 (s, 6 H), 1.66-2.09 (m, 16 H), 2.11-2.18 (m, 1 H), 2.18 (s, 3 H), 3.98 (d, J = 6.6 Hz, 2 H), 4.03-4.07 (m, 2 H), 4.17-4.22 (m, 1 H), 6.46 (d, J = 7.8 Hz, 1 H), 7.73 (s, 1 H) |
| C-140 | Chiral | (CDCl3); 1.07 (d, J = 6.6 Hz, 6 H), 1.12 (s, 9 H), 1.42 (s, 3 H), 1.44 (s, 3 H), 1.67-2.10 (m, 14 H), 2.10-2.19 (m, 1 H), 3.52-3.57 (m, 1 H), 3.84-3.88 (m, 1 H), 4.00 (d, J = 6.6 Hz, 2 H), 4.18-4.22 (m, 1 H), 4.58-4.64 (m, 1 H), 6.50 (d, J = 14.1 Hz, 1 H), 6.49-6.52 (m, 1 H), 6.62 (d, J = 7.8 Hz, 1 H), 6.94 (d, J = 14.1 Hz, 1 H), 7.84 |
| C-141 | ClH | (DMSO-d6): 0.97 (d, J = 6.4 Hz, 6 H), 1.31 (s, 6 H), 1.01-2.06 (m, 14 H), 2.79-2.87 (m, 2 H), 3.27-3.35 (m, 2 H), 3.86-3.91 (m, 1 H), 4.11 (d, J = 5.6 Hz, 2 H), 6.36 (d, J = 15.2 Hz, 1 H), 6.81 (d, J = 15.2 Hz, 1 H), 7.38 (d, J = 6.4 Hz, 1 H), 7.83-7.89 (m, 1 H), 7.98 (s, 1 H), 8.02-8.11 (br, 2 H) |
| C-142 | 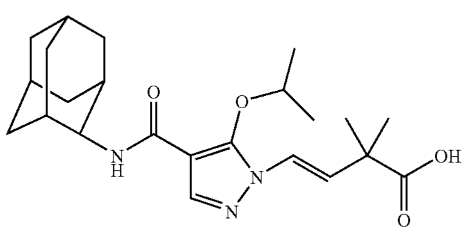 | (DMSO-d6): 1.25 (d, J = 6.0 Hz, 6 H), 1.27 (s, 6 H), 1.51-2.04 (m, 13 H), 3.97-4.02 (m, 1 H), 4.84-4.91 (m, 1 H), 6.45 (d, J = 14.4 Hz, 1 H), 6.76 (d, J = 14.4 Hz, 1 H), 7.35 (d, J = 6.9 Hz, 1 H), 8.01 (s, 1 H) |
| C-143 | 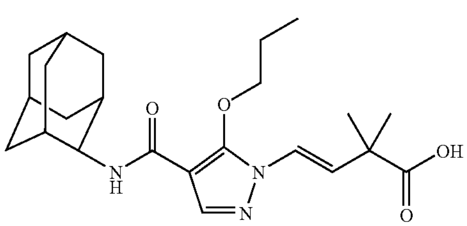 | (DMSO-d6) 0.96 (t, J = 7.4 Hz, 3 H), 1.32 (s, 6 H), 1.45-2.05 (m, 16 H), 3.97 (m, 1 H), 4.27 (t, J = 6.4 Hz, 2 H), 6.36 (d, J = 14.4 Hz, 1 H), 6.82 (d, J = 14.4 Hz, 1 H), 7.41 (d, J = 7.1 Hz, 1 H), 7.98 (s, 1 H), 12.49 (brs, 1 H) |

TABLE 36-continued

| No. | Structure | NMR (CDCl3 or d6-DMSO) |
|---|---|---|
| C-144 | 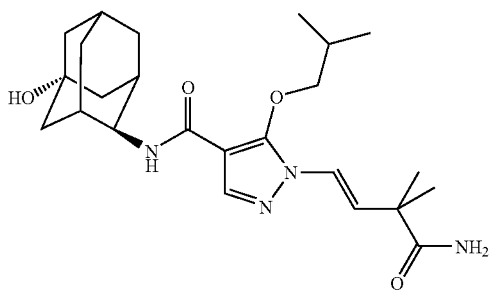 | (DMSO-d6); 0.98 (d, J = 6.8 Hz, 6 H), 1.27 (s, 6 H), 1.34 (d, J = 12.4 Hz, 2 H), 1.61-2.04 (m, 12 H), 3.89 (brs, 1 H), 4.10 (d, J = 6.4 Hz, 2 H), 4.42 (s, 1 H), 6.37 (d, J = 14.4 Hz, 1 H), 6.81 (d, J =14.0 Hz, 1 H), 6.92 (s, 1 H), 7.14 (s, 1 H), 7.37 (d, J = 6.4 Hz, 1 H), |

TABLE 37

| No. | Structure | NMR (CDCl3 or d6-DMSO) |
|---|---|---|
| C-145 | 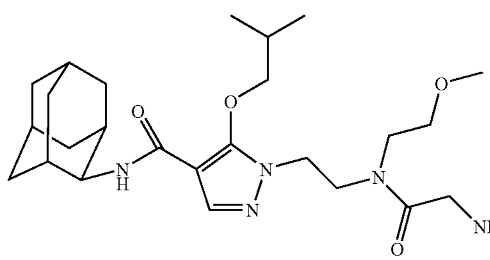 | (DMSO-d6); 0.97 (d, J = 6.9 Hz, 6 H), 1.49-2.04 (m, 15 H), 3.45 (s, 3 H), 3.35-4.15 (m, 13 H), 7.32 (d, J = 6.9 Hz, 1 H), 7.86 (s, 1 H), 8.12 (bs, 2 H) |
| C-146 | 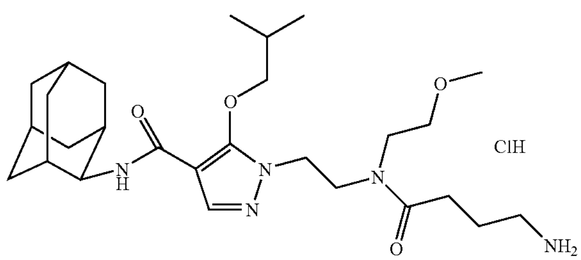 | (DMSO-d6); 1.03 (d, J = 6.9 Hz, 6 H), 1.57-2.11 (m, 15 H), 2.30-2.51 (m, 2 H), 2.71-2.90 (m, 2 H), 3.29 (s, 3 H), 3.57-4.20 (m, 13 H), 7.37 (d, J = 7.2 Hz, 1 H), 787 (bs, 2 H), 7.95 (s, 1 H) |
| C-147 | 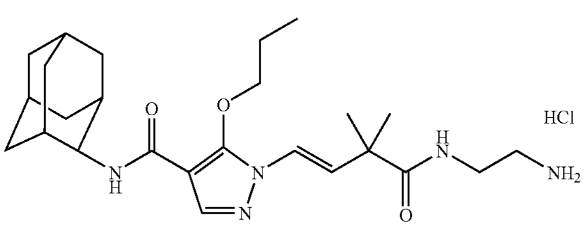 | (DMSO-d6) 0.97 (t, J = 7.3 Hz, 3 H), 1.31 (s, 6 H), 1.45-2.05 (m, 14 H), 2.50 (m, 2 H), 2.82 (m, 2 H), 3.29 (m, 2 H), 3.99 (m, 1 H), 4.28 (t, J = 6.5 Hz, 2 H), 6.36 (d, J = 14.3 Hz, 1 H), 6.80 (d, J = 14.3 Hz, 1 H), 7.40 (d, J = 6.9 Hz, 1 H), 7.80 (brs, 1 H), 7.89 (brs, 2 H), 7.99 |
| C-148 | 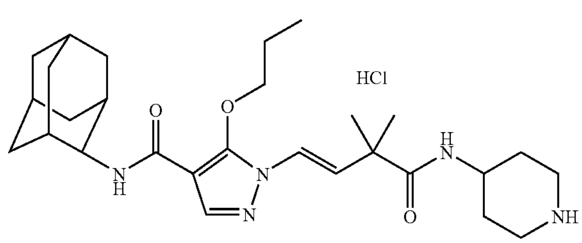 | (DMSO-d6) 0.96 (t, J = 7.4 Hz, 3 H), 1.29 (s, 6 H), 1.45-2.05 (m, 20 H), 2.80-3.00 (m, 2 H), 3.20-3.30 (m, 2 H), 3.81 (m, 1 H), 3.97 (m, 1 H), 4.27 (t, J = 6.5 Hz, 2 H), 6.39 (d, J = 14.3 Hz, 1 H), 6.76 (d, J = 14.3 Hz, 1 H), 7.42 (d, J = 7.0 Hz, 1 H), 7.62 (d, J = 7.8 Hz, 1 H), |

TABLE 37-continued

| No. | Structure | NMR (CDCl3 or d6-DMSO) |
|---|---|---|
| C-149 | 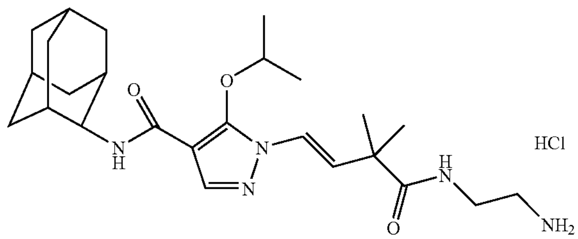 | (DMSO-d6): 1.04 (d, J = 6.2 Hz, 6 H), 1.09 (s, 6 H), 1.28-1.81 (m, 15 H), 2.55-2.64 (m, 2 H), 3.04-3.10 (m, 2 H), 3.73-3.77 (m, 1 H), 4.64-4.73 (m, 1 H), 6.15 (d, J = 14.4 Hz, 1 H), 6.56 (d, J = 14.4 Hz, 1 H), 7.12 (d, J = 6.9 Hz, 1 H), 7.59 (t, J = 5.5 Hz, 1 H), 7.71 (br, s, 2 H), 7.81 (s, 1 H) |
| C-150 | 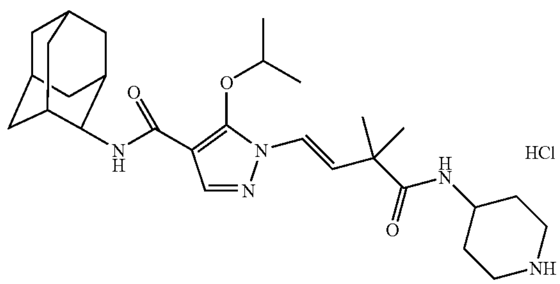 | (DMSO-d6): 1.12 (d, J = 6.0 Hz, 6 H), 1.15 (s, 6 H), 1.40-1.89 (m, 17 H), 2.73-2.85 (m, 2 H), 3.08-3.21 (m, 2 H), 3.66-3.70 (m, 1 H), 3.82-3.85 (m, 1 H), 4.73-4.82 (m, 1 H), 6.25 (d, J = 14.3 Hz, 1 H), 6.61 (d, J = 14.3 Hz, 1 H), 7.22 (d, J = 6.9 Hz, 1 H), 7.46 (d, J = 7.6 Hz, 1 H), 7.88 (s, 1 H), 7.46 (d, J = 7.6 Hz, 1 H), 7.88 (s, 1 H), 8.63 (br.s, 2 H) |

TABLE 38

| No. | Structure | NMR (CDCl3 or d6-DMSO) |
|---|---|---|
| C-151 | 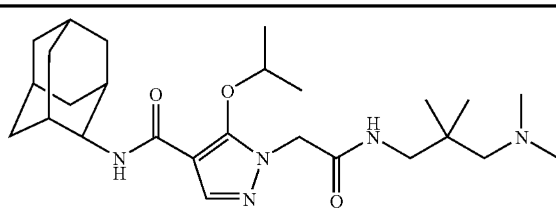 | (DMSO-d6) 0.80 (s, 6 H), 1.23 (d, J = 6.2 Hz, 6 H), 1.45-2.13 (m, 16 H), 2.16 (s, 6 H), 2.98 (d, J = 5.9 Hz, 2 H), 3.99 (m, 1 H), 4.61 (s, 2 H), 4.95 (m, 1 H), 7.26 (d, J = 6.7 Hz, 1 H), 7.91 (s, 1 H), 7.95 (brs, 1 H) |
| C-152 | 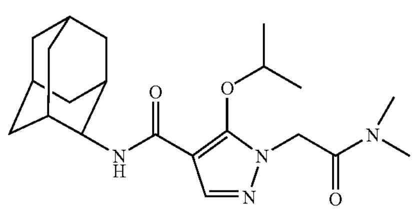 | (DMSO-d6) 1.22 (d, J = 6.1 Hz, 6 H), 1.45-2.10 (m, 14 H), 2.84 (s, 3 H), 3.05 (s, 3 H), 3.98 (m, 1 H), 4.87 (s, 2 H), 4.90 (m, 1 H), 7.26 (d, J = 7.0 Hz, 1 H), 7.85 (s, 1 H) |
| C-153 | 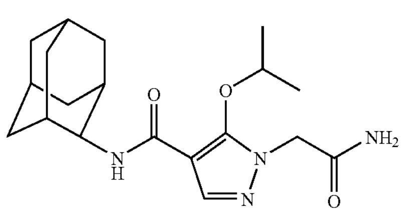 | (DMSO-d6) 1.23 (d, J = 6.0 Hz, 6 H), 1.45-2.05 (m, 14 H), 3.98 (m, 1 H), 4.53 (s, 2 H), 4.91 (sep, J = 6.1 Hz, 1 H), 7.21 (brs, 1 H), 7.24 (brs, 1 H), 7.47 (brs, 1 H), 7.86 (s, 1 H) |
| C-154 | 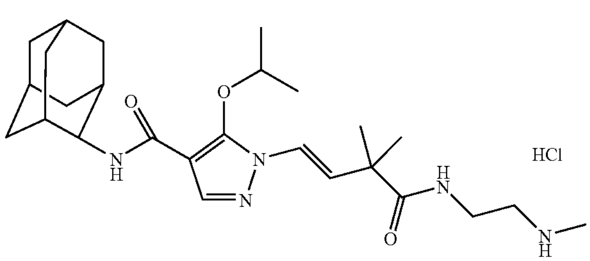 | (DMSO-d6): 1.23 (d, J = 6.2 Hz, 6 H), 1.28 (s, 6 H), 1.47-2.00 (m, 13 H), 2.50 (t, J = 6.0 Hz, 3 H), 2.87-2.91 (m, 2 H), 3.28-3.32 (m, 2 H), 3.94-3.96 (m, 1 H), 4.85-4.91 (m, 1 H), 6.34 (d, J = 14.4 Hz, 1 H), 6.76 (d, J = 14.4 Hz, 1 H), 7.33 (d, J = 7.0 Hz, 1 H), 7.85 (t, J = 5.5 Hz, 1 H), 8.00 (s, 1 H), 8.78 (br, s, |

TABLE 38-continued

| No. | Structure | NMR (CDCl3 or d6-DMSO) |
|---|---|---|
| C-155 | 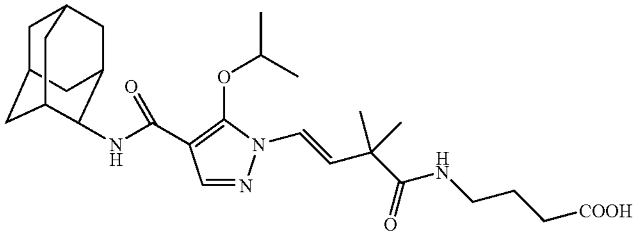 | (DMSO-d6): 1.27 (d, J = 6.3 Hz, 6 H), 1.28 (s, 6 H), 1.50-3.09 (m, 19 H), 3.97-4.01 (m, 1 H), 4.86-4.94 (m, 1 H), 6.35 (d, J = 14.3 Hz, 1 H), 6.76 (d, J = 14.3 Hz, 1 H), 7.36 (d, J = 6.9 Hz, 1 H), 7.63 (t, J = 5.6, 1 H), 8.02 (s, 1 H) |
| C-156 | 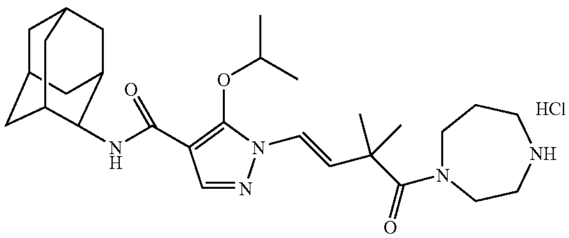 | (DMSO-d6): 1.07 (d, J = 6.0 Hz, 6 H), 1.16 (s, 6 H), 1.32-1.84 (m, 15 H), 2.94-3.47 (m, 8 H), 3.77-3.81 (m, 1 H), 4.70-4.74 (m, 1 H), 6.34 (d, J = 14.4 Hz, 1 H), 6.63 (d, J = 14.4 Hz, 1 H), 7.17 (d, J = 6.9 Hz, 1 H), 7.85 (s, 1 H), 8.68 (br, s, 2 H) |

TABLE 39

| No. | Structure | NMR (CDCl3 or d6-DMSO) |
|---|---|---|
| C-157 | 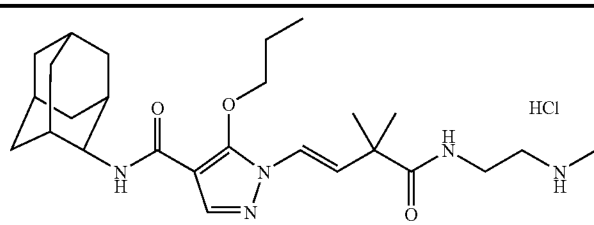 | (DMSO-d6) 0.97 (t, J = 7.4 Hz, 3 H), 1.32 (s, 6 H), 1.45-2.10 (m, 17 H), 2.54 (m, 2 H), 2.85-3.00 (m, 2 H), 3.30-3.40 (m, 2 H), 3.96 (m, 1 H), 4.28 (t, J = 6.5 Hz, 2 H), 6.37 (d, J = 14.1 Hz, 1 H), 6.80 (d, J = 14.1 Hz, 1 H), 7.40 (d, J = 6.7 Hz, 1 H), 7.88 (t, J = 5.3 Hz, 1 H), 7.99 (s, 1 H), 8.76 (brs, 1 H) |
| C-158 | 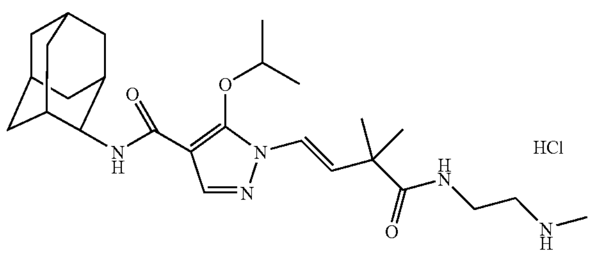 | (DMSO-d6): 1.08 (s, 6 H), 1.16 (d, J = 6.2 Hz, 6 H), 1.41-1.99 (m, 15 H), 2.45-2.48 (t, J = 5.5 Hz, 3 H), 2.84-2.88 (m, 2 H), 3.26-3.31 (m, 2 H), 3.72-3.77 (m, 2 H), 3.88-3.89 (m, 1 H), 4.76-4.82 (m, 1 H), 7.12 (d, J = 7.1 Hz, 1 H), 7.76 (s, 1 H), 7.86 (t, J = 6.0 Hz, 1 H), 8.78 (br, 2 H) |
| C-159 | 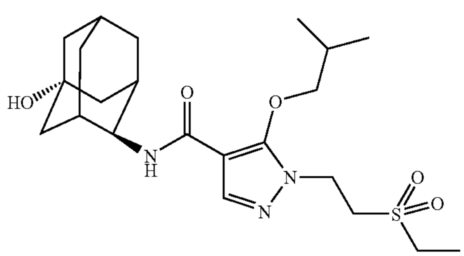 | (DMSO-d6); 0.98 (d, J = 6.8 Hz, 6 H), 1.19 (t, J = 7.2 Hz, 3 H), 1.34 (d, J = 12.0 Hz, 2 H), 1.58-1.72 (m, 6 H), 1.88-2.07 (m, 6 H), 3.06 (q, J = 7.2 Hz, 2 H), 3.60 (t, J = 6.8 Hz, 2 H), 3.88 (brs, 1 H), 4.10 (d, J = 6.8 Hz, 2 H), 4.35 (t, J = 6.8 Hz, 2 H), 4.43 (s, 1 H), 7.30 (d, J = 6.4 Hz, 1 H), 7.89 (s, 1 H) |
| C-160 | 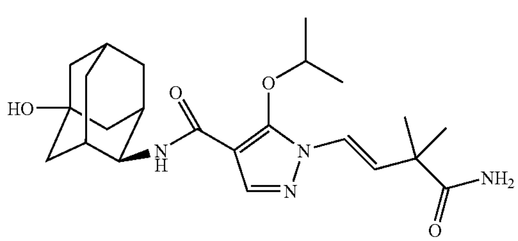 | (CDCl3): 1.38 (d, J = 6.0 Hz, 6 H), 1.42 (s, 6 H), 1.54-2.19 (m, 13 H), 4.13-4.20 (m, 1 H), 4.74 (ddd, J = 6.0 Hz, 1 H), 5.52 (bs, 1 H), 5.81 (bs, 1 H), 6.34 (d, J = 7.8 Hz, 1 H), 6.49 (d, J = 14.4 Hz, 1 H), 6.87 (d, J = 14.4 Hz, 1 H), 7.84 (s, 1 H) |

TABLE 39-continued

| No. | Structure | NMR (CDCl3 or d6-DMSO) |
|---|---|---|
| C-161 | 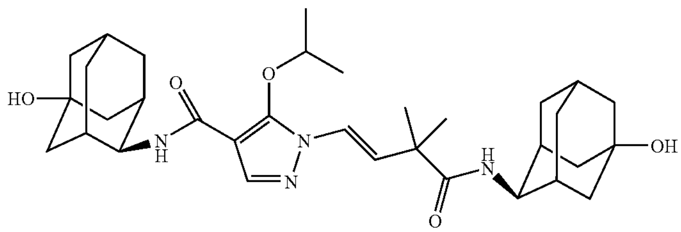 | (CDCl3); 1.39 (d, J = 6.0 Hz, 6 H), 1.42 (s, 6 H), 1.49-2.20 (m, 26 H), 3.94-3.97 (m, 1 H), 4.15-4.19 (m, 1 H), 4.76 (ddd, J = 6.0 Hz, 1 H), 5.94 (d, J = 7.8 Hz, 1 H), 6.34 (d, J = 7.8 Hz, 1 H), 6.50 (d, J = 14.1 Hz, 1 H), 6.89 (d, J = 14.1 Hz, 1 H), 7.85 (s, 1 H) |
| C-162 | 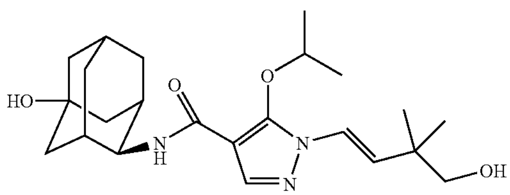 | (CDCl3): 1.15 (s, 6 H), 1.39 (d, J = 6.0 Hz, 6 H), 1.55-2.20 (m, 13 H), 3.45 (s, 2 H), 4.16-4.19 (m, 1 H), 4.72 (ddd, J = 6.0 Hz, 1 H), 6.31 (d, J = 14.4 Hz, 1 H), 6.39 (d, J = 6.6 Hz, 1 H), 6.74 (d, J = 14.4 Hz, 1 H), 7.85' s, 1 H) |

TABLE 40

| No. | Structure | NMR (CDCl3 or d6-DMSO) |
|---|---|---|
| C-163 | 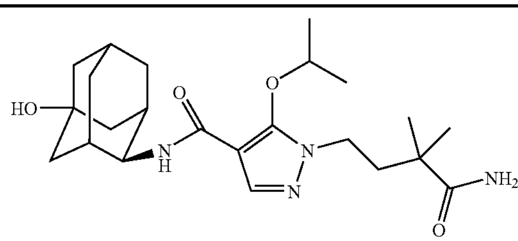 | (CDCl3); 1.28 (s, 6 H), 1.37 (d, J = 6.0 Hz, 6 H), 1.53-2.19 (m, 15 H), 4.00-4.06 (m, 2 H), 4.12-4.20 (m, 1 H), 4.78 (ddd, J = 6.0 Hz, 1 H), 5.40 (bs, 1 H), 5.84 (bs, 1 H), 6.33 (d, J = 6.6 Hz, 1 H), 7.76 (s, 1 H) |
| C-164 | 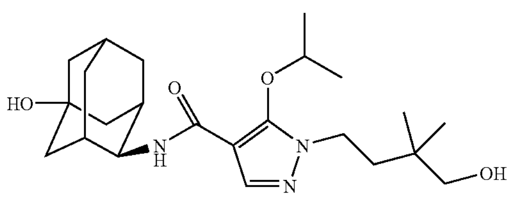 | (CDCl3); 0.96 (s, 6 H), 1.38 (d, J = 6.3 Hz, 6 H), 1.54-2.20 (m, 15 H), 3.34 (s, 2 H), 4.00-4.05 (m, 2 H), 4.15-4.18 (m, 1 H), 4.81 (ddd, J = 6.3 Hz, 1 H), 6.33 (d, J = 7.8 Hz, 1 H), 7.78 (s, 1 H) |
| C-165 | 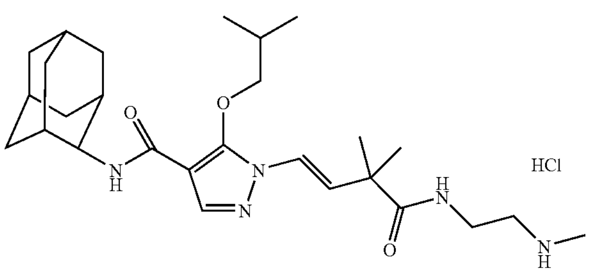 | (DMSO-d6): 1.04 (d, J = 6.0 Hz, 6 H), 1.31 (s, 6 H), 1.50-2.96 (m, 21 H), 3.95-3.99 (m, 1 H), 4.11 (d, J = 6.4 Hz, 2 H), 6.37 (d, J = 14.3 Hz, 1 H), 6.82 (d, J = 14.3 Hz, 1 H), 7 42 (d, J = 7.2 Hz, 1 H), 7.86 (t, J = 5.3 Hz, 1 H), 7.99 (s, 1 H), 8.67 (br, s, 2 H) |
| C-166 | 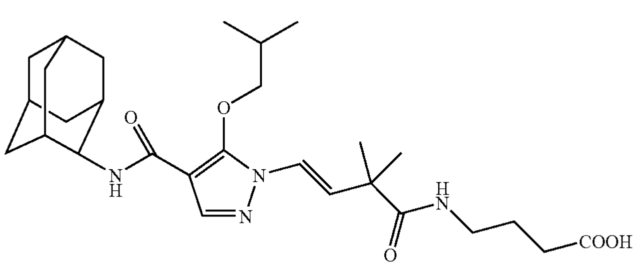 | (DMSO-d6): 0.97 (d, J = 6.6 Hz, 6 H), 1.27 (s, 6 H), 1.50-3.14 (m, 20 H), 3.97-3.99 (m, 1 H), 4.10 (d, J = 6.4 Hz, 2 H), 6.35 (d, J = 14.3 Hz, 1 H), 6.79 (d, J = 14.3 Hz, 1 H), 7.41 (d, J = 6.9 Hz, 1 H), 7.66 (t, J = 6.0 Hz, 1 H), 7.97 (s, 1 H) |

TABLE 40-continued

| No. | Structure | NMR (CDCl3 or d6-DMSO) |
|---|---|---|
| C-167 | 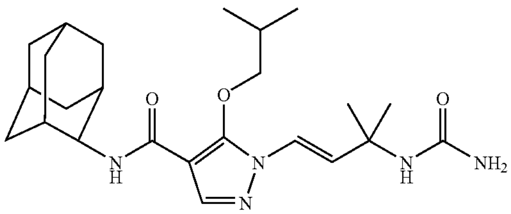 | (DMSO-d6); 0.98 (d, J = 6.4 Hz, 6 H), 1.38 (s, 6 H), 1.52 (d, J = 12.4 Hz, 2 H), 1.70-2.04 (m, 13 H), 3.98 (brs, 1 H), 4.07 (d, J = 6.4 Hz, 2 H), 5.31 (s, 2 H), 6.09 (s, 1 H), 6.37 (d, J = 14.4 Hz, 1 H), 6.81 (d, J = 14.0 Hz, 1 H), 7.40 (d, J = 6.8 Hz, 1 H), 7.95 (s, 1 H) |
| C-168 | 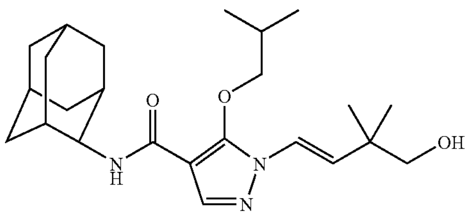 | (DMSO-d6): 0.98 (d, J = 6.8 Hz, 6 H), 1.03 (s, 6 H), 1.52 (d, J = 12.4 Hz, 2 H), 1.71-2.04 (m, 13 H), 3.23 (d, J = 5.2 Hz, 2 H), 3.98 (brs, 1 H), 4.08 (d, J = 6.4 Hz, 2 H), 4.75 (t, J = 5.6 Hz, 1 H), 6.22 (d, J = 14.4 Hz, 1 H), 6.74 (d, J = 14.4 Hz, 1 H), 7.39 (d, J = 7.2 Hz, 1 H), 7.95 (s, 1 H) |

TABLE 41

| No. | Structure | NMR (CDCl3 or d6-DMSO) |
|---|---|---|
| C-169 | 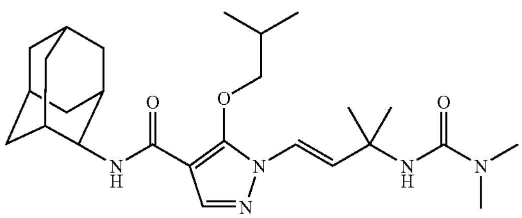 | (DMSO-d6); 0.97 (d, J = 6.8 Hz, 6 H), 1.42 (s, 6 H), 1.52 (d, J = 12.0 Hz, 2 H), 1.70-2.08 (m, 13 H), 2.78 (s, 6 H), 3.98 (brs, 1 H), 4.06 (d, J = 6.0 Hz, 2 H), 5.79 (s, 1 H), 6.40 (d, J = 14.4 Hz, 1 H), 6.80 (d, J = 14.8 Hz, 1 H), 7.37 (d, J = 6.8 Hz, 1 H), 7.95 (s, 1 H) |
| C-170 | 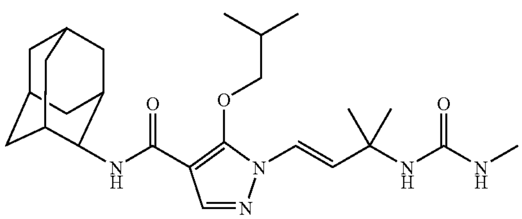 | (DMSO-d6); 0.97 (d, J = 6.8 Hz, 6 H), 1.38 (s, 6 H), 1.52 (d, J = 12.8 Hz, 2 H), 1.71-2.04 (m, 13 H), 2.50 (s, 3 H), 3.99 (brs, 1 H), 4.06 (d, J = 6.4 Hz, 2 H), 5.58-5.62 (m, 1 H), 5.98 (s, 1 H), 6.35 (d, J = 14.0 Hz, 1 H), 6.79 (d, J = 14.4 Hz, 1 H), 7.38 (d, J = 6.8 Hz, 1 H), 7.94 (s, 1 H) |
| C-171 | 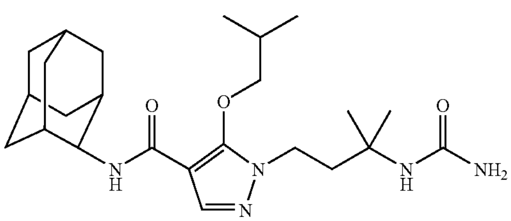 | (DMSO-d6): 0.98 (d, J = 6.4 Hz, 6 H), 1.20 (s, 6 H), 1.52 (d, J = 11.6 Hz, 2 H), 1.70-2.11 (m, 15 H), 3.88-3.93 (m, 2 H), 3.98 (brs, 1 H), 4.02 (d, J = 6.8 Hz, 2 H), 5.24 (s, 2 H), 5.80 (s, 1 H), 7.22 (d, J = 6.4 Hz, 1 H), 7.79 (s, 1 H) |
| C-172 | 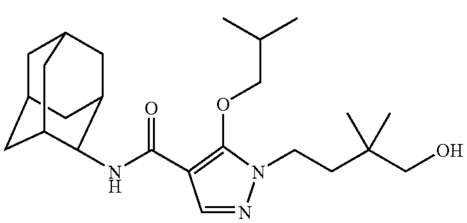 | (DMSO-d6): 0.85 (s, 6 H), 0.98 (d, J = 6.4 Hz, 6 H), 1.52 (d, J = 12.4 Hz, 2 H), 1.59-2.05 (m, 15 H), 3.13 (brs, 2 H), 3.91-3.99 (m, 3 H), 4.04 (d, J = 6.4 Hz, 2 H), 4.60 (brs, 1 H), 7.23 (d, J = 6.4 Hz, 1 H), 7.79 (s, 1 H) |

TABLE 41-continued

| No. | Structure | NMR (CDCl3 or d6-DMSO) |
|---|---|---|
| C-173 | 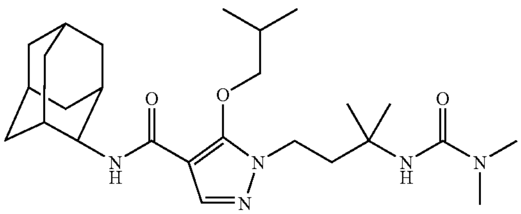 | (DMSO-d6); 0.97 (d, J = 6.8 Hz, 6 H), 1.26 (s, 6 H), 1.53 (d, J = 12.8 Hz, 2 H), 1.70-2.04 (m, 13 H), 2.13 (t, J = 7.6 Hz, 2 H), 2.76 (s, 6 H), 3.89 (t, J = 7.6 Hz, 2 H), 3.98-4.02 (m, 3 H), 5.41 (s, 1 H), 7.21 (d, J = 6.4 Hz, 1 H), 7.80 (s, 1 H) |
| C-174 | 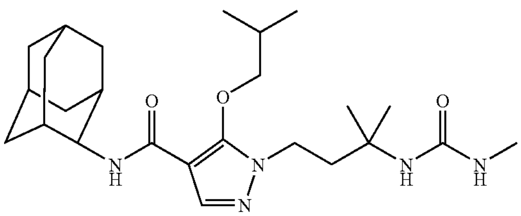 | (DMSO-d6); 0.98 (d, J = 6.4 Hz, 6 H), 1.20 (s, 6 H), 1.53 (d, J = 12.4 Hz, 2 H), 1.70-2.04 (m, 13 H), 2.09 (t, J = 8.0 Hz, 2 H), 2.51 (s, 3 H), 3.90 (t, J = 7.6 Hz, 2 H), 3.96-4.02 (m, 3 H), 5.51-5.57 (brm, 1 H), 5.66 (s, 1 H), 7.21 (d, J = 6.4 Hz, 1 H), 7.79 (s, 1 H) |

TABLE 42

| No. | Structure | NMR (CDCl3 or d6-DMSO) |
|---|---|---|
| C-175 | 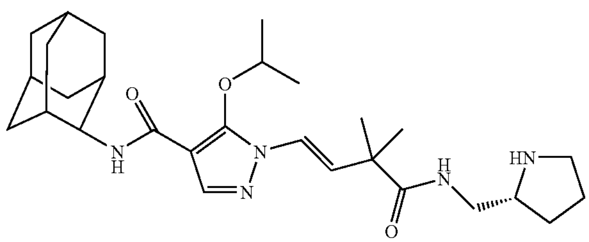 | (DMSO-d6): 1.26 (d, J = 6.0 Hz, 6 H), 1.29 (s, 6 H), 1.51-3.11 (m, 21 H), 3.97-3.99 (m, 1 H), 4.87-4.93 (m, 1 H), 6.36 (d, J = 14.4 Hz, 1 H), 6.79 (J = 14.4 Hz, 1 H), 7.35 (d, J = 7.1 Hz, 1 H), 7.44 (t, J = 5.5 Hz, 1 H), 8.0 (s, 1 H) |
| C-176 | 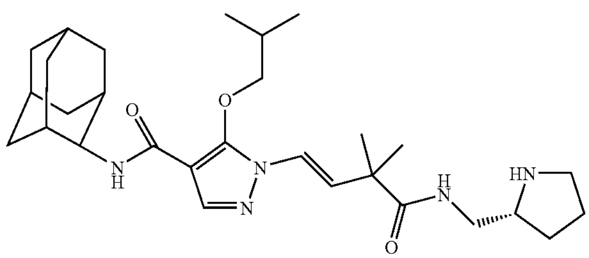 | (DMSO-d6): 097 (d, J = 6.7 Hz, 6 H), 1.28 (s, 6 H), 1.50-3.23 (m, 22 H), 3.96-3.98 (m, 1 H), 4.10 (d, J = 6.4 Hz, 2 H), 6.35 (d, J = 14.3 Hz, 1 H), 6.80 (d, J = 14.3 Hz, 1 H), 7.41-7.45 (m, 2 H), 7.97 (s, 1 H) |
| C-177 | 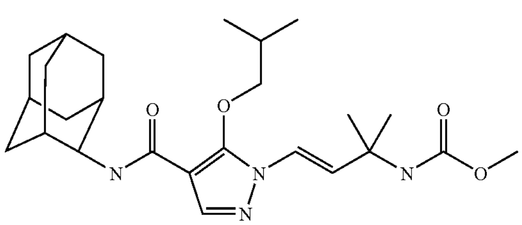 | (DMSO-d6): 0.97 (d, J = 6.8 Hz, 6 H), 1.39 (s, 6 H), 1.52 (d, J = 13.2 Hz, 2 H), 1.70-2.04 (m, 13 H), 3.49 (s, 3 H), 3.97 (brs, 1 H), 4.08 (d, J = 6.4 Hz, 2 H), 6.30 (d, J = 14.0 Hz, 1 H), 6.79 (d, J = 14.0 Hz, 1 H), 7.25 (s, 1 H), 7.41 (d, J = 6.8 Hz, 1 H), 7.95 (s, 1 H) |
| C-178 | 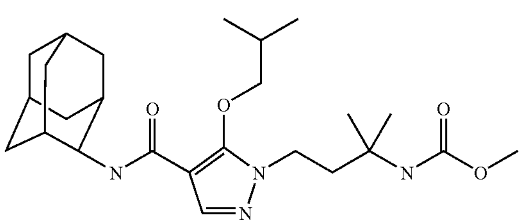 | (DMSO-d6); 0.97 (d, J = 6.8 Hz, 6 H), 1.22 (s, 6 H), 1.52 (d, J = 12.0 Hz, 2 H), 1.70-2.08 (m, 15 H), 3.49 (s, 3 H), 3.89 (t, J = 8.0 Hz, 2 H), 3.97 (brs, 1 H), 4.02 (d, J = 6.4 Hz, 2 H), 6.93 (s, 1 H), 7.24 (d, J = 6.8 Hz, 1 H), 7.80 (s, 1 H) |

TABLE 42-continued

| No. | Structure | NMR (CDCl3 or d6-DMSO) |
|---|---|---|
| C-179 | 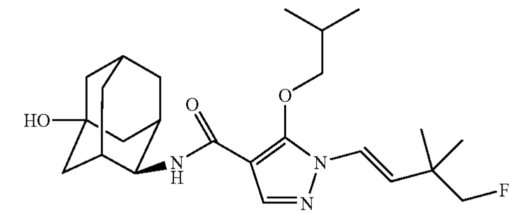 | (CDCl3); 1.06 (d, J = 6.6 Hz, 6 H), 1.37 (s, 3 H), 1.44 (s, 3 H), 1.54-2.20 (m, 14 H), 2.45-2.54 (m, 2 H), 3.99 (d, J = 6.6 Hz, 2 H), 4.18-4.20 (m, 1 H), 6.30 (d, J = 14.4 Hz, 1 H), 6.25-6.35 (m, 1 H), 6.79 (d, J = 14.4 Hz, 1 H), 7.80 (s, 1 H) |
| C-180 | 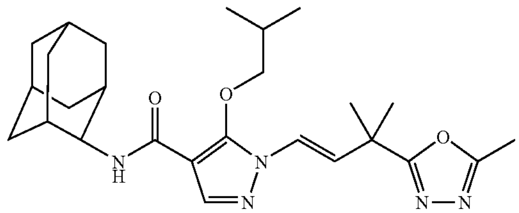 | (DMSO-d6); 0.94 (d, J = 6.8 Hz, 6 H), 1.50-1.56 (m, 8 H), 1.70-2.04 (m, 13 H), 2.48 (s, 3 H), 3.97 (brs, 1 H), 4.10 (d, J = 6.4 Hz, 2 H), 6.40 (d, J = 14.0 Hz, 1 H), 6.79 (d, J = 14.4 Hz, 1 H), 7.44 (d, J = 6.4 Hz, 1 H), 7.99 (s, 1 H) |

TABLE 43

| No. | Structure | NMR (CDCl3 or d6-DMSO) |
|---|---|---|
| C-181 | 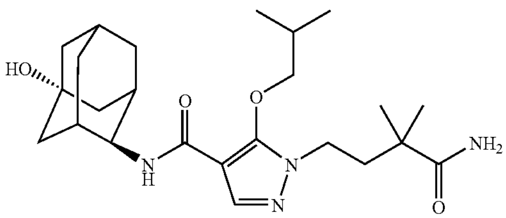 | (DMSO-d6); 0.97 (d, J = 6.8 Hz, 6 H), 1.12 (s, 6 H), 1.34 (d, J = 12.0 Hz, 2 H), 1.61-2.03 (m, 14 H), 3.84-3.90 (m, 3 H), 4.02 (d, J = 6.4 Hz, 2 H), 4.41 (s, 1 H), 6.87 (s, 1 H), 7.14 (s, 1 H), 7.20 (d, J = 6.4 Hz, 1 H), 7.79 (s, 1 H) |
| C-182 | 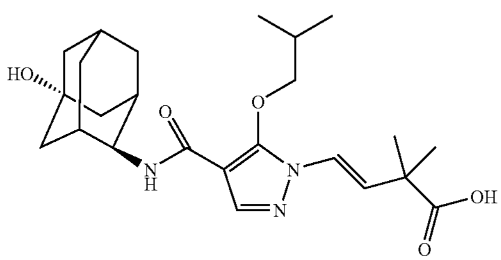 | (DMSO-d6): 0.97 (d, J = 6.7 Hz, 6 H), 1.09 (s, 6 H), 1.40-2.10 (m, 14 H), 3.79 (s, 2 H), 3.93-3.96 (m, 1 H), 4.09 (d, J = 6.4 Hz, 2 H), 6.22 (br,d, J = 14.4 Hz, 3 H), 6.48 (br, s, 2 H), 6.76 (d, J = 14.4 Hz, 1 H), 7.43 (d, J = 6.7 Hz, 1 H), 8.00 (s, 1 H) |
| C-183 | 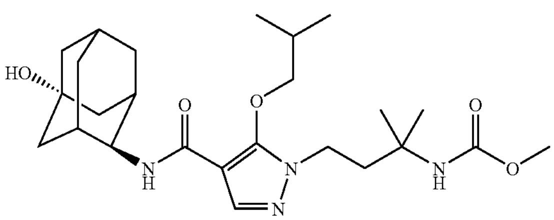 | (DMSO-d6): 0.97 (d, J = 6.8 Hz, 6 H), 1.22 (s, 6 H), 1.34 (d, J = 11.6 Hz, 2 H), 1.61-2.06 (m, 14 H), 3.48 (s, 3 H), 3.88 (brs, 3 H), 4.01 (d, J = 6.8 Hz, 2 H), 4.42 (s, 1 H), 6.92 (s, 1 H), 7.20 (d, J = 6.4 Hz, 1 H), 7.79 (s, 1 H) |
| C-184 | 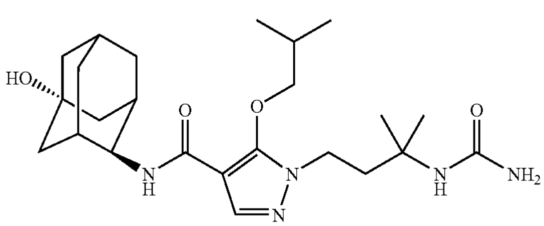 | (DMSO-d6); 0.98 (d, J = 6.4 Hz, 6 H), 1.20 (s, 6 H), 1.34 (d, J = 12.4 Hz, 2 H), 1.61-2.11 (m, 14 H), 3.89 (brs, 3 H), 4.02 (d, J = 6.4 Hz, 2 H), 4.42 (s, 1 H), 5.24 (s, 2 H), 5.81 (s, 1 H), 7.19 (d, J = 6.4 Hz, 1 H), 7.79 (s, 1 H) |

TABLE 43-continued

| No. | Structure | NMR (CDCl3 or d6-DMSO) |
|---|---|---|
| C-185 | 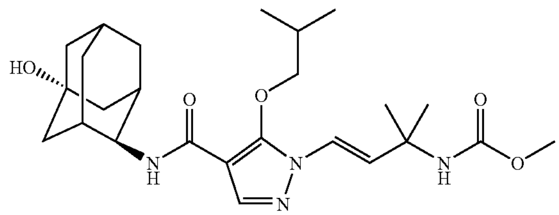 | (DMSO-d6): 0.97 (d, J = 6.8 Hz, 6 H), 1.34 (d, J = 13.2 Hz, 2 H), 1.38 (s, 6 H), 1.61-2.04 (m, 12 H), 3.49 (s, 3 H), 3.90 (brs, 1 H), 4.08 (d, J = 6.4 Hz, 2 H), 4.42 (s, 1 H), 6.30 (d, J = 14.4 Hz, 1 H), 6.79 (d, J = 14.4 Hz, 1 H), 7.25 (s, 1 H), 7.37 (d, J = 6.4 Hz, 1 H), 7.95 (s, 1 H) |
| C-186 | 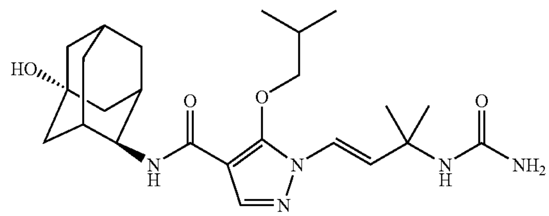 | (DMSO-d6); 0.98 (d, J = 6.8 Hz, 6 H), 1.32-1.41 (m, 8 H), 1.61-2.04 (m, 12 H), 3.88 (brs, 1 H), 4.07 (d, J = 6.4 Hz, 2 H), 4.42 (s, 1 H), 5.29 (s, 2 H), 6.08 (s, 1 H), 6.37 (d, J = 14.0 Hz, 1 H), 6.81 (d, J = 14.4 Hz, 1 H), 7.35 (d, J = 6.0 Hz, 1 H), 7.95 (s, 1 H) |

TABLE 44

| No. | Structure | NMR (CDCl3 or d6-DMSO) |
|---|---|---|
| C-187 | 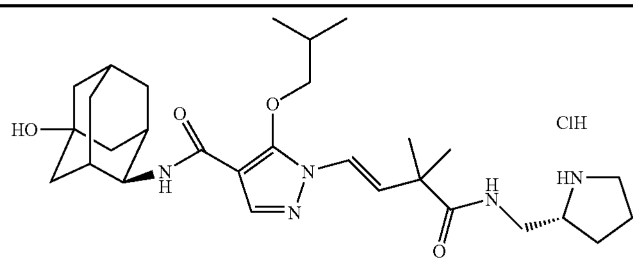 | (DMSO-d6); 0.98 (d, J = 6.6 Hz, 6 H), 1.33 (s, 6 H), 1.18-2.03 (m, 18 H), 3.11-3.23 (m, 2 H), 3.12-3.50 (m, 3 H), 3.88-3.95 (m, 1 H), 4.12 (d, J = 6.3 Hz, 2 H), 6.36 (d, J = 14.4 Hz, 1 H), 6.84 (d, J = 14.4 Hz, 1 H), 7.40 (d, J = 6.6 Hz, 1 H), 8.00 (s, 1 H), 8.00-8.05 (m, 1 H), 8.84 (bs, 1 H), 9.26 (bs, 1 H) |
| C-188 | 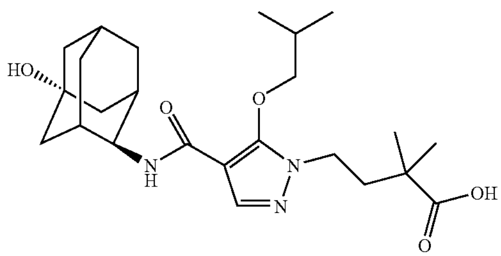 | (DMSO-d6): 097 (d, J = 6.7 Hz, 6 H), 1.14 (s, 6 H), 1.32-2.01 (m, 14 H), 3.86-3.99 (m, 3 H), 4.03 (d, J = 6.5 Hz, 2 H), 4.41 (s, 1 H), 7.22 (d, J = 6.7 Hz, 1 H), 7.80 (s, 1 H) |
| C-189 | 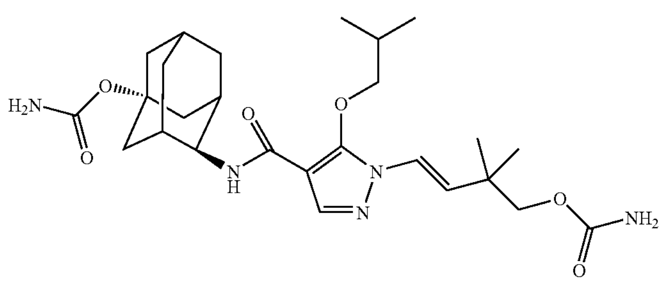 | (DMSO-d6): 0.97 (d, J = 6.7 Hz, 6 H), 1.09 (s, 6 H), 1.40-2.01 (m, 14 H), 3.79 (s, 2 H), 3.93-3.96 (m, 1 H), 4.09 (d, J = 6.4 Hz, 2 H), 6.22 (br,d, J = 14.4 Hz, 3 H), 6.48 (br, s, 2 H), 6.76 (d, J = 14.4 Hz, 1 H), 7.43 (d, J = 6.7 Hz, 1 H), 8.00 (s, 1 H) |
| C-190 | 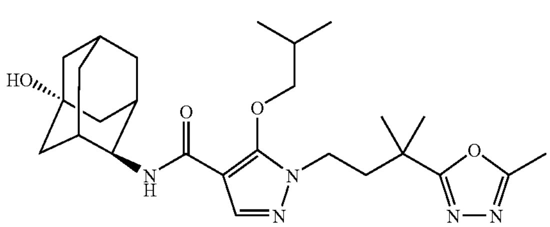 | (DMSO-d6); 0.94 (d, J = 6.8 Hz, 6 H), 1.31-1.37 (m, 8 H), 1.61-2.02 (m, 12 H), 2.11 (t, J = 7.6 Hz, 2 H), 2.42 (s, 3 H), 3.89-3.95 (m, 3 H), 4.01 (d, J = 6.4 Hz, 2 H), 4.42 (s, 1 H), 7.18 (d, J = 7.2 Hz, 1 H), 7.78 (s, 1 H) |

TABLE 44-continued

| No. | Structure | NMR (CDCl3 or d6-DMSO) |
|---|---|---|
| C-191 | 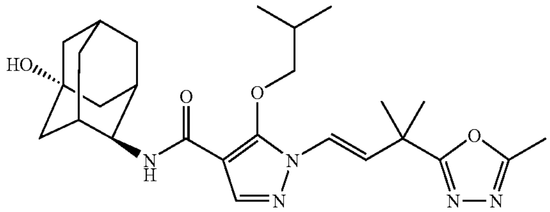 | (DMSO-d6): 0.94 (d, J = 6.8 Hz, 6 H), 1.34 (d, J = 12.8 Hz, 2 H), 1.55 (s, 6 H), 1.61-2.04 (m, 12 H), 2.47 (s, 3 H), 3.89 (brs, 1 H), 4.10 (d, J = 6.0 Hz, 2 H), 4.42 (s, 1 H), 6.40 (d, J = 14.0 Hz, 1 H), 6.79 (d, J = 14.4 Hz, 1 H), 7.41 (d, J = 6.4 Hz, 1 H), 7.99 (s, 1 H) |
| C-192 | 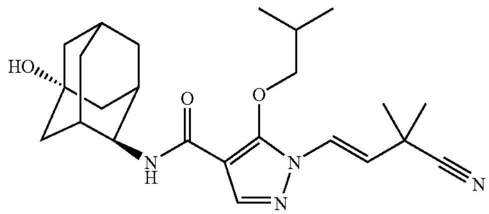 | (DMSO-d6); 0.98 (d, J = 6.8 Hz, 6 H), 1.34 (d, J = 11.6 Hz, 2 H), 1.52 (s, 6 H), 1.61-2.04 (m, 12 H), 3.89 (brs, 1 H), 4.15 (d, J = 6.4 Hz, 2 H), 4.42 (s, 1 H), 6.24 (d, J = 14.0 Hz, 1 H), 7.10 (d, J = 14.4 Hz, 1 H), 7.46 (d, J = 6.8 Hz, 1 H), 8.02 (s, 1 H) |

TABLE 45

| No. | Structure | NMR (CDCl3 or d6-DMSO) |
|---|---|---|
| C-193 | Chiral | (DMSO-d6): 0.97 (d, J = 6.6 Hz, 6 H), 1.02 (s, 6 H), 1.25-2.02 (m, 14 H), 3.22 (d, J = 5.5 Hz, 2 H), 3.84-3.90 (m, 1 H), 4.08 (d, J = 6.6 Hz, 2 H), 4.43 (s, 1 H), 4.74 (t, J = 5.3 Hz, 1 H), 6.21 (d, J = 14.3 Hz, 1 H), 6.74 (d, J = 14.3 Hz, 1 H), 7.36 (d, J = 6.9 Hz, 1 H), 7.95 (s, 1 H) |
| C-194 | 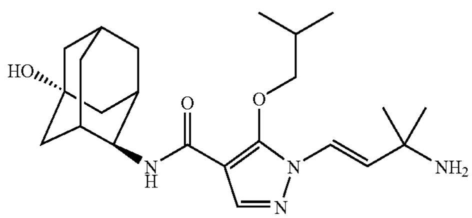 | (DMSO-d6); 0.98 (d, J = 6.8 Hz, 6 H), 1.20 (s, 6 H), 1.34 (d, J = 12.4 Hz, 2 H), 1.61-2.04 (m, 12 H), 3.88 (brs, 1 H), 4.08 (d, J = 6.4 Hz, 2 H), 4.42 (brs, 1 H), 6.30 (d, J = 14.0 Hz, 1 H), 6.91 (d, J = 14.0 Hz, 1 H), 7.34 (d, J = 6.8 Hz, 1 H), 7.93 (s, 1 H) |
| C-195 | 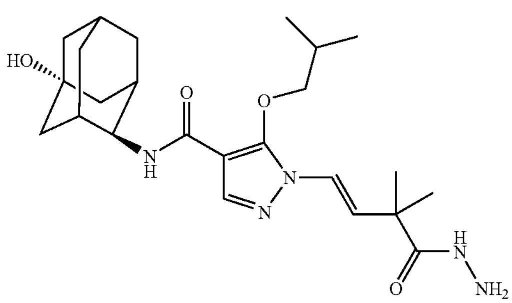 | (DMSO-d6); 0.98 (d, J = 6.8 Hz, 6 H), 1.29 (s, 6 H), 1.34 (d, J = 12.4 Hz, 2 H), 1.61-2.04 (m, 12 H), 3.88 (brs, 1 H), 4.10 (d, J = 6.4 Hz, 2 H), 4.20 (brs, 2 H), 4.42 (brs, 1 H), 6.33 (d, J = 14.4 Hz, 1 H), 6.79 (d, J = 14.4 Hz, 1 H), 7.36 (d, J = 6.4 Hz, 1 H), 7.97 (s, 1 H), 8.90 (s, 1 H) |
| C-196 | 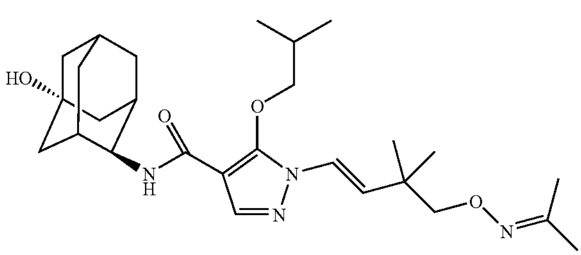 | (CDCl3-d1): 1.07 (d, J = 6.9 Hz, 6 H), 1.17 (s, 6 H), 1.56-2.20 (m, 20 H), 3.92 (s, 2 H), 3.96 (d, J = 6.5 Hz, 2 H), 4.15-4.19 (m, 1 H), 6.34 (d, J = 8.4 Hz, 1 H), 6.38 (d, J = 14.3 Hz, 1 H), 6.76 (d, J = 14.3 Hz, 1 H), 7.80 (s, 1 H) |

TABLE 45-continued

| No. | Structure | NMR (CDCl3 or d6-DMSO) |
|---|---|---|
| C-197 | 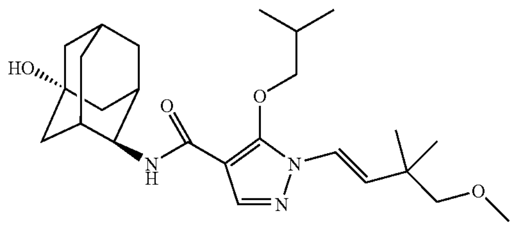 | (CDCl3-d1): 1.08 (d, J = 6.7 Hz, 6 H), 1.14 (s, 6 H), 1.54-2.20 (m, 14 H), 3.21 (s, 2 H), 3.35 (s, 3 H), 3.97 (d, J = 6.5 Hz, 2 H), 4.15-4.20 (m, 1 H), 6.35 (d, J = 14.3 Hz, 1 H), 6.37 (d, J = 6.0, 1 H), 6.76 (d, J = 14.3 Hz, 1 H), 7.81 (s, 1 H) |
| C-198 | 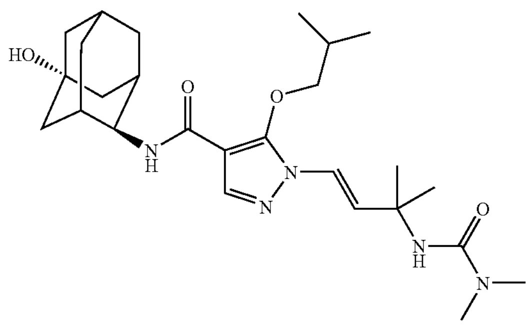 | (DMSO-d6); 0.97 (d, J = 6.4 Hz, 6 H), 1.34 (d, 14.0 Hz, 2 H), 1.42 (s, 6 H), 1.61-2.05 (m, 12 H), 2.77 (s, 6 H), 3.89 (brs, 1 H), 4.06 (d, J = 6.4 Hz, 2 H), 4.43 (s, 1 H), 5.79 (s, 1 H), 6.39 (d, J = 14.4 Hz, 1 H), 6.76 (d, J = 14.4 Hz, 1 H), 7.34 (d, J = 6.4 Hz, 1 H), 7.94 (s, 1 H) |

TABLE 46

| No. | Structure | NMR (CDCl3 or d6-DMSO) |
|---|---|---|
| C-199 | 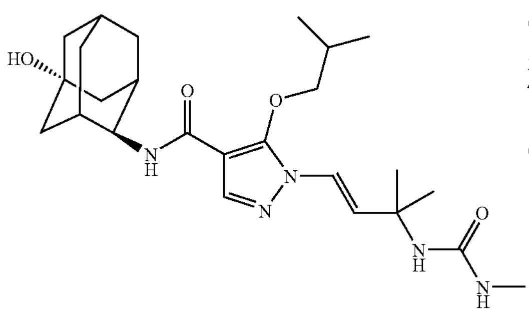 | (DMSO-d6); 0.97 (d, J = 6.8 Hz, 6 H), 1.32-1.38 (m, 8 H), 1.61-2.05 (m, 12 H), 2.50 (s, 3 H), 3.88 (brs, 1 H), 4.06 (d, J = 6.4 Hz, 2 H), 4.42 (s, 1 H), 5.56-5.61 (brm, 1 H), 5.97 (s, 1 H), 6.35 (d, J = 14.4 Hz, 1 H), 6.79 (d, J = 14.4 Hz, 1 H), 7.35 (d, J = 6.8 Hz, 1 H), 7.94 (s, 1 H) |
| C-200 | 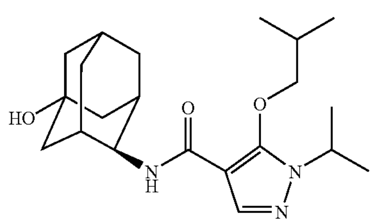 | (DMSO-d6) 0.95 (d, J = 6.7 Hz, 6 H), 1.32 (d, J = 6.6 Hz, 6 H), 1.55-2.05 (m, 14 H), 3.85 (brs, 1 H), 4.01 (d, J = 6.7 Hz, 2 H), 4.43 (s, 1 H), 4.48 (sep, J = 6.7 Hz, 1 H), 7.25 (d, J = 6.7 Hz, 1 H), 7.77 (s, 1 H) |
| C-201 | 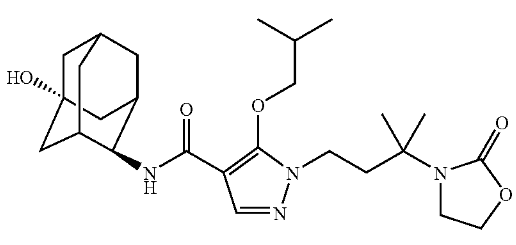 | (DMSO-d6); 0.98 (d, J = 6.8 Hz, 6 H), 1.30-1.36 (m, 8 H), 1.61-2.03 (m, 12 H), 2.19 (t, J = 8.0 Hz, 2 H), 3.60 (t, J = 7.6 Hz, 2 H), 3.88 (brs, 1 H), 3.95 (t, J = 8.4 Hz, 2 H), 4.03 (d, J = 6.4 Hz, 2 H), 4.16 (t, J = 8.0 Hz, 2 H), 4.40 (s, 1 H), 7.21 (d, J = 6.4 Hz, 1 H), 7.81 (s, 1 H) |

TABLE 46-continued

| No. | Structure | NMR (CDCl3 or d6-DMSO) |
|---|---|---|
| C-202 | 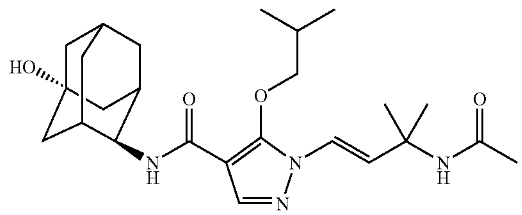 | (DMSO-d6); 0.97 (d, J = 6.8 Hz, 6 H), 1.34 (d, 11.6 Hz, 2 H), 1.40 (s, 6 H), 1.61-2.04 (m, 15 H), 3.89 (brs, 1 H), 4.07 (d, J = 6.0 Hz, 2 H), 4.41 (s, 1 H), 6.36 (d, J = 14.4 Hz, 1 H), 6.77 (d, J = 14.4 Hz, 1 H), 7.36 (d, J = 6.0 Hz, 1 H), 7.77 (s, 1 H), 7.95 (s, 1 H) |
| C-203 | 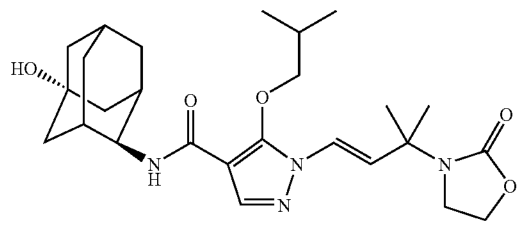 | (DMSO-d6); 0.97 (d, J = 6.4 Hz, 6 H), 1.34 (d, 13.2 Hz, 2 H), 1.51 (s, 6 H), 1.61-2.04 (m, 12 H), 3.61 (t, J = 8.0 Hz, 2 H), 3.88 (brs, 1 H), 4.07 (d, J = 6.0 Hz, 2 H), 4.18 (t, J = 7.6 Hz, 2 H), 4.41 (s, 1 H), 6.37 (d, J = 14.8 Hz, 1 H), 6.87 (d, J = 14.0 Hz, 1 H), 7.39 (d, J = 6.8 Hz, 1 H), 7.98 (s, 1 H) |
| C-204 | 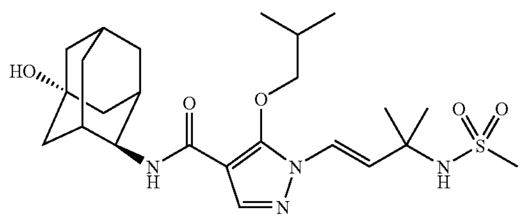 | (DMSO-d6); 0.97 (d, J = 6.8 Hz, 6 H), 1.34 (d, 12.0 Hz, 2 H), 1.44 (s, 6 H), 1.61-2.04 (m, 12 H), 2.90 (s, 3 H), 3.89 (brs, 1 H), 4.10 (d, J = 6.4 Hz, 2 H), 4.41 (s, 1 H), 6.33 (d, J = 14.4 Hz, 1 H), 6.92 (d, J = 13.2 Hz, 1 H), 7.22 (s, 1 H), 7.41 (d, J = 6.0 Hz, 1 H), 7.96 (s, 1 H) |

TABLE 47

| No. | Structure | NMR (CDCl3 or d6-DMSO) |
|---|---|---|
| C-205 | 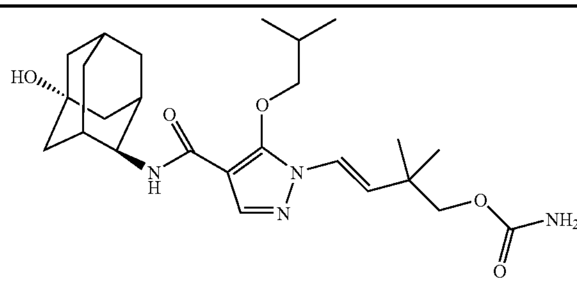 | (CDCl3-d1): 1.08 (d, J = 6.7 Hz, 6 H), 1.17 (s, 6 H), 1.59-2.20 (m, 14 H), 3.95 (s, 2 H), 3.99 (d, J = 6.5 Hz, 2 H), 4.17-4.19 (m, 1 H), 4.62 (br, s, 2 H), 6.33 (d, J = 5.4 Hz, 1 H), 6.36 (d, J = 14.4 Hz, 1 H), 6.76 (d, J = 14.4 Hz, 1 H), 7.80 (s, 1 H) |
| C-206 | 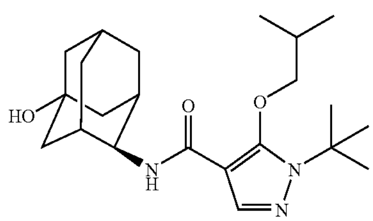 | (DMSO-d6) 0.80 (d, J = 6.5 Hz, 6 H), 1.20-1.50 (m, 2 H), 1.35 (s, 9 H), 1.40-1.90 (m, 12 H), 3.69 (brs, 1 H), 3.88 (d, J = 6.5 H, 2 H), 4.26 (s, 1 H), 7.20 (d, J = 6.0 Hz, 1 H), 7.49 (s, 1 H) |
| C-207 | 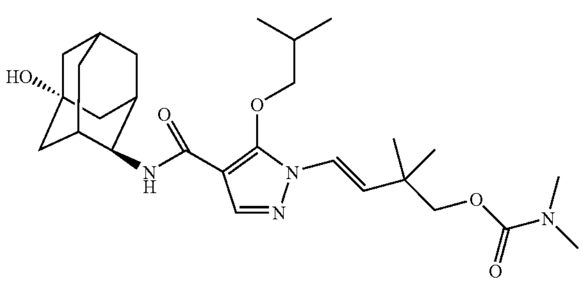 | (CDCl3-d1): 1.07 (d, J = 6.5 Hz, 6 H), 1.18 (s, 6 H), 1.55-2.20 (m, 14 H), 2.91 (s, 6 H), 3.94 (s, 2 H), 3.98 (d, J = 6.7 Hz, 2 H), 4.14-4.19 (m, 1 H), 6.31 (d, J = 7.7 Hz, 1 H), 6.36 (d, J = 14.3 Hz, 1 H), 6.76 (d, J = 14.3 Hz, 1 H), 7.79 (s, 1 H) |

TABLE 47-continued

| No. | Structure | NMR (CDCl3 or d6-DMSO) |
|---|---|---|
| C-208 | 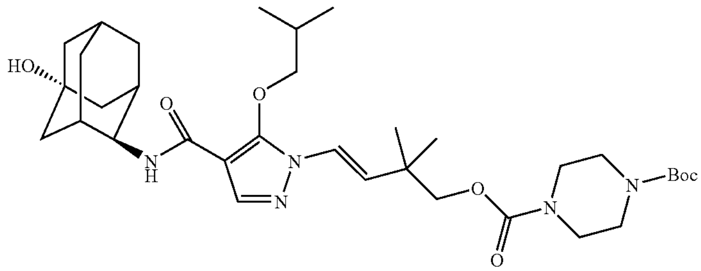 | (CDCl3-d1): 1.08 (d, J = 6.6 Hz, 6 H), 1.18 (s, 6 H), 1.46 (s, 9 H), 1.57-2.21 (m, 14 H), 3.40-3.44 (m, 8 H), 3.97 (s, 2 H), 4.00 (d, J = 6.0 Hz, 2 H), 4.13-4.21 (m, 1 H), 6.30 (d, J = 8.2 Hz, 1 H), 6.36 (d, J = 14.3 Hz, 1 H), 6.76 (d, J = 14.3 Hz, 1 H), 7.80 (s, 1 H) |
| C-209 | 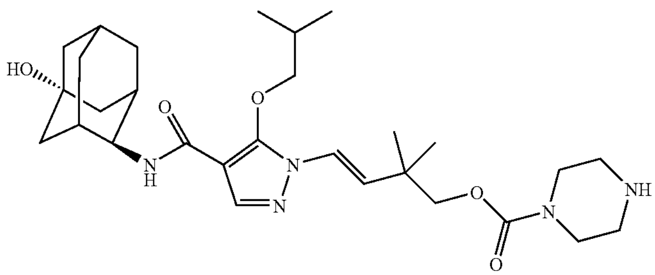 | (CDCl3-d1): 1.07 (d, J = 6.7 Hz, 6 H), 1.18 (s, 6 H), 1.54-3.67 (m, 23 H), 3.98 (s, 2 H), 4.00 (d, J = 6.0 Hz, 2 H), 4.14-4.19 (m, 1 H), 6.23 (d, J = 8.2 Hz, 1 H), 6.33 (d, J = 14.4 Hz, 1 H), 6.75 (d, J = 14.4 Hz, 1 H), 7.79 (s, 1 H) |
| C-210 | 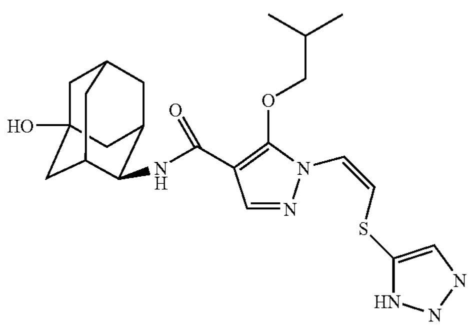 | (CDCl3); 1.06 (d, J = 6.6 Hz, 6 H), 1.55-2.22 (m, 14 H), 4.03 (d, J = 6.6 Hz, 2 H), 4.17-4.20 (m, 1 H), 6.34 (d, J = 7.2 Hz, 1 H), 6.40 (d, J = 8.4 Hz, 1 H), 6.89 (d, J = 8.4 Hz, 1 H), 7.72 (s, 1 H), 7.95 (s, 1 H) |

TABLE 48

| No. | Structure | NMR (CDCl3 or d6-DMSO) |
|---|---|---|
| C-211 | 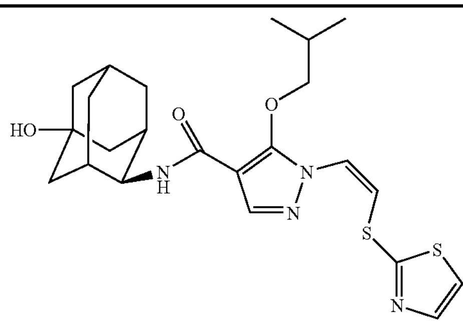 | (CDCl3); 1.07 (d, J = 6.6 Hz, 6 H), 1.58-2.21 (m, 14 H), 4.03 (d, J = 6.6 Hz, 2 H), 4.18-4.23 (m, 1 H), 6.32 (d, J = 7.5 Hz, 1 H), 6.97 (s, 2 H), 7.30 (d, J = 3.3 Hz, 1 H), 7.74 (d, J = 3.3 Hz, 1 H), 7.95 (s, 1 H) |
| C-212 | 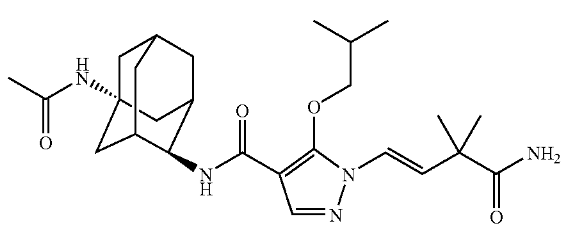 | (DMSO-d6); 0.98 (d, J = 6.8 Hz, 6 H), 1.27 (s, 6 H), 1.42 (d, J = 12.4 Hz, 2 H), 1.75 (s, 3 H), 1.93-2.03 (m, 12 H), 3.93 (brs, 1 H), 4.10 (d, J = 6.4 Hz, 2 H), 6.37 (d, J = 14.4 Hz, 1 H), 6.81 (d, J = 14.0 Hz, 1 H), 6.92 (brs, 1 H), 7.14 (brs, 1 H), 7.35 (s, 1 H), 7.41 (d, J = 6.4 Hz |

TABLE 48-continued

| No. | Structure | NMR (CDCl3 or d6-DMSO) |
|---|---|---|
| C-213 | 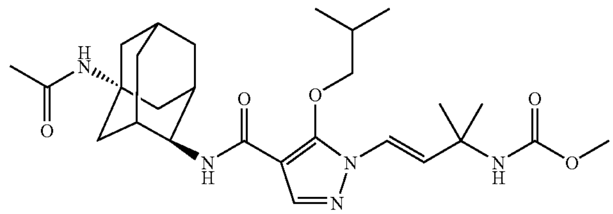 | (DMSO-d6); 0.97 (d, J = 6.8 Hz, 6 H), 1.38-1.43 (m, 8 H), 1.75 (s, 3 H), 1.93-2.02 (m, 12 H), 3.49 (s, 3 H), 3.92-3.94 (brm, 1 H), 4.08 (d, J = 6.4 Hz, 2 H), 6.30 (d, J = 14.4 Hz, 1 H), 6.79 (d, J = 14.0 Hz, 1 H), 7.25 (brs, 1 H), 7.35 (s, 1 H), 7.42 (d, J = 6.8 Hz, 1 H), 7.96 (s, 1 H) |
| C-214 | 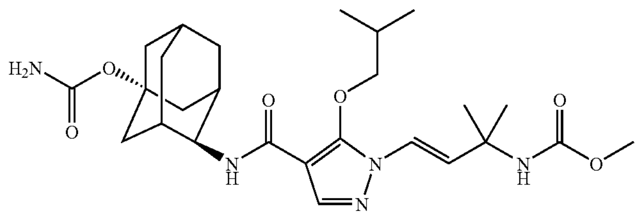 | (DMSO-d6); 0.97 (d, J = 6.8 Hz, 6 H), 1.38-1.44 (m, 8 H), 1.93-2.12 (m, 12 H), 3.49 (s, 3 H), 3.94-3.96 (brm, 1 H), 7.44 (d, J = 6.8 Hz, 2 H), 6.19 (brs, 2 H), 6.30 (d, J = 14.0 Hz, 1 H), 6.79 (d, J = 14.4 Hz, 1 H), 7.25 (s, 1 H), 7.44 (d, 6.8 Hz, 1 H), 7.96 (s, 1 H) |
| C-215 | 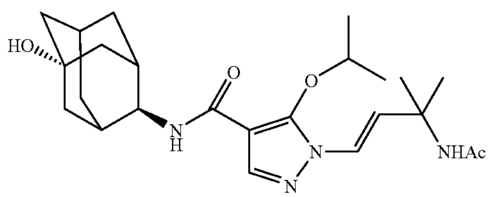 | (DMSO-d6); 1.24 (d, J = 6.1 Hz, 6 H), 1.25-1.35 (m, 2 H), 1.36 (s, 6 H) 1.60-1.75 (m, 8 H), 1.80-1.94 (m, 4 H), 2.03 (s, 3 H), 3.87 (brs, 1 H), 4.43 (s, 1 H), 4.85 (hept, J = 6.1 Hz, 1 H), 6.35 (d, J = 14.3 Hz, 1 H), 6.75 (d, J = 14.3 Hz, 1 H), 7.29 (d, J = 6.6 Hz, 1 H), |
| C-216 | 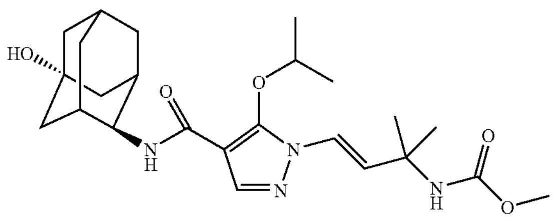 | (CDCl3); 1.38 (d, J = 6.1 Hz, 6 H), 1.51 (s, 6 H), 1.54-2.20 (m, 14 H), 3.62 (s, 3 H), 4.15-4.19 (m, 1 H), 4.66-4.75 (m, 1 H), 4.83 (s, 1 H), 6.36 (d, J = 14.2 Hz, 1 H), 6.44 (d, J = 7.3 Hz, 1 H), 6.82 (d, J = 14.2 Hz, 1 H), 7.85 (s, 1 H) |

TABLE 49

| No. | Structure | NMR (CDCl3 or d6-DMSO) |
|---|---|---|
| C-217 | 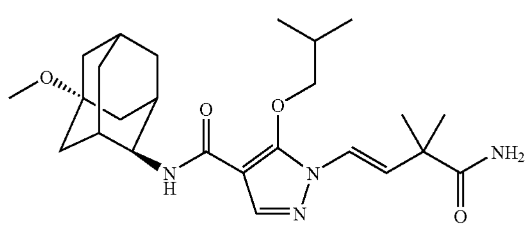 | (DMSO-d6); 0.98 (d, J = 6.7 Hz, 6 H), 1.28 (s, 6 H), 1.30-1.42 (m, 2 H), 1.62-2.18 (m, 12 H), 3.12 (s, 3 H), 3.90 (m, 1 H), 4.10 (d, J = 6.4 Hz, 2 H), 6.36 (d, J = 14.3 Hz, 1 H), 6.80 (d, J = 14.3 Hz, 1 H), 6.96 (brs, 1 H), 7.16 (brs, 1 H), 7.43 (d, J = 6.6 Hz, 1 H), 7.99 (s, 1 H) |
| C-218 | 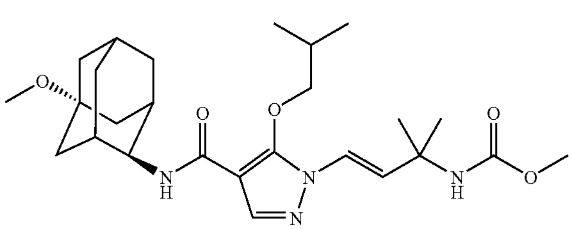 | (DMSO-d6); 0.97 (d, J = 6.7 Hz, 6 H), 1.35-1.37 (m, 2 H), 1.38 (s, 6 H), 1.65-2.17 (m, 12 H), 3.11 (s, 3 H), 3.49 (s, 3 H), 3.90 (m, 1 H), 4.08 (d, J = 6.4 Hz, 2 H), 6.29 (d, J = 14.3 Hz, 1 H), 6.79 (d, J = 14.3 Hz, 1 H), 7.26 (brs, 1 H), 7.42 (d, J = 6.7 Hz, 1 H), 7.96 (s, 1 H) |

TABLE 49-continued

| No. | Structure | NMR (CDCl3 or d6-DMSO) |
|---|---|---|
| C-219 | 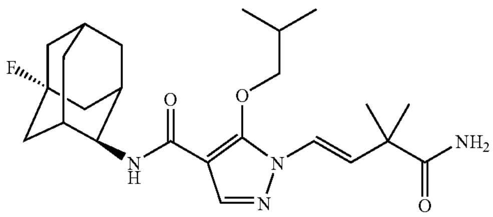 | (DMSO-d6); 0.97 (d, J = 6.9 Hz, 6 H), 1.27 (s, 6 H), 1.35-1.50 (m, 2 H), 1.80-2.22 (m, 12 H), 3.95 (m, 1 H), 4.10 (d, J = 6.3 Hz, 2 H), 6.37 (d, J = 14.3 Hz, 1 H), 6.80 (d, J = 14.3 Hz, 1 H), 6.95 (brs, 1 H), 7.16 (brs, 1 H), 7.47 (d, J = 6.3 Hz, 1 H), 7.99 (s, 1 H) |
| C-220 | 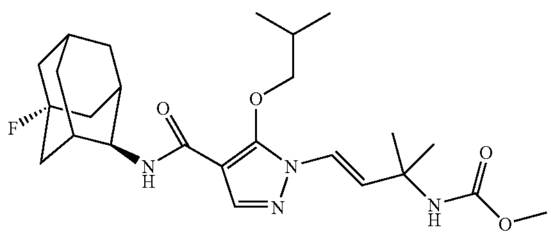 | (CDCl3): 1.08 (d, J = 6.9 Hz, 6 H), 1.51 (s, 6 H), 1.53-2.32 (m, 14 H), 3.62 (s, 3 H), 3.99 (d, J = 6.6 Hz, 3 H), 4.19 (m, 1 H), 4.83 (br.s, 1 H), 6.34 (d, J = 7.5 Hz), 6.38 (d, J = 14.1 Hz, 1 H), 6.87 (d, J = 14.1 Hz, 1 H), 7.82 (s, 1 H) |
| C-221 | 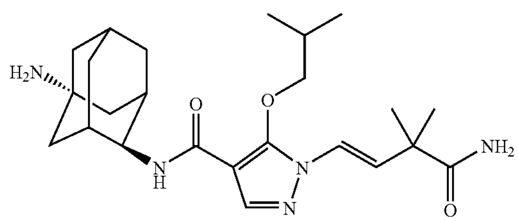 | (DMSO-d6); 0.98 (d, J = 6.8 Hz, 6 H), 1.27 (s, 6 H), 1.34 (d, J = 12.0 Hz, 2 H), 1.52-1.63 (m, 6 H), 1.90-1.99 (m, 6 H), 3.88 (brs, 1 H), 4.10 (d, J = 6.0 Hz, 2 H), 6.37 (d, J = 14.4 Hz, 1 H), 6.81 (d, J = 14.4 Hz, 1 H), 6.93 (brs, 1 H), 7.14 (brs, 1 H), 7.36 (d, J = 6.8 Hz, 1 H), 7.9 |
| C-222 | 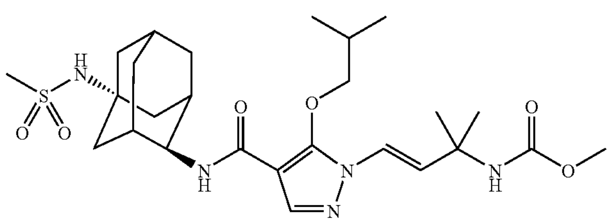 | (DMSO-d6); 0.97 (d, J = 6.4 Hz, 6 H), 1.38-1.42 (m, 8 H), 1.89-2.05 (m, 12 H), 2.92 (s, 3 H), 3.49 (s, 3 H), 3.91 (brs, 1 H), 4.08 (d, J = 6.4 Hz, 2 H), 6.30 (d, J = 14.4 Hz, 1 H), 6.79 (d, J = 14.0 Hz, 1 H), 6.87 (s, 1 H), 7.25 (s, 1 H), 7.44 (d, J = 6.0 Hz, 1 H), 7.96 (s, 1 H) |

TABLE 50

| No. | Structure | NMR(CDCl3 or d6-DMSO) |
|---|---|---|
| C-223 | 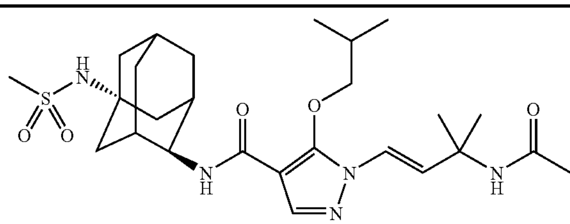 | (DMSO-d6); 0.97(d, J = 6.8 Hz, 6H), 1.40(s, 8H), 1.79(s, 3H), 1.90-2.06(m, 12H), 2.95(s, 3H), 3.91(brs, 1H), 4.08(d, J = 6.4 Hz, 2H), 6.36(d, J = 14.4 Hz, 1H), 6.78(d, J = 14.4 Hz, 1H), 6.87(s, 1H), 7.43(d, J = 6.8 Hz, 1H), 7.77(s, 1H), 7.96(s, 1H) |
| C-224 | 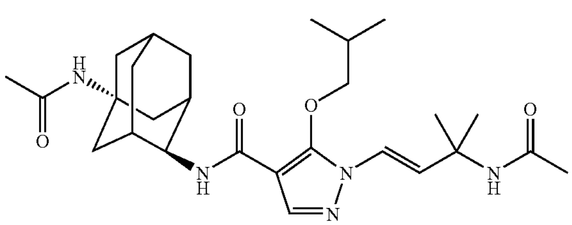 | (DMSO-d6); 0.97(d, J = 6.8 Hz, 6H), 1.40-1.44(m, 8H), 1.75(s, 3H), 1.79(s, 3H), 1.93-2.09(m, 12H), 3.93(brs, 1H), 4.08(d, J = 6.0 Hz, 2H), 6.36(d, J = 14.4 Hz, 1H), 6.78(d, J = 14.4 Hz, 1H), 7.36(s, 1H), 7.40(d, J = 6.4 Hz, 1H), 7.77(s, 1H), 7.96(s, 1H) |

TABLE 50-continued

| No. | Structure | NMR(CDCl3 or d6-DMSO) |
|---|---|---|
| C-225 | 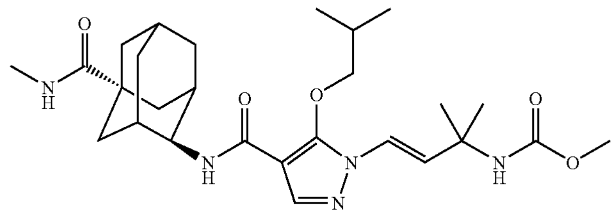 | (DMSO-d6); 0.97(d, J = 6.4 Hz, 6H), 1.29(s, 6H), 1.44(d, J = 12.4 Hz, 2H), 1.75-2.02(m, 12H), 2.56(d, J = 4.0 Hz, 3H). 3.49(s, 3H), 3.93(brs, 1H), 4.08(d, J = 6.0 Hz, 2H), 6.30(d, J = 14.0 Hz, 1H), 6.79(d, J = 14.4 Hz, 1H), 7.25(s, 1H), 7.38(d, J = 4.4 Hz, 1H), |
| C-226 | 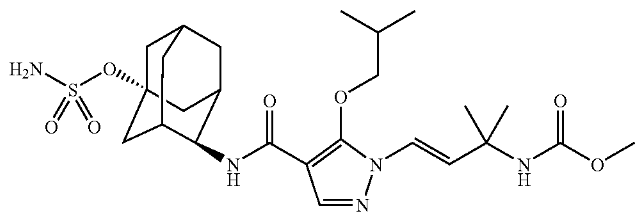 | (DMSO-d6); 0.97(d, J = 6.8 Hz, 6H), 1.38(s, 6H), 1.43(d, J = 13.2 Hz, 2H), 1.93-2.20(m, 12H), 3.49(s, 3H), 3.95(brs, 1H), 4.09(d, J = 6.4 Hz, 2H), 6.30(d, J = 14.4 Hz, 1H), 6.79(d, J = 14.4 Hz, 1H), 7.25(s, 1H), 7.35(s, 2H), 7.48(d, J = 6.0 Hz, 1H), 7.96(s, 1H) |
| C-227 | 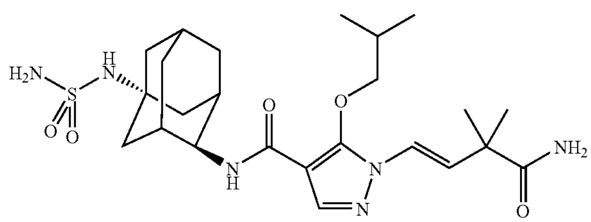 | (DMSO-d6): 0.98(d, J = 6.4 Hz, 6H), 1.27(s, 6H), 1.39(d, J = 11.7 Hz, 2H), 1.90-2.03(m, 12H), 3.92(brs, 1H), 4.10(d, J = 6.4 Hz, 2H), 6.35-6.39(m, 2H), 6.46(s, 2H), 6.81(d, J = 14.4 Hz, 1H), 6.92(s, 1H), 7.14(s, 1H), 7.14(d, J = 7.2 Hz, 1H), 7.97(s, 1H) |
| C-228 | 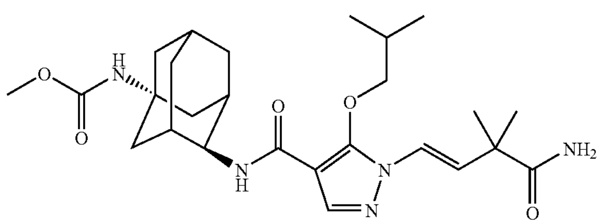 | (DMSO-d6); 0.98(d, J = 6.8 Hz, 6H), 1.27(s, 6H), 1.40(d, J = 11.6 Hz, 2H), 1.86-2.10(m, 12H), 3.47(s, 3H), 3.93(brs, 1H), 4.10(d, J = 6.4 Hz, 2H), 6.37(d, J = 14.4 Hz, 1H), 6.81(d, J = 14.4 Hz, 1H), 6.84(s, 1H), 6.92(s, 1H), 7.14(s, 1H), 7.42(d, J = 6.4 Hz, 1H) |

TABLE 51

| No. | Structure | NMR(CDCl3 or d6-DMSO) |
|---|---|---|
| C-229 | 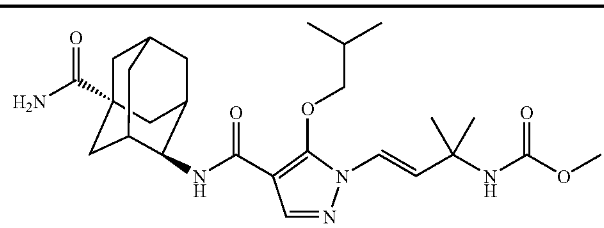 | (DMSO-d6); 0.97(d, J = 6.4 Hz, 6H), 1.39(s, 6H), 1.44(d, J = 12.0 Hz, 2H), 1.76-2.08(m, 12H), 3.49(s, 3H), 3.93(brs, 1H), 4.08(d, J = 6.4 Hz, 2H), 6.30(d, J = 14.4 Hz, 1H), 6.71(s, 1H), 6.79(d, J = 14.4 Hz, 1H), 7.00(s, 1H), 7.25(s, 1H), 7.43(d, J = 7.2 Hz, 1H) |
| C-230 | 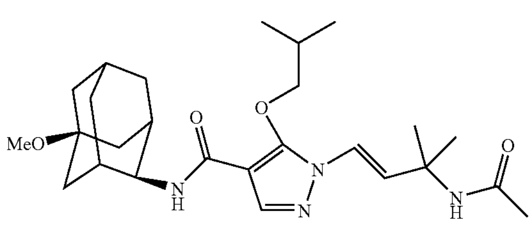 | (CDCl3); 1.09(d, J = 6.6 Hz, 6H), 1.54(s, 6H), 1.57-2.26(m, 14H), 1.95(s, 3H), 3.25(s, 3H), 3.96(d, J = 6.9 Hz, 2H), 4.16(m, 1H), 5.47(br.s, 1H), 6.39(d, J = 14.1 Hz, 1H), 6.40(d, J = 7.5 Hz, 1H), 6.87(d, J = 4.1 Hz, 1H), 7.82(s, 1H) |

TABLE 51-continued

| No. | Structure | NMR(CDCl3 or d6-DMSO) |
|---|---|---|
| C-231 | 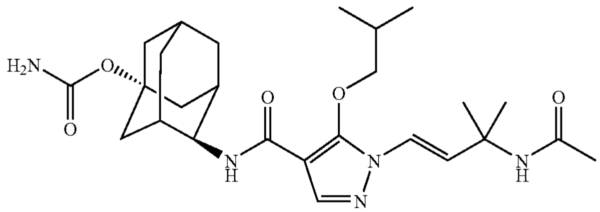 | (DMSO-d6); 0.97(d, J = 6.8 Hz, 6H), 1.40-1.44(m, 8H), 1.79(s, 3H), 1.93-2.12(m, 12H), 3.95(brs, 1H), 4.08(d, J = 6.4 Hz, 2H), 6.20(brs, 2H), 6.36(d, J = 14.0 Hz, 1H), 6.77(d, J = 14.4 Hz, 1H), 7.43(d, J = 6.4 Hz, 1H), 7.77(s, 1H), 7.96(s, 1H) |
| C-232 | 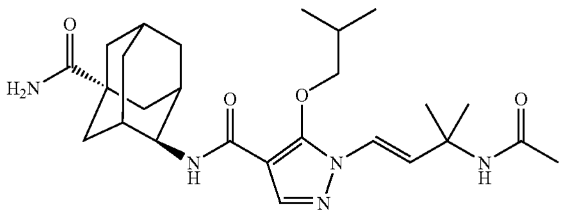 | (DMSO-d6); 0.98(d, J = 6.8 Hz, 6H), 1.40-1.46(m, 8H), 1.75-2.02(m, 15H), 3.93(brs, 1H), 4.08(d, J = 6.4 Hz, 2H), 6.36(d, J = 14.4 Hz, 1H), 6.71(s, 1H), 6.77(d, J = 14.0 Hz, 1H), 6.99(s, 1H), 7.42(d, J = 6.4 Hz, 1H), 7.77(s, 1H), 7.96(s, 1H) |
| C-233 | 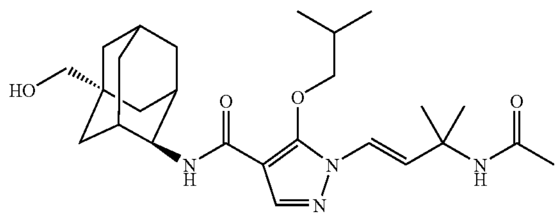 | (DMSO-d6); 0.98(d, J = 6.8 Hz, 6H), 1.40-1.51(m, 14H), 1.79(s, 3H), 1.87-2.04(m, 6H), 3.00(d, J = 5.6 Hz, 2H), 3.87(brs, 1H), 4.08(d, J = 6.4 Hz, 2H), 4.38(t, J = 5.2 Hz, 1H), 6.36(d, J = 14.4 Hz, 1H), 6.77(d, J = 14.4 Hz, 1H), 7.40(d, J = 6.4 Hz, 1H), 7.79(s, 1 |
| C-234 | 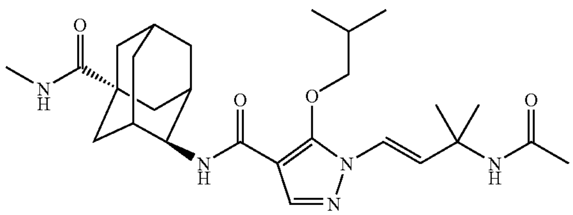 | (DMSO-d6); 0.97(d, J = 6.8 Hz, 6H), 1.40-1.45(m, 8H), 1.74-2.03(m, 12H), 2.56(d, J = 4.0 Hz, 3H), 3.92(brs, 1H), 4.08(d, J = 6.4 Hz, 2H), 6.35(d, J = 14.4 Hz, 1H), 6.77(d, J = 14.4 Hz, 1H), 7.39(d, J = 4.4 Hz, 1H), 7.44(d, J = 6.4 Hz, 1H), 7.79(s, 1H), 7.96(s, 1 |

TABLE 52

| No. | Structure | NMR(CDCl3 or d6-DMSO) |
|---|---|---|
| C-235 | 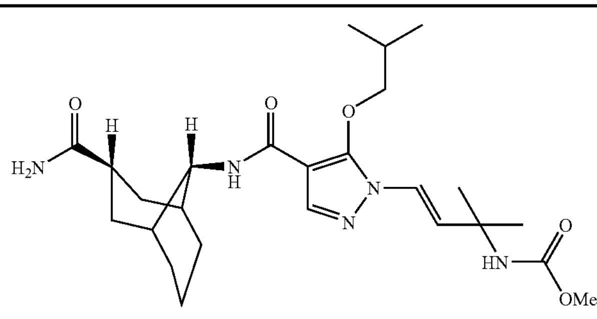 | (DMSO-d6); 0.96(s, 3H), 0.99(s, 3H), 1.15-1.20(m, 2H), 1.30-1.32(m, 1H), 1.38(s, 6H), 1.53-1.60(m, 2H), 1.74-1.78(m, 3H), 1.96-2.06(m, 5H), 2.52-2.61 (m, 1H), 3.49(s, 3H), 4.03-4.08 (m, 1H), 4.07(d, 2H, J = 6.0 Hz), 6.30(d, J = 14.1 Hz, 1H), 6.73(br s, 1H), 6.78 |
| C-236 | 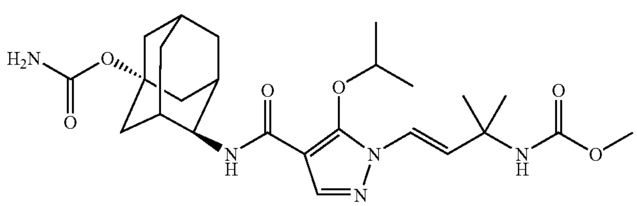 | (DMSO-d6); 1.25(d, J = 6.0 Hz, 6H), 1.38-1.44(m, 8H), 1.92-2.10(m, 11H), 3.49(s, 3H), 3.95(brs, 1H), 4.82-4.90(m, 1H), 6.20(brs, 2H), 6.31(d, J = 14.0 Hz, 1H), 6.78(d, J = 14.4 Hz, 1H), 7.27(s, 1H), 7.38(d, J = 6.0 Hz, 1H), 8.02(s, 1H) |

TABLE 53

| No. | Structure | retention time | LC-MS |
|---|---|---|---|
| D-1 | 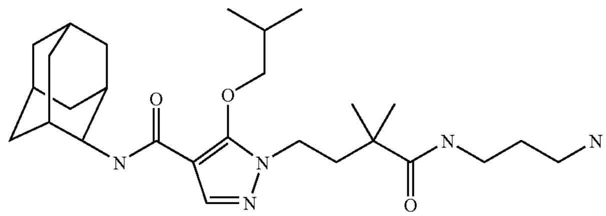 | 1.48 | 489.4 |
| D-2 | 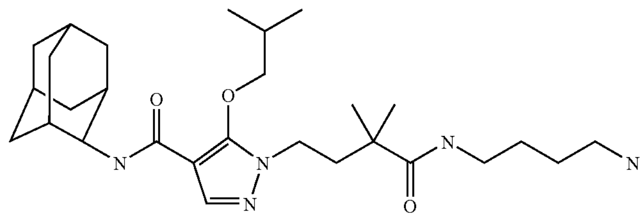 | 1.44 | 503.5 |
| D-3 | 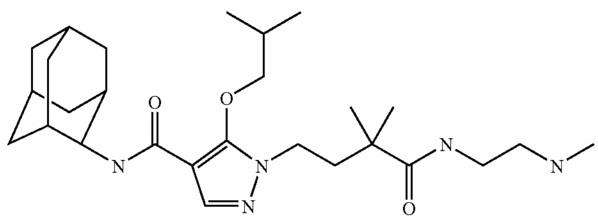 | 1.49 | 489.7 |
| D-4 | 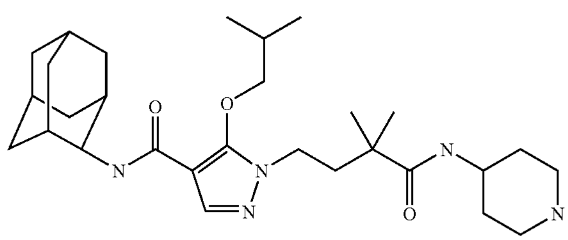 | 1.45 | 515.2 |
| D-5 | 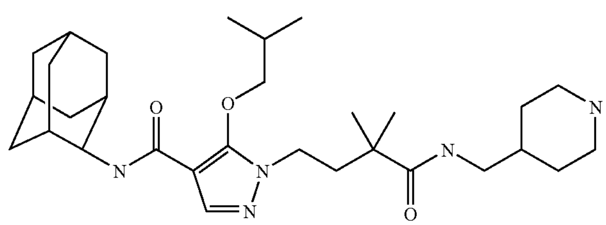 | 1.45 | 529.5 |
| D-6 | 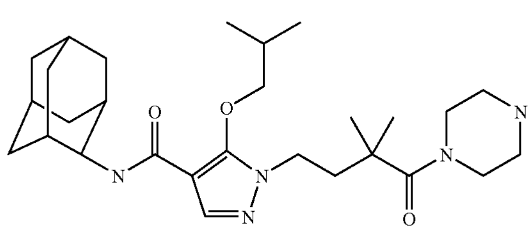 | 1.56 | 500 |

TABLE 54

| No. | Structure | retention time | LC-MS |
|---|---|---|---|
| D-7 | 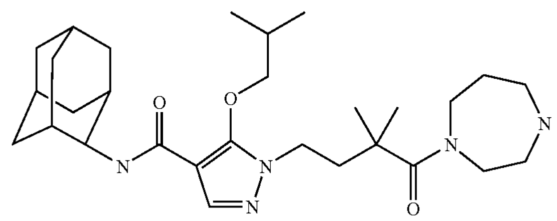 | 1.5 | 515.3 |
| D-8 | 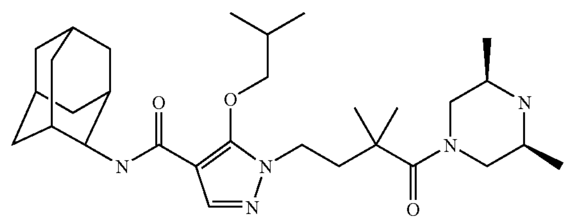 | 1.52 | 529.2 |
| D-9 | 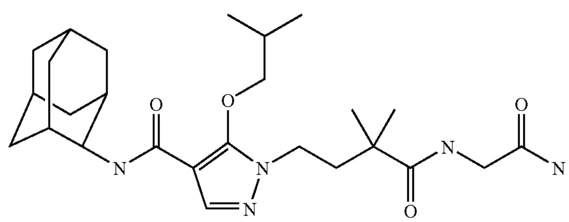 | 1.99 | 489.2 |
| D-10 | 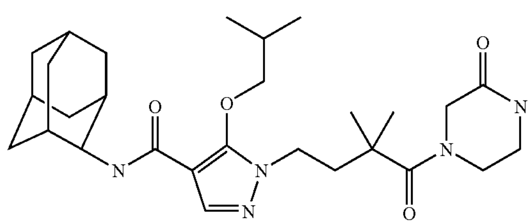 | 2.06 | 515.2 |
| D-11 | 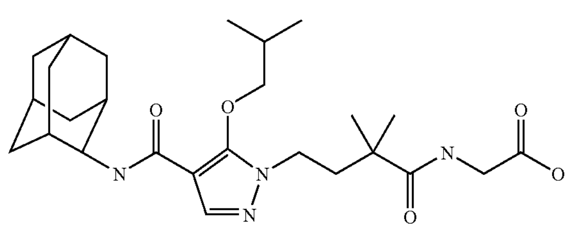 | 2.11 | 490.1 |
| D-12 | 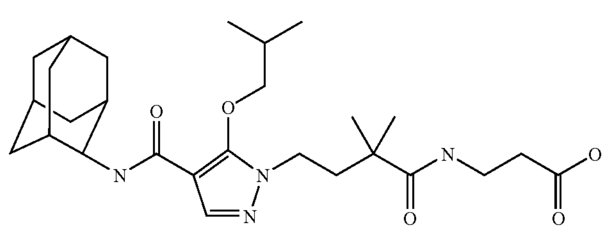 | 2.12 | 504 |

TABLE 55

| No. | Structure | retention time | LC-MS |
|---|---|---|---|
| D-13 | 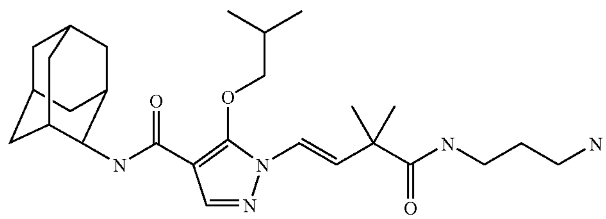 | 1.56 | 486.1 |
| D-14 | 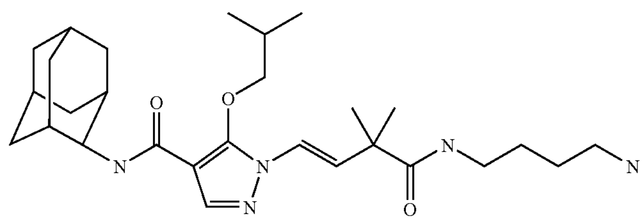 | 1.56 | 500.7 |
| D-15 | 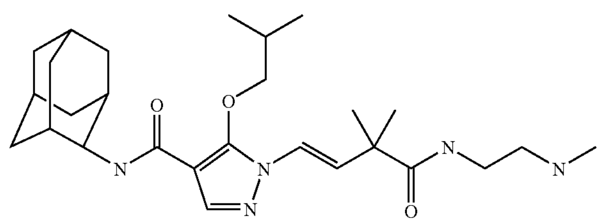 | 1.57 | 486.6 |
| D-16 | 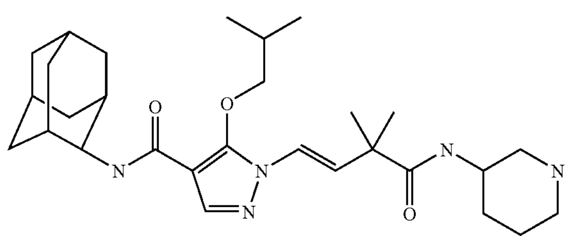 | 1.63 | 512.8 |
| D-17 | 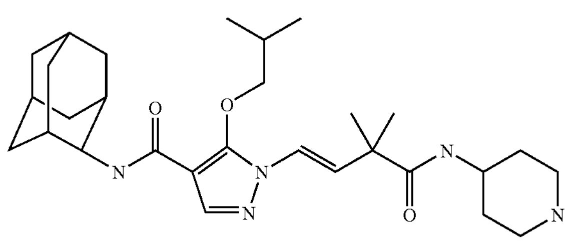 | 1.6 | 512.7 |
| D-18 | 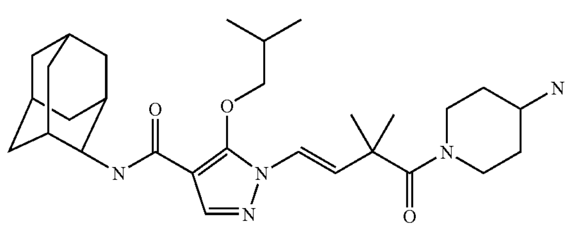 | 1.57 | 513.3 |

TABLE 56

| No. | Structure | | retention time | LC-MS |
|---|---|---|---|---|
| D-19 | 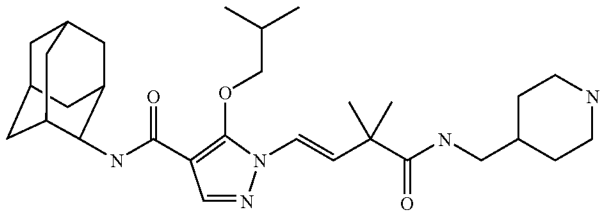 | | 1.65 | 527.3 |
| D-20 | 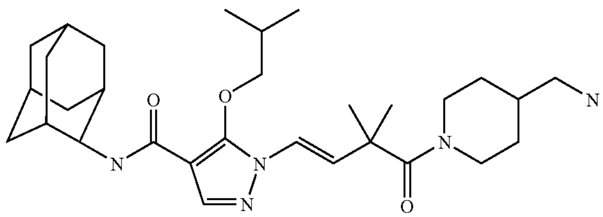 | | 1.56 | 527.3 |
| D-21 | 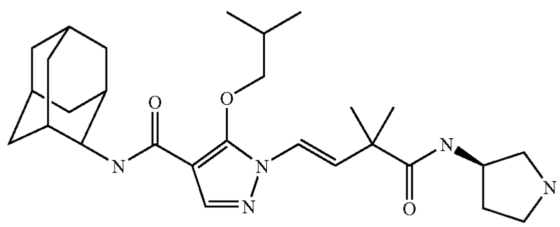 | Chiral | 1.68 | 499.3 |
| D-22 | 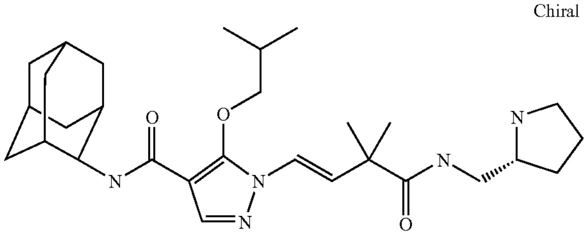 | Chiral | 1.6 | 513.3 |
| D-23 | 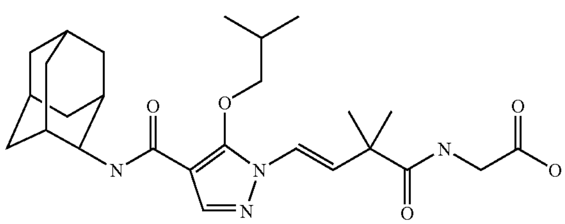 | | 2.23 | 487.6 |
| D-24 | 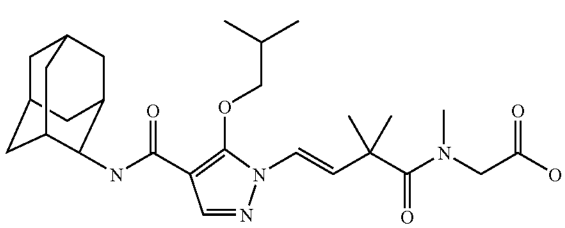 | | 2.3 | 501.6 |

TABLE 57
| No. | Structure | | retention time | LC-MS |
|---|---|---|---|---|
| D-25 | 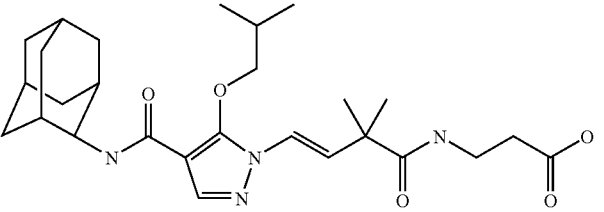 | | 2.25 | 501.1 |
| D-26 | 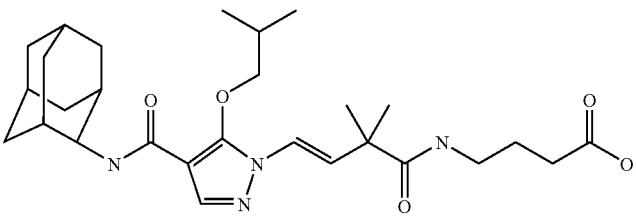 | | 2.31 | 515.6 |
| D-27 | 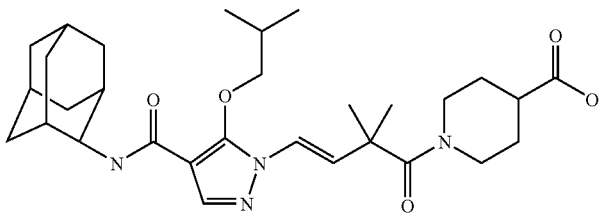 | | 2.33 | 541.6 |
| D-28 | 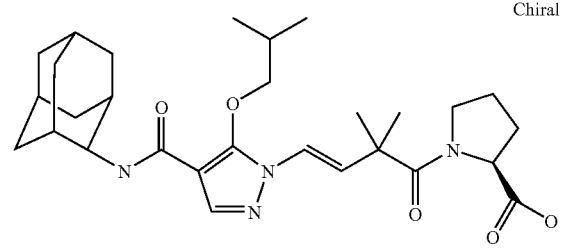 | Chiral | 2.37 | 527.7 |
| D-29 | 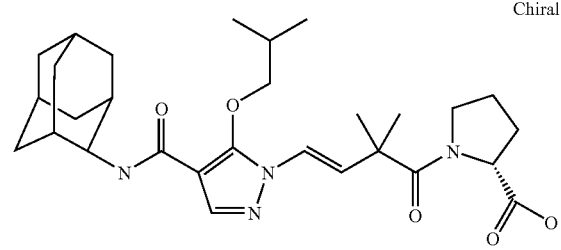 | Chiral | 2.39 | 527.7 |
| D-30 | 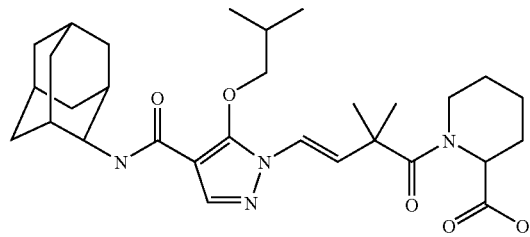 | | 2.53 | 541.1 |

TABLE 58

| No. | Structure | retention time | LC-MS |
|---|---|---|---|
| D-31 | 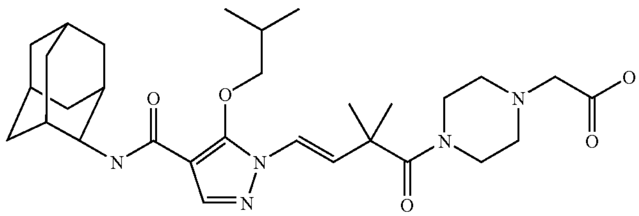 | 1.84 | 556 |
| D-32 | 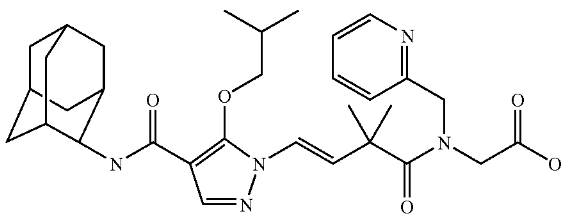 | 2.26 | 578.1 |
| D-33 | 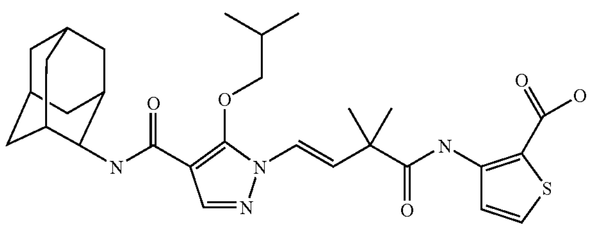 | 2.81 | 555 |
| D-34 | 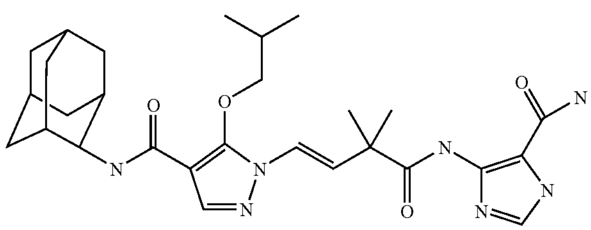 | 2.29 | 539.2 |
| D-35 | Chiral | 1.58 | 567.6 |

TABLE 59

| No. | Structure |
|---|---|
| E-1 | (structure) |
| E-2 | (structure) |
| E-3 | (structure) |
| E-4 | (structure) |
| E-5 | (structure) |
| E-6 | (structure) |

TABLE 59-continued
| No. | Structure |
|---|---|
| E-7 | 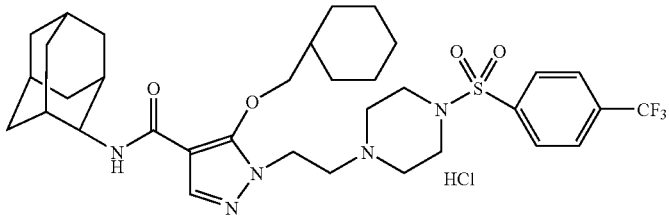 HCl |
| E-8 | 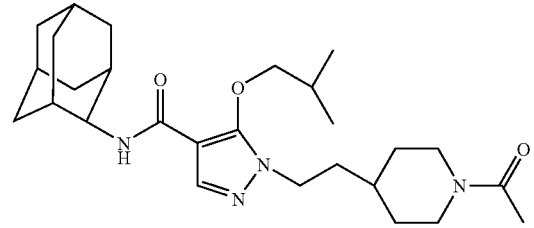 |
| E-9 | 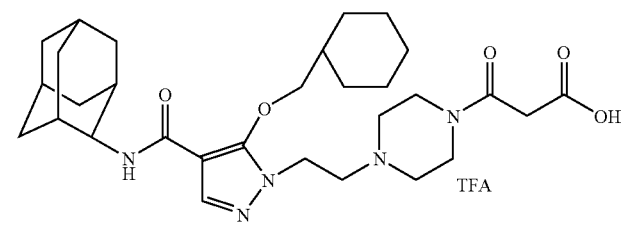 TFA |
| E-10 | 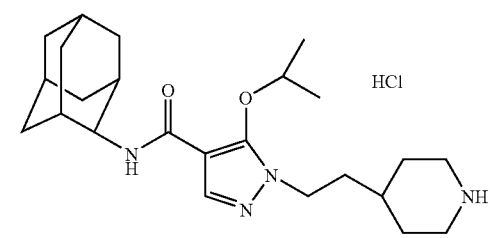 HCl |
| E-11 | 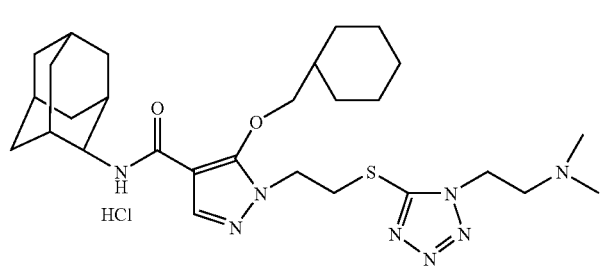 HCl |
| E-12 | 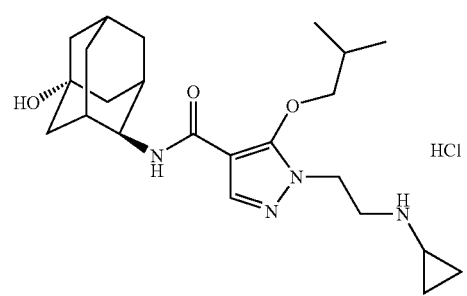 HCl |

TABLE 60

| No. | Structure |
|---|---|
| E-13 | 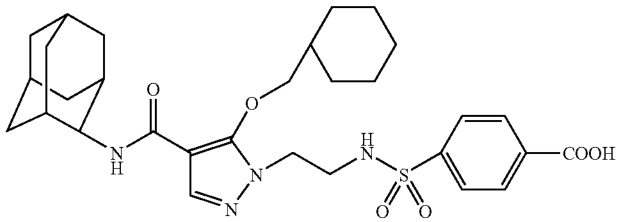 |
| E-14 | 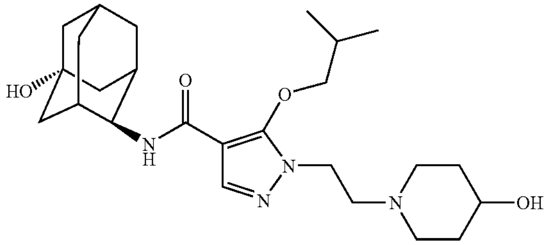 |
| E-15 | 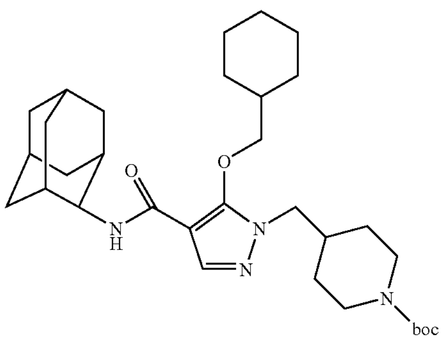 |
| E-16 | 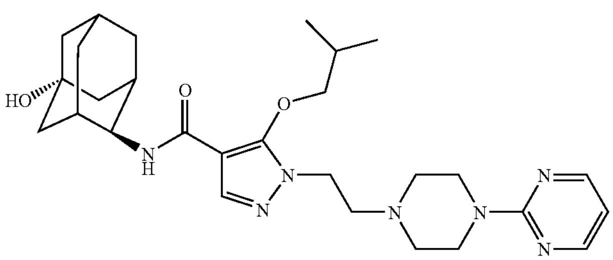 |
| E-17 | 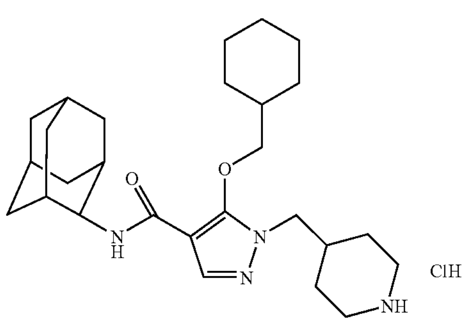 |

TABLE 60-continued
| No. | Structure |
|---|---|
| E-18 | 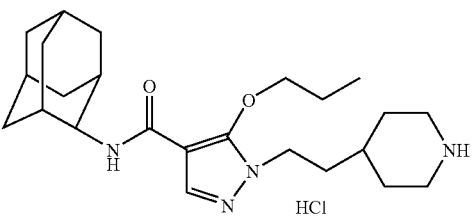 HCl |
| E-19 | 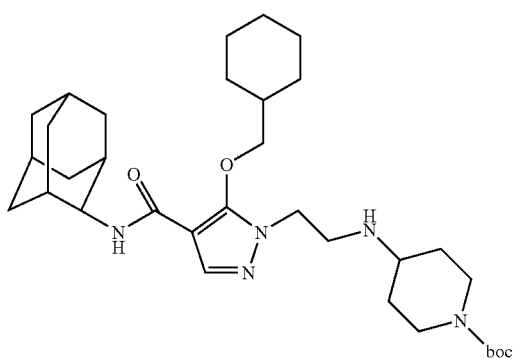 |
| E-20 | 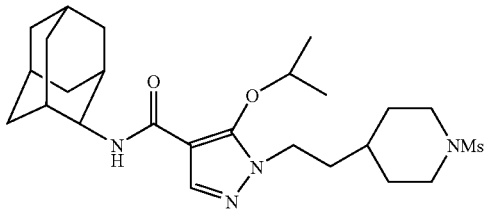 |
| E-21 | 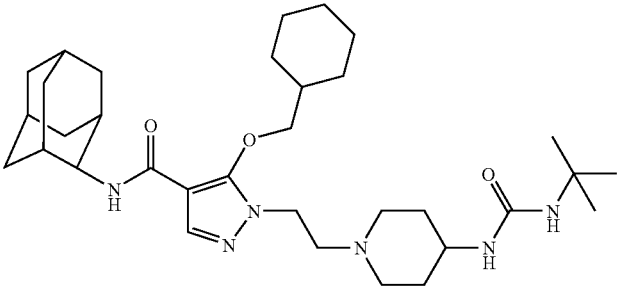 |
| E-22 | 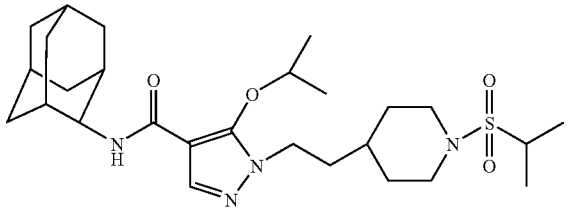 |
| E-23 | 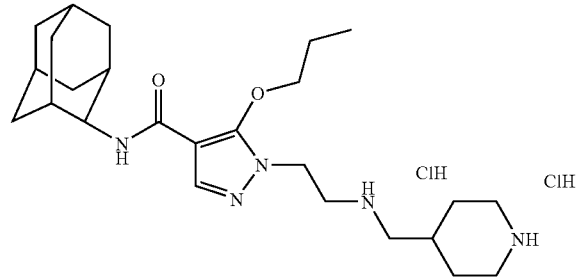 |

TABLE 60-continued

| No. | Structure |
|---|---|
| E-24 | (structure) |

TABLE 61

| No. | Structure |
|---|---|
| E-25 | (structure) |
| E-26 | (structure) |
| E-27 | (structure) |
| E-28 | (structure) |
| E-29 | (structure) |

US 8,324,265 B2
229
230
TABLE 61-continued
| No. | Structure |
|---|---|
| E-30 | 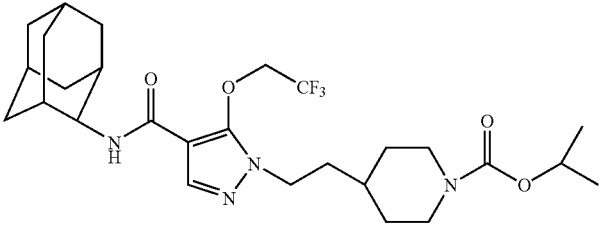 |
| E-31 | 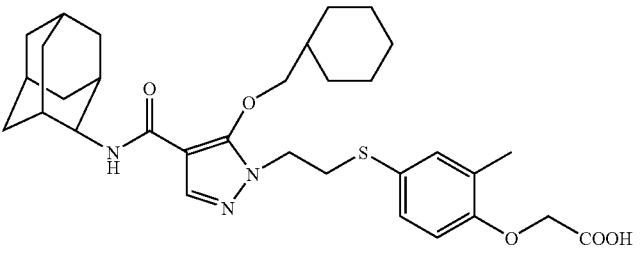 |
| E-32 | 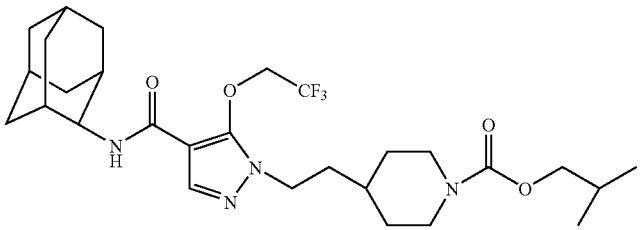 |
| E-33 | 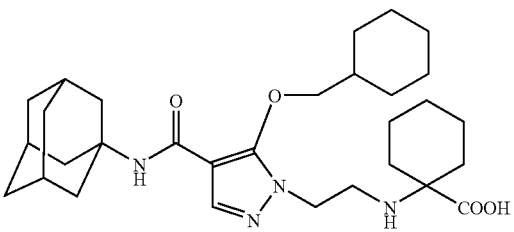 |
| E-34 | 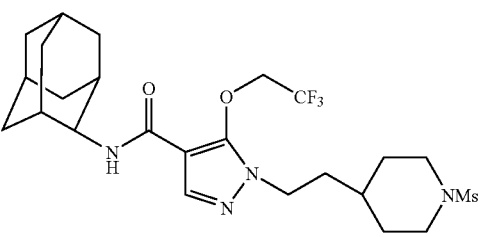 |
| E-35 | 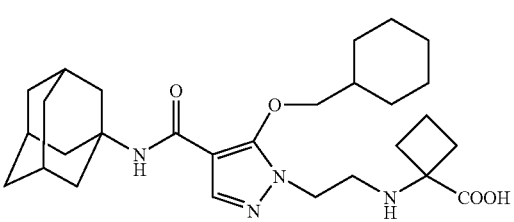 |

TABLE 61-continued

| No. | Structure |
|---|---|
| E-36 | (structure) |

TABLE 62

| No. | Structure |
|---|---|
| E-37 | (structure) |
| E-38 | (structure) |
| E-39 | (structure) |
| E-40 | (structure) |
| E-41 | (structure) |

TABLE 62-continued
| No. | Structure |
|---|---|
| E-42 | 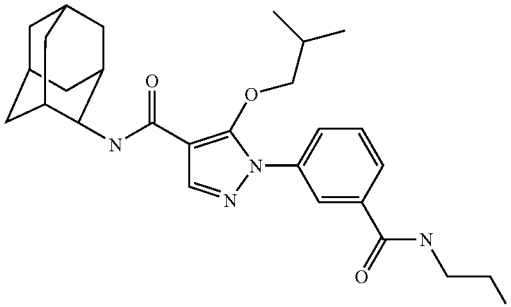 |
| E-43 | 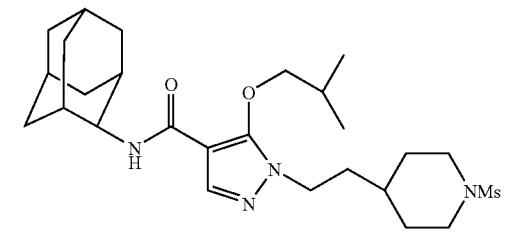 |
| E-44 | 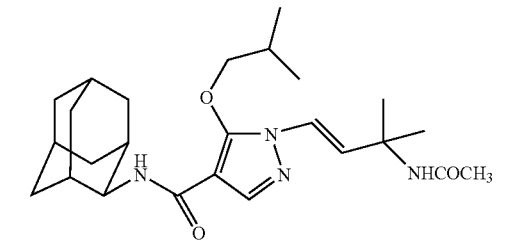 |
| E-45 | 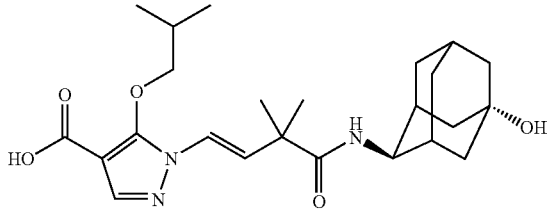 |
| E-46 | 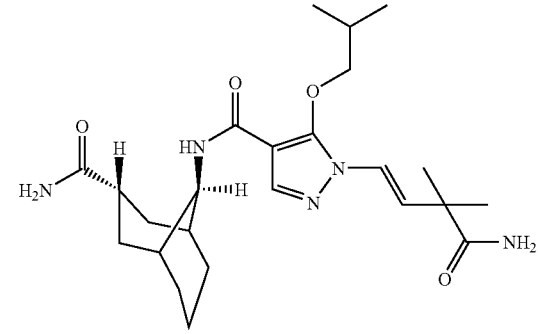 |
| E-47 | 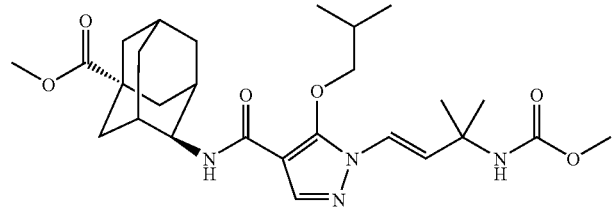 |

TABLE 62-continued

| No. | Structure |
|---|---|
| E-48 | 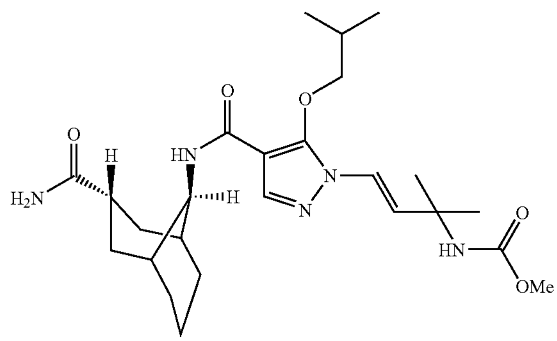 |

TABLE 63

| No. | Structure |
|---|---|
| E-49 | 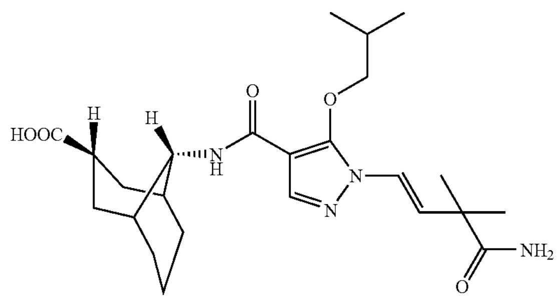 |
| E-50 | 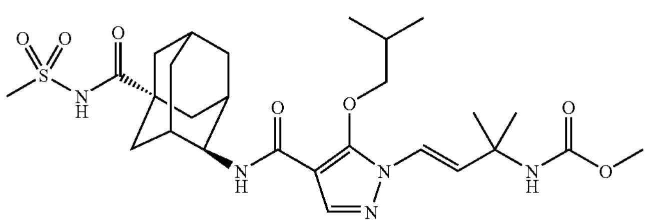 |
| E-51 | 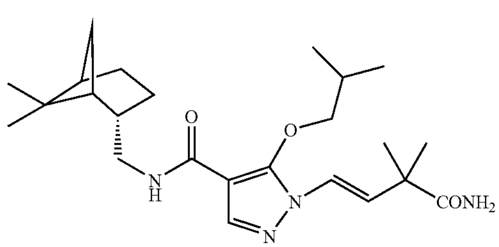 |
| E-52 | 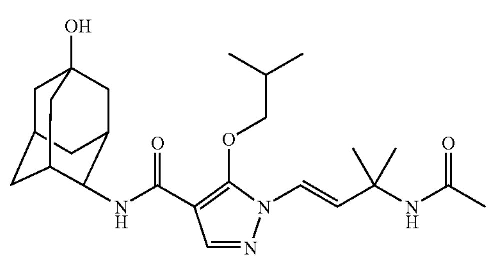 |

TABLE 63-continued

| No. | Structure |
| --- | --- |
| E-53 | 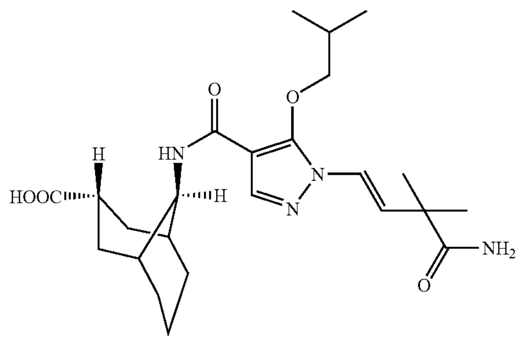 |
| E-54 | 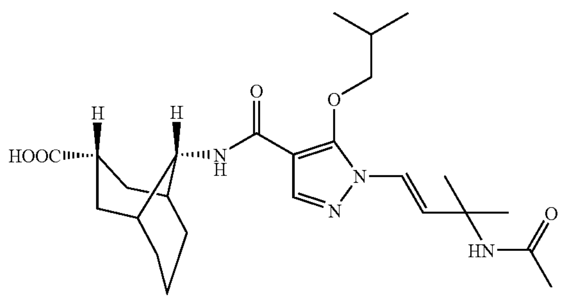 |
| E-55 | 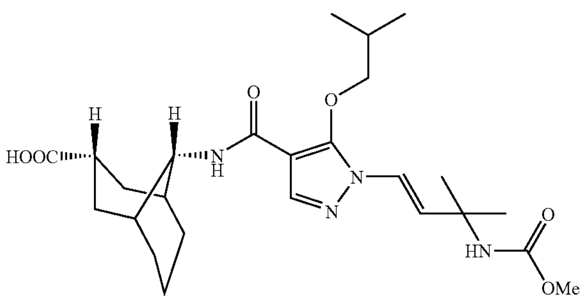 |
| E-56 | 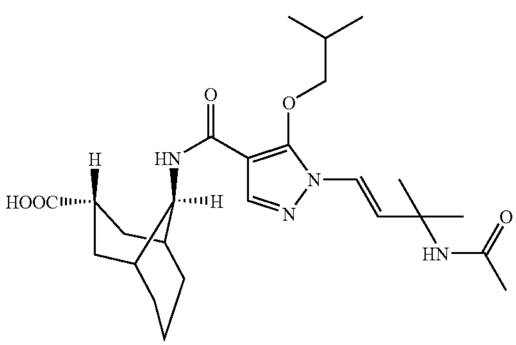 |
| E-57 | 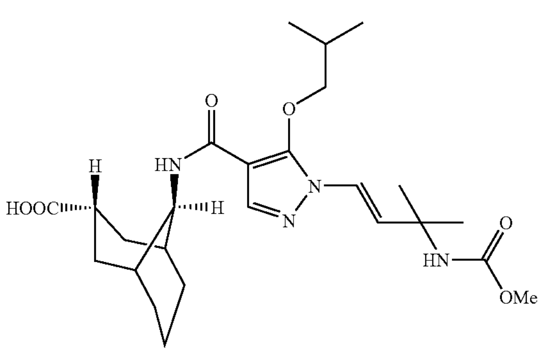 |

TABLE 63-continued

| No. | Structure |
|---|---|
| E-58 | 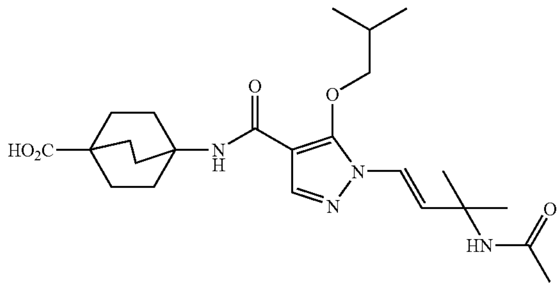 |
| E-59 | 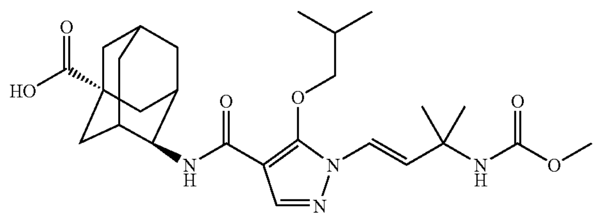 |
| E-60 | 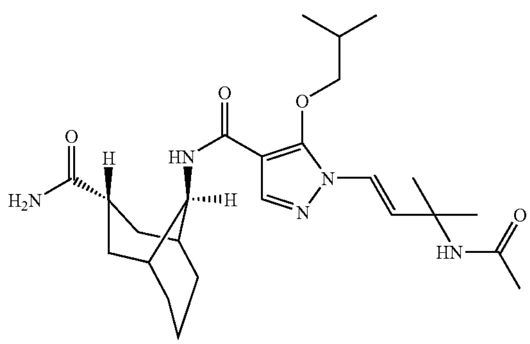 |

TABLE 64

| No. | Structure |
|---|---|
| E-61 | 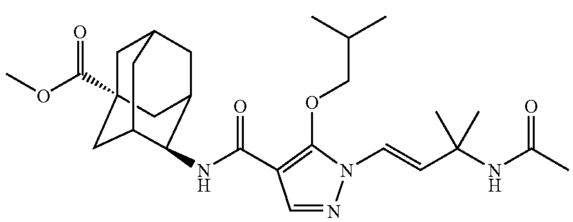 |
| E-62 | 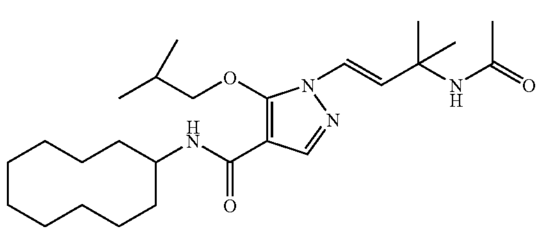 |

TABLE 64-continued

| No. | Structure |
|---|---|
| E-63 | 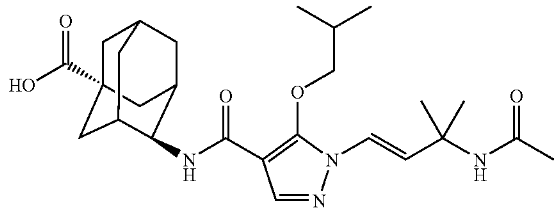 |
| E-64 | 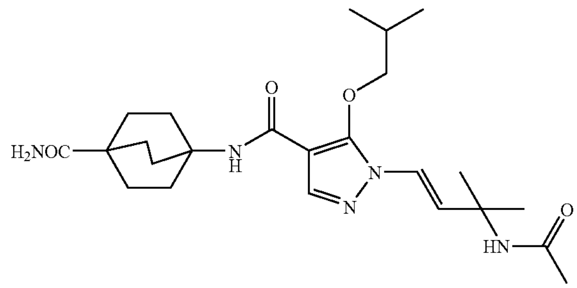 |
| E-65 | (+)- |
| E-66 | 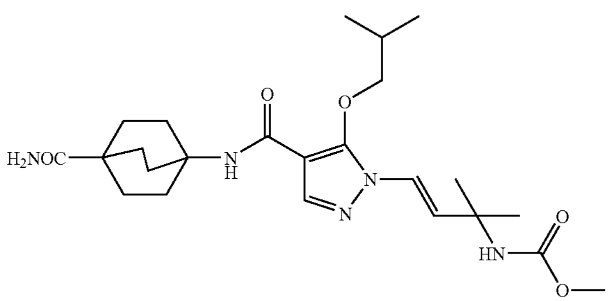 |
| E-67 | (-)- |

EXPERIMENTAL EXAMPLE 1

Evaluation of 11β-HSD1 Inhibitors (Enzyme Activity Assay on Human 11β-HSD1)

Enzymatic activity for human 11β-HSD1 was determined in a 10 μl final volume of assay mixture containing 50 mM sodium phosphate buffer (pH 7.6), 1 mg/ml bovine serum albumin, 0.42 mg/ml NADPH, 1.26 mg/ml glucose-6-phosphate, glucose-6-phosphate dehydrogenase, test compound, recombinant human 11β-HSD1, and 5μM cortisone as substrate. The reaction was started with the addition of cortisone. After incubation for 2 hours at 37° C., 5μl of europium cryptate-labelled anti-cortisol antibody and 5μl of XL665-labeled cortisol were added. After further incubation for 2 hours at room temperature, the homogeneous time-resolved fluorescence (HTRF) signal was measured. The cortisol production was quantitated by a standard curve generated with several known concentrations of cortisol in each assay.

The amount of cortisol production without compounds was served as control, and the percent inhibition by test compound at each concentration was calculated. The IC50 value of the compound for 11β-HSD1 was obtained using the inhibition curve generated by plotting the percent inhibition versus the concentration of test compound.

EXPERIMENTAL EXAMPLE 2

Evaluation of 11β-HSD1 Inhibitors (Enzyme Activity Assay on Mouse 11β-HSD1)

Enzymatic activity for mouse 11β-HSD1 activity was determined in a 10μl final volume of assay mixture containing 50 mM sodium phosphate buffer (pH 7.6), 1 mg/ml bovine serum albumin, 0.42 mg/ml NADPH, 1.26 mg/ml glucose-6-phosphate, glucose-6-phosphate dehydrogenase, test compound, recombinant mouse 11β-HSD1, and 2μM 11-dehydrocorticosterone as substrate. The reaction was started with the addition of 11-dehydrocorticosterone. After incubation for 2 hours at 37° C., 5μl of europium cryptate-labelled anti-cortisol antibody and 5μl of XL665-labeled cortisol were added. After further incubation for 2 hours at room temperature, the HTRF signal was measured. The corticosterone production was quantitated by a standard curve generated with several known concentrations of corticosterone in each assay.

The amount of corticosterone production without compounds was served as control, and the percent inhibition by compound at each concentration was calculated. The IC50 value of the compound for 11β-HSD1 was obtained using the inhibition curve generated by plotting the percent inhibition versus the concentration of test compound.

The results of experimental example 1 and 2 are shown in the following table.

TABLE 65

| No. | humanIC50(μM) | mouseIC50(μM) |
|-----|---------------|---------------|
| A-1 | 0.19 | 5.9 |
| A-2 | 0.27 | 11 |
| A-3 | 0.3 | 24.1 |
| A-4 | 0.037 | 1.6 |
| A-5 | 0.71 | >30 |
| A-6 | 0.0083 | 0.94 |
| A-7 | 0.018 | 0.71 |

EXPERIMENTAL EXAMPLE 3

Materials and Methods in Oral Absorption of 11β-HSD1 Inhibitor (1) Animals

Male C57BL/6J Jcl mice were purchased from CLEA Japan at the age of 6 weeks. After 1-week preliminary rearing, the mice were used for this study at the age of 7 weeks (2) Rearing Conditions The mice were placed at an animal room, where was set at room temperature of 23±2° C. and humidity of 55±10%, and lighting cycle time was 12 hours [light (8:00-20:00)/dark (20:00-8:00)]. The mice were allowed free access to solid laboratory food (CE-2, CLEA Japan) and sterile tap water through the preliminary rearing and experimental periods.

(3) Identification of Animals and Cages

The mice were identified by tail marking with an oil marker pen. Labels identifying the study director, purchased date, strain, sex and supplier were placed on each cage. The mice were housed by 20 mice/cage in the preliminary rearing period, and 3 mice/cage in the experimental period.

(4) Group Composition

Oral administration: 20 mg/kg (n=3)

Intravenous administration: 5 mg/kg (n=3)

(5) Preparation of Dosing Formulation

Dosing suspension for oral administration was prepared using 0.5% methyl cellulose (1500 cP) aqueous solution. Dosing solution for intravenous administration was prepared using N-dimethylacetamide/polyethyleneglycol 400 (1/2).

(6) Dosing Method

As to oral administration, the dosing suspension at 10 mL/kg was administered into the stomach using a feeding tube. As to intravenous administration, the dosing solution at 2.5 mL/kg was administered into the caudal vein using a glass syringe.

(7) Evaluation Items

The blood samples were collected from the heart at each sampling point. The drug concentration in plasma was measured using HPLC or LC/MS/MS.

(8) Statistical Analysis

The area under the plasma concentration-time curve (AUC) was calculated by WinNonlin®, and the bioavailability was calculated by the AUC values after oral and intravenous administration.

The following formulation examples 1 to 8 are provided to further illustrate the present invention and are not intended to limit the scope of the present invention. The term of "active ingredient" means a compound of the present invention, a pharmaceutical acceptable salt, or a hydrate thereof.

FORMULATION EXAMPLE 1

Hard gelatin capsules are prepared with the following ingredients:

| | Dose (mg/capsule) |
|---|---|
| Active ingredient | 250 |
| Starch (dried) | 200 |
| Magnesium stearate | 10 |
| Total | 460 mg |

FORMULATION EXAMPLE 2

Tablets are prepared with the following ingredients:

| | Dose (mg/tablet) |
|---|---|
| Active ingredient | 250 |
| Cellulose (microcrystal) | 400 |
| Silicon dioxide, fumed | 10 |
| Stearic acid | 5 |
| Total | 665 mg |

The ingredients are blended and compressed to form tablets each weighing 665 mg.

FORMULATION EXAMPLE 3

Tablets, each containing 60 mg of active ingredient, are made as follows.

| Active ingredient | 60 mg |
|---|---|
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the obtained powder, and then the admixture is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are added to the granules, mixed, and then compressed on a tablet machine to yield tablets each weighing 150 mg.

FORMULATION EXAMPLE 4

Capsules, each containing 80 mg of active ingredient, are made as follows:

| Active ingredient | 80 mg |
|---|---|
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION EXAMPLE 5

Suppositories, each containing 225 mg of active ingredient, are made as follows:

| Active ingredient | 225 mg |
|---|---|
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION EXAMPLE 6

Suspensions, each containing 50 mg of active ingredient, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 U.S. sieve, and mixed with the sodium carboxymethyl cellulose and syrup to form a smooth paste. The benzoic acid solution and flavor are diluted with a portion of the water, added and stirred. Then sufficient water is added to produce the required volume.

FORMULATION EXAMPLE 7

An intravenous formulation may be prepared as follows:

| Active ingredient | 100 mg |
|---|---|
| Saturated fatty acid glycerides | 1000 mL |

The solution of the above ingredients is generally administered intravenously to a patient at a rate of 1 mL per minute.

The invention claimed is:

1. A compound represented by formula (I) or a pharmaceutically acceptable salt thereof,

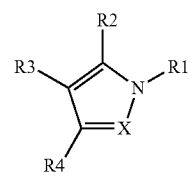

(I)

wherein $R^1$ optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle, $R^2$ is a group of formula: —Y—$R^5$, wherein Y is —O— or —S—, and $R^5$ is branched alkyl, $R^3$ is a group of formula: —C(=O)—Z—$R^6$, wherein Z is —$NR^7$— or —$NR^7$—W—, and $R^6$ is optionally substituted cycloalkyl, optionally substituted cycloalkenyl, or optionally substituted heterocycle, $R^7$ is hydrogen or optionally substituted alkyl, and W is optionally substituted alkylene, $R^4$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, or optionally substituted heterocycle, and X is =N.

2. The compound according to claim 1 or a pharmaceutically acceptable salt thereof, wherein Y is —O—.

3. The compound according to claim 1 or a pharmaceutically acceptable salt thereof, wherein Z is —NR$^7$—, and R$^7$ has the same meaning as defined in claim 1.

4. The compound according to claim 3 or a pharmaceutically acceptable salt thereof, wherein R$^7$ is hydrogen.

5. The compound according to claim 1 or a pharmaceutically acceptable salt thereof, wherein R$^6$ is optionally substituted cycloalkyl.

6. A compound represented by formula (I) or a pharmaceutically acceptable salt thereof,

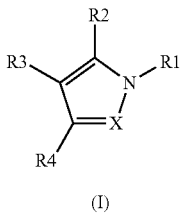

(I)

wherein
R$^1$ is optionally substituted alkyl, optionally substituted alkenyl, optionally substituted alkynyl, optionally substituted cycloalkenyl, optionally substituted cycloalkenyl, optionally substituted aryl, optionally substituted heteroaryl or optionally substituted heterocycle,
R$^2$ is a group of formula: —Y—R$^5$, wherein Y is —O— or —S—, and
R$^5$ is (i) substituted straight alkyl, wherein the substituent of said substituted straight alkyl is optionally substitute cycloalkyl or optionally substituted cycloalkenyl,
(ii) optionally substituted branched alkyl,
(iii) optionally substituted alkenyl,
(iv) optionally substituted alkynyl,
(v) optionally substituted cycloalkyl,
(vi) optionally substituted cycloalkenyl,
(vii) optionally substituted aryl,
(viii) optionally substituted heteroaryl, or
(iv) optionally substituted heterocycle, and
R$^3$ is a group of formula: —C(=O)—Z—R$^6$,
wherein Z is —NR$^7$— or —NR$^7$—W—, and
R$^6$ is optionally substituted adamantyl,
R$^7$ is hydrogen or optionally substituted alkyl, and
W is optionally substituted alkylene,
R$^4$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, or optionally substituted heterocycle, and
X is =N.

7. A compound represented by formula (I) or a pharmaceutically acceptable salt thereof,

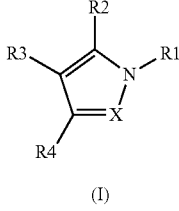

(I)

wherein R$^1$ is a group of formula:) —CH=CH—C(R$^9$R$^{10}$)—R$^{11}$—R$^{12}$,
wherein R$^9$ and R$^{10}$ are each independently hydrogen, optionally substituted alkyl or halogen, or R$^9$ and R$^{10}$ taken together with the carbon atom to which they are attached form an optionally substituted ring,
R$^{11}$ is —(CH$_2$)n-, wherein n is an integer of 0 to 3, and
R$^{12}$ is hydrogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkyloxycarbonyl, optionally substituted arylalkylcarbonyl, optionally substituted carbamoyl, optionally substituted thiocarbamoyl, optionally substituted alkylsulfonyl, optionally substituted arylsulfonyl, optionally substituted sulfamoyl, optionally substituted amino, optionally substituted carbamoyloxy, optionally substituted alkyloxy, or optionally substituted alkylthio, or
a group of formula: —C(=O)—NR$^{13}$R$^{14}$,
wherein R$^{13}$ and R$^{14}$ are each independently hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted arylsulfonyl, optionally substituted heteroarylsulfonyl or optionally substituted heterocyclesulfonyl, or R$^{13}$ and R$^{14}$ taken together with the nitrogen atom to which they are attached form an optionally substituted ring, or
a group of formula: —NR$^{15}$R$^{16}$,
wherein R$^{15}$ and R$^{16}$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted arylsulfonyl, optionally substituted alkyloxycarbonyl or optionally substituted sulfamoyl, or R$^{15}$ and R$^{16}$ taken together with the nitrogen atom to which they are attached form an optionally substituted ring,
R$^2$ is a group of formula: —Y—R$^5$, wherein Y is —O— or —S—, and
R$^5$ is (i) substituted straight alkyl, wherein the substituent of said substituted straight alkyl is optionally substituted cycloalkyl or optionally substituted cycloalkenyl,
(ii) optionally substituted branched alkyl,
(iii) optionally substituted alkenyl,
(iv) optionally substituted alkynyl,
(v) optionally substituted cycloalkyl,
(vi) optionally substituted cycloalkenyl,
(vii) optionally substituted aryl,
(viii) optionally substituted heteroaryl, or
(iv) optionally substituted heterocycle,
R$^3$ is a group of formula: —C(=O)—Z—R$^6$,
wherein Z is —NR$^7$— or —NR$^7$—W—, and
R$^6$ is optionally substituted cycloalkyl, optionally substituted cycloalkenyl, or optionally substituted heterocycle,
R$^7$ is hydrogen or optionally substituted alkyl, and
W is optionally substituted alkylene, R$^4$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, or optionally substituted heterocycle, and X is =N.

8. The compound according to claim 7 or a pharmaceutically acceptable salt thereof, wherein R$^9$ and R$^{10}$ are each independently optionally substituted alkyl or R$^9$ and R$^{10}$ taken together with the carbon atom to which they are attached form an optionally substituted ring.

9. The compound according to claim 7 or a pharmaceutically acceptable salt thereof, wherein R$^{11}$ is —(CH$_2$)n-, wherein n is an integer of 0 to 1.

10. The compound according to claim 7 or a pharmaceutically acceptable salt thereof,
wherein R$^{12}$ is a group of formula: —NR$^{15}$R$^{16}$, and
wherein R$^{15}$ and R$^{16}$ have the same meaning as defined in claim 7.

11. The compound according to claim 10 or a pharmaceutically acceptable salt thereof,
wherein R$^{15}$ is a group of formula: —C(=O)R', and
wherein R' is optionally substituted alkyl, optionally substituted alkenyl, optionally substituted cycloalkyl, optionally substituted aryl, optionally substituted amino or optionally substituted alkyloxy.

12. A pharmaceutical composition which comprises the compound according to claim 1 or a pharmaceutically acceptable salt thereof as an active ingredient.

13. The pharmaceutical composition according to claim 12, wherein the composition includes the compound according to claim 10 or the pharmaceutically acceptable salt thereof in an amount effective for treating type 2 diabetes.

14. A compound represented by formula (I):

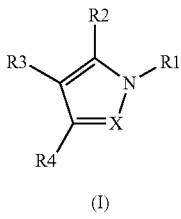

(I)

or a pharmaceutically acceptable salt thereof,
wherein R$^1$ is a group of formula:) —CH=CH—C(R$^9$R$^{10}$)—R$^{11}$—R$^{12}$,
wherein R$^9$ and R$^{10}$ are each independently optionally substituted alkyl or R$^9$ and R$^{10}$ taken together with the carbon atom to which they are attached form an optionally substituted ring,
R$^{11}$ is —(CH$_2$)$_n$-, wherein n is an integer of 0 to 1, and
R$^{12}$ is a group of formula: —NR$^{15}$R$^{16}$,
wherein R$^{15}$ is a group of formula: —C(=O)R',
wherein R' is optionally substituted alkyl, optionally substituted alkenyl, optionally substituted cycloalkyl, optionally substituted aryl, optionally substituted amino or optionally substituted alkyloxy, and
R$^{16}$ is hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted arylsulfonyl, optionally substituted alkyloxycarbonyl, or optionally substituted sulfamoyl,
wherein one of R$^2$ and R$^4$ is a group of formula: —Y—R$^5$,
wherein Y is —O— or —S—, and
R$^5$ is (i) substituted straight alkyl, wherein the substituent of said substituted straight alkyl is optionally substituted cycloalkyl or optionally substituted cycloalkenyl,
(ii) optionally substituted branched alkyl,
(iii) optionally substituted alkenyl,
(iv) optionally substituted alkynyl,
(v) optionally substituted cycloalkyl,
(vi) optionally substituted cycloalkenyl,
(vii) optionally substituted aryl,
(viii) optionally substituted heteroaryl, or
(iv) optionally substituted heterocycle, and
wherein the other of R$^2$ and R$^4$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, or optionally substituted heterocycle,
wherein R$^3$ is a group of formula: —C(=O)—Z—R$^6$,
wherein R$^6$ is optionally substituted cycloalkyl, optionally substituted cycloalkenyl, or optionally substituted heterocycle, and
Z is —NR$^7$— or —NR$^7$—W—,
wherein R$^7$ is hydrogen or optionally substituted alkyl, and
W is optionally substituted alkylene, and
wherein X is =N.

* * * * *